US010287557B2

(12) United States Patent
Geysens et al.

(10) Patent No.: US 10,287,557 B2
(45) Date of Patent: May 14, 2019

(54) YEAST STRAINS PRODUCING MAMMALIAN-LIKE COMPLEX N-GLYCANS

(71) Applicant: Oxyrane UK Limited, Manchester (GB)

(72) Inventors: Steven Christian Jozef Geysens, Wannegem-Lede (BE); Wouter Vervecken, Landskouter (BE)

(73) Assignee: Oxyrane UK Limited, Manchester (GB)

( * ) Notice: Subject to any disclaimer, the term of this patent is extended or adjusted under 35 U.S.C. 154(b) by 0 days.

(21) Appl. No.: 14/641,002

(22) Filed: Mar. 6, 2015

(65) Prior Publication Data

US 2015/0337273 A1 Nov. 26, 2015

Related U.S. Application Data

(63) Continuation of application No. 13/510,527, filed as application No. PCT/IB2010/003154 on Nov. 19, 2010, now abandoned.

(60) Provisional application No. 61/262,828, filed on Nov. 19, 2009.

(51) Int. Cl.
| | |
|---|---|
| *C12N 9/10* | (2006.01) |
| *C12N 9/24* | (2006.01) |
| *C12N 9/60* | (2006.01) |
| *C12N 15/81* | (2006.01) |
| *C12P 21/00* | (2006.01) |
| *C07K 16/32* | (2006.01) |

(52) U.S. Cl.
CPC ............ *C12N 9/1051* (2013.01); *C07K 16/32* (2013.01); *C12N 9/2402* (2013.01); *C12N 9/2488* (2013.01); *C12N 9/60* (2013.01); *C12N 15/81* (2013.01); *C12P 21/005* (2013.01); *C07K 2317/14* (2013.01); *C07K 2317/41* (2013.01); *C12Y 204/01* (2013.01); *C12Y 204/01133* (2013.01); *C12Y 302/01024* (2013.01); *C12Y 302/01084* (2013.01); *C12Y 302/01114* (2013.01)

(58) Field of Classification Search
None
See application file for complete search history.

(56) References Cited

U.S. PATENT DOCUMENTS

| | | | |
|---|---|---|---|
| 4,307,717 A | 12/1981 | Hymes et al. | |
| 4,352,883 A | 10/1982 | Lim | |
| 4,353,888 A | 10/1982 | Sefton | |
| 4,407,957 A | 10/1983 | Lim | |
| 4,704,362 A | 11/1987 | Itakura et al. | |
| 4,837,148 A | 6/1989 | Cregg | |
| 4,879,231 A | 11/1989 | Stroman et al. | |
| 4,882,279 A | 11/1989 | Cregg | |
| 4,883,666 A | 11/1989 | Sabel et al. | |
| 4,929,555 A | 5/1990 | Cregg et al. | |
| 4,968,733 A | 11/1990 | Miller et al. | |
| 4,976,859 A | 12/1990 | Wechs | |
| 5,084,350 A | 1/1992 | Chang et al. | |
| 5,158,881 A | 10/1992 | Aebischer et al. | |
| 5,272,070 A | 12/1993 | Lehrman et al. | |
| 5,284,761 A | 2/1994 | Aebischer et al. | |
| 5,585,089 A | 12/1996 | Queen et al. | |
| 5,798,113 A | 8/1998 | Dionne et al. | |
| 5,800,828 A | 9/1998 | Dionne et al. | |
| 6,110,703 A | 8/2000 | Egel et al. | |
| 6,265,185 B1 | 7/2001 | Muller et al. | |
| 6,699,658 B1 | 3/2004 | Wittrup et al. | |
| 6,803,225 B2 | 10/2004 | Contreras et al. | |
| 6,872,392 B2 | 3/2005 | Nakamura et al. | |
| 7,029,872 B2 | 4/2006 | Gerngross | |
| 7,259,007 B2 | 8/2007 | Bobrowicz et al. | |
| 7,262,287 B2 | 8/2007 | Kang et al. | |
| 7,326,681 B2 | 2/2008 | Gerngross | |
| 7,390,884 B2 | 6/2008 | Segal et al. | |
| 7,422,742 B2 | 9/2008 | Greenfeder et al. | |
| 7,422,890 B2 | 9/2008 | Gopalakrishnakone et al. | |
| 7,431,927 B2 | 10/2008 | Couto et al. | |
| 7,442,772 B2 | 10/2008 | Goddard et al. | |
| 7,449,308 B2 | 11/2008 | Gerngross et al. | |
| 7,488,591 B2 | 2/2009 | Miura et al. | |
| 7,785,856 B2 | 8/2010 | LeBowitz et al. | |
| 8,026,083 B2 | 9/2011 | Callewaert et al. | |
| 8,597,906 B2 | 12/2013 | Callewaert et al. | |
| 9,206,408 B2 | 12/2015 | Callewaert et al. | |
| 9,222,083 B2 | 12/2015 | Callewaert et al. | |
| 9,249,399 B2 | 2/2016 | Vervecken et al. | |
| 9,347,050 B2 | 5/2016 | Piens et al. | |
| 9,598,682 B2 | 3/2017 | Callewaert et al. | |
| 9,689,015 B2 | 6/2017 | Piens et al. | |
| 10,011,857 B2 | 7/2018 | Piens et al. | |
| 2002/0127219 A1 | 9/2002 | Okkels et al. | |
| 2002/0137125 A1 | 9/2002 | Zhu | |
| 2003/0147868 A1 | 8/2003 | Treco et al. | |
| 2003/0186374 A1 | 10/2003 | Hufton et al. | |
| 2004/0018588 A1 | 1/2004 | Contreras et al. | |
| 2004/0018590 A1 | 1/2004 | Gerngross et al. | |
| 2005/0014270 A1 | 1/2005 | Picataggio et al. | |
| 2005/0064539 A1 | 3/2005 | Chiba et al. | |
| 2005/0170452 A1 | 8/2005 | Wildt et al. | |
| 2005/0265988 A1 | 12/2005 | Choi et al. | |
| 2006/0014264 A1 | 1/2006 | Sauer et al. | |
| 2006/0030521 A1 | 2/2006 | Defrees et al. | |

(Continued)

FOREIGN PATENT DOCUMENTS

| | | |
|---|---|---|
| AU | 2012 206 984 | 8/2012 |
| AU | 2012206984 | 8/2012 |

(Continued)

OTHER PUBLICATIONS

Pourcq et al., Plos, vol. 7, Issue 6, pp. 1-12. (Year: 2012).*

(Continued)

*Primary Examiner* — Daniel E Kolker
*Assistant Examiner* — Jegatheesan Seharaseyon
(74) *Attorney, Agent, or Firm* — Fish & Richardson P.C.

(57) ABSTRACT

Described herein are methods and genetically engineered fungal cells useful for producing target molecules containing mammalian-like complex N-glycans or containing intermediates in a mammalian glycosylation pathway.

16 Claims, 45 Drawing Sheets

Specification includes a Sequence Listing.

(56) References Cited

U.S. PATENT DOCUMENTS

| | | |
|---|---|---|
| 2006/0040353 A1 | 2/2006 | Davidson et al. |
| 2006/0148039 A1 | 7/2006 | Kobayashi et al. |
| 2006/0286637 A1 | 12/2006 | Hamilton |
| 2007/0037248 A1 | 2/2007 | Bobrowicz et al. |
| 2008/0081035 A1 | 4/2008 | Parmely et al. |
| 2008/0171359 A1 | 7/2008 | Botes et al. |
| 2009/0069232 A1 | 3/2009 | Callewaert et al. |
| 2009/0186011 A1 | 7/2009 | Vellard et al. |
| 2010/0291059 A1 | 11/2010 | Sakuraba et al. |
| 2011/0201540 A1 | 8/2011 | Callewaert et al. |
| 2011/0207676 A1 | 8/2011 | Callewaert et al. |
| 2012/0135461 A1 | 5/2012 | Cook et al. |
| 2013/0053550 A1 | 2/2013 | Geysens et al. |
| 2013/0096281 A1 | 4/2013 | Rychaert et al. |
| 2013/0158239 A1 | 6/2013 | Callewaert et al. |
| 2013/0190253 A1 | 7/2013 | Callewaert et al. |
| 2013/0195835 A1 | 8/2013 | Callewaert et al. |
| 2013/0243746 A1 | 9/2013 | Vervecken et al. |
| 2013/0267473 A1 | 10/2013 | Piens et al. |
| 2013/0295603 A1 | 11/2013 | Piens et al. |
| 2015/0031081 A1 | 1/2015 | Vervecken et al. |
| 2016/0279254 A1 | 9/2016 | Vervecken et al. |
| 2017/0226493 A1 | 8/2017 | Callewaert et al. |
| 2017/0306379 A1 | 10/2017 | Piens et al. |

FOREIGN PATENT DOCUMENTS

| | | |
|---|---|---|
| EP | 1408117 | 4/2004 |
| FR | 2954349 | 6/2011 |
| JP | 57-054588 | 4/1982 |
| JP | 2002-369679 | 12/2002 |
| JP | 2004-313074 | 11/2004 |
| KR | 10-2004-0026663 | 3/2004 |
| KR | 20040062304 | 7/2004 |
| WO | WO 1992/19195 | 11/1992 |
| WO | WO 1995/05452 | 2/1995 |
| WO | WO 1996/04378 | 2/1996 |
| WO | WO 1996/21038 | 7/1996 |
| WO | WO 1998/01473 | 1/1998 |
| WO | WO 1998/01535 | 1/1998 |
| WO | WO 1998/48025 | 10/1998 |
| WO | WO 1999/036569 | 7/1999 |
| WO | WO 1999/37758 | 7/1999 |
| WO | WO 2001/49830 | 7/2001 |
| WO | WO 2001/088143 | 11/2001 |
| WO | WO 2002/18570 | 3/2002 |
| WO | WO 2003/029456 | 4/2003 |
| WO | WO 2003/056914 | 7/2003 |
| WO | WO 2004/003194 | 1/2004 |
| WO | WO 2004/074458 | 9/2004 |
| WO | WO 2004/074461 | 9/2004 |
| WO | WO 2004/074498 | 9/2004 |
| WO | WO 2004/074499 | 9/2004 |
| WO | WO 2005/100584 | 10/2005 |
| WO | WO 2005/106010 | 11/2005 |
| WO | WO 2007/035930 | 3/2007 |
| WO | WO 2008/100816 | 8/2008 |
| WO | WO 2008/120107 | 10/2008 |
| WO | WO 2009/033507 | 3/2009 |
| WO | WO 2009/105357 | 8/2009 |
| WO | WO 2009/137721 | 11/2009 |
| WO | WO 2010/099195 | 9/2010 |
| WO | WO 2011/039634 | 4/2011 |
| WO | WO 2011/061629 | 5/2011 |
| WO | WO 2012/042386 | 4/2012 |
| WO | WO 2012/042387 | 4/2012 |
| WO | WO 2013/098651 | 7/2013 |

OTHER PUBLICATIONS

Jacobs et al., Nat. Protocols, vol. 4, No. 1, pp. 58-70. (Year: 2009).*

Ekici et al., "Unconventional serine proteases: variations on the catalytic Ser/His/Asp triad configuration," *Protein Sci.*, 17(12):2023-2037, Epub Sep. 29, 2008.

GenBank Accession No. AAO78636, "putative alpha-1,2-mannosidase [Bacteroides thetaiotaomicron VPI-5482]," 1 page, Oct. 24, 2007.

GenBank Accession No. NP_630514, "secreted protein [Streptomyces coelicolor A3(2)]," 2 pages, Sep. 26, 2008.

Hedstrom, "Serine protease mechanism and specificity," *Chem Rev.*, 102(12):4501-4524, Dec. 2002.

Jaafar et al., "Isolation of the MNN9 gene of Yarrowia lipolytica (Y1MNN9) and phenotype analysis of a mutant ylmnn9 Delta strain," *Yeast*, 20(7):633-644, May 2003.

Liang et al., "The crystal structures of two cuticle-degrading proteases from nematophagous fungi and their contribution to infection against nematodes," *FASEB J.*, 24(5):1391-1400, Epub Dec. 9, 2009.

Lobsanov et al., "Structure of Penicillium citrinum alpha 1,2-mannosidase reveals the basis for differences in specificity of the endoplasmic reticulum and Golgi class I enzymes," *J Biol Chem.*, 277(7):5620-5630, Epub Nov. 19, 2001.

Morya et al., "In silico characterization of alkaline proteases from different species of Aspergillus," *Appl Biochem Biotechnol.*, 166(1):243-257, Epub Nov. 10, 2011.

Perona and Craik et al., "Structural basis of substrate specificity in the serine proteases," *Protein Sci.*, 4(3):337-360, Mar. 1995.

Rawlings and Barrett, "Evolutionary families of peptidases," *Biochem J.*, 290 ( Pt 1):205-218, Feb. 15, 1993.

Siezen et al., "Subtilases: the superfamily of subtilisin-like serine proteases," *Protein Sci.*, 6(3):501-523, Mar. 1997.

Wright et al., "Structure of subtilisin BPN' at 2.5 angström resolution," *Nature*, 221(5177):235-242, Jan. 18, 1969.

Zhu et al., "Mechanistic insights into a Ca2+-dependent family of alpha-mannosidases in a human gut symbiont," *Nat. Chem. Biol.*, 6(2):125-132. Supplementary Information, 25 pages. Epub 2009 Dec. 27, 2010.

"Glycoside Hydrolase Family 38," cazy.org [online] retrieved on Dec. 1, 2016. Retrieved from the Internet: <URL: http://www.cazy.org/GH38.html>, 1 page.

"Glycoside Hydrolase Family 47," cazy.org [online] retrieved on Dec. 1, 2016. Retrieved from the Internet: <URL: http://www.cazy.org/GH47.html>, 1 page.

"Glycoside Hydrolase Family 92," cazy.org [online] retrieved on Dec. 1, 2016. Retrieved from the Internet: <URL: http://www.cazy.org/GH92.html>, 1 page.

Abe et al., "In vitro oligosaccharide synthesis using intact yeast cells that display glycosyltransferases at the cell surface through cell wall-anchored protein Pir.," *Glycobiology*, 13(2):87-95, print Feb. 2003, ePub Nov. 2002.

Ackerman et al., "Highly avid magnetic bead capture: an efficient selection method for de novo protein engineering utilizing yeast surface display," *Biotechnol Prog.*, 25(3):774-783, May-Jun. 2009.

Almeciga et al., "Production of an active recombinant human N-acetylgalactosamine-6-sulfate sulfatase enzyme in Pichia Pastoris," *Molecular Genetics and Metabolism*, 111(2):S19, Abstract 11, Jan. 27, 2014.

Andrés et al., "Use of the cell wall protein Pir4 as a fusion partner for the expression of Bacillus sp. BP-7 xylanase A in Saccharomyces cerevisiae," *Biotechnol Bioeng*, 89(6): 690-697, Mar. 2005.

Boder and Wittrup, "Yeast surface display for screening combinatorial polypeptide libraries," *Nat. Biotechnol.*, 15, 553-557, Jun. 1997.

Boder et al. "Directed evolution of antibody fragments with monovalent femtomolar antigen-binding affinity," *Proc Natl Acad Sci U S A.*, 97(20):10701-5, Sep. 2000.

Brady, "Enzyme replacement for lysosmal diseases," *Annu Rev. Med.*, 57:283-296, 2006.

Brady, "The lipid storage diseases: new concepts and control," *Ann Intern Med.*, 82(2):257-61, Feb. 1975.

Cantarel et al., "The Carbohydrate-Active EnZymes database (CAZy): an expert resource for Glycogenomics," Nucleic Acids Res., 37(Database issue):D233-D238, Epub Oct. 5, 2008.

Carlson et al., "Function and structure of a prokaryotic formylglycine-generating enzyme," J Biol Chem., 283(29):20117-20125, Epub Apr. 4, 2008.

(56) References Cited

OTHER PUBLICATIONS

Chao et al., "Isolating and engineering human antibodies using yeast surface display," *Nat. Protoc.*, 1(2):755-768, 2006.
Chiba et al., "Production of human compatible high mannose-type (Man5GlcNAc2) sugar chains in *Saccharomyces cerevisiae*," *J Biol Chem.*, 273(41):26298-26304, Oct. 9, 1998.
Cho et al., "Structure of the extracellular region of HER2 alone and in complex with the Herceptin," Nature, 421(6924):756-760, Feb. 2003.
Cregg et al., "Transformation," Molecular Biology: Pichia Protocols, Chapter 3, Humana Press, Totowa, N.J., pp. 27-39 (1998).
Database Geneseq, "Aspergillus oryzae alkaline protease, SEQ ID 1.", retrieved from EBI accession No. GSP:ARW11112, Database accession No. ARW11112, 1 page, Aug. 7, 2008.
Davidow et al., "Cloning and sequencing of the alkaline extracellular protease gene of Yarrowia lipolytica," J. Bacteriol., 169(10):4621-4629, Oct. 1987.
Devos and Valencia, "Practical limits of function prediction," *Proteins.*, 41(1):98-107, Oct. 1, 2000.
Dierks et al., "Multiple sulfatase deficiency is caused by mutations in the gene encoding the human C(alpha)-formylglycine generating enzyme," *Cell*, 113(4):435-444, May 16, 2003.
Dierks et al., "Sequence determinants directing conversion of cysteine to formylglycine in eukaryotic sulfatases," *EMBO J.*, 18(8):2084-2091, Apr. 15, 1999.
Diez-Roux and Ballabio, "Sulfatases and human disease," *Annu Rev Genomics Hum Genet.*, 6:355-379, 2005.
Dragosits et al., "The effect of temperature on the proteome of recombinant Pichia pastoris," *J. Proteome Res.*, 8(3):1380-1392, Mar. 2009.
Floudas, "Computational methods in protein structure prediction," Biotechnology and Bioengineering, 97(2): 207-213, Jun. 1, 2007.
Fournier et al., "Scarcity of ars sequences isolated in a morphogenesis mutant of the yeast Yarrowia lipolytica," *Yeast*, 7(1):25-36, Jan. 1991.
Fraldi et al., "Multistep, sequential control of the trafficking and function of the multiple sulfatase deficiency gene product, SUMF1 by PDI, ERGIC-53 and ERp44," *Hum Mol Genet.*, 17(17):2610-2621, Epub May 28, 2008.
Fujii, "Antibody Affinity Maturation by Random Mutagenesis," Antibody Engineering, vol. 248, pp. 345-359, 2004.
Gande et al., "Paralog of the formylglycine-generating enzyme—retention in the endoplasmic reticulum by canonical and noncanonical signals," FEBS J., 275(6):1118-1130, Epub Feb. 6, 2008.
Garcia-Gómez et al., "Advantages of a proteolytic extract by Aspergillus oryzae from fish flour over a commercial proteolytic preparation," *Food Chemistry*, 112(3):604-608, Feb. 1, 2009.
Gasser et al., "Engineering of Pichia pastoris for improved production of antibody fragments," *Biotechnol. Bioeng.*, 94(2):353-361, Jun. 2006.
Gatlin et al., "Automated identification of amino acid sequence variations in proteins by HPLC/microspray tandem mass spectrometry," Anal Chem., 72(4):757-763, Feb. 15, 2000.
GenBank Accession No. AA034683, "mi41c04.r1 Soares mouse embryo NbME13.5 14.5 Mus musculus cDNA clone IMAGE:466086 5-, mRNA sequence," Aug. 23, 1996, 2 pages.
GenBank Accession No. BAA00258.1 GI:217809, "alkaline protease, partial [Aspergillus oryzae],"Dec. 20, 2002, 2 pages.
GenBank Accession No. BAJ83907, "sulfatase modifying factor 1 [Hemicentrotus pulcherrimus]," Nov. 10, 2011, 2 pages.
GenBank Accession No. ELW48757.1, GI: 444707484, "Sulfatase-modifying factor 1 [Tupaia chinensis]," Jan. 31, 2013, 2 pages.
GenBank Accession No. ENN77245.1, GI: 478257082, "hypothetical protein YQE_06075, partial [Dendroctonus ponderosae]," Apr. 10, 2013, 2 pages.
GenBank Accession No. NP_001069544, "sulfatase-modifying factor 1 precursor [Bos taurus]," Jan. 23, 2012, 2 pages.
GenBank Accession No. NP_215226.1, "unnamed protein product [*Mycobacterium tuberculosis* H37Rv]," Jan. 19, 2012, 2 pages.
GenBank Accession No. NP_631591.1, "hypothetical protein SCO7548 [Streptomyces coelicolor A3(2)]," Jan. 19, 2012, 2 pages.
GenBank Accession No. XP_001374411, GI: 126336367, "Predicted: sulfatase-modifying factor 1-like [Monodelphis domestica]," May 31, 2011, 1 page.
GenBank Accession No. XP_003642070.1, GI: 363738801, "Predicted: sulfatase-modifying factor 1-like [Gallus gallus]," Dec. 16, 2011, 1 pages.
GenBank Accession No. XP_005511340.1, GI: 543740918, "Predicted: sulfatase-modifying factor 1 [Columba livia]," Sep. 15, 2013, 2 pages.
GenBank Accession No. XP_504265.1, GI: 50553708, "YALI0E22374p [Yarrowia lipolytica CLIB122]," Oct. 29, 2008, 2 pages.
GenBank Accession: CAC87611.1, "ERp44 protein [*Homo sapiens*]," 2 pages, Oct. 7, 2008.
Gilbert, "Glycoside Hydrolase Family 92," CAZypedia [online], Mar. 4, 2010. Retrieved from the Internet: <URL: http://www.cazypedia.org/index.php/Glycoside_Hydrolase_Family_92>, 3 pages.
Grove et al., "In vitro characterization of AtsB, a radical SAM formylglycine-generating enzyme that contains three [4Fe-4S] clusters," *Biochemistry*, 47(28):7523-7538, Epub Jun. 18, 2008 [author manuscript].
Grubb et al., "New strategies for enzyme replacement therapy for lysosomal storage diseases," *Rejuvenation Res.*, 13(2-3):229-236, Apr.-Jun. 2010.
Guo et al., "Protein tolerance to random amino acid change," Proc Natl Acad Sci U S A., 101(25):9205-9210, Epub Jun. 14, 2004.
Henrissat, "A classification of glycosyl hydrolases based on amino acid sequence similarities," Biochem J., 280 ( Pt 2):309-316, Dec. 1, 1991.
InterPro—Protein sequence anaylsis and classification, "Species: Sulfatase-modifying factor enzyme (IPR005532)," EMBL-EBI, [online]. Retrieved from the Internet: <URL: http://www.ebi.ac.uk/interpro/entry/IPR005532/taxonomy:jsessionid= A50B4C8B868FB85867E9D179F3959BED>, 2 pages, retrieved on Nov. 3, 2015.
Jaafar et al., "Isolation of the MNN9 gene of Yarrowia lipolytica (Y1MNN9) and phenotype analysis of a mutant y1mnn9 Delta strain," Yeast, 20(7):633-644, May 2003.
Kim et al., "Functional characterization of the Hansenula polymorpha HOC1, OCH1, and OCR1 genes as members of the yeast OCH1 mannosyltransferase family involved in protein glycosylation," *J Biol Chem.*, 281(10):6261-6272, Epub Jan. 10, 2006.
Klis et al., "Cell wall construction in *Saccharomyces cerevisiae*," *Yeast*, 23(3):185-202, 2006.
Landgrebe et al., "The human SUMF1 gene, required for post-translational sulfatase modification, defines a new gene family which is conserved from pro- to eukaryotes," Gene., 316:47-56, Oct. 16, 2003.
Lin et al., "Display of a functional hetero-oligomeric catalytic antibody on the yeast cell surface," App. Microbiol Biotechol., 62(2-3): 226-232, print Aug. 2003, Epub Mar. 2003.
Mariappan et al., "ERp44 mediates a thiol-independent retention of formylglycine-generating enzyme in the endoplasmic reticulum," J Biol Chem., 283(10):6375-6383, Epub Jan. 4, 2008.
Mast and Moremen, "Family 47 alpha-mannosidases in N-glycan processing," *Methods Enzymol.*, 415:31-46, 2006.
Matsuoka et al., "Analysis of regions essential for the function of chromosomal replicator sequences from Yarrowia lipolytica," *Mol. Gen. Genet.*, 237(3):327-333, Mar. 1993.
Moreland et al., "Species-specific differences in the processing of acid α-glucosidase are due to the amino acid identity at position 201," Gene, 491(1):25-30, Jan. 1, 2012.
NCBI Reference Sequence: NP_000909.2, "protein disulfide-isomerase precursor [*Homo sapiens*]," Mar. 24, 2012, 4 pages.
NCBI Reference Sequence: XP_502492.1, "YALI0D06589p [Yarrowia lipolytica CLM122]," 2 pages, Oct. 29, 2008.
NCBI Reference Sequence: XP_502939.1, "YALI0D17424p [Yarrowia lipolytica CLM122]," 2 pages, Oct. 29, 2008.
Nett et al., "A combinatorial genetic library approach to target heterologous glycosylation enzymes to the endoplasmic reticulum or the Golgi apparatus of Pichia pastoris," *Yeast.*, 28(3):237-252, Epub Jan. 6, 2011.

(56) References Cited

OTHER PUBLICATIONS

Nicaud et al., "Protein expression and secretion in the yeast Yarrowia lipolytica," FEMS Yeast Res., 2(3):371-379, Aug. 2002.
Pignède et al., "Characterization of an extracellular lipase encoded by LIP2 in Yarrowia lipolytica," J. Bacteriol., 182(10):2802-10, May 2000.
Rabuka et al., "Site-specific chemical protein conjugation using genetically encoded aldehyde tags," Nat Protoc., 7(6):1052-1067, May 10, 2012.
Rakestraw and Wittrup, "Contrasting secretory processing of simultaneously expressed heterologous proteins in Saccharomyces cerevisiae," Biotechnol. Bioeng., 93(5):896-905, Apr. 2006.
Rodriguez et al., "Production of recombinant human N-acetylgalactosamine-6-sulfate sulfatase enzyme in Pichia pastoris," Molecular Genetics and Metabolism, 108(2):S79-S80, Abstract 197, Feb. 1, 2013.
Roeser et al., "A general binding mechanism for all human sulfatases by the formylglycine-generating enzyme," Proc Natl Acad Sci U S A., 103(1):81-86, Epub Dec. 20, 2005.
Rose, "Glycoside Hydrolase Family 38," CAZypedia [online], Feb. 2, 2010. Retrieved from the Internet: <URL: http://www.cazypedia.org/index.php/Glycoside_Hydrolase_Family_38>, 3 pages.
Ruiz-Herrera and Sentandreu, "Different effectors of dimorphism in Yarrowia lipolytica," Arch. Microbiol., 178(6): 477-483, print Dec. 2002, Epub Oct. 2002.
Ryckaert et al., "Isolation of antigen-binding camelid heavy chain antibody fragments (nanobodies) from an immune library displayed on the surface of Pichia pastoris," J Biotechnol., 145(2):93-98, Epub Oct. 2009, print Jan. 2010.
Sakuma et al., "HpSumf1 is involved in the activation of sulfatases responsible for regulation of skeletogenesis during sea urchin development," Dev Genes Evol., 221(3):157-166, Epub Jun. 27, 2011.
Sardiello et al., "Sulfatases and sulfatase modifying factors: an exclusive and promiscuous relationship," Hum Mol Genet., 14(21):3203-3217, Epub Sep. 20, 2005.
Shusta et al., "Increasing the secretory capacity of Saccharomyces cerevisiae for production of single-chain antibody fragments," Nat. Biotechnol., 16(8): 773-777, Aug. 1998.
Shusta et al., "Yeast polypeptide fusion surface display levels predict thermal stability and soluble secretion efficiency," J. Mol. Biol., 292(5):949-956, Oct. 1999.
Swennen et al., "Secretion of active anti-Ras single-chain Fv antibody by the yeasts Yarrowia lipolytica and Kluyveromyces lactis," Microbiology, 148(Pt 1):41-50, Jan. 2002.
Tajima et al., "Use of a modified alpha-N-acetylgalactosaminidase in the development of enzyme replacement therapy for Fabry disease," Am J Hum Genet., 85(5):569-580 Epub Oct. 22, 2009.
Tanino et al., "Construction of a Pichia pastoris cell-surface display system using Flo 1p anchor system," Biotechnol. Prog., 22(4): 989-993, Jul.-Aug. 2006.
Ueda et al., "Cell surface engineering of yeast: construction of arming yeast with biocatalyst," J. Biosci. Bioeng., 90(2): 125-136, 2000.
UniProtKB/Swiss-Prot: P01588, "Erythropoietin precursor (Epoetin)," Jul. 21, 1986, 7 pages.
UniProtKB/Swiss-Prot: P04062, "Glucosylceramidase precursor (Beta-glucocerebrosidase) (Acid beta-glucosidase) (D-glucosyl-N-acylsphingosine glucohydrolase) (Alglucerase) (Imiglucerase)," Nov. 1, 1986, 31 pages.
Van den Elsen et al., "Structure of Golgi alpha-mannosidase II: a target for inhibition of growth and metastasis of cancer cells," EMBO J., 20(12):3008-3017, Jun. 15, 2001.
VanAntwerp and Wittrup, "Fine affinity discrimination by yeast surface display and flow cytometry," Biotechnol. Prog., 16(1): 31-7, Jan.-Feb. 2000.
Vega et al., "Partial characterization of α-mannosidase from Yarrowia lipolytica," J Basic Microbiol., 28(6):371-379, 1988.
Vernis et al., "An origin of replication and a centromere are both needed to establish a replicative plasmid in the yeast Yarrowia lipolytica," Mol. Cell Biol., 17(4): 1995-2004, Apr. 1997.
Voznyi et al., "A fluorimetric enzyme assay for the diagnosis of MPS II (Hunter disease)," J Inherit Metab Dis., 24(6):675-680, Nov. 2001.
Wang and Shusta, "The use of scFv-displaying yeast in mammalian cell surface selections," J. Immunol. Methods, 304(1-2):30-42, Sep. 2005.
Wang et al., "A new yeast display vector permitting free scFv amino termini can augment ligand binding affinities," Protein Eng. Des. Sel., 18(7): 337-343, print Jul. 2005, Epub Jun. 2005.
Wang et al., "Construction of a novel Pichia pastoris cell-surface display system based on the cell wall protein Pir1," Curr. Microbiol., 56(4): 352-357, Apr. 2008.
Whisstock and Lesk, "Prediction of protein function from protein sequence and structure," Q Rev Biophys., 36(3):307-340, Aug. 2003.
Yeung and Wittrup, "Quantitative screening of yeast surface-displayed polypeptide libraries by magnetic bead capture," Biotechnol. Prog., 18(2):212-220, Mar.-Apr. 2002.
Ying et al., "Soluble monomeric IgG1 Fc," J Biol Chem., 287(23):19399-19408, Epub Apr. 19, 2012.
Zito et al., "Sulphatase activities are regulated by the interaction of sulphatase-modifying factor 1 with SUMF2," EMBO Rep., 6(7):655-660, Jul. 2005.
U.S. Appl. No. 61/387,924, filed Apr. 5, 2012, Piens et al.
"Arxula adeninivorans," Wikipedia [online] Jan. 13, 2010 [retrieved on Jan. 31, 2010]. Retrieved from the Internet: <URL: http://en.wikipedia.org/wiki/Arxula_adeninivorans>, 2 pages.
"Eukaryotes Genomes—Yarrowia Lipolytica," The European Bioinformatics Institute [online] [retrieved on Jun. 26, 2012]. Retrieved from the Internet: <URL: http://www.ebi.ac.uk/2can/genomes/eukaryotes/Yarrowia_lipolytica.html>, 1 page.
Aebi et al., "Cloning and characterization of the ALG3 gene of Saccharomyces cerevisiae," Glycobiology, vol. 6, No. 4, (1996), pp. 439-444.
Akcapinar et al., "Effect of codon optimization on the expression of Trichoderma reesei endoglucanase 1 in Pichia pastoris." Biotechnol Prog., Sep.-Oct. 2011; 27(5):1257-1263. doi: 10.1002/btpr.663. Epub Jul. 2011.
Akeboshi et al., "Production of Recombinant Beta-Hexosaminidase A, a Potential Enzyme for Replacement Therapy for Tay-Sachs and Sandhoff Diseases, in the Methylotrophic Yeast Ogataea minuta", Appl. Environ. Microbiol., 73( 15):4805-4812 (2007).
Alessandrini et al., "Alterations of Glucosylceramide-b-Glucosidase Levels in the Skin of Patients with Psoriasis Vulgaris," J. Invest. Dermatol, 23(6):1030-1036, 2004.
Aravind and Koonin, "The fukutin family—predicted enzymes modifying cell-surface molecules," Curr Biol., 9(22):R836-R837, Nov. 18, 1999.
Bagiyan et al., "The Action of α-Mannosidase from Oerskovia sp. on the Mannose-Rich O-Linked Sugar Chains of Glycoproteins," Eur. J. Biochem., 249(1):286-292, 1997.
Baharaeen and Vishniac, "A fixation method for visualization of yeast ultrastructure in the electron microscope ," Mycopathologia, 77(1):19-22, 1982.
Ballou, "Isolation, characterization, and properties of Saccharomyces cerevisiae mnn mutants with nonconditional protein glycosylation defects," Methods in Enzymology, vol. 185, (1990) pp. 440-470.
Barnay-Verdier et al., "Identification and characterization of two alpha-1,6-mannosyltransferases, An11p and Och1p, in the yeast yarrowia lipolytica", Microbiology, 150:2185-2195 (2004).
Barth and Gaillardin, "Physiology and genetics of the dimorphic fungus Yarrowia lipolytica," FEMS Microbiology Reviews, 19(4):219-237, Apr. 1997 [print], Jan. 2006 [online].
Bennetzen and Hall, "Codon Selection in Yeast," J. Biol. Chem., 257(6):3026-3031, 1982.
Bentley et al., "Complete genome sequence of the model actinomycete Streptomyces coelicolor A3(2)," Nature, 417:141-147, (May 2002).

(56) References Cited

OTHER PUBLICATIONS

Bijvoet et al., "Recombinant human acid alpha-glucosidase: high level production in mouse milk, biochemical characteristics, correction of enzyme deficiency in GSDII KO mice," *Hum Mol Genet.*, 7(11):1815-1824, Oct. 1998.
Bobrowicz et al., "Engineering of an artificial glycosylation pathway blocked in core oligosaccharide assembly in the yeast Pichia pastoris: production of complex humanized glycoproteins with terminal galactose," *Glycobiology*, 14(9):757-766 (2004).
Boisrame et al. "Sls1p, an endoplasmic reticulum component, is involved in the protein translocation process in the yeast Yarrowia lipolytica," *J. Biol. Chem.* 271(20):11668-75, 1996.
Bourbonnais et al., "Production of full-length human pre-elafin, an elastase specific inhibitor, from yeast requires the absence of a functional yapsin 1 (Yps1p) endoprotease," *Protein Expr Purif.*, 20(3):485-491, Dec. 2000.
Bretthauer, "Genetic engineering of Pichia pastoris to humanize N-glycosylation of proteins," *Trends in Biotechnology*, 21(11): 459-462 (Nov. 2003).
Burda et al., "Ordered assembly of the asymmetrically branched lipid-linked oligosaccharide in the endoplasmic reticulum is ensured by the substrate specificity of the individual glycosyltransferases", *Glycobiology*, 9(6):617-625 (1999).
Burton and Harding, "Hydrophobic charge induction chromatography: salt independent protein adsorption and facile elution with aqueous buffers.," *J. Chromatogr. A* 814(1-2):71-81, Jul. 1998.
Callewaert et al, "Use of HDEL-tagged Trichoderma reesei mannosyl oligosaccharide 1,2-alpha-D-mannosidase for N-glycan engineering in Pichia pastoris.," *FEBS Lett.*, 503(2-3):173-178, (Aug. 2001).
Callewaert et al., "Ultrasensitive profiling and sequencing of N-linked oligosaccharides using standard DNA-sequencing equipment," *Glycobiology* 11(4):275-281, Apr. 2001.
Cardone et al., "Abnormal mannose-6-phosphate receptor trafficking impairs recombinant alpha-glucosidase uptake in Pompe disease fibroblasts," *Pathogenetics*, 1(1):6, Dec. 1, 2008.
Carter et al., "Humanization of an anti-p185HER2 antibody for human cancer therapy," *Proc Natl Acad Sci USA*, 89(10): 4285-4289, (May 1992).
Chiba et al., "Production in yeast of alpha-galactosidase A, a lysosomal enzyme applicable to enzyme replacement therapy for Fabry disease," *Glycobiology*, 12(12):821-828 (2002).
Choi et al. "Use of combinatorial genetic libraries to humanize N-linked glycosylation in the yeast Pichia pastoris," *Proc. Natl. Acad. Sci. USA*, 100(9):5022-5027, Apr. 2003.
Choi, "Structural analysis of N-linked oligosaccharides assembled on recombinant proteins secreted from Yarrowia lipolytica Yloch1 and Yloch1 Y1mnn4 mutants," Thesis, Chungnam National University: Department of Microbiology, Republic of Korea, pp. 1-39, XP008160421, Retrieved from the Internet: URL: http://www.riss.kr/search/detail/DetailView.do?p_mat_type=75f99de66db18cf6 &control_no=4cbf0006e9061fb5ffe0bdc3ef48d419 (2006).
Choi, et al., "Structural analysis of N-linked oligosaccharides assembled on recombinant proteins secreted from Yarrowia lypolytica Yloch1 and Yloch1 Y1mnn4 mutants.," XXIIth International Conference on Yeast Genetics and Molecular Biology, 09—Protein biosynthesis, maturation, modification and degradation, *Yeast*, 22:S131, 9-35, 2005.
Cipollo and Trimble, "The accumulation of Man(6)GlcNAc(2)-PP-dolichol in the *Saccharomyces cerevisiae* Deltaalg9 mutant reveals a regulatory role for the Alg3p alpha1,3-Man middle-arm addition in downstream oligosaccharide-lipid and glycoprotein glycan processing," *J Biol Chem.*, 275(6):4267-4277, (Feb. 2000).
Cobucci-Ponzano et al., "The molecular characterization of a novel GH38 alpha-mannosidase from the crenarchaeon Sulfolobus solfataricus revealed its ability in de-mannosylating glycoproteins," *Biochimie.*, 92(12):1895-1907, (Aug. 2010).

Codon usage table: Yarrowia lipolytica CLIB122 [gbpln]: 5967 CD's (2945919 codons), *Codon Usage Database* [online], [retrieved on Jul. 10, 2012]. Retrieved from the Internet:<URL: http://www.kazusa.or.jp/codon/cgi-bin/showcodon.cgi?species=284591>, 1 page.
Connock et al., "A systematic review of the clinical effectiveness and cost-effectiveness of enzyme replacement therapies for Fabry's disease and mucopolysaccharidosis type 1," *Health Technol Assess.*, 10(20):iii-iv, ix-113, 2006.
Database Accession No. P41546, UniProt (online), "RecName: Full Transcriptionmanal Activator HAC1"; XP002509286, Nojima et al., Nov. 1, 1995, 3 pages.
Database UniProt[Online] Aug. 1, 1998 (Aug. 1, 1998), "SubName: Full= Putative secreted protein;" XP002628929 retrieved from EBI accession No. UNIPROT:O69822 Database accession No. O69822, 3 pages.
Database UniProt[Online] Jul. 11, 2006 (Jul. 11, 2006), "SubName: Full= Alpha-1, 2-mannosidase, putative; Flags: Precursor;" XP002628931 retrieved from EBI accession No. UNIPROT:Q1ASW5 Database accession No. Q1ASW5, 2 pages.
Database UniProt[Online] Apr. 29, 2008 (Apr. 29, 2008), "SubName: Full= Putative uncharacterized protein;" XP002628930 retrieved from EBI accession No. UNIPROT:B1BZG6 Database accession No. B1BZG6, 2 pages.
Davies et al, "Nomenclature for sugar-binding subsites in glycosyl hydrolases," *Biochem. J.*, 321:557-559 (1997).
De Pourcq et al, "Engineering Yarrowia lipolytica to produce glycoproteins homogeneously modified with the universal Man3GlcNAc2 N-glycan core," *PLoS One*, 7(6):e39976, 12 pages, Epub Jun. 29, 2012.
De Pourcq et al., "Engineering of glycosylation in yeast and other fungi: current state and perspectives," *Appl Microbiol Biotechnol.*, 87(5):1617-1631. Epub Jun. 29, 2010.
De Pourcq et al., "Engineering the yeast Yarrowia lipoytica for the production of therapeutic proteins homogeneously glycosylated with Man8GlcNAc2 and MansGlcNAc2," *Microbial Cell Factories*, 11:53, 1-12, May 1, 2012.
Ettinger et al., "Intrathecal methotrexate overdose without neurotoxicity: case report and literature review," *Cancer*, 41(4):1270-1273, Apr. 1978.
Fickers et al. "New disruption cassettes for rapid gene disruption and marker rescue in the yeast Yarrowia lipolytica," *J. Microbiol. Methods.* 55(3):727-737, Dec. 2003.
Fickers et al., "Carbon and nitrogen sources modulate lipase production in the yeast Yarrowia lipolytica," *J. of Applied Microbiology*, vol. 96, No. 4 (2004), pp. 742-749.
Fickers, P. et al. "Hydrophobic substrate utilization by the yeast Yarrowia lipolytica and its potential applications," *FEMS Yeast Research*, Apr. 2005, vol. 5, No. 6-7, pp. 527-543.
Freire et al. "Efficient monitoring of enzymatic conjugation reaction by surface-enhanced laser desorption/ionization time of flight mass spectrometry for process optimization," *Bioconjug. Chem.* 17(2):559-564, 2006.
Fujita and Takegawa, "Chemoenzymatic Synthesis of Neoglycoproteins Using Transglycosylation with Endo-Beta-N-acetylglucosaminidase A," *Biochem. Biophys. Res. Commun.*, 282(3):678-682, (Apr. 2001).
Gagnon-Arsenault et al., "Activation mechanism, functional role and shedding of glycosylphosphatidylinositol-anchored Yps1p at the *Saccharomyces cerevisiae* cell surface," *Mol Microbiol.*, 69(4):982-993, Epub Jun. 28, 2008.
Gagnon-Arsenault et al., "Fungal yapsins and cell wall: a unique family of aspartic peptidases for a distinctive cellular function," *FEMS Yeast Res.*, 6(7):966-978, Nov. 2006.
Gao et al. "UpGene: Application of a web-based DNA codon optimization algorithm," *Biotechnol. Prog.*, 20(2): 443-448, 2004.
Gellissen, et al., "New yeast expression platforms based on methylotrophic Hansenula polymorpha and Pichia pastoris and on dimorphic Arxula adeninivorans and Yarrowia lipolytica—A comparison," *FEMS Yeast Res.*, 5(11): 1079-1096, 2005.
Genbank Acccession No. XM_502922 GI:50550898, "Yarrowia lipolytica YALI0D17028p (YALI0D17028g) mRNA, complete cds," Oct. 29, 2008, 2 pages.

(56) References Cited

OTHER PUBLICATIONS

Genbank Acccession No. XM_503217 GI:50551486, "Yarrowia lipolytica YALI0D24101p (YALI0D24101g) mRNA, complete cds," Oct. 29, 2008, 2 pages.
Genbank Accession No. AAF34579 GI:6979644, "1,2-a-D-mannosidase [Trichoderma reesei]" Feb. 16, 2000, 1 page.
Genbank Accession No. AAO78636.1 GI:29340846, putative alpha-1,2-mannosidase [Bacteroides thetaiotaomicron VPI-5482] Feb. 8, 2011, 2 pages.
Genbank Accession No. AAO79070.1 GI:29341282, "putative alpha-1,2-mannosidase [Bacteroides thetaiotaomicron VPI-5482]," Feb. 8, 2011, 2 pages.
Genbank Accession No. AAO79099.1, "putative alpha-1,2-mannosidase [Bacteroides thetaiotaomicron VPI-5482]," Feb. 8, 2011, 2 pages.
Genbank Accession No. AF212153 GI:6979643, "Hypocrea jecorina 1,2-a-D-mannosidase (MDS1) mRNA, complete cds," Feb. 16, 2000, 2 pages.
GenBank Accession No. AF441127 GI:16974782, "Yarrowia lipolytica Mnn9p (mnn9) gene, complete cds," Apr. 11, 2003, 2 pages.
GenBank Accession No. AJ563920 GI:38488499, "Yarrowia lipolytica och1 gene for alpha 1,6 mannosyltransferase," Nov. 20, 2003, 2 pages.
GenBank Accession No. AJ865333 GI:56266607, "Trypanosoma brucei brucei glcaseIIa gene for glucosidase II alpha subunit precursor," Oct. 25, 2005, 2 pages.
GenBank Accession No. BAA08634 GI:1171477, "alpha-mannosidase [Aspergillus saitoi]" Feb. 10, 1999, 1 page.
GenBank Accession No. NP_630514 GI:21224735, "hypothetical protein SCO6428 [Streptomyces coelicolor A3(2)]," Jan. 19, 2012, 3 pages.
GenBank Accession No. NP_812442 GI:29348939, "alpha-1,2-mannosidase [Bacteroides thetaiotaomicron VPI-5482]" Jan. 20, 2012, 2 pages.
Genbank Accession No. XM_499811 GI:50543289, "Yarrowia lipolytica YALI0A06589p (YALI0A06589g) mRNA, complete cds," Oct. 29, 2008, 2 pages.
GenBank Accession No. XM_500574 GI:50546093, "Yarrowia lipolytica YALI0B06600p (YALI0B06600g) mRNA, complete cds," Oct. 29, 2008, 2 pages.
Genbank Accession No. XM_500811 GI:50546682, "Yarrowia lipolytica YALI0B12716p (YALI0B12716g) mRNA, complete cds," Oct. 29, 2008, 2 pages.
GenBank Accession No. XM_503488 GI:50552026, "Yarrowia lipolytica YALI0E03190p (YALI0E03190g) mRNA, complete cds," Oct. 29, 2008, 2 pages.
GenBank Accession No. XP_503768, GI: 50552716, "YALI0E10175p [Yarrowia lipolytica CLIB122]," Oct. 29, 2008, 2 pages.
GenBank Accession No. YP_003013376 YP_003013376, "alpha-1,2-mannosidase [Paenibacillus sp. JDR-2]" Jun. 15, 2012, 3 pages.
GenBank Accession No. YP_003120664 GI:256420011, "alpha-1,2-mannosidase [Chitinophaga pinensis DSM 2588]," Jun. 18, 2012, 2 pages.
GenBank Accession No. YP_003584502 GI:295133826, "alpha-1,2-mannosidase [Zunongwangia profunda SM-A87]," Nov. 21, 2011, 2 pages.
GenBank Accession No. Z49631 GI:1015863, "S.cerevisiae chromosome X reading frame ORF YJR131w," Aug. 11, 1997, 2 pages.
GenBank Accession No. ZP_01061975 GI:86143590, "putative alpha-1,2-mannosidas [Leeuwenhoekiella blandensis MED217]," Nov. 9, 2010, 1 page.
GenBank Accession No. ZP_01885202 GI:149279069, "putative alpha-1,2-mannosidase [Pedobacter sp. BAL39]," Nov. 9, 2010, 1 page.
GenBank Accession No. ZP_02866543 GI:169349605, "hypothetical protein CLOSPI_00343 [Clostridium spiroforme DSM 1552]," Nov. 9, 2010, 2 pages.
GenBank Accession No. ZP_03677957 GI: 224537418, "hypothetical protein BACCELL_02296 [Bacteroides cellulosilyticus DSM 14838]," Nov. 10, 2010, 1 page.

GenBank Accession No. ZP_04848482 GI:253571075, "conserved hypothetical protein [Bacteroides sp. 1_1_6]" Jun. 9, 2010, 2 pages.
GenBank Accession No. ZP_05522540 GI:256784109, "secreted protein [Streptomyces lividans TK24]," Dec. 9, 2010, 2 pages.
GenBank Accession No. ZP_06527366 GI:289767988, "secreted protein [Streptomyces lividans TK24]" Oct. 26, 2010, 3 pages.
GenBank Accession No. ZP_07083984 GI:300774115, "probable alpha-1,2-mannosidase [Sphingobacterium spiritivorum ATCC 33861]," Dec. 1, 2010, 1 page.
GenBank, "Yarrowia lipolytica CLIB122 [gbpln]: 5967 CDS's (2945919 codons)," Codon Usage Database, [online], Jun. 15 2007 [retrieved on Aug. 15, 2014]. Retrieved from the Internet: <URL:http://www.kazusa.or.jp/codon/cgi-bin/showcodon.cgi?species=284591>, 1 page.
Gentzsch and Tanner, "The PMT gene family: protein O-glycosylation in Saccharomyces cerevisiae is vital," Embo J, 15(21):5752-5759, (1996).
Gerngross, "Advances in the production of human therapeutic proteins in yeasts and filamentous fungi," Nature Biotech., 22(11):1409-1414, (2004).
Ghaemmaghami et al., "Global analysis of protein expression in yeast." Nature. vol. 425, No. 6959 (Oct. 2003) pp. 737-741.
Gonzalez and Jordan, "The alpha-mannosidases: Phylogeny and adaptive diversification," Mol Biol Evol., 17(2):292-300, (Feb. 2000).
Gossen and Bujard, "Studying gene function in eukaryotes by conditional gene inactivation," Ann. Rev. Genetics 36:153-173, (2002).
Grinna and Robbins, "Substrate specificities of rat liver microsomal glucosidases which process glycoproteins," J. Biol. Chem., 255(6):2255-2258, (1980).
Guarente et al., "A GAL10-CYC1 hybrid yeast promoter identifies the GAL4 regulatory region as an upstream site," Proc. Natl. Acad. Sci. USA 79(23):7410-7414, (1982).
Hamilton and Gerngross, "Glycosylation engineering in yeast: the advent of fully humanized yeast," Curr Opin Biotechnol., 18(5):387-392, (Oct. 2007).
Hamilton et al, "Production of complex human glycoproteins in yeast.," Science, 301(5637):1244-1246, Aug. 2003.
Henderson and Finn, "Human tumor antigens are ready to fly," Advances in Immunology, 62:217-256 (1996).
Hermans et al., "Human lysosomal alpha-glucosidase: functional characterization of the glycosylation sites," Biochem J., 289 ( Pt 3):681-686, (Feb. 1993).
Hinnen et al. "Transformation of yeast," Proc. Nat. Acad. Sci. USA 75(4):1929-1933, (1978).
Howard et al., "Identification of the Active Site Nucleophile in Jack Bean alpha-Mannosidase Using 5-Fluoro-beta-L-Gulosyl Fluoride," J. Biol. Chem., 273(4):2067-2072, 1998.
Hudson and Kortt, "High avidity scFv multimers; diabodies and triabodies," J. Immunol. Methods, 231(1-2):177-189, (1999).
Huston et al. "Engineered antibodies take center stage," Hum. Antibodies, 10(3-4):127-142, (2001).
Ichishima et al., "Molecular and enzymic properties of recombinant 1,2-alpha-mannosidase from Aspergillus saitoi overexpressed in Aspergillus oryzae cells," Biochem. J., 339: 589-597, (1999).
Inoue et al., "Molecular cloning and nucleotide sequence of the 1,2-alpha-D-mannosidase gene, msdS, from Aspergillus saitoi and expression of the gene in yeast cells," Biochim Biophys Acta. 1253(2):141-145, Dec. 6, 1995.
Ito et al., "Transformation of intact yeast cells treated with alkali cations," J. Bacteriol., 153(1):163-168, (1983).
Jacobs et al. "Engineering complex-type N-glycosylation in Pichia pastoris using GlycoSwitch technology," Nat Protoc., 2009;4(1):58-70., Epub Dec. 18, 2008.
Komeda et al., "Construction of protease-deficient Candida boidinii strains useful for recombinant protein production: cloning and disruption of proteinase A gene (PEP4) and proteinase B gene (PRBI)," Biosci Biotechnol Biochem., 66(3):628-631, Mar. 2002.
Kornfeld and Kornfeld, "Assembly of asparagine-linked oligosaccharides," Annu Rev Biochem., 54:631-664, (1985).

(56) References Cited

OTHER PUBLICATIONS

Kotula and Curtis, "Evaluation of foreign gene codon optimization in yeast: expression of a mouse IG kappa chain," *Biotechnology (N Y).*, 9(12):1386-1389, (1991).
Kuroda et al., "Production of Man5GlcNAc2-type sugar chain by the methylotrophic yeast Ogataea minuta," *FEMS Yeast Res.*, 6:1052-1062 (2006).
Kuroda et al., "Antibody expression in protease-deficient strains of the methylotrophic yeast Ogataea minuta," *FEMS Yeast Res.*, 7(8):1307-1316. Epub Aug. 22, 2007.
Laroy et al., "Glycome mapping on DNA sequencing equipment," *Nature Protocols*, 1: 397-405 (2006).
Le Dall et al., "Multiple-copy integration in the yeast Yarrowia lipolytica," *Curr Genet.*, 26(1):38-44, Jul. 1994.
Lee and Park, "Enzymatic in vitro glycosylation using peptide-N-glycosidase F," *Enzyme and Microbial Technology*, 30(6):716-720, (2002).
Li et al., "Optimization of humanized IgGs in glycoengineered Pichia pastoris," *Nat Biotechnol.*, 24(2):210-215, Epub Jan. 22, 2006.
Liao et al., "Cloning, expression, purification, and characterization of the human broad specificity lysosomal acid alpha-mannosidase," *J. Biol Chem.*, 271(45):28348-28358, (Nov. 1996).
Liu et al., "Disruption of the OCH1 and MNN1 genes decrease N-glycosylation on glycoprotein expressed in Kluyveromyces lactis," *J Biotechnol.*, 143(2):95-102, Epub Jun. 24, 2009.
Lobsanov et al., "Modulation of activity by Arg407: structure of a fungal alpha-1,2-mannosidase in complex with a substrate analogue," *Acta Crystallogr D Biol Crystallogr.*, 64(Pt 3):227-236, (2008).
Luer and Hatton, "Vancomycin administration into the cerebrospinal fluid: a review ," *Annals of Pharmacotherapy*, 27:912-921, 1993.
Madzak et al., "Heterologous protein expression and secretion in the non-conventional yeast Yarrowia lipolytica: a review," *J Biotechnol.*, 109(1-2):63-81, Apr. 8, 2004.
Madzak et al., "Strong hybrid promoters and integrative expression/secretion vectors for quasi-constitutive expression of heterologous proteins in the yeast Yarrowia lipolytica," *J Mol Microbiol Biotechnol.*, 2(2):207-216, (Apr. 2000).
Maras et al., "Molecular cloning and enzymatic characterization of a Trichoderma reesei 1, 2-alpha-D-mannosidase," *J. Biotechnol*, 77: 255-263 (2000).
Martinet et al., "Protection of mice against a lethal influenza challenge by immunization with yeast-derived recombinant influenza neuraminidase," *Eur J Biochem.*, 247(1):332-338, (Jul. 1997).
Merkle et al., Cloning, expression, purification, and characterization of the murine lysosomal acid alpha-mannosidase, *Biochim Biophys Acta.*, 1336(2):132-146, (Aug. 1997).
Mille et al., "Identification of a new family of genes involved in beta-1,2-mannosylation of glycans in Pichia pastoris and Candida albicans," *J Biol Chem.*, 283(15):9724-9736. Epub Jan. 30, 2008.
Moreau et al. "Cell-free transfer of membrane lipids. Evidence for lipid processing," *J. Biol. Chem.* 266(7):4329-4333, (1991).
Moreau et al. "Trafficking of lipids from the endoplasmic reticulum to the Golgi apparatus in a cell-free system from rat liver," *J. Biol. Chem.*, 266(7):4322-4328, (1991).
Moreland et al., "Lysosomal acid alpha-glucosidase consists of four different peptides processed from a single chain precursor," *J Biol Chem.*, 280(8):6780-6791, Epub Nov. 1, 2004.
Mori et al., "Signalling from endoplasmic reticulum to nucleus: transcription factor with a basic-leucine zipper motif is required for the unfolded protein-response pathway," *Genes Cells*, vol. 1, No. 9 (Sep. 1996), pp. 803-817.
Nakadai et al., "Purification and Properties of Alkaline Proteinase from Aspergillus oryzae," *Agr. Biol. Chem.*, 37(12): 2685-2694, 1973.
Newman and Ferro-Novick, "Characterization of new mutants in the early part of the yeast secretory pathway isolated by a [3H]mannose suicide selection," *J. Cell Biol.*, 105(4):1587-1594, (1987).

Orlean et al., "Cloning and sequencing of the yeast gene for dolichol phosphate mannose synthase, an essential protein," *J. Biol. Chem.*, vol. 263, (Nov. 1988), pp. 17499-17507.
Park et al, "Essential role of Y1MPO1, a novel Yarrowia lipolytica homologue of *Saccharomyces cerevisiae* MNN4, in mannosylphosphorylation of N- and O-linked glycans," *Appl Environ Microbiol.*, 77(4):1187-1195, Epub Dec. 23, 2010.
Paulik et al., "Cell-free transfer of the vesicular stomatitis virus G protein from an endoplasmic reticulum compartment of baby hamster kidney cells to a rat liver Golgi apparatus compartment for Man8-9 to Man5 processing," *Arch. Biochem. Biophys.*, 367(2):265-273, (1999).
Peberdy et al., "Protein secretion by fungi," *Applied Micology and Biotechnology, Agriculture and Food Production*, 1:73-114, 2001.
Penttilä et al., "Expression of two Trichoderma reesei endoglucanases in the yeast *Saccharomyces cerevisiae*," *Yeast.*, 3(3):175-185, Sep. 1987.
Platt and Lachmann, "Treating lysosomal storage disorders: Current practice and future prospects," *Biochim Biophys Acta*, 1793(4):737-745, 2009.
Poljak, "Production and structure of diabodies," *Structure*, 2(12):1121-1123, (1994).
Potgieter et al., "Production of monoclonal antibodies by glycoengineered Pichia pastoris," *J Biotechnol.*, Feb. 23, 2009;139(4):318-325, Epub Dec. 27, 2008.
Protein Data Bank, "Structure of the GH92 Family Glycosylhydrolase CCMAN5" Deposition: Sep. 29, 2010 [retrieved on Jul. 17, 2012]. Retrieved from the Internet: <URL: http://www.pdb.org/pdb/explore/explore.do?structureId=2XSG>, 2 pages.
Rexach and Schekman, "Distinct biochemical requirements for the budding, targeting, and fusion of ER-derived transport vesicles," *J. Cell Biol.*, 114(2):219-229, (1991).
Richard et al., "Tagging morphogenetic genes by insertional mutagenesis in the yeast Yarrowia lipolytica," *J Bacteriol.*, 183(10):3098-3107, (May 2001).
Seffernick et al., "Melamine deaminase and atrazine chlorohydrolase: 98 percent identical but functionally different," *J Bacteriol.*, 183(8):2405-2410, Apr. 2001.
Smith and Waterman, "Comparison of biosequences," *Adv. Appl. Math.*, 2(4):482-489, (Dec. 1981).
Song et al., "Characterization of Genes Involved in N-glycosylation in Yarrowia lipolytica," *Yeast*, 20:S147 (2003).
Song et al., "Engineering of the Yeast Yarrowia lipolytica for the Production of Glycoproteins Lacking the Outer-Chain Mannose Residues of N-Glycans," *Appl Environ Microbiol.*, vol. 73, No. 14 (Jul. 2007), pp. 4446-4454.
Sreekrishna et al., "Invertase gene (SUC2) of *Saccharomyces cerevisiae* as a dominant marker for transformation of Pichia pastoris," *Gene*, 59(1):115-125, (1987).
Stocks, "Intrabodies: production and promise," *Drug Discov. Today* 9(22): 960-966, (Nov. 2004).
Swennen et al., "Folding proteome of Yarrowia lipolytica targeting with uracil permease mutants," *J Proteome Res.*, 9(12):6169-6179, Epub Nov. 12, 2010.
Swiss Protein Accession No. P15291, Nov. 30, 2010, 9 pages.
Swiss Protein Accession No. P26572, Nov. 30, 2010, 4 pages.
Swiss Protein Accession No. P38069, Nov. 30, 2010, 3 pages.
Swiss Protein Accession No. Q09326, Nov. 30, 2010, 3 pages.
Swiss Protein Accession No. Q24451, Nov. 30, 2010, 12 pages.
Tiels et al., "A bacterial glycosidase enables mannose-6-phosphate modification and improved cellular uptake of yeast-produced recombinant human lysosomal enzymes," *Nat Biotechnol.*, 30(12):1225-1231, Epub Nov. 18, 2012.
Tremblay and Herscovics, "Cloning and expression of a specific human alpha 1,2-mannosidase that trims Man9GlcNAc2 to Man8GlcNAc2 isomer B during N-glycan biosynthesis," *Glycobiology.*, 9(10):1073-1078, (Oct. 1999).
UniProtKB/Swiss-Prot: P06280.1 GI:113499, "RecName: Full=Alpha-galactosidase A; AltName: Full=Alpha-D-galactosidase A; AltName: Full=Alpha-D-galactoside galactohydrolase; AltName: Full=Melibiase; AltName: INN=Agalsidase; Flags: Precursor," Jun. 13, 2012, 26 pages.

(56) References Cited

OTHER PUBLICATIONS

UniProtKB/Swiss-Prot: P15291.5 GI:116241264, "RecName: Full=Beta-1,4-galactosyltransferase 1; Short=Beta-1,4-GalTase 1; Short=Beta4Gal-T1; Short=b4Gal-T1; AltName: Full=UDP-Gal:beta-GlcNAc beta-1,4-galactosyltransferase 1; AltName: Full=UDP-galactose:beta-N-acetylglucosamine beta-1,4-galactosyltransferase . . . " Jun. 13, 2012, 10 pages.
UniProtKB/Swiss-Prot: P26572.2 GI:311033399, "RecName: Full=Alpha-1,3-mannosyl-glycoprotein 2-beta-N-acetyl-glucosaminyltransferase; AltName: Full=N-glycosyl-oligosaccharide-glycoprotein N-acetylglucosaminyltransferase I; Short=GNT-I; Short=GlcNAc-T I," Apr. 18, 2012, 6 pages.
UniProtKB/Swiss-Prot: P27809.1 GI:127214, "RecName: Full=Glycolipid 2-alpha-mannosyltransferase; AltName: Full=Alpha-1,2-mannosyltransferase," Jun. 13, 2012, 8 pages.
UniProtKB/Swiss-Prot: P38069.1 GI:586137, "RecName: Full=Alpha-1,2-mannosyltransferase MNN2; AltName: Full=Calcium resistance and vanadate sensitivity protein 4; AltName: Full=Mannan synthesis protein MNN2," Jun. 13, 2012, 5 pages.
UniProtKB/Swiss-Prot: Q09326.1 GI:1169978, "RecName: Full=Alpha-1,6-mannosyl-glycoprotein 2-beta-N-acetylglucosaminyltransferase; AltName: Full=Beta-1,2-N-acetylglucosaminyltransferase II; AltName: Full=GlcNAc-T II; Short=GNT-II; AltName: Full=Mannoside acetylglucosaminyltransferase 2; AltName: Full=N-g . . . ," Jun. 13, 2012, 3 pages.
UniProtKB/Swiss-Prot: Q24451.2 GI:32130434, "RecName: Full=Alpha-mannosidase 2; AltName: Full=Golgi alpha-mannosidase II; Short=AMan II; Short=Man II; AltName: Full=Mannosyl-oligosaccharide 1,3-1,6-alpha-mannosidase," Apr. 18, 2012, 13 pages.
UniProtKB/Swiss-Prot: Q9Y7X5.1 GI:74698597, "RecName: Full=Uncharacterized protein C365.14c," May 16, 2012, 2 pages.
Van Hove et al., "High-level production of recombinant human lysosomal acid alpha-glucosidase in Chinese hamster ovary cells which targets to heart muscle and corrects glycogen accumulation in fibroblasts from patients with Pompe disease," *Proc Natl Acad Sci U S A.*, 93(1):65-70, Jan. 9, 1996.
Vandersall-Nairn et al., "Cloning, expression, purification, and characterization of the acid α-mannosidase from Trypanosoma cruzi," *Glycobiology*, 8(12):1183-1194, (1998).
Verostek et al., "Glycoprotein biosynthesis in the alg3 *Saccharomyces cerevisiae* mutant. I. Role of glucose in the initial glycosylation of invertase in the endoplasmic reticulum," *The Journal of Biological Chemistry*, vol. 268, (Jun. 5, 1993), pp. 12095-12103.
Verostek et al., "Glycoprotein biosynthesis in the alg3 *Saccharomyces cerevisiae* mutant. II. Structure of novel Man6-10GlcNAc2 processing intermediates on secreted invertase," *The Journal of Biological Chemistry*, vol. 268, pp. 12104-12115, (Jun. 5, 1993).
Vervecken et al. "In Vivo Synthesis of Mammalian-Like, Hybrid-Type N-Glycans in Pichia pastoris," *Appl. Environ. Microb.*, 70(5):2639-2646, (May 2004).
Vervecken et al., "Modification of the N-glycosylation pathway to produce homogeneous, human-like glycans using GlycoSwitch plasmids," *Methods Mol Biol.*, 389:119-138, 2007.
Vocadlo et al., "Mechanistic insights into glycosidase chemistry," *Curr. Opin. Chem. Biol.*, 12:539-555 (2008).
Ward et al., "Characterization of Humanized Antibodies Secreted by Aspergillus niger," *Appl. Environ. Microbiol.*, 70(5):2567-2576, (May 2004).
Wheeler et al. "Intrabody and Intrakine Strategies for Molecular Therapy," *Mol. Ther.*, 8(3):355-366, (Sep. 2003).
Witkowski et al. "Conversion of a beta-ketoacyl synthase to a malonyl decarboxylase by replacement of the active-site cysteine with glutamine," *Biochemistry*, 38(36):11643-11650, Sep. 7, 1999.
Wu et al., Asparagine-linked glycosylational modifications in yeast, *Cell Engineering*, 3:215-232, 2002.
YALI0A16819g YALI0A16819p[Yarrowia lipolytica CLIB122] Gene ID: 2906333, created on Jul. 24, 2004, 2 pages.

YALI0C10135g YALI0C10135p[Yarrowia lipolytica CLIB122] Gene ID: 7009445, created on Oct. 29, 2008, 2 pages.
YALI0D10835g YALI0D10835p[Yarrowia lipolytica CLIB122] Gene ID: 2910442, created on Jul. 24, 2004, 2 pages.
YALI0E10175g YALI0E10175p[Yarrowia lipolytica CLIB122] Gene ID: 2912589, created on Jul. 28, 2004, 2 pages.
YALI0E20823g YALI0E20823p[Yarrowia lipolytica CLIB122] Gene ID: 2911836, created on Jul. 28, 2004, 2 pages.
YALI0E22374g YALI0E22374p[Yarrowia lipolytica CLIB122] Gene ID: 2912981, created on Jul. 28, 2004, 2 pages.
YALI0E24981g YALI0E24981p[Yarrowia lipolytica CLIB122 Gene ID: 2912672, created on Jul. 28, 2004, 2 pages.
YALI0E34331g YALI0E34331p[Yarrowia lipolytica CLIB122] Gene ID: 2912367, created on Jul. 28, 2004, 2 pages.
Yang et al., "Cell-surface display of the active mannanase in Yarrowia lipolytica with a novel surface-display system," *Biotechnol Appl Biochem*, vol. 54, No. 3 (Oct. 2009), pp. 171-176.
Yao et al., "Degradation of HSA-AX15(R13K) when expressed in Pichia pastoris can be reduced via the disruption of YPS1 gene in this yeast," *J Biotechnol.*, Jan. 15, 2009;139(2):131-136. Epub Oct. 8, 2008.
Yue et al., "Construction of a new plasmid for surface display on cells of Yarrowia lipolytica," *J Microbiol Methods*, vol. 72, No. 2 (Feb. 2008), pp. 116-123.
Zhu and Zhang, "SCPD: a promotor database of the yeast *Saccharomyces cerevisiae*," *Bioinformatics*, 15(7-8):607-611, (1999).
Zhu et al., "Glycoengineered acid alpha-glucosidase with improved efficacy at correcting the metabolic aberrations and motor function deficits in a mouse model of Pompe disease," *Mol Ther.*, 17(6):954-963, Epub Mar. 10, 2009.
Zhu et al., "Mechanistic insights into a Ca2+-dependent family of alpha-mannosidases in a human gut symbiont," *Nat. Chem. Biol.*, 6(2):125-132. Epub Dec. 27, 2009 (2010).
Zimm et al., "Cerebrospinal fluid pharmacokinetics of intraventricular and intravenous aziridinylbenzoquinone," *Cancer Research*, 44(4):1698-1701, Apr. 1984.
International Search Report and Written Opinion in PCT/IB2010/003154, dated Sep. 15, 2011, 21 pages.
International Preliminary Report on Patentability in PCT/IB2010/003154, dated May 31, 2012, 12 pages.
"Glycoside Hydrolase Family 38," cazy.org [online] captured Sep. 11, 2010. Retrieved from the Internet: <URL: http://www.cazy.org/GH38.html>, 1 page.
"Glycoside Hydrolase Family 47," cazy.org [online] captured Sep. 12, 2010. Retrieved from the Internet: <URL: http://www.cazy.org/GH47.html>, 1 page.
"Glycoside Hydrolase Family 92," cazy.org [online] captured Sep. 12, 2010. Retrieved from the Internet: <URL: http://www.cazy.org/GH92.html>, 1 page.
Vega et al., "Partial characterization of α-mannosidase from Yarrowia lipolytica," *J Basic Microbiol.*, 28(6):371-379, ePub Jan. 10, 2007.
Wang et al., "Construction of a novel Pichia pastoris cell-surface display system based on the cell wall protein Pir1," *Curr. Microbiol.*, 56(4): 352-357, Apr. 2008.
U.S. Appl. No. 13/620,259, filed Sep. 14, 2012, Callewaert.
U.S. Appl. No. 13/499,061, filed Sep. 6, 2012, Callewaert.
U.S. Appl. No. 14/641,002, filed Mar. 6, 2015, Geysens et al.
U.S. Appl. No. 15/087,201, filed Mar. 31, 2016, Piens.
U.S. Appl. No. 14/981,123, filed Dec. 28, 2015, Vervecken.
U.S. Appl. No. 14/773,234, filed Sep. 4, 2015, Vervecken.
Makde et al., "Structure and Mutational Analysis of the PhoN Protein of *Salmonella typhimurium* Provide Insight into Mechanistic Details," *Biochemistry.*, 46:2079-2090, 2007.
U.S. Appl. No. 12/062,469, filed Apr. 3, 2008, Callewaert.
U.S. Appl. No. 13/095,532, filed Apr. 27, 2011, Callewaert.
U.S. Appl. No. 13/094,606, filed Apr. 26, 2011, Callewaert.
U.S. Appl. No. 13/620,306, filed Sep. 14, 2012, Callewaert.
U.S. Appl. No. 13/574,126, filed Nov. 12, 2012, Ryckaert.
U.S. Appl. No. 15/350,648, filed Dec. 14, 2016, Callewaert.
U.S. Appl. No. 13/510,527, filed Oct. 31, 2012, Geysens.
U.S. Appl. No. 13/876,730, filed Mar. 28, 2013, Piens.
U.S. Appl. No. 13/876,769, filed Jun. 19, 2013, Piens et al.

(56) References Cited

OTHER PUBLICATIONS

U.S. Appl. No. 14/369,324, filed Jun. 27, 2014, Vervecken.
U.S. Appl. No. 13/831,368, filed Mar. 14, 2013, Vervecken.
European Office Action in International Application No. EP 13729065.6, dated Oct. 17, 2017, 4 pages.
Korean Office Action in International Application No. 10-2013-7011113, dated Nov. 14, 2017, 13 pages (with English Translation).
Korean Office Action in International Application No. 10-2013-7011110, dated Nov. 14, 2017, 16 pages (with English Translation).
Japanese Office Action in International Application No. 2017-000348, dated Jan. 17, 2018, 12 pages (with English Translation).
Japanese Office Action in International Application No. 2016-042290, dated Jan. 24, 2018, 19 pages (with English Translation).
glycoforum.gr.jp' [online] "α-Mannosidases and EDEM homolog proteins: their roles in glycoprotein ERAD," Jun. 5, 2006, Retrieved online Feb. 15, 2018, Retrieved URL: http://www.glycoforum.gr.jp/science/word/qualitycontrol/QS-A02E.html, 2 pages.
Song et al., "Glycan Microarray analysis of P-type lectins reveals distinct phosphomannose glycan recognition," *J Biol Chem.*, 284(50):35201-35214, Dec. 11, 2009.
Bohnsack et al., "Cation-independent mannose 6-phosphate receptor," *J Biol Chem.*, 284(50):35215-35226, Dec. 11, 2009.
Zhu et al., "Conjugation of mannose 6-Phosphate-containing Oligosaccharides to acid α-Glucosidase improves the clearance of glycogen in pompe mice," *J Biol Chem.*, 279(48):50336-50341, Nov. 26, 2004.
Wisselaar et al., "Structural and functional changes of lysosomal acid a-glucosidase during intracellular transport and maturation," J Biol Chem., 268(3):2223-2231, Jan. 25, 1993.
Chinese Office Action in International Application No. 201410681757.1, dated Aug. 11, 2017, 5 pages (with English Translation).
Bones et al., "Identification of N-Glycans Displaying Mannose-6-Phosphate and their Site of Attachment on Therapeutic Enzymes for Lysosomal Storage Disorder Treatment," Analytical Chemistry, 83(13):5344-5352, May 23, 2011.

European Office Action in European Application No. EP10782375.9, dated Jun. 16, 2017, 6 pages.
Herscovics, "Processing glycosidases of *Saccharomyces cerevisiae*," Biochimica Biophysica Acta, 1426(2):275-285, Jan. 6, 1999.
Korean Grounds for Rejection in Korean Patent Application No. 10-2009-7022979, dated Feb. 10, 2017, 4 pages with English translation.
Korean Grounds for Rejection in Korean Patent Application No. 10-2015-7035851, dated Feb. 10, 2017, 4 pages with English translation.
Lee et al., "A biochemical and pharmacological comparison of enzyme replacement therapies for the glycolipid storage disorder Fabry disease," Glycobiology, 13:305-313, 2003.
Odani et al., "Cloning and analysis of the MNN4 gene required for phosphorylation of N-linked oligosaccharides in *Saccharomyces cerevisiae*," *Glycobiology*, 6(8):805-810, Dec. 1996.
Odani et al., "Mannosylphosphate transfer to cell wall mannan is regulated by the transcriptional level of the MNN4 gene in *Saccharomyces cerevisiae*," FEBS Letters, 420(2-3):186-190, Dec. 29, 1997.
Prince et al., "Lipoprotein Receptor Binding, Cellular Uptake, and Lysosomal Delivery of Fusions between the Receptor associated Protein (RAP) and alpha-L-Iduronidase or Acid alpha-Glucosidase," J. Biol. Chem., 279:35037-35046, 2004.
Zhu et al., "Carbohydrate-remodeled acid a-glucosidase with higher affinity for the cation-independent mannose 6-phosphate receptor demonstrates improved delivery to muscles of Pompe mice," Biochem. J., 389:619-628, 2005.
Glycoside Hydrolase Family 38, accessed Jul. 30, 2017 at URL cazypedia.org/index.php/Glycoside_Hydrolase_Family_38, 1 page.
Tatsumi et al., "Cloning and Sequencing of the Alkaline Protease cDNA from Aspergillus Oryzae," *Agric Biol Chem.*, 52(7): 1887-1888, 1988.
Russian Office Action in International Application No. 2014139953, dated May 10, 2017, 6 pages (with English translation).

\* cited by examiner

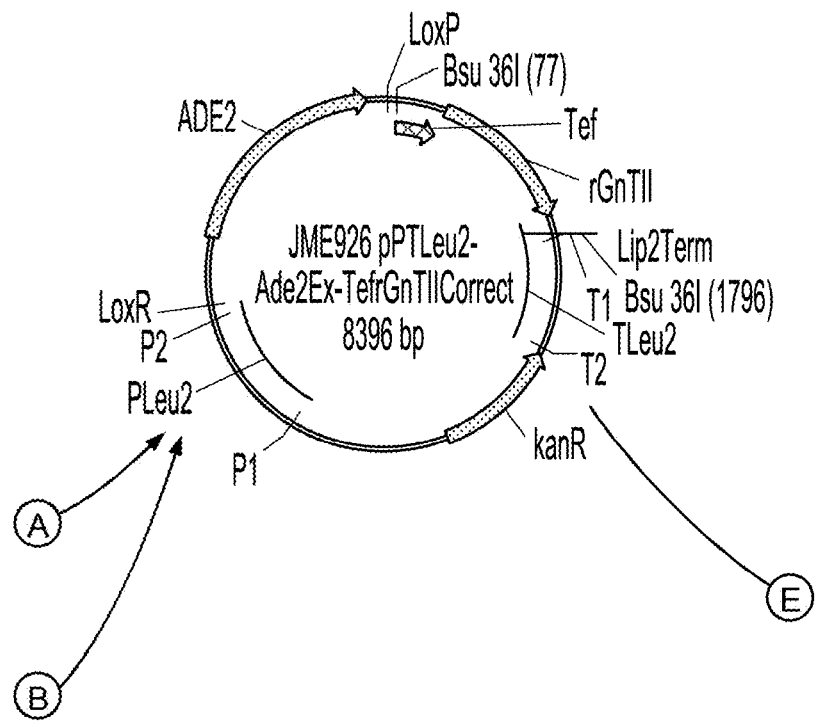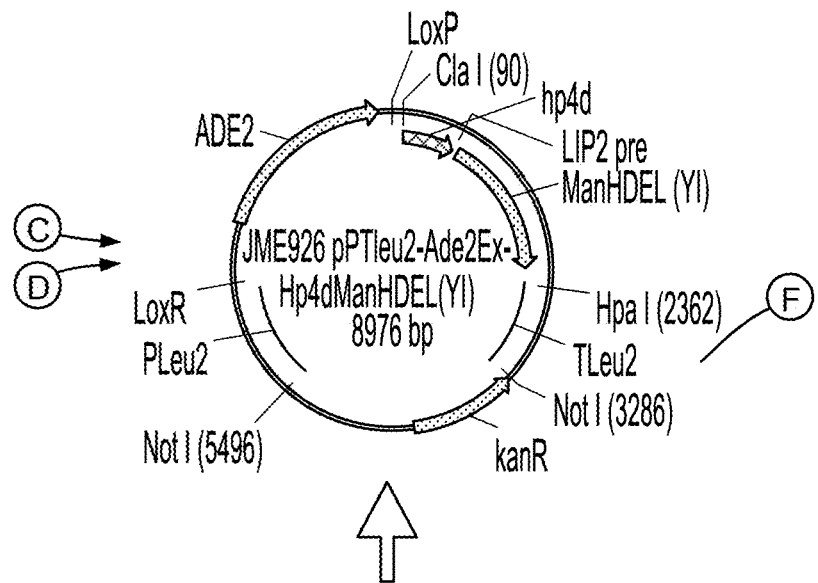
FIG. 5 (Cont.)

MALFLSKRLLRFTVIAGAVIVLLLTLNSNSRTQQYIPSSISAAFDFTSGSISPEQQVISE
ENDAKKLEQSALNSEASEDSEAMDEESKALKAAAEKADAPPAVIPILVIACDRSTVRRCL
DKLLHYRPSAELFPIIVSQDCGHEETAQAIASYGSAVTHIRQPDLSSIAVPPDHRKFQGY
YKIARHYRWALGQVFRQFRFPAAVVVEDDLEVAPDFFEYFRATYPLLKADPSLMCVSAWN
DNGKEQMVDASRPELLYRTDFFPGLGWLLLAELWAELEPKWPKAFWDDWMRRPEQRQGRA
CIRPEISRTMTFGRKGVSHGQFFDQHLKFIKLNQQFVHFTQLDLSYLQREAYDRDFLARV
YGAPQLQVEKVRTNDRKELGEVRVQYTGRDSFKAFAKALGVMDDLKSGVPRAGYRGIVTF
QFRGRRVHLAPPPTWEGYDPSWN (SEQ ID NO:3)

ATGGCCCTGTTTCTGTCTAAGCGACTGCTGCGATTCACCGTGATCGCCGGTGCCGTGATCGTGCTGCTGCTGACCCTGAACTCTAACTCTCGAACC
CAGCAGTACATCCCCTCCTCTTCTGCCGCCTTCGACTTCACCTCTGGCTCTATCTCTCCCGAGCAGCAGGTGATCTCTGAGGAGAACGACGCC
AAGAAGCTGGAGCAGTCTGCCCTGAACTCTGAGGCTTCTGAGGACTCCGAGGACAGCGAGGCCATGGACGAGGAGTCTAAGGCCCTGAAGGCCGCTGCCGAGAAG
GCTGACGACGCTCCGGCCGGCTGTGATCCCCATCCTGGTCATCGCCTGTGACCGATCGCCGTGCCACAGCTGCTCTGGACAAGCTGCTGCACTACCGACCG
TCTGCCGAGCTGTTCCCCATCATCGTGTCTCAGGACTGTGGCCACGAGGAGACCGCCCAGGCCATTGCCTCTTACGGCTCTGCCGTGACCCACATC
CGACAGCCCGACCTGTCCTCTATCGCCGTGCCCCCTGACCACCGGAAAGTTCCAGGGCTACTACAAGATCGCCCGACACTACCATGGGCCCTGGC
CAGGTGTTCCGACAGTTCCGATTCCCCGCTGCCGTGGTGTGTCTGCCTGGGGGCGTGATTCTCCGAGCCCACCTAC
CCCCTGCTGAAGGCCGACCCTCTTCCCCGGGCCTGATGTGTGTCGTGCCGTGCTGGCGCAAGTGGCCCAAGTCGAGCCCAAGCCTTCTGAGCTCTG
TACCGAACCGACTTCTTCCCCGAGCAGCAGCAGCCTGAACTCTGAGGCCCTGAACCCAGACATCTCTGAACCAGTCTCTGAACCTTCGGCCGAAAGGGCGTCGTGCTCACGGC
TGGATGCGACGACCGGAGCAGCAGCGACAGCCTGAAGTTCATCAAGCTGAACCAGCAGTTCGTGCACTTCACCCAGCTGGACCTGTCTTACCTGCAGAGGAGGCCTAC
GACCGAGACTTCCTGGCCCGAGTCGTTCGCCTCCCAGGCGCTGTACGGCCCTCAAGGCCTTCGCCAAGGCCCTGGGCGTGATGGACGACCTGAAGTCTGGCGTGCCCGAGCCTGGCGAGGC
CAGTACACCGGCGAGACTCGTTCAAGGCCTTCGCCAAGGCCCTGGGCGTGATGGACGACCTGAAGTCTGGCGTGCCCGAGCCTGGCGAGGC
ATCGTGACCTTCCAGTTCCGAGGCCGACGAGTGCACCTGGCCCTCCACCCCACCTGGAGGGCTACGACCCCTCTTGGAACTAG (SEQ ID
NO:4)

MLLTKRFSKLFKLTFIVLILCGLFVITNKYMDENTSRDDPIRPPLKVARSPRPGQCQDVV
QDVPNVDVQMLELYDRMSFKDIDGGVWKQGWNIKYDPLKYNAHHKLKVFVPHSHNDPGW
IQTFEEYYQHDTKHILSNALRHLHDNPEMKFIWAEISYFARFYHDLGENKKLQMKSIVKN
GQLEFVTGGWVMPDEANSHWRNVLLQLTEGQTWLKQFMNVTPTASWAIDPFGHSPTMPYI
LQKSGFKNMLIQRTHYSVKKELAQQRQLEFLWRQIWDNKGDTALFTHMMPFYSYDIPHTC
GPDPKVCCQFDFKRMGSFGLSCPWKVPPRTISDQNVAARSDLLVDQWKKKAELYRTNVLL
IPLGDDERFKQNTEMDVQRVNYERLFEHINSQAHFNVQAQFGTLQEYFDAVHQAERAGQA
EFPTLSGDFFTYADRSDNYWSGYYTSRPYHKRMDRVLMHYVRAAEMLSAWHSWDGMARIE
ERLEQARRELSLFQHHDGITGTAKTHVVVDYEQRMQEALKACQMVMQQSVYRLLTKPSIY
SPDFSFSYFTLDDSRWPGSGVEDSRTTIILGEDILPSKHVVMHNTLPHWREQLVDFYVSS
PFVSVTDLANNPVEAQVSPVWSWHHDTLTKTIHPQGSTTKYRIIFKARVPPMGLATYVLT
ISDSKPEHTSYASNLLLRKNPTSLPLGQYPEDVKFGDPREISLRVGNGPTLAFSEQGLLK
SIQLTQDSPHVPVHFKFLKYGVRSHGDRSGAYLFLPNGPASPVELGQPVVLVTKGKLESS
VSVGLPSVHQTIMRGGAPEIRNLVDIGSLDNTEIVMRLETHIDSGDIFYTDLNGLQFIK
RRRLDKLPLQANYPIPSGMFIEDANTRLTLLTGQPLGGSSLASGELEIMQDRRLASDDE
RGLGQGVLDNKPVLHIYRLVLEKVNNCVRPSKLHPAGYLTSAAHKASQSLLDPLDKFIFA
ENEWIGAQGQFGGDHPSAREDLDVSVMRRLTKSSAKTQRVGYVLHRTNLMQCGTPEEHTQ
KLDVCHLLPNVARCERTTLTFLQNLEHLDGMVAPEVCPMETAAYVSSHS

SEQ ID NO:7)

FIG. 10 (continued)

```
ATGGCTGCTGACCAAGCGATTCTCTAAGCTGTTCAAGCTTCATCGTGCTGATCCTGTTCGTGATCACCAACAAGTACATGGACGA
GAACACCTCCGGGATGACCCCATCCGACCCCTGAAGGTGCCCGATCTCCCGACCTGTCAGGACGTGGTGCAGGACGTGCCAACG
TGGACGTGCAGATGCTGGAGCTGTACGACGCCAAGGTGTCTTTCAAGGACATCGACGTGCTGGAAGCAGGGCTGGAACATCAAGTACGACCCCTG
AAGTACAACGCCCCACCACAAGCTGAAGGTGTTCGTGGTGCCGTGCCCCACTGTGACACCTGCGACGAACGACCCCGAGGAGTACTACCAGCACGA
CACCAAGCACATCCTGTCTAAGCCCTGCACCATGCTGACAACCTGAGATGAAGTTTATCTGGGCCGAGATCTCTTACTTCGCCCGATTCTACC
ACGAACTGGGCGAGAACAAGAAGTGCTGCTGCAGGTCTATCGTGCAGGGCCAGCTGGCTGGAGTTCGTGACCGGCTGGTGATGCCCGACGAGGCC
AACTCTCACTGGGCACTCTCCACCATGGCCTGCGAGGGCTGCAGAAGTGCTGGCTTCAAGAACATGCTGATCAGCGAACATGTCTGTGAAGAAGAGC
CCCCTTCGGCCAGCAGCGACAGCTGGAGTTTCTGTGGCCGACAGATCTGGACAACAAGGGCGACACCCGCTGTTCACCCCACATGATGCCCTTCACTCTTAC
TGGCCCAGCAGCGACAGCTGGAGTTTCTGTGGCCGACAGATCTGGACAACAAGGGCGACACCCGCTGTTCACCCCACATGATGCCCTTTCACTCTTAC
GACATCCCCACACCTGTGCCCCAGAACGTGGCCGCTCAGAACGTGTGTTGTCAGTTGACCTGCTGGTTGACCAGCCGAGCTCTTTCGCCTGCTCCTGTCTTGTCCCCCTGGAAGGTGCCCC
CCCTCGAACCATCTGACCAGAACGTGGCCGCTCAGAACGTGGTTGTCAGTTGACCTGCTGGTTGACCAGCCGAGCTCTTTCGCCTGTGCTGTGTGTTCCGCCCTGAACCAACGTCCTGC
TGATCCCCCTGGGCGACGACTTCGATTCAAGCAGAACGACGCTCAGTTCGGCACTTCGACCGCTGGAGAGTAACCTGAGAGCCGACTGTGCCAGGCCCGAGTGCCCCCACCCT
GCCCACTTCAAGCTGCAGGCTCAGTTCGCCGACGTACTTCGACGCCGTGACCCTCTGACAATCGACAACGGCGAATGGACCAGGCCCGAGTGCCCGAGTGCTGA
GTCTGGCGACTTTTTCACCTACGCCGAGCCGCCGAGATGCTGTCTCGCCGAGAACCCCAAGAGCCCCACCTGAGCGACCCCGCGAATGGACCAGGCCGGACGAGTCGAGAGCTG
TGCACTACGTGCGAGCAGCTGCAGCCACCACGACGCATGCCGGACGAGCTGGAGTGGTGGGACTACGACGGCGAATGCACCGACACCCGTCAGAAGCCGCTCAGCAGGCCCTGTCA
TCTCTGTTCCAGCACCAGACCAGTCTGCTCTACCCGGCACGTGAGTTCGGCGACCTCTTCCCACGACCCTGACCTTCACCGTGCTGACGACCCCACCCCGAGGCCGACTCTCGAT
GATGGTGATGCAGTCAGCAGCTGTCTACCGACTCCTGACCTACATGCCCTATCTCCCCCGACTTCTCTTTCTCTTAAGCACGTGATGCACAACACCCTGCCCCAC
GGCCCGGCCTCTGCGTGGAGAAGCAGCTGGTCGACTTCTACGTGTCCTCCCTTCGTGTGCCTGCGCTACCACAGTGAAGCCGCTGCTGAAACAACCCGGGAGGCTGCAGATCCTGTGTG
TGGCGAGAGCAGCTGGTCGCCAACGACACCCGAGACCTGGACCACCGAGAAGACTACCCAAGAGCTCTTCAAGGCCGAGGTGCCCCCAGGTGTCTCCGGTG
GTCTTGGCCACCTACGTGCGACCATCTCCGACCTCCGACCGAGCCACTCAGCAGCTTCAACCTGCTGCTGGACCTGTCCTCTCTCAGGCCTCTAACCTGCTGCTCCCAGGCTTCAAGGCCACCTCCGCCCATGGGCC
TGGCCACTACGTGCTGACCATCTCCGACCTCCGACCGAGCCACTCAGCAGCTTCTCGCTCTCCGACCGAGACCGGCTCTGCTGGGCGGCAACCCGCTGGGGCAACCTGAGGTCAGGGCCCTGCT
GGCCAGTACCCCGAGGACGTGAAGTTCGGCGACGTGAAGTTCGGCGAGTGGCGCAACGGCGTGCAACCGCGTGCCGATCTGCACTTCAAGTTCTCGAAGTACGCGGGTGGAACGGCGTGCCGATCTCGGCGCCT
GAAGTCTATCCAGCTGACCCAGGACTCTCCCCACGTGCCCACGTGCCCGATCTGCACTTCAAGTTCTCGAAGTACGCGGGCTGCTGGACCAGCAAGCTGGAGTCCTGTCTGTCTGTGGGC
ACCTGTTCCTGAGACCTGCCAACGACGCCGCTCCGCCCTCTCCCGTGGAGGCGGAGCATCTTCTACGAGGCGGGACATCCGGAAACCTGGTGGTGACAGTTCATCAACCTGGTGACAGTCAGGCTGACCAACCTGGCTGCTGGCTGCGAACACCGAGATCGTGAT
CTGCCCCTCTGTGGTGCACCAGACCATCAGCGGAGGCGGACACTCCATGCGGGACATCCGAAAACCTGGTGAGTTCATCAACCTGGTGACAGTTCATCAACCTGACAGAAGCCGACGCACACCCGAGGATCGTGTGAT
CCGACTGGAGACCTATCCCAGACACCCCACATGCCGACATCTTTGACAACCTGGGCAACATGGACACTTCATCATCGCAGACGACTGAAGCGACGACGACACCCGAGCCCCAGCCTGC
AGGCCAACTACTACCCCTGCACCTGAGCATGGTCATCAATGTCATCATCTGCGAGATCCATGGTCATCATCGACGGAGATCATGTTCATCATGCGACGACCTGAGGGAGGAGCCGACCGACCTGGGGGCTGAAGGCCTGAGGGCCAAGTCTGTGCACAGCCCCTGCA
GCCCTCGGCGGGCGAGCTGGAGATCATGTGCATGGAGAGCATCGGAGATCATGCACGACCAGGCTCTCTGACCCCGCTGAGTGTGACCTGGGGGCAAGTCTGTGCAGTCGTGGAGGGCTACCGGCCCGACGTGGAAAAGGCCTCTC
CATCTACCGACTGGTGCTGCTGGAGAAGTGAACAACTGTGTGCCGAGAACTGTGGGCGATCGGCCAGAACCGAGTGCTGTACGAGCTGTCACCGCCCCGAACCAAGGCCTCTC
AGTCTCTGCTGAGACGTGTCTGTATGCGACGACCTGAAGTTCATCTTGCCCGAGAACGAGTGGATCGGCAACACCAGCGCCAGTGCCGATCCGACCCTGAGGGGCTACGTTCCGAGGAGCTCGTGTAGCGTACGTTCCGAGGGCTACGTGGAGGGCTACGTTCAGCGTGGTGG
CACCCCCGAGGACACACCCAGGACGTGCTGACTGAAGCAACTGGTGCCCCAGCAGCGTGCCCAACCGAACTGCGAAAGGAGTCTGAGGCCCGAAGCTGTGACCGAACCGCTGTGACTGGTGG
AGCCACCTGAGACGGCATGGTGCCCCGAGGTGTGTGCCGAGAAATGAGAGACCGCCGCTACCGTCGTCCACTCTTCTTAG (SEQ ID NO:8)
```

MLLTKRFSKLFKLTFIVLILCGLFVITNKYMDENTSVKEYKEYLDRGRAMTGVHEGTVLV
TGGAGYIGSHTCVVLLEKGYDVIVDNLCNSRVEAVHRIEKLTGKKVIFHQVDLLDEPAL
DKVFANQNISAVIHFAGLKAVGESVQVPLSYYKNNISGTINLIECMKKYNVRDFVFSSSA
TVYGDPTRPGGTIPIPESCPREGTSPYGRTKLFIENIIEDETKVNKSLNAALLRYFNPGG
AHPSGELGEDPLGIPNNLLPYIAQVAVGRLDHLNVFGDDYPTSDGTFIRDYIHVCDLAEA
HVAALDYLRQHFVSCRPWNLGSGTGSTVFQVLNAFSKAVGRDLPYKVTPRRAGDVVNLTA
NPTRANEELKWKTSRSIYEICVDTWRWQQKYPYGFDLTHTKTYKGSGGRDLSRLPQLVG
VSTPLQGGSNSAAAIGQSSGELRTGGARPPPLGASSQPRPGGDSSPVVDSGPPASNLT
SVPVPHTTALSLPACPEESPLLVGPMLIEFNMPVDLELVAKQNPNVKMGGRYAPRDCVSP
HKVAIIPFRNRQEHLKVWLYLHPVLQRQQLDYGIYVINQAGDTIFNRAKLINVGFQEA
LKDYDYTCFVFSDVDLIPMNDHNAYRCFSQPRHISVAMDKFGFSLPYVQYFGGVSALSKQ
QFLTINGFPNNYWGWGGEDDDIFNRLVFRGMSISRPNAVVGRCRMIRHSRDKKNEPNPQR
FDRIAHTKETMLSDGLNSLTYQVLDVQRYPLYTQITVDIGTPS (SEQ ID NO:9)

ATGCTGCTGACCAAGCGATTCTCTAAGCTGTTCAAGCTGACCTTCATCGTGCTGATCCTGTGTGGCCTGTTCGTGATCACCAACAAGTACATGGACGAGAACACCTCTG
TGAAGGAATACAAGGAGTACCTGGACCGTGGAGCCATGACCGGCGTGCACGAGGGCACCGTGCTGGTGACCGGAGGAATACAAGGAGTACCTGGACCGTGGAGCCATGACCGGCGTG
GGTGCTGCTGGAGAAGGCTACGACGTGATCGTGGACAACCTGTGTAACTCTCGAGTGGAGGCCGTGCACGAGGGCATCGAGAAGCTGACAGGCAAGAAGGTGATCTTC
CACCAGGTGGACCTGCTGGACGAGCCTGCCCTGGACAAGGTGTTCGCCAACCAGAACATCTCTGCCGTGATCCACTTCGCCGGGCTGAAGGCCGTGGGCGAGTCTGTGC
AGTGCCCCTGTCTTACTACAAGAACAACATCTCTGGCACCATCAACCTGATCGAGTGTATGAAGAAGTACAACGTCCGAGACCTTCGTGTTCTCTTCTGCCACCGT
GTACGGCGACCCCACCCGGCCAGGCGGAACCATCCCCATCCCCGAGTCTTGTCCCAGAGAGGCACCTCTCCCTACGGCCGGACCAAGCTGTTCATCGAGAACATCATC
GAGGACGAAACCAAGGTGAACAAGTCTCTGAACGCCGCCCTCCTGCGGTACTTCAACCCGGTGGCGCCCCACCCTGAAGCTGTTTGGCGACGACTACCTGTTTGCCC
CAACCAGGTGCTGCCCTGGACTGGCGGCCAGTCCACATGACGGTGAACGGTGCAGCACTTCGTGTCTGTCTTGTGACCCGGACAGCCAGGATGCCAGGTGGAAACCTCTAC
GTGTTCCAGGTGCTGAACGCTGAAGTGGAAGACCTCTCGATCTATCGACGAGATCTGTCTGACTGCTGGACCACTGGAGATCGTGTGAGACATCGTGGTGATCGCC
GAGCTAACGAGGAGCTCTGGCGGACGCTGGAGATCTGTCTGACTGCTGGACCACTGGAGATCGTGTGAGACATCGTGGTGATCGCC
CAAGACCTACAAGGGCTCTGGCGGACGCTGGAGATCTGTCTGACTGCTGCCTCAGCTGGCGTGTCTACCTCGGCCGACTCTTTCTCCGTGGTGACTCTGGCC
CAGTCCTCCGGCGAGCTGCGGACCACTGAACCTGTGTGCCGTGCCCGGCGGCAAGCAGAACCCAACGTGAAGATGGCGCGCTACCTGCCCGTCCCGAGATGGCC
GTTCAACATGGCCGTGGAGCTGGTGCCAAGCTGAAGTGGCACCTGAAGGAGCCGTGCAGCACGCTGATACCGCACCGTGTCCACCGCATCTACGTGATCAACCAGG
ATCATCCCTTTCAGAAACCGACAGGAGCACCGAGCGCAAGCTGTGAACGTGCTGAACGTGGGCTTCCAGGAGGCCCTGAAGACTACGACTACACCTGTTTCGTGTTCTCTCGCGCCAT
CCGGCGACACCATCTTCAACCGAGCCAAGCTGATCAACGTGGGCTTCCAGGAGGCCCTGAAGACTACGACTACACCTGTTTCGTGTTCTCTGACGTGGACCTGATCCCC
ATGAACGACCACAACGCCTACCGATGTTTCTCCCAGCCCCGACACATCTCTGTGGCCATGGACAAGTTCGGTTTCTCTCTGCCCTACGTGCAGTACTTCGGCGGCGTT
TCTGCCCTGTCTAAGCAGCAGTTCCTGACCATCAACGGCTTCCCCAACAACTACTGGGGCTGGGCCGGAGAGGACGACGACATTTTCAACCGACTGGTGTTCCGAGGCA
TGTCCTATCCTCGACCAACGCCGTGGTGGGCCGATGTCGAATGATCCGACACTCTCGAGACAAGAAGAACGAGCCCAACCCCAGCCAGATTTGACCGAATTCTCACAC
TAAGGAAACCATGCTGTCTGACGGCCTGAACTCTCGAACCTGACCTACCAGGTGCTGGACGTGCAGCGGTACCCCCTGTACACCCAGATCACCGTGGACATCGGCACACCCTCT
TAG (SEQ ID NO:10)

FIG. 13

MLLTKRFSKLFKLTFIVLILCGLFVITNKYMDENTSSLVYQLNFDQMLRNVDKDGTWSPG
ELVLVVQVHNRPEYLRLLIDSLRKAQGIREVLVIFSHDFWSAEINSLISSVDFCPVLQVF
FPFSIQLYPSEFPGSDPRDCPRDLKKNAALKLGCINAEYPDSFGHYREAKFSQTKHHWWW
KLHFVWERVKVLQDYTGLILFLEEDHYLAPDFYHVFKKMWKLKQQECPGCDVLSLGTYTT
IRSFYGIADKVDVKTWKSTEHNMGLALTRDAYQKLIECTDTFCTYDDYNWDWTLQYLTLA
CLPKVMKVLVPQAPRIFHAGDCGMHHKKTCRPSTQSAQIESLLNNNKQYLFPETLVIGEK
FPMAAISPPRKNGGWGDIRDHELCKSYRRLQ (SEQ ID NO:17)

<u>ATG</u>CTGCTGACCAAGCGATTCTCTAAGCTGTTCAAGCTGACCTTCATCGTGCTGATCCTGTGCTGGCCTGTTC
GTGATCACCAACAAGTACATGGACGAGAACACCTCGAGCCTGGTGTACCAGTGAACTTCGACCAGATGCTGC
GAAACGTGGACAAGGACGGCACCTGGTCTCCCGGCGAGCTGGTGCTCGTGGTGCAGGTGCACAACCGACCCAGT
ACCTGCGACTGCTGATCGACTCTCTGCGAAAGGCCCAGGGCATCCGAGAGGTGCTGGTGATCTTCTCACGACTT
CTGGTCTGCCGAGATCAACTCCCTGATCTCTTCTGGACCCCCGAGTCCCGAGACTGTCCCGAGACCTGAAGAACGCCGCCT
TCCAGCTGTACCCCTGAGTTCCCCGACGTAGTTACCCCGACTCTTCGCCACTACGGAGAGCAAGTTCTCTCAGACCAAG
GAAGCTGGGCTGTATCAACGCGACTGCACTTCGGTGTGGAGCGAGTGAAGGTGCTGCAGGACTACACCGGCCTGATCTG
CACCACTGGGAGGAGGACCACTACCTGGCCCCCGACTTCTACCAGTGTTCAAGAAGATGTGAAGCTGAAGCAGCAG
TTCCTGGAGGAGGACCACTACCTGGCCCCCGACTGTCTCTGGCCACTACAACATCGATCTTTCTACGGCATCGCCGACAAGG
GAGTGTCCCCGGCTGCGACTGCGAAGTCTACGAAGGTCTACCGAGCAGCACAACATGGGCTGGCCTGACCGAGATGCTACCAGAAGCTGA
TGGACGTCAAGACCTGAAGACACCTTCGTAGTCTACCCCTGAAGACCAGCTTCCCATGGCGCAGGACTGGACTGCTGACCCGACCCCGACCCTGGCCTG
TCGAGTGTACCGACCACACCTTCGGTGGAAGGTGCTGGTGCCCCAAGTCTGCCCAGGTCGCCAATCTTCCACGCCGGGCACTGTTGGCATGCACCAC
TCTGCCCCAAGGTGGGAAGGTGTGGGTTGCCCTACCAGTCTGCGCCAGATCGAGTCTGTCTGAACAACAACAAGCAGTACCTGTTTCC
AAGAAGACCTGTGCGACCCCTGGTGATCGGCGAGAAGTTCCCCAGTCTCGCCTGCGCCATCTCCGCTCCCCCCGAAAGAACGGCGGCTGGGCCG
CTGAGACCCTGGTGATCGGCGAGAAGTTCCCCATGGCCGCCATCTCCGCTCCCCCCGAAAGAACGGCGGCTGGGCCG
ACATCCGAGACCACGAACTCTGTAAGTCTTACGACGAGACTGCAG<u>TAG</u>

FIG. 22

ATGAAGCTTTCCACCATCCTTTTCACAGCCTGCGCTACCCTGGCTG
CCGCCCTCCCTTCCCCCATCACTCCTTCTGAGGCCGCAGTTCTCCA
GAAGCGAGGCGGCGGCGACATTCAGATGACTCAGTCTCCCTCTTC
TCTGTCTGCTTCTGTGGGTGACCGAGTGACCATTACCTGTCGAGCT
TCTCAGGACGTGAACACTGCTGTTGCTTGGTATCAGCAGAAGCCT
GGAAAGGCTCCTAAGCTGCTGATCTACTCTGCCTCTTTCCTGTACT
CTGGCGTGCCTTCTCGATTTTCTGGCTCTCGATCTGGAACCGACTT
CACCCTGACCATTTCTTCTCTGCAGCCTGAGGACTTTGCTACCTAC
TACTGTCAGCAGCATTACACCACCCCTCCTACTTTTGGACAGGGC
ACCAAGGTTGAGATTAAGCGAACCGTGGCTGCTCCTTCTGTGTTC
ATTTTCCCCCCTCTGACGAGCAGCTGAAGTCTGGAACTGCTTCTG
TTGTGTGCCTGCTGAACAACTTTTACCCCGAGAGGCTAAGGTTC
AGTGGAAGGTGGACAACGCTCTGCAGTCTGGAAACTCTCAGGAG
TCTGTTACTGAGCAGGACTCTAAGGACTCGACCTACTCTCTCTT
CTACCCTGACCCTGTCTAAGGCTGACTACGAAGCATAAGGTGT
ACGCTTGTGAGGTTACCCATCAGGGACTGTCCTCTCCCGTGACCA
AGTCTTTTAACCGAGGCGAGTGCTAA

FIG. 30A

MKLSTILFTACATLAAALPSPITPSEAAVLQKRGGGDIQMTQSPSSLSA
SVGDRVTITCRASQDVNTAVAWYQQKPGKAPKLLIYSASFLYSGVPS
RFSGSRSGTDFTLTISSLQPEDFATYYCQQHYTTPPTFGQGTKVEIKRT
VAAPSVFIFPPSDEQLKSGTASVVCLLNNFYPREAKVQWKVDNALQS
GNSQESVTEQDSKDSTYSLSSTLTLSKADYEKHKVYACEVTHQGLSS
PVTKSFNRGEC

FIG. 30B

```
ATGAAGCTTTCCACCATCCTTTTCACAGCCTGCGCTACCCTGGCTGCC
GCCCTCCCTTCCCCCATCACTCCTTCTGAGGCCGCAGTTCTCCAGAAG
CGAGGCGGCGGCGAGGTTCAGCTGGTTGAGTCTGGTGGAGGACTGG
TTCAGCCTGGTGGATCTCTGCGACTGTCTTGTGCTGCTTCTGGCTTCA
ACATCAAGGACACCTACATTCATTGGGTCCGACAGGCTCCCGGAAAG
GGACTGGAGTGGGTTGCCCGAATCTACCCTACCAACGGCTACACTCG
ATACGCTGACTCTGTGAAGGGACGATTCACCATTTCTGCCGACACCT
CTAAGAACACTGCCTACCTGCAGATGAACTCTCTGCGAGCTGAGGAC
ACTGCTGTGTACTACTGTTCTGATGGGGAGGTGACGGTTTTTACGCC
ATGGACTACTGGGGACAGGGAACTCTGGTGACCGTTTCTTCTGCTTC
TACCAAGGGACCTTCTGTGTTTCCTCTGGCCCCTCTTCTAAGTCTAC
CTCTGGTGGAACTGCTGCTCTGGGATGTCTGGTGAAGGACTACTTTC
CTGAGCCTGTGACTGTGTCTTGGAACTCTGGCGCTCTGACTTCTGGTG
TTCACACCTTCCCTGCTGTTCTGCAGTCCTCTGGACTGTACTCTCTC
TTCTGTGGTGACCGTGCCTTCTTCTTCTCTGGGAACCCAGACCTACAT
CTGTAACGTGAACCACAAGCCCTCTAACACTAAGGTGGACAAGAAG
GTGGAGCCTAAGTCTTGTGACAAGACCCATACCTGTCCCCCTTGTCCT
GCTCCTGAGCTGCTGGGAGGACCCTCTGTTTTCTGTTCCCCCCCAAG
CCTAAGGACACCCTGATGATTTCTCGAACCCCTGAGGTGACCTGTGT
TGTGGTGGACGTTTCTCATGAGGACCCTGAGGTGAAGTTTAACTGGT
ACGTGGACGGTGTTGAGGTTCACAACGCTAAGACTAAGCCCCGAGA
GGAGCAGTACAACTCTACTTACCGAGTGGTGTCTGTGCTGACTGTTC
TGCATCAGGACTGGCTGAACGGAAAGGAATACAAGTGTAAGGTCTC
CAACAAGGCTCTGCCTGCTCCATTGAAAAGACCATCTCTAAGGCTA
AGGGACAGCCCAGAGAGCCTCAGGTTTACACTCTGCCCCCTTCCCGA
GAGGAGATGACCAAGAACCAGGTGTCCCTGACTTGTCTGGTCAAGG
GATTCTACCCCTCTGACATTGCTGTTGAGTGGGAGTCTAACGGACAG
CCTGAGAACAACTACAAGACCACCCCTCCTGTTCTGGACTCTGACGG
CTCTTTCTTCCTGTACTCTAAGCTGACCGTGGACAAGTCTCGATGGCA
GCAGGGAAACGTGTTCTCTTGTTCCGTGATGCATGAGGCTCTGCACA
ACCACTACACCCAGAAGTCTCTGTCTCTGTCTCCCGGCAAGTAA
```

FIG. 31A

MKLSTILFTACATLAAALPSPITPSEAAVLQKRGGGEVQLVESGGGLVQPGGSLRLSCAA
SGFNIKDTYIHWVRQAPGKGLEWVARIYPTNGYTRYADSVKGRFTISADTSKNTAYLQMN
SLRAEDTAVYYCSRWGGDGFYAMDYWGQGTLVTVSSASTKGPSVFPLAPSSKSTSGGTAA
LGCLVKDYFPEPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKC
KVSNKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQKSL
SLSPGK

FIG. 31B

SEQUENCE LISTING

```
<160> NUMBER OF SEQ ID NOS: 35

<210> SEQ ID NO 1
<211> LENGTH: 19
<212> TYPE: DNA
<213> ORGANISM: Artificial Sequence
<220> FEATURE:
<223> OTHER INFORMATION: oligonucleotide

<400> SEQUENCE: 1
tcgctatcac gtctctagc                                                    19

<210> SEQ ID NO 2
<211> LENGTH: 29
<212> TYPE: DNA
<213> ORGANISM: Artificial Sequence
<220> FEATURE:
<223> OTHER INFORMATION: oligonucleotide

<400> SEQUENCE: 2
actctgtata cttgtatgta ctgtgagac                                         29

<210> SEQ ID NO 3
<211> LENGTH: 443
<212> TYPE: PRT
<213> ORGANISM: Artificial Sequence
<220> FEATURE:
<223> OTHER INFORMATION: fusion of N-terminal portion of the S.
      cerevisiae Kre2 protein and catalytic domain of human
      GlcNAc-transferase I

<400> SEQUENCE: 3

Met Ala Leu Phe Leu Ser Lys Arg Leu Leu Arg Phe Thr Val Ile Ala
 1               5                  10                  15

Gly Ala Val Ile Val Leu Leu Leu Thr Leu Asn Ser Asn Ser Arg Thr
            20                  25                  30
```

-continued

```
Gln Gln Tyr Ile Pro Ser Ser Ile Ala Ala Phe Asp Phe Thr Ser
         35                  40                  45
Gly Ser Ile Ser Pro Glu Gln Val Ile Ser Glu Glu Asn Asp Ala
 50                  55                  60
Lys Lys Leu Glu Gln Ser Ala Leu Asn Ser Glu Ala Ser Glu Asp Ser
 65                  70                  75                  80
Glu Ala Met Asp Glu Ser Lys Ala Leu Lys Ala Ala Glu Lys
                 85                  90                  95
Ala Asp Ala Pro Pro Ala Val Ile Pro Ile Leu Val Ile Ala Cys Asp
                100                 105                 110
Arg Ser Thr Val Arg Arg Cys Leu Asp Lys Leu Leu His Tyr Arg Pro
                115                 120                 125
Ser Ala Glu Leu Phe Pro Ile Ile Val Ser Gln Asp Cys Gly His Glu
                130                 135                 140
Glu Thr Ala Gln Ala Ile Ala Ser Tyr Gly Ser Ala Val Thr His Ile
145                 150                 155                 160
Arg Gln Pro Asp Leu Ser Ser Ile Ala Val Pro Pro Asp His Arg Lys
                165                 170                 175
Phe Gln Gly Tyr Tyr Lys Ile Ala Arg His Tyr Arg Trp Ala Leu Gly
                180                 185                 190
Gln Val Phe Arg Gln Phe Arg Phe Pro Ala Ala Val Val Glu Asp
                195                 200                 205
Asp Leu Glu Val Ala Pro Asp Phe Phe Glu Tyr Phe Arg Ala Thr Tyr
                210                 215                 220
Pro Leu Leu Lys Ala Asp Pro Ser Leu Trp Cys Val Ser Ala Trp Asn
225                 230                 235                 240
Asp Asn Gly Lys Glu Gln Met Val Asp Ala Ser Arg Pro Glu Leu Leu
                245                 250                 255
Tyr Arg Thr Asp Phe Phe Pro Gly Leu Gly Trp Leu Leu Leu Ala Glu
                260                 265                 270
Leu Trp Ala Glu Leu Glu Pro Lys Trp Pro Lys Ala Phe Trp Asp Asp
                275                 280                 285
Trp Met Arg Arg Pro Glu Gln Arg Gln Gly Arg Ala Cys Ile Arg Pro
                290                 295                 300
Glu Ile Ser Arg Thr Met Thr Phe Gly Arg Lys Gly Val Ser His Gly
305                 310                 315                 320
Gln Phe Phe Asp Gln His Leu Lys Phe Ile Lys Leu Asn Gln Gln Phe
                325                 330                 335
Val His Phe Thr Gln Leu Asp Leu Ser Tyr Leu Gln Arg Glu Ala Tyr
                340                 345                 350
Asp Arg Asp Phe Leu Ala Arg Val Tyr Gly Ala Pro Gln Leu Gln Val
                355                 360                 365
Glu Lys Val Arg Thr Asn Asp Arg Lys Glu Leu Gly Glu Val Arg Val
                370                 375                 380
Gln Tyr Thr Gly Arg Asp Ser Phe Lys Ala Phe Ala Lys Ala Leu Gly
385                 390                 395                 400
Val Met Asp Asp Leu Lys Ser Gly Val Pro Arg Ala Gly Tyr Arg Gly
                405                 410                 415
Ile Val Thr Phe Gln Phe Arg Gly Arg Arg Val His Leu Ala Pro Pro
                420                 425                 430
Pro Thr Trp Glu Gly Tyr Asp Pro Ser Trp Asn
                435                 440
```

```
<210> SEQ ID NO 4
<211> LENGTH: 1332
<212> TYPE: DNA
<213> ORGANISM: Artificial Sequence
<220> FEATURE:
<223> OTHER INFORMATION: encodes fusion protein of SEQ ID NO:3

<400> SEQUENCE: 4
atggccctgt ttctgtctaa gcgactgctg cgattcaccg tgatcgccgg tgccgtgatc      60
gtgctgctgc tgaccctgaa ctctaactct cgaacccagc agtacatccc ctcttctatc     120
tctgccgcct tcgacttcac ctctggctct atctctcccg agcagcaggt gatctctgag     180
gagaacgacg ccaagaagct ggagcagtct gccctcaact ctgaggcttc tgaggactcc     240
gaggccatgg acgaggagtc taaggccctg aaggccgctg ccgagaaggc tgacgctccg     300
ccggctgtga tccccatcct ggtcatcgcc tgtgaccgat ctaccgtgcg acgatgtctg     360
gacaagctgc tgcactaccg accctctgcc gagctgttcc ccatcatcgt gtctcaggac     420
tgtggccacg aggagaccgc ccaggccatt gcctcttacg gctctgccgt gacccacatc     480
cgacagcccg acctgtcctc tatcgccgtg ccccccgacc accgaaagtt ccagggctac     540
tacaagatcg cccgacacta ccgatgggcc ctgggccagg tgttccgaca gttccgattc     600
cccgctgccg tggtggtgga ggacgacctg gaggtggccc ccgacttctt cgagtacttc     660
cgagccacct acccccctgct gaaggccgac ccctctctgt ggtgtgtgtc tgcctggaac     720
gacaacggca aggaacagat ggtcgacgcc tctcgacctg agctgctgta ccgaaccgac     780
ttcttccccg gcctgggctg gctgctgctg gctgagctgt gggccgagct ggagcccaag     840
tggcccaagg ccttctggga cgactggatg cgacgacccg agcagcgaca gggccgagcc     900
tgtatccgac ccgagatctc tcgaaccatg accttcggcc gaaagggcgt gtctcacggc     960
cagttcttcg accagcacct gaagttcatc aagctgaacc agcagttcgt gcacttcacc    1020
cagctggacc tgtcttacct gcagcgagag gcctacgacc gagacttcct ggcccgagtg    1080
tacggcgctc cccagctgca ggtggagaag gtgcgaacca cgaccgaaa ggagctgggc    1140
gaggtccgag tgcagtacac cggccgagac tcgttcaagg ccttcgccaa ggccctgggc    1200
gtgatggacg acctgaagtc tggcgtgccc cgagccggat accgaggcat cgtgaccttc    1260
cagttccgag ccgacgagt gcacctggcc cctccaccca cctgggaggg ctacgacccc    1320
tcttggaact ag                                                         1332

<210> SEQ ID NO 5
<211> LENGTH: 28
<212> TYPE: DNA
<213> ORGANISM: Artificial Sequence
<220> FEATURE:
<223> OTHER INFORMATION: oligonucleotide

<400> SEQUENCE: 5
ggatgatcac acaatggccc tgtttctg                                         28

<210> SEQ ID NO 6
<211> LENGTH: 27
<212> TYPE: DNA
<213> ORGANISM: Artificial Sequence
<220> FEATURE:
<223> OTHER INFORMATION: oligonucleotide

<400> SEQUENCE: 6
tgctctagac tagttccaag aggggtc                                          27
```

```
<210> SEQ ID NO 7
<211> LENGTH: 1069
<212> TYPE: PRT
<213> ORGANISM: Artificial Sequence
<220> FEATURE:
<223> OTHER INFORMATION: fusion of N-terminal portion of the S.
      cerevisiae Mnn2 protein and catalytic domain of Drosophila
      melanogaster mannosidase II

<400> SEQUENCE: 7

Met Leu Leu Thr Lys Arg Phe Ser Lys Leu Phe Lys Leu Thr Phe Ile
 1               5                  10                  15

Val Leu Ile Leu Cys Gly Leu Phe Val Ile Thr Asn Lys Tyr Met Asp
                20                  25                  30

Glu Asn Thr Ser Arg Asp Asp Pro Ile Arg Pro Pro Leu Lys Val Ala
             35                  40                  45

Arg Ser Pro Arg Pro Gly Gln Cys Gln Asp Val Val Gln Asp Val Pro
         50                  55                  60

Asn Val Asp Val Gln Met Leu Glu Leu Tyr Asp Arg Met Ser Phe Lys
 65                  70                  75                  80

Asp Ile Asp Gly Gly Val Trp Lys Gln Gly Trp Asn Ile Lys Tyr Asp
                 85                  90                  95

Pro Leu Lys Tyr Asn Ala His His Lys Leu Lys Val Phe Val Val Pro
                100                 105                 110

His Ser His Asn Asp Pro Gly Trp Ile Gln Thr Phe Glu Glu Tyr Tyr
            115                 120                 125

Gln His Asp Thr Lys His Ile Leu Ser Asn Ala Leu Arg His Leu His
        130                 135                 140

Asp Asn Pro Glu Met Lys Phe Ile Trp Ala Glu Ile Ser Tyr Phe Ala
145                 150                 155                 160

Arg Phe Tyr His Asp Leu Gly Glu Asn Lys Lys Leu Gln Met Lys Ser
                165                 170                 175

Ile Val Lys Asn Gly Gln Leu Glu Phe Val Thr Gly Gly Trp Val Met
                180                 185                 190

Pro Asp Glu Ala Asn Ser His Trp Arg Asn Val Leu Leu Gln Leu Thr
            195                 200                 205

Glu Gly Gln Thr Trp Leu Lys Gln Phe Met Asn Val Thr Pro Thr Ala
        210                 215                 220

Ser Trp Ala Ile Asp Pro Phe Gly His Ser Pro Thr Met Pro Tyr Ile
225                 230                 235                 240

Leu Gln Lys Ser Gly Phe Lys Asn Met Leu Ile Gln Arg Thr His Tyr
                245                 250                 255

Ser Val Lys Lys Glu Leu Ala Gln Gln Arg Gln Leu Glu Phe Leu Trp
            260                 265                 270

Arg Gln Ile Trp Asp Asn Lys Gly Asp Thr Ala Leu Phe Thr His Met
        275                 280                 285

Met Pro Phe Tyr Ser Tyr Asp Ile Pro His Thr Cys Gly Pro Asp Pro
    290                 295                 300

Lys Val Cys Cys Gln Phe Asp Phe Lys Arg Met Gly Ser Phe Gly Leu
305                 310                 315                 320

Ser Cys Pro Trp Lys Val Pro Pro Arg Thr Ile Ser Asp Gln Asn Val
                325                 330                 335

Ala Ala Arg Ser Asp Leu Leu Val Asp Gln Trp Lys Lys Lys Ala Glu
            340                 345                 350

Leu Tyr Arg Thr Asn Val Leu Leu Ile Pro Leu Gly Asp Asp Phe Arg
        355                 360                 365
```

-continued

```
Phe Lys Gln Asn Thr Glu Trp Asp Val Gln Arg Val Asn Tyr Glu Arg
370                 375                 380

Leu Phe Glu His Ile Asn Ser Gln Ala His Phe Asn Val Gln Ala Gln
385                 390                 395                 400

Phe Gly Thr Leu Gln Glu Tyr Phe Asp Ala Val His Gln Ala Glu Arg
                405                 410                 415

Ala Gly Gln Ala Glu Phe Pro Thr Leu Ser Gly Asp Phe Phe Thr Tyr
            420                 425                 430

Ala Asp Arg Ser Asp Asn Tyr Trp Ser Gly Tyr Tyr Thr Ser Arg Pro
        435                 440                 445

Tyr His Lys Arg Met Asp Arg Val Leu Met His Tyr Val Arg Ala Ala
    450                 455                 460

Glu Met Leu Ser Ala Trp His Ser Trp Asp Gly Met Ala Arg Ile Glu
465                 470                 475                 480

Glu Arg Leu Glu Gln Ala Arg Arg Glu Leu Ser Leu Phe Gln His His
                485                 490                 495

Asp Gly Ile Thr Gly Thr Ala Lys Thr His Val Val Asp Tyr Glu
                500                 505                 510

Gln Arg Met Gln Glu Ala Leu Lys Ala Cys Gln Met Val Met Gln Gln
            515                 520                 525

Ser Val Tyr Arg Leu Leu Thr Lys Pro Ser Ile Tyr Ser Pro Asp Phe
530                 535                 540

Ser Phe Ser Tyr Phe Thr Leu Asp Asp Ser Arg Trp Pro Gly Ser Gly
545                 550                 555                 560

Val Glu Asp Ser Arg Thr Thr Ile Ile Leu Gly Glu Asp Ile Leu Pro
                565                 570                 575

Ser Lys His Val Val Met His Asn Thr Leu Pro His Trp Arg Glu Gln
            580                 585                 590

Leu Val Asp Phe Tyr Val Ser Ser Pro Phe Val Ser Val Thr Asp Leu
        595                 600                 605

Ala Asn Asn Pro Val Glu Ala Gln Val Ser Pro Val Trp Ser Trp His
    610                 615                 620

His Asp Thr Leu Thr Lys Thr Ile His Pro Gln Gly Ser Thr Thr Lys
625                 630                 635                 640

Tyr Arg Ile Ile Phe Lys Ala Arg Val Pro Pro Met Gly Leu Ala Thr
                645                 650                 655

Tyr Val Leu Thr Ile Ser Asp Ser Lys Pro Glu His Thr Ser Tyr Ala
            660                 665                 670

Ser Asn Leu Leu Leu Arg Lys Asn Pro Thr Ser Leu Pro Leu Gly Gln
        675                 680                 685

Tyr Pro Glu Asp Val Lys Phe Gly Asp Pro Arg Glu Ile Ser Leu Arg
    690                 695                 700

Val Gly Asn Gly Pro Thr Leu Ala Phe Ser Glu Gln Gly Leu Leu Lys
705                 710                 715                 720

Ser Ile Gln Leu Thr Gln Asp Ser Pro His Val Pro Val His Phe Lys
                725                 730                 735

Phe Leu Lys Tyr Gly Val Arg Ser His Gly Asp Arg Ser Gly Ala Tyr
            740                 745                 750

Leu Phe Leu Pro Asn Gly Pro Ala Ser Pro Val Glu Leu Gly Gln Pro
        755                 760                 765

Val Val Leu Val Thr Lys Gly Lys Leu Glu Ser Ser Val Ser Val Gly
    770                 775                 780
```

```
Leu Pro Ser Val Val His Gln Thr Ile Met Arg Gly Gly Ala Pro Glu
785                 790                 795                 800

Ile Arg Asn Leu Val Asp Ile Gly Ser Leu Asp Asn Thr Glu Ile Val
                805                 810                 815

Met Arg Leu Glu Thr His Ile Asp Ser Gly Asp Ile Phe Tyr Thr Asp
            820                 825                 830

Leu Asn Gly Leu Gln Phe Ile Lys Arg Arg Leu Asp Lys Leu Pro
        835                 840                 845

Leu Gln Ala Asn Tyr Tyr Pro Ile Pro Ser Gly Met Phe Ile Glu Asp
    850                 855                 860

Ala Asn Thr Arg Leu Thr Leu Thr Gly Gln Pro Leu Gly Gly Ser
865                 870                 875                 880

Ser Leu Ala Ser Gly Glu Leu Glu Ile Met Gln Asp Arg Arg Leu Ala
                885                 890                 895

Ser Asp Asp Glu Arg Gly Leu Gly Gln Gly Val Leu Asp Asn Lys Pro
            900                 905                 910

Val Leu His Ile Tyr Arg Leu Val Leu Glu Lys Val Asn Asn Cys Val
        915                 920                 925

Arg Pro Ser Lys Leu His Pro Ala Gly Tyr Leu Thr Ser Ala Ala His
930                 935                 940

Lys Ala Ser Gln Ser Leu Leu Asp Pro Leu Asp Lys Phe Ile Phe Ala
945                 950                 955                 960

Glu Asn Glu Trp Ile Gly Ala Gln Gly Gln Phe Gly Gly Asp His Pro
                965                 970                 975

Ser Ala Arg Glu Asp Leu Asp Val Ser Val Met Arg Arg Leu Thr Lys
            980                 985                 990

Ser Ser Ala Lys Thr Gln Arg Val Gly Tyr Val Leu His Arg Thr Asn
        995                 1000                1005

Leu Met Gln Cys Gly Thr Pro Glu Glu His Thr Gln Lys Leu Asp Val
    1010                1015                1020

Cys His Leu Leu Pro Asn Val Ala Arg Cys Glu Arg Thr Thr Leu Thr
1025                1030                1035                1040

Phe Leu Gln Asn Leu Glu His Leu Asp Gly Met Val Ala Pro Glu Val
                1045                1050                1055

Cys Pro Met Glu Thr Ala Ala Tyr Val Ser Ser His Ser
            1060                1065

<210> SEQ ID NO 8
<211> LENGTH: 3213
<212> TYPE: DNA
<213> ORGANISM: Artificial Sequence
<220> FEATURE:
<223> OTHER INFORMATION: encodes fusion protein of SEQ ID NO:7

<400> SEQUENCE: 8
atgctgctga ccaagcgatt ctctaagctg ttcaagctga ccttcatcgt gctgatcctg      60
tgtggcctgt tcgtgatcac caacaagtac atggacgaga cacctcccg ggatgacccc      120 atccgacccc ccctgaaggt ggcccgatct ccccgacccg ccagtgtca ggacgtggtg       180 caggacgtgc ccaacgtgga cgtgcagatg ctggagctgt acgaccgaat gtctttcaag      240
gacatcgacg cggcgtgtg aagcagggc tggaacatca gtacgaccc cctgaagtac        300 aacgcccacc acaagctgaa ggtgttcgtg gtgcccact ctcacaacga ccccggctgg      360
attcagacct cgaggagta ctaccagcac gacaccaagc acatcctgtc taacgccctg      420
cgacacctgc acgacaaccc tgagatgaag tttatctggg ccgagatctc ttacttcgcc    480
```

```
cgattctacc acgacctggg cgagaacaag aagctgcaga tgaagtctat cgtgaagaac    540
ggccagctgg agttcgtgac cggcggctgg gtgatgcccg acgaggccaa ctctcactgg    600
cgaaacgtgc tgctgcagct gaccgagggc cagacctggc tgaagcagtt catgaacgtg    660 accccccaccg cctcttgggc catcgacccc ttcggccact ctcccaccat gccctacatc    720
ctgcagaagt ctggcttcaa gaacatgctg atccagcgaa cccactactc tgtgaagaag    780
gagctggccc agcagcgaca gctggagttt ctgtggcgac agatctggga caacaagggc    840
gacaccgccc tgttcaccca catgatgccc ttctactctt acgacatccc ccacacctgt    900
ggccccgacc ccaaggtgtg ttgtcagttc gacttcaagc gaatgggctc tttcggcctg    960
tcttgtccct ggaaggtgcc ccctcgaacc atctctgacc agaacgtggc cgctcgatct   1020
gacctgctgg ttgaccagtg gaagaagaag gccgagctgt accgaaccaa cgtcctgctg   1080 atcccccctgg gcgacgactt ccgattcaag cagaacaccg agtgggacgt gcagcgagtg   1140
aactacgagc gactgttcga gcacatcaac tctcaggccc acttcaacgt gcaggctcag   1200
ttcggcactc tgcaggagta cttcgacgcc gtccaccagg ccgagcgagc cggccaggcc   1260
gagttcccca ccctgtctgg cgactttttc acctacgccg accgatctga caactactgg   1320
tctggctact acacctctcg accctaccac aagcgaatgg accgagtgct gatgcactac   1380
gtgcgagccg ccgagatgct gtctgcctgg cactcttggg acggcatggc ccgaatcgag   1440
gagcgactgg agcaggcccg acgagagctg tctctgttcc agcaccacga cggcatcacc   1500
ggcaccgcca agacccacgt ggtggtggac tacgagcagc gaatgcagga ggccctgaag   1560
gcctgtcaga tggtgatgca gcagtctgtc taccgactcc tgactaagcc ctctatctac   1620
tctcccgact tctctttctc ttacttcacc ctggacgact ctcgatggcc cggctctggc   1680
gtggaggact ctcgaaccac catcatcctg ggcgaggaca tcctgccctc taagcacgtg   1740
gtgatgcaca acaccctgcc ccactggcga gagcagctgg tcgacttcta cgtgtcctct   1800
cccttcgtgt ctgtgaccga cctggccaac aaccccgtgg aggcccaggt gtctcccgtg   1860
tggtcttggc accacgacac cctgaccaag accatccacc cccagggctc taccaccaag   1920
taccgaatca tcttcaaggc ccgagtgccc cccatgggcc tggccaccta cgtgctgacc   1980
atctccgact ctaagcccga gcacacctct tacgcctcta acctgctgct gcgaaagaac   2040
cccacctctc tgcccctggg ccagtacccc gaggacgtga agttcggcga ccccgagag    2100 atctctctgc gagtgggcaa cggccccacc ctggccttct ctgagcaggg cctgctgaag   2160
tctatccagc tgacccagga ctctcccac gtgcccgtgc acttcaagtt ctgaagtac    2220 ggcgtgcgat ctcacggcga ccgatctggc gcctacctgt tcctgcccaa cggacccgcc   2280 tctccccgtgg agctgggaca gcccgtggtg ctggtgacca agggcaagct ggagtcctct   2340
gtgtctgtgg gcctgccctc tgtggtgcac cagaccatca tgcgaggcgg agccccccgag  2400 atccgaaacc tggtggacat cggatctctg gacaacaccg agatcgtgat gcgactggag   2460
acccacatcg actctggcga catcttctac accgacctga acggcctgca gttcatcaag   2520
cgacgacgac tggacaagct gccctgcag gccaactact accccatccc ctctggcatg   2580
ttcatcgagg acgccaacac ccgactgacc ctgctgaccg ccagcccct gggcggatct    2640 tctctggcct ctggcgagct ggagatcatg caggaccgac gactggcctc tgacgacgag   2700
cgaggcctgg gccagggcgt gctggacaac aagcccgtgc tgcacatcta ccgactggtg   2760
ctggagaagg tgaacaactg tgtgcgaccc tctaagctgc accccgctgg ctacctgacc   2820
tctgccgccc acaaggcctc tcagtctctg ctggaccccc tggacaagtt catcttcgcc   2880
```

-continued

```
gagaacgagt ggatcggcgc ccagggccag ttcggaggcg accacccctc tgcccgagag    2940
gacctggacg tgtctgtgat gcgacgactg accaagtcct ctgccaagac ccagcgagtg    3000
ggctacgtgc tgcaccgaac caacctgatg cagtgtggca ccccgagga gcacacccag    3060 aagctggacg tctgtcacct gctgcccaac gtcgcccgat gtgagcgaac caccctgacc    3120
tttctgcaga acctggagca cctggacggc atggtggccc ccgaggtgtg tcccatggag    3180
accgccgcct acgtgtcgtc ccactcttct tag                                  3213
```

<210> SEQ ID NO 9
<211> LENGTH: 763
<212> TYPE: PRT
<213> ORGANISM: Artificial Sequence
<220> FEATURE:
<223> OTHER INFORMATION: fusion of N-terminal portion of the S. cerevisiae Mnn2 protein, the S. pombe Gal10-like protein, and catalytic domain of human GalT I

<400> SEQUENCE: 9

```
Met Leu Leu Thr Lys Arg Phe Ser Lys Leu Phe Lys Leu Thr Phe Ile
 1               5                  10                  15

Val Leu Ile Leu Cys Gly Leu Phe Val Ile Thr Asn Lys Tyr Met Asp
            20                  25                  30

Glu Asn Thr Ser Val Lys Glu Tyr Lys Glu Tyr Leu Asp Arg Gly Arg
        35                  40                  45

Ala Met Thr Gly Val His Glu Gly Thr Val Leu Val Thr Gly Gly Ala
    50                  55                  60

Gly Tyr Ile Gly Ser His Thr Cys Val Val Leu Leu Glu Lys Gly Tyr
65                  70                  75                  80

Asp Val Val Ile Val Asp Asn Leu Cys Asn Ser Arg Val Glu Ala Val
                85                  90                  95

His Arg Ile Glu Lys Leu Thr Gly Lys Lys Val Ile Phe His Gln Val
            100                 105                 110

Asp Leu Leu Asp Glu Pro Ala Leu Asp Lys Val Phe Ala Asn Gln Asn
        115                 120                 125

Ile Ser Ala Val Ile His Phe Ala Gly Leu Lys Ala Val Gly Glu Ser
    130                 135                 140

Val Gln Val Pro Leu Ser Tyr Tyr Lys Asn Asn Ile Ser Gly Thr Ile
145                 150                 155                 160

Asn Leu Ile Glu Cys Met Lys Lys Tyr Asn Val Arg Asp Phe Val Phe
                165                 170                 175

Ser Ser Ser Ala Thr Val Tyr Gly Asp Pro Thr Arg Pro Gly Gly Thr
            180                 185                 190

Ile Pro Ile Pro Glu Ser Cys Pro Arg Glu Gly Thr Ser Pro Tyr Gly
        195                 200                 205

Arg Thr Lys Leu Phe Ile Glu Asn Ile Ile Glu Asp Glu Thr Lys Val
    210                 215                 220

Asn Lys Ser Leu Asn Ala Ala Leu Leu Arg Tyr Phe Asn Pro Gly Gly
225                 230                 235                 240

Ala His Pro Ser Gly Glu Leu Gly Glu Asp Pro Leu Gly Ile Pro Asn
                245                 250                 255

Asn Leu Leu Pro Tyr Ile Ala Gln Val Ala Val Gly Arg Leu Asp His
            260                 265                 270

Leu Asn Val Phe Gly Asp Asp Tyr Pro Thr Ser Asp Gly Thr Pro Ile
        275                 280                 285
```

```
Arg Asp Tyr Ile His Val Cys Asp Leu Ala Glu Ala His Val Ala Ala
290                 295                 300

Leu Asp Tyr Leu Arg Gln His Phe Val Ser Cys Arg Pro Trp Asn Leu
305                 310                 315                 320

Gly Ser Gly Thr Gly Ser Thr Val Phe Gln Val Leu Asn Ala Phe Ser
                325                 330                 335

Lys Ala Val Gly Arg Asp Leu Pro Tyr Lys Val Thr Pro Arg Arg Ala
                340                 345                 350

Gly Asp Val Val Asn Leu Thr Ala Asn Pro Thr Arg Ala Asn Glu Glu
                355                 360                 365

Leu Lys Trp Lys Thr Ser Arg Ser Ile Tyr Glu Ile Cys Val Asp Thr
370                 375                 380

Trp Arg Trp Gln Gln Lys Tyr Pro Tyr Gly Phe Asp Leu Thr His Thr
385                 390                 395                 400

Lys Thr Tyr Lys Gly Ser Gly Gly Arg Asp Leu Ser Arg Leu Pro
                405                 410                 415

Gln Leu Val Gly Val Ser Thr Pro Leu Gln Gly Gly Ser Asn Ser Ala
                420                 425                 430

Ala Ala Ile Gly Gln Ser Ser Gly Glu Leu Arg Thr Gly Gly Ala Arg
                435                 440                 445

Pro Pro Pro Leu Gly Ala Ser Ser Gln Pro Arg Pro Gly Gly Asp
450                 455                 460

Ser Ser Pro Val Val Asp Ser Gly Pro Gly Pro Ala Ser Asn Leu Thr
465                 470                 475                 480

Ser Val Pro Val Pro His Thr Thr Ala Leu Ser Leu Pro Ala Cys Pro
                485                 490                 495

Glu Glu Ser Pro Leu Leu Val Gly Pro Met Leu Ile Glu Phe Asn Met
                500                 505                 510

Pro Val Asp Leu Glu Leu Val Ala Lys Gln Asn Pro Asn Val Lys Met
                515                 520                 525

Gly Gly Arg Tyr Ala Pro Arg Asp Cys Val Ser Pro His Lys Val Ala
530                 535                 540

Ile Ile Ile Pro Phe Arg Asn Arg Gln Glu His Leu Lys Tyr Trp Leu
545                 550                 555                 560

Tyr Tyr Leu His Pro Val Leu Gln Arg Gln Gln Leu Asp Tyr Gly Ile
                565                 570                 575

Tyr Val Ile Asn Gln Ala Gly Asp Thr Ile Phe Asn Arg Ala Lys Leu
                580                 585                 590

Leu Asn Val Gly Phe Gln Glu Ala Leu Lys Asp Tyr Asp Tyr Thr Cys
                595                 600                 605

Phe Val Phe Ser Asp Val Asp Leu Ile Pro Met Asn Asp His Asn Ala
610                 615                 620

Tyr Arg Cys Phe Ser Gln Pro Arg His Ile Ser Val Ala Met Asp Lys
625                 630                 635                 640

Phe Gly Phe Ser Leu Pro Tyr Val Gln Tyr Phe Gly Gly Val Ser Ala
                645                 650                 655

Leu Ser Lys Gln Gln Phe Leu Thr Ile Asn Gly Phe Pro Asn Asn Tyr
                660                 665                 670

Trp Gly Trp Gly Gly Glu Asp Asp Ile Phe Asn Arg Leu Val Phe
                675                 680                 685

Arg Gly Met Ser Ile Ser Arg Pro Asn Ala Val Val Gly Arg Cys Arg
690                 695                 700
```

```
Met Ile Arg His Ser Arg Asp Lys Lys Asn Glu Pro Asn Pro Gln Arg
705                 710                 715                 720

Phe Asp Arg Ile Ala His Thr Lys Glu Thr Met Leu Ser Asp Gly Leu
            725                 730                 735

Asn Ser Leu Thr Tyr Gln Val Leu Asp Val Gln Arg Tyr Pro Leu Tyr
        740                 745                 750

Thr Gln Ile Thr Val Asp Ile Gly Thr Pro Ser
        755                 760
```

<210> SEQ ID NO 10
<211> LENGTH: 2292
<212> TYPE: DNA
<213> ORGANISM: Artificial Sequence
<220> FEATURE:
<223> OTHER INFORMATION: encodes fusion protein of SEQ ID NO:9

<400> SEQUENCE: 10

| | | |
|---|---|---|
| atgctgctga ccaagcgatt ctctaagctg ttcaagctga ccttcatcgt gctgatcctg | 60 |
| tgtggcctgt tcgtgatcac caacaagtac atggacgaga cacctctgt gaaggaatac | 120 |
| aaggagtacc tggaccgcgg ccgagccatg accggcgtgc acgagggcac cgtgctggtg | 180 |
| accggcggag ccggctacat cggctctcac acctgtgtgg tgctgctgga aagggctac | 240 |
| gacgtggtga tcgtggacaa cctgtgtaac tctcgagtgg aggccgtgca ccgaatcgag | 300 |
| aagctgaccg gcaagaaggt gatcttccac caggtggacc tgctggacga gcccgccctg | 360 |
| gacaaggtgt cgccaacca gaacatctct gccgtgatcc acttcgccgg cctgaaggct | 420 |
| gtgggcgagt ctgtgcaggt gccctgtct tactacaaga caacatctc tggcaccatc | 480 |
| aacctgatcg agtgtatgaa gaagtacaac gtccgagact tcgtgttctc ttcttctgcc | 540 |
| accgtgtacg cgaccccac ccgacccggc ggaaccatcc ccatccccga gtcttgtccc | 600 |
| cgagagggca cctctcccta cggccgaacc aagctgttca tcgagaacat catcgaggac | 660 |
| gaaaccaagg tgaacaagtc tctgaacgcc gccctgctgc atacttcaa ccccggtggc | 720 |
| gctcacccct ctggcgagct gggcgaggac cctctgggca tccccaacaa cctgctgccc | 780 |
| tacattgctc aggtggctgt gggccgactg gaccacctga cgtgttggg cgacgactac | 840 |
| cctacctctg acggcacccc catccgagac tacatccacg tgtgtgacct ggccgaggcc | 900 |
| cacgtggccg ctctggacta cctgcgacag cacttcgtgt cttgtcgacc ctggaacctg | 960 |
| ggctctggca ccggctctac cgtgttccag gtgctgaacg ccttctctaa ggctgtcggc | 1020 |
| cgagatctgc cctacaaggt gaccccccga cgagccggcg acgtcgtgaa cctgaccgcc | 1080 |
| aaccctaccc gagctaacga ggagctgaag tggaagacct ctcgatctat ctacgagatc | 1140 |
| tgtgtggaca cctggagatg gcagcagaag taccctacg gcttcgacct gacccatacc | 1200 |
| aagacctaca agggctctgg cggaggacga gatctgtctc gactgcctca gctggtcggc | 1260 |
| gtgtctaccc ctctgcaggg cggctctaac tctgccgccg ctatcggcca gtcctccggc | 1320 |
| gagctgcgaa ccggtggagc ccgacctccc cctcccctgg gcgcctcttc tcagccccga | 1380 |
| cccggtggcg actcttctcc cgtggtggac tctggccccg acccgcctc taacctgacc | 1440 |
| tctgtgcccg tgcccacac caccgccctg tctctgcccg cctgtcccga ggagtctccc | 1500 |
| ctgctcgtcg gcccccatgct gatcgagttc aacatgcccg tggacctgga gctggtcgcc | 1560 |
| aagcagaacc caacgtgaa gatgggcgga cgatacgctc ccgagactg tgtgtctccc | 1620 |
| cacaaggtgg ccatcatcat ccctttcaga aaccgacagg agcacctgaa gtactggctg | 1680 |
| tactacctgc accccgtgct gcagcgacag cagctggact acggcatcta cgtgatcaac | 1740 |

| | | |
|---|---|---|
| caggccggcg acaccatctt caaccgagcc aagctgctga acgtgggctt ccaggaggcc | 1800 | |
| ctgaaggact acgactacac ctgtttcgtg ttctccgacg tggacctgat ccccatgaac | 1860 | |
| gaccacaacg cctaccgatg tttctcccag ccccgacaca tctctgtggc catggacaag | 1920 | |
| ttcggcttct ctctgcccta cgtgcagtac ttcggcggcg tttctgccct gtctaagcag | 1980 | |
| cagttcctga ccatcaacgg cttccccaac aactactggg gctggggcgg agaggacgac | 2040 | |
| gacattttca accgactggt gttccgaggc atgtctatct ctcgacccaa cgccgtggtg | 2100 | |
| ggccgatgtc gaatgatccg acactctcga gacaagaaga acgagcccaa ccccagcga | 2160 | |
| tttgaccgaa ttgctcacac taaggaaacc atgctgtctg acggcctgaa ctctctgacc | 2220 | |
| taccaggtgc tggacgtgca gcgataccc ctgtacaccc agatcaccgt ggacatcggc | 2280 | |
| acaccctctt ag | 2292 | |

<210> SEQ ID NO 11
<211> LENGTH: 28
<212> TYPE: DNA
<213> ORGANISM: Artificial Sequence
<220> FEATURE:
<223> OTHER INFORMATION: oligonucleotide

<400> SEQUENCE: 11
ggatgatcac acaatggccc tgtttctg                                28

<210> SEQ ID NO 12
<211> LENGTH: 27
<212> TYPE: DNA
<213> ORGANISM: Artificial Sequence
<220> FEATURE:
<223> OTHER INFORMATION: oligonucleotide

<400> SEQUENCE: 12
tgctctagac tagttccaag aggggtc                                 27

<210> SEQ ID NO 13
<211> LENGTH: 35
<212> TYPE: DNA
<213> ORGANISM: Artificial Sequence
<220> FEATURE:
<223> OTHER INFORMATION: oligonucleotide

<400> SEQUENCE: 13
cgacgataga gcaggtctca ctgttgggaa tgctg                        35

<210> SEQ ID NO 14
<211> LENGTH: 35
<212> TYPE: DNA
<213> ORGANISM: Artificial Sequence
<220> FEATURE:
<223> OTHER INFORMATION: oligonucleotide

<400> SEQUENCE: 14
ctacactgac gaagtggaca tcccggcttg gactg                        35

<210> SEQ ID NO 15
<211> LENGTH: 28
<212> TYPE: DNA
<213> ORGANISM: Artificial Sequence
<220> FEATURE:
<223> OTHER INFORMATION: oligonucleotide

<400> SEQUENCE: 15
ggatgatcac acaatggccc tgtttctg                                28

-continued

```
<210> SEQ ID NO 16
<211> LENGTH: 27
<212> TYPE: DNA
<213> ORGANISM: Artificial Sequence
<220> FEATURE:
<223> OTHER INFORMATION: oligonucleotide

<400> SEQUENCE: 16
tgctctagac tagttccaag agggtc                                           27

<210> SEQ ID NO 17
<211> LENGTH: 391
<212> TYPE: PRT
<213> ORGANISM: Artificial Sequence
<220> FEATURE:
<223> OTHER INFORMATION: fusion of N-terminal portion of the S.
      cerevisiae Mnn2 protein and catalytic domain of rat GlcNAc-
      transferase II

<400> SEQUENCE: 17
```

Met Leu Leu Thr Lys Arg Phe Ser Lys Leu Phe Lys Leu Thr Phe Ile
1               5                   10                  15

Val Leu Ile Leu Cys Gly Leu Phe Val Ile Thr Asn Lys Tyr Met Asp
            20                  25                  30

Glu Asn Thr Ser Ser Leu Val Tyr Gln Leu Asn Phe Asp Gln Met Leu
        35                  40                  45

Arg Asn Val Asp Lys Asp Gly Thr Trp Ser Pro Gly Glu Leu Val Leu
    50                  55                  60

Val Val Gln Val His Asn Arg Pro Glu Tyr Leu Arg Leu Leu Ile Asp
65                  70                  75                  80

Ser Leu Arg Lys Ala Gln Gly Ile Arg Glu Val Leu Val Ile Phe Ser
                85                  90                  95

His Asp Phe Trp Ser Ala Glu Ile Asn Ser Leu Ile Ser Val Asp
            100                 105                 110

Phe Cys Pro Val Leu Gln Val Phe Phe Pro Phe Ser Ile Gln Leu Tyr
        115                 120                 125

Pro Ser Glu Phe Pro Gly Ser Asp Pro Arg Asp Cys Pro Arg Asp Leu
    130                 135                 140

Lys Lys Asn Ala Ala Leu Lys Leu Gly Cys Ile Asn Ala Glu Tyr Pro
145                 150                 155                 160

Asp Ser Phe Gly His Tyr Arg Glu Ala Lys Phe Ser Gln Thr Lys His
                165                 170                 175

His Trp Trp Trp Lys Leu His Phe Val Trp Glu Arg Val Lys Val Leu
            180                 185                 190

Gln Asp Tyr Thr Gly Leu Ile Leu Phe Leu Glu Glu Asp His Tyr Leu
        195                 200                 205

Ala Pro Asp Phe Tyr His Val Phe Lys Lys Met Trp Lys Leu Lys Gln
    210                 215                 220

Gln Glu Cys Pro Gly Cys Asp Val Leu Ser Leu Gly Thr Tyr Thr Thr
225                 230                 235                 240

Ile Arg Ser Phe Tyr Gly Ile Ala Asp Lys Val Asp Val Lys Thr Trp
                245                 250                 255

Lys Ser Thr Glu His Asn Met Gly Leu Ala Leu Thr Arg Asp Ala Tyr
            260                 265                 270

Gln Lys Leu Ile Glu Cys Thr Asp Thr Phe Cys Thr Tyr Asp Asp Tyr
        275                 280                 285

Asn Trp Asp Trp Thr Leu Gln Tyr Leu Thr Leu Ala Cys Leu Pro Lys
    290                 295                 300

```
Val Trp Lys Val Leu Val Pro Gln Ala Pro Arg Ile Phe His Ala Gly
305                 310                 315                 320

Asp Cys Gly Met His His Lys Lys Thr Cys Arg Pro Ser Thr Gln Ser
                325                 330                 335

Ala Gln Ile Glu Ser Leu Leu Asn Asn Asn Lys Gln Tyr Leu Phe Pro
            340                 345                 350

Glu Thr Leu Val Ile Gly Glu Lys Phe Pro Met Ala Ala Ile Ser Pro
        355                 360                 365

Pro Arg Lys Asn Gly Gly Trp Gly Asp Ile Arg Asp His Glu Leu Cys
    370                 375                 380

Lys Ser Tyr Arg Arg Leu Gln
385                 390
```

<210> SEQ ID NO 18
<211> LENGTH: 1176
<212> TYPE: DNA
<213> ORGANISM: Artificial Sequence
<220> FEATURE:
<223> OTHER INFORMATION: encodes fusion protein of SEQ ID NO:17

<400> SEQUENCE: 18

```
atgctgctga ccaagcgatt ctctaagctg ttcaagctga ccttcatcgt gctgatcctg      60
tgtggcctgt cgtgatcac caacaagtac atggacgaga cacctcgag cctggtgtac      120
cagctgaact tcgaccagat gctgcgaaac gtggacaagg acggcacctg gtctcccggc      180
gagctggtgc tcgtggtgca ggtgcacaac cgacccgagt acctgcgact gctgatcgac      240
tctctgcgaa aggcccaggg catccgagag gtgctggtga tcttctctca cgacttctgg      300
tctgccgaga tcaactcccct gatctcttct gtggacttct gtcccgtgct gcaggtgttc      360
ttcccattca gcatccagct gtaccctct gagttccccg ctctgaccc ccgagactgt      420
ccccgagacc tgaagaagaa cgccgccctg aagctgggct gtatcaacgc cgagtacccc      480
gactctttcg ccactaccg agaggccaag ttctctcaga ccaagcacca ctggtggtgg      540
aagctgcact tcgtgtggga cgagtgaag gtgctgcagg actacaccgg cctgatcctg      600
ttcctggagg aggaccacta cctggccccc gacttctacc acgtgttcaa gaagatgtgg      660
aagctgaagc agcaggagtg tcccggctgc gacgtgctgt ctctgggcac ctacaccacc      720
atccgatctt tctacggcat cgccgacaag gtggacgtca agacctggaa gtctaccgag      780
cacaacatgg gcctggccct gacccgagat gcctaccaga gctgatcga gtgtaccgac      840
accttctgta cctacgacga ctacaactgg gactggactc tgcagtacct gaccctggcc      900
tgtctgccca aggtgtggaa ggtgctggtg cccccaggccc ctcgaatctt ccacgccggc      960
gactgtggca tgcaccacaa gaagacctgt cgaccctcta cccagtctgc ccagatcgag     1020
tctctgctga acaacaacaa gcagtacctg ttccctgaga ccctggtgat cggcgagaag     1080
ttccccatgg ccgccatctc gcctccccga aagaacggcg gctggggcga catccgagac     1140
cacgaactct gtaagtctta ccgacgactg cagtag                                1176
```

<210> SEQ ID NO 19
<211> LENGTH: 19
<212> TYPE: DNA
<213> ORGANISM: Artificial Sequence
<220> FEATURE:
<223> OTHER INFORMATION: oligonucleotide

<400> SEQUENCE: 19

```
gtccccgaat tacctttcc                                                    19
```

```
<210> SEQ ID NO 20
<211> LENGTH: 21
<212> TYPE: DNA
<213> ORGANISM: Artificial Sequence
<220> FEATURE:
<223> OTHER INFORMATION: oligonucleotide

<400> SEQUENCE: 20
aggtagaagt tgtaaagagt g                                              21

<210> SEQ ID NO 21
<211> LENGTH: 4
<212> TYPE: PRT
<213> ORGANISM: Artificial Sequence
<220> FEATURE:
<223> OTHER INFORMATION: protein tag

<400> SEQUENCE: 21

His Asp Glu Leu
 1

<210> SEQ ID NO 22
<211> LENGTH: 31
<212> TYPE: DNA
<213> ORGANISM: Artificial Sequence
<220> FEATURE:
<223> OTHER INFORMATION: oligonucleotide

<400> SEQUENCE: 22
gccttccaga cctcttggaa cgcctaccac c                                   31

<210> SEQ ID NO 23
<211> LENGTH: 32
<212> TYPE: DNA
<213> ORGANISM: Artificial Sequence
<220> FEATURE:
<223> OTHER INFORMATION: oligonucleotide

<400> SEQUENCE: 23
gccaggtggc cgcctcgtcg agaagaagat cg                                  32

<210> SEQ ID NO 24
<211> LENGTH: 20
<212> TYPE: DNA
<213> ORGANISM: Artificial Sequence
<220> FEATURE:
<223> OTHER INFORMATION: oligonucleotide

<400> SEQUENCE: 24
gctggactct tcttctatcc                                                20

<210> SEQ ID NO 25
<211> LENGTH: 19
<212> TYPE: DNA
<213> ORGANISM: Artificial Sequence
<220> FEATURE:
<223> OTHER INFORMATION: oligonucleotide

<400> SEQUENCE: 25
ggtctccttc agagacagg                                                 19

<210> SEQ ID NO 26
<211> LENGTH: 20
<212> TYPE: DNA
<213> ORGANISM: Artificial Sequence
<220> FEATURE:
<223> OTHER INFORMATION: oligonucleotide
```

<400> SEQUENCE: 26
ccaagttcta caaggacacc                                                    20

<210> SEQ ID NO 27
<211> LENGTH: 19
<212> TYPE: DNA
<213> ORGANISM: Artificial Sequence
<220> FEATURE:
<223> OTHER INFORMATION: oligonucleotide

<400> SEQUENCE: 27
cccttgacga ccttagagg                                                     19

<210> SEQ ID NO 28
<211> LENGTH: 19
<212> TYPE: DNA
<213> ORGANISM: Artificial Sequence
<220> FEATURE:
<223> OTHER INFORMATION: oligonucleotide

<400> SEQUENCE: 28
gaccagatgc tgcgaaacg                                                     19

<210> SEQ ID NO 29
<211> LENGTH: 19
<212> TYPE: DNA
<213> ORGANISM: Artificial Sequence
<220> FEATURE:
<223> OTHER INFORMATION: oligonucleotide

<400> SEQUENCE: 29
cttgacgtcc accttgtcg                                                     19

<210> SEQ ID NO 30
<211> LENGTH: 32
<212> TYPE: DNA
<213> ORGANISM: Artificial Sequence
<220> FEATURE:
<223> OTHER INFORMATION: oligonucleotide

<400> SEQUENCE: 30
gcctgaacgg cacgatgcga tcgtggcaat cc                                      32

<210> SEQ ID NO 31
<211> LENGTH: 31
<212> TYPE: DNA
<213> ORGANISM: Artificial Sequence
<220> FEATURE:
<223> OTHER INFORMATION: oligonucleotide

<400> SEQUENCE: 31
caagaagcct caggctcggc gaatctccat c                                       31

<210> SEQ ID NO 32
<211> LENGTH: 753
<212> TYPE: DNA
<213> ORGANISM: Artificial Sequence
<220> FEATURE:
<223> OTHER INFORMATION: encodes fusion protein of SEQ ID NO:33

<400> SEQUENCE: 32
atgaagcttt ccaccatcct tttcacagcc tgcgctaccc tggctgccgc cctcccttcc        60
cccatcactc cttctgaggc cgcagttctc cagaagcgag gcggcggcga cattcagatg       120
actcagtctc cctcttctct gtctgcttct gtgggtgacc gagtgaccat tacctgtcga       180

```
gcttctcagg acgtgaacac tgctgttgct tggtatcagc agaagcctgg aaaggctcct    240
aagctgctga tctactctgc ctcttcctg tactctggcg tgccttctcg attttctggc    300
tctcgatctg gaaccgactt caccctgacc atttcttctc tgcagcctga ggactttgct    360
acctactact gtcagcagca ttacaccacc cctcctactt ttggacaggg caccaaggtt    420
gagattaagc gaaccgtggc tgctccttct gtgttcattt tcccccctc tgacgagcag    480
ctgaagtctg gaactgcttc tgttgtgtgc ctgctgaaca cttttaccc ccgagaggct    540
aaggttcagt ggaaggtgga caacgctctg cagtctggaa actctcagga gtctgttact    600
gagcaggact ctaaggactc gacctactct ctctcttcta ccctgaccct gtctaaggct    660
gactacgaga agcataaggt gtacgcttgt gaggttaccc atcagggact gtcctctccc    720
gtgaccaagt cttttaaccg aggcgagtgc taa                                753

<210> SEQ ID NO 33
<211> LENGTH: 250
<212> TYPE: PRT
<213> ORGANISM: Artificial Sequence
<220> FEATURE:
<223> OTHER INFORMATION: fusion of Lip2 protein prepro signal and
      anti-HER2 antibody light chain

<400> SEQUENCE: 33

Met Lys Leu Ser Thr Ile Leu Phe Thr Ala Cys Ala Thr Leu Ala Ala
 1               5                  10                  15

Ala Leu Pro Ser Pro Ile Thr Pro Ser Glu Ala Ala Val Leu Gln Lys
             20                  25                  30

Arg Gly Gly Gly Asp Ile Gln Met Thr Gln Ser Pro Ser Ser Leu Ser
         35                  40                  45

Ala Ser Val Gly Asp Arg Val Thr Ile Thr Cys Arg Ala Ser Gln Asp
     50                  55                  60

Val Asn Thr Ala Val Ala Trp Tyr Gln Gln Lys Pro Gly Lys Ala Pro
 65                  70                  75                  80

Lys Leu Leu Ile Tyr Ser Ala Ser Phe Leu Tyr Ser Gly Val Pro Ser
                 85                  90                  95

Arg Phe Ser Gly Ser Arg Ser Gly Thr Asp Phe Thr Leu Thr Ile Ser
            100                 105                 110

Ser Leu Gln Pro Glu Asp Phe Ala Thr Tyr Tyr Cys Gln Gln His Tyr
        115                 120                 125

Thr Thr Pro Pro Thr Phe Gly Gln Gly Thr Lys Val Glu Ile Lys Arg
    130                 135                 140

Thr Val Ala Ala Pro Ser Val Phe Ile Phe Pro Pro Ser Asp Glu Gln
145                 150                 155                 160

Leu Lys Ser Gly Thr Ala Ser Val Val Cys Leu Leu Asn Asn Phe Tyr
                165                 170                 175

Pro Arg Glu Ala Lys Val Gln Trp Lys Val Asp Asn Ala Leu Gln Ser
            180                 185                 190

Gly Asn Ser Gln Glu Ser Val Thr Glu Gln Asp Ser Lys Asp Ser Thr
        195                 200                 205

Tyr Ser Leu Ser Ser Thr Leu Thr Leu Ser Lys Ala Asp Tyr Glu Lys
    210                 215                 220

His Lys Val Tyr Ala Cys Glu Val Thr His Gln Gly Leu Ser Ser Pro
225                 230                 235                 240

Val Thr Lys Ser Phe Asn Arg Gly Glu Cys
                245                 250
```

<210> SEQ ID NO 34
<211> LENGTH: 1461
<212> TYPE: DNA
<213> ORGANISM: Artificial Sequence
<220> FEATURE:
<223> OTHER INFORMATION: encodes fusion protein of SEQ ID NO:35

<400> SEQUENCE: 34

```
atgaagcttt ccaccatcct tttcacagcc tgcgctaccc tggctgccgc cctcccttcc     60
cccatcactc cttctgaggc cgcagttctc cagaagcgag gcggcggcga ggttcagctg    120
gttgagtctg gtgaggact ggttcagcct ggtggatctc tgcgactgtc ttgtgctgct    180
tctggcttca acatcaagga cacctacatt cattgggtcc gacaggctcc cggaaaggga    240
ctggagtggg ttgcccgaat ctaccctacc aacggctaca ctcgatacgc tgactctgtg    300
aagggacgat tcaccatttc tgccgacacc tctaagaaca ctgcctacct gcagatgaac    360
tctctgcgag ctgaggacac tgctgtgtac tactgttctc gatggggagg tgacggtttt    420
tacgccatgg actactgggg acagggaact ctggtgaccg tttcttctgc ttctaccaag    480
ggaccttctg tgtttcctct ggcccctct tctaagtcta cctctggtgg aactgctgct    540
ctgggatgtc tggtgaagga ctactttcct gagcctgtga ctgtgtcttg aactctggc    600
gctctgactt ctggtgttca caccttccct gctgttctgc agtcctctgg actgtactct    660
ctctcttctg tggtgaccgt gccttcttct tctctgggaa cccagaccta catctgtaac    720
gtgaaccaca agccctctaa cactaaggtg gacaagaagg tggagcctaa gtcttgtgac    780
aagacccata cctgtccccc ttgtcctgct cctgagctgc tgggaggacc ctctgttttt    840
ctgttccccc caagcctaa ggacaccctg atgatttctc gaacccctga ggtgacctgt    900
gttgtggtgg acgtttctca tgaggaccct gaggtgaagt ttaactggta cgtggacggt    960
gttgaggttc acaacgctaa gactaagccc cgagaggagc agtacaactc tacttaccga   1020
gtggtgtctg tgctgactgt tctgcatcag actggctga acggaaagga atacaagtgt   1080
aaggtctcca acaaggctct gcctgctcct attgaaaaga ccatctctaa ggctaaggga   1140
cagcccagag agcctcaggt ttacactctg ccccttccc gagaggagat gaccaagaac   1200
caggtgtccc tgacttgtct ggtcaaggga ttctacccct ctgacattgc tgttgagtgg   1260
gagtctaacg gacagcctga gaacaactac aagaccaccc ctcctgttct ggactctgac   1320
ggctctttct tcctgtactc taagctgacc gtggacaagt ctcgatggca gcagggaaac   1380
gtgttctctt gttccgtgat gcatgaggct ctgcacaacc actacaccca gaagtctctg   1440
tctctgtctc ccggcaagta a                                            1461
```

<210> SEQ ID NO 35
<211> LENGTH: 486
<212> TYPE: PRT
<213> ORGANISM: Artificial Sequence
<220> FEATURE:
<223> OTHER INFORMATION: fusion of Lip2 protein prepro signal and
      anti-HER2 antibody heavy chain

<400> SEQUENCE: 35

Met Lys Leu Ser Thr Ile Leu Phe Thr Ala Cys Ala Thr Leu Ala Ala
1               5                   10                  15

Ala Leu Pro Ser Pro Ile Thr Pro Ser Glu Ala Ala Val Leu Gln Lys
            20                  25                  30

Arg Gly Gly Gly Glu Val Gln Leu Val Glu Ser Gly Gly Gly Leu Val
        35                  40                  45

```
Gln Pro Gly Gly Ser Leu Arg Leu Ser Cys Ala Ala Ser Gly Phe Asn
     50                  55                  60
Ile Lys Asp Thr Tyr Ile His Trp Val Arg Gln Ala Pro Gly Lys Gly
 65                  70                  75                  80
Leu Glu Trp Val Ala Arg Ile Tyr Pro Thr Asn Gly Tyr Thr Arg Tyr
                 85                  90                  95
Ala Asp Ser Val Lys Gly Arg Phe Thr Ile Ser Ala Asp Thr Ser Lys
            100                 105                 110
Asn Thr Ala Tyr Leu Gln Met Asn Ser Leu Arg Ala Glu Asp Thr Ala
            115                 120                 125
Val Tyr Tyr Cys Ser Arg Trp Gly Gly Asp Gly Phe Tyr Ala Met Asp
130                 135                 140
Tyr Trp Gly Gln Gly Thr Leu Val Thr Val Ser Ser Ala Ser Thr Lys
145                 150                 155                 160
Gly Pro Ser Val Phe Pro Leu Ala Pro Ser Ser Lys Ser Thr Ser Gly
                165                 170                 175
Gly Thr Ala Ala Leu Gly Cys Leu Val Lys Asp Tyr Phe Pro Glu Pro
            180                 185                 190
Val Thr Val Ser Trp Asn Ser Gly Ala Leu Thr Ser Gly Val His Thr
            195                 200                 205
Phe Pro Ala Val Leu Gln Ser Ser Gly Leu Tyr Ser Leu Ser Ser Val
210                 215                 220
Val Thr Val Pro Ser Ser Ser Leu Gly Thr Gln Thr Tyr Ile Cys Asn
225                 230                 235                 240
Val Asn His Lys Pro Ser Asn Thr Lys Val Asp Lys Lys Val Glu Pro
                245                 250                 255
Lys Ser Cys Asp Lys Thr His Thr Cys Pro Pro Cys Pro Ala Pro Glu
            260                 265                 270
Leu Leu Gly Gly Pro Ser Val Phe Leu Phe Pro Pro Lys Pro Lys Asp
            275                 280                 285
Thr Leu Met Ile Ser Arg Thr Pro Glu Val Thr Cys Val Val Val Asp
290                 295                 300
Val Ser His Glu Asp Pro Glu Val Lys Phe Asn Trp Tyr Val Asp Gly
305                 310                 315                 320
Val Glu Val His Asn Ala Lys Thr Lys Pro Arg Glu Glu Gln Tyr Asn
                325                 330                 335
Ser Thr Tyr Arg Val Val Ser Val Leu Thr Val Leu His Gln Asp Trp
            340                 345                 350
Leu Asn Gly Lys Glu Tyr Lys Cys Lys Val Ser Asn Lys Ala Leu Pro
            355                 360                 365
Ala Pro Ile Glu Lys Thr Ile Ser Lys Ala Lys Gly Gln Pro Arg Glu
370                 375                 380
Pro Gln Val Tyr Thr Leu Pro Pro Ser Arg Glu Glu Met Thr Lys Asn
385                 390                 395                 400
Gln Val Ser Leu Thr Cys Leu Val Lys Gly Phe Tyr Pro Ser Asp Ile
                405                 410                 415
Ala Val Glu Trp Glu Ser Asn Gly Gln Pro Glu Asn Asn Tyr Lys Thr
            420                 425                 430
Thr Pro Pro Val Leu Asp Ser Asp Gly Ser Phe Phe Leu Tyr Ser Lys
            435                 440                 445
Leu Thr Val Asp Lys Ser Arg Trp Gln Gln Gly Asn Val Phe Ser Cys
450                 455                 460
```

```
Ser Val Met His Glu Ala Leu His Asn His Tyr Thr Gln Lys Ser Leu
465                 470                 475                 480

Ser Leu Ser Pro Gly Lys
                485
```

YEAST STRAINS PRODUCING MAMMALIAN-LIKE COMPLEX N-GLYCANS

CROSS-REFERENCE TO RELATED

This application is a continuation, and claims priority, of U.S. application Ser. No. 13/510,527, filed Oct. 31, 2012, which is a U.S. National Stage application, and claims priority of International Application No. PCT/IB2010/003154, filed Nov. 19, 2010, 2002, which claims priority of U.S. Provisional Application Ser. No. 61/262,828, filed Nov. 19, 2009. The contents of all of the prior applications are incorporated herein by reference in their entirety.

TECHNICAL FIELD

The invention relates to methods and materials for producing glycoproteins in fungal cells, and more particularly, to genetically engineering fungal cells to produce proteins containing mammalian-like complex N-glycans or proteins containing intermediates within a mammalian glycosylation pathway.

BACKGROUND

High performance expression systems are required to produce most biopharmaceuticals (e.g., recombinant proteins) currently under development. The biological activity of many of these biopharmaceuticals is dependent on their post-translational modification (e.g., phosphorylation or glycosylation). A yeast-based expression system combines the ease of genetic manipulation and fermentation of a microbial organism with the capability to secrete and to modify proteins. However, recombinant glycoproteins produced in yeast cells exhibit mainly heterogeneous high-mannose and hyper-mannose glycan structures, which can be detrimental to protein function, downstream processing, and subsequent therapeutic use, particularly where glycosylation plays a biologically significant role.

SUMMARY

The methods and genetically engineered fungal cells described herein can be used to produce target molecules (e.g., target proteins) that contain mammalian-like N-glycans or contain intermediates within the mammalian (e.g., human) glycosylation pathway. Target molecules isolated from such engineered cells can be used for biopharmaceutical applications including antibody production, cytokine production, and for treatment of metabolic disorders such as lysosomal storage disorders.

In one aspect, this document features a method of producing a fungal cell (e.g., *Yarrowia lipolytica* or *Arxula adeninivorans*) capable of producing proteins comprising GlcNAcMan$_5$GlcNAc$_2$ N-glycans. The method includes providing a fungal cell genetically engineered to produce proteins comprising Man$_5$GlcNAc$_2$ N-glycans; and introducing into the cell a nucleic acid encoding a GlcNAc-transferase I, wherein the nucleic acid includes a nucleotide targeting sequence to target the encoded GlcNAc-transferase I to an intracellular compartment (e.g., Golgi apparatus), wherein expression of the GlcNAc-transferase I in the fungal cell produces proteins including GlcNAcMan$_5$GlcNAc$_2$ N-glycans. The method further can include introducing into the cell a nucleic acid encoding a target protein, wherein the cell produces the target protein modified to include the GlcNAcMan$_5$GlcNAc$_2$ N-glycans. The target protein can bind to an Fc receptor. The target protein can be an antibody or fragment thereof. The target protein can be a therapeutic glycoprotein. The target protein can be Interferon-β, GM-CSF, Interferon γ, or erythropoietin.

The fungal cell genetically engineered to produce proteins containing Man$_5$GlcNAc$_2$ N-glycans can be deficient in OCH1 activity and include a nucleic acid encoding an α-1,2-mannosidase, wherein the nucleic acid encoding the α-1,2-mannosidase includes a nucleotide sequence encoding a targeting sequence to target the encoded α-1,2-mannosidase to the endoplasmic reticulum. The targeting sequence can be an HDEL sequence.

The method further can include introducing into a cell a nucleic acid encoding a mannosidase II, wherein the nucleic acid encoding the mannosidase II includes a nucleotide sequence encoding a targeting sequence to target the encoded mannosidase II to the Golgi apparatus, wherein expression of the mannosidase II in the fungal cell produces proteins containing GlcNAcMan$_3$GlcNAc$_2$ N-glycans.

The method further can include introducing into a cell a nucleic acid encoding a galactosyltransferase, wherein the nucleic acid encoding the galactosyltransferase includes a nucleotide sequence encoding a targeting sequence to target the encoded galactosyltransferase to the Golgi apparatus, wherein expression of the galactosyltransferase in the fungal cell produces proteins containing GalGlcNAcMan$_5$GlcNAc$_2$ or GalGlcNAcMan$_3$GlcNAc$_2$ N-glycans. The galactosyltransferase can be a fusion of a UDP-Glc-4-epimerase and the catalytic domain of a β-1,4-galactosyltransferase I. Such a method further can include introducing into the cell a nucleic acid encoding a target protein, wherein the cell produces the target protein modified to contain GalGlcNAcMan$_5$GlcNAc$_2$ or GalGlcNAcMan$_3$GlcNAc$_2$ N-glycans. The methods can include isolating the target protein modified to contain the GalGlcNAcMan$_5$GlcNAc$_2$ or GalGlcNAcMan$_3$GlcNAc$_2$ N-glycans.

In another aspect, this document features a method of producing a target protein containing GlcNAcMan$_3$GlcNAc$_2$ N-glycans. The method includes providing a fungal cell (e.g., *Yarrowia lipolytica* or *Arxula adeninivorans*) genetically engineered to include a nucleic acid encoding a GlcNAc-transferase I, an α-1,2-mannosidase, and a mannosidase II, wherein the nucleic acid includes a nucleotide sequence encoding a targeting sequence, or nucleotide sequences encoding targeting sequences, to target each encoded protein to an intracellular compartment, wherein the fungal cell is deficient in OCH1 activity; and introducing into the cell a nucleic acid encoding a target protein, wherein the cell produces the target protein containing GlcNAcMan$_3$GlcNAc$_2$ N-glycans. The nucleic acid encoding the α-1,2-mannosidase can include an endoplasmic reticulum targeting sequence to target the encoded α-1,2-mannosidase to the endoplasmic reticulum. For example, the targeting sequence can be an HDEL sequence. The nucleic acid encoding the GlcNAc-transferase I and the mannosidase II can include a Golgi targeting sequence, or Golgi targeting sequences, to target the encoded GlcNAc-transferase I and mannosidase II to the Golgi apparatus. The target protein can bind to an Fc receptor. The target protein can be an antibody or fragment thereof. The target protein can be a therapeutic glycoprotein. The target protein can be Interferon-β, GM-CSF, Interferon γ, or erythropoietin.

In some embodiments, the method further can include introducing into the cell a nucleic acid encoding a galactosyltransferase, wherein the nucleic acid encoding the galactosyltransferase includes a nucleotide sequence encoding a targeting sequence to target the encoded galactosyltransferase to the Golgi apparatus, wherein expression of the galactosyltransferase in the fungal cell produces the target protein modified to contain GalGlcNAcMan$_3$GlcNAc$_2$ N-glycans. The target protein modified to contain GalGlcNAcMan$_3$GlcNAc$_2$ N-glycans can be isolated from the fungal cell.

This document also features a method of making a fungal cell (e.g., *Yarrowia lipolytica* or *Arxula adeninivorans*) capable of producing proteins containing GlcNAcMan$_3$GlcNAc$_2$ N-glycans. The method includes providing a fungal cell genetically engineered to produce proteins containing Man$_3$GlcNAc$_2$ N-glycans; introducing into the cell a nucleic acid encoding a GlcNAc-transferase I, wherein the nucleic acid includes a nucleotide sequence encoding a targeting sequence to target the encoded GlcNAc-transferase I to an intracellular compartment (e.g., Golgi apparatus), wherein expression of the GlcNAc-transferase I in the fungal cell produces proteins containing GlcNAcMan$_3$GlcNAc$_2$ N-glycans. The method further can include introducing into the cell a nucleic acid encoding a target protein, wherein the cell produces the target protein modified to contain GlcNAcMan$_3$GlcNAc$_2$ N-glycans. The target protein can bind to an Fc receptor. The target protein can be an antibody or fragment thereof. The target protein can be a therapeutic glycoprotein. The target protein can be Interferon-β, GM-CSF, Interferon γ, or erythropoietin.

The fungal cell genetically engineered to produce proteins containing Man$_3$GlcNAc$_2$ N-glycans can be deficient in ALG3 activity, and include a nucleic acid encoding an α-1,2-mannosidase, wherein the nucleic acid includes a nucleotide sequence encoding a targeting sequence to target the encoded α-1,2-mannosidase to the endoplasmic reticulum. Such a fungal cell further can be deficient in OCH1 activity and/or further include a nucleic acid encoding α-1,3-glucosyltransferase (e.g., ALG6).

The method further can include introducing into the cell a nucleic acid encoding a GlcNAc-transferase II, wherein the nucleic acid encoding the GlcNAc-transferase II includes a nucleotide sequence encoding a targeting sequence to target the encoded GlcNAc-transferase II to an intracellular compartment, wherein expression of the GlcNAc-transferase II in the fungal cell produces proteins containing GlcNAc$_2$Man$_3$GlcNAc$_2$ N-glycans.

The method further can include introducing into the cell a nucleic acid encoding a galactosyltransferase, wherein the nucleic acid encoding the galactosyltransferase includes a nucleotide sequence encoding a targeting sequence to target the encoded galactosyltransferase to the Golgi apparatus, wherein expression of the galactosyltransferase in the fungal cell produces proteins containing GalGlcNAcMan$_3$GlcNAc$_2$ or Gal$_2$GlcNAc$_2$Man$_3$GlcNAc$_2$ N-glycans. The galactosyltransferase can be a fusion of a UDP-Glc-4-epimerase and catalytic domain of a β-1,4-galactosyltransferase I. The method further can include introducing into the cell a nucleic acid encoding a target protein, wherein the cell produces the target protein modified to contain GalGlcNAcMan$_3$GlcNAc$_2$ or Gal$_2$GlcNAc$_2$Man$_3$GlcNAc$_2$ N-glycans.

The method further can include introducing into the cell a nucleic acid encoding the α and β subunits of a Glucosidase II, wherein expression of the α and β subunits of the Glucosidase II in the fungal cell produces proteins including GalGlcNAcMan$_3$GlcNAc$_2$ or Gal$_2$GlcNAc$_2$Man$_3$GlcNAc$_2$ N-glycans.

This document also features a method of producing a target protein containing Gal$_2$GlcNAc$_2$Man$_3$GlcNAc$_2$ N-glycans. The method includes providing a fungal cell genetically engineered to be deficient in ALG3 activity and including a nucleic acid encoding a GlcNAc-transferase I, a GlcNAc-transferase II, and a galactosyltransferase, wherein the nucleic acid encoding the GlcNAc-transferase I, the GlcNAc-transferase II, and the galactosyltransferase include a nucleotide sequence encoding a targeting sequence, or nucleotide sequences encoding targeting sequences, to target each encoded protein to an intracellular compartment (e.g., the Golgi apparatus); and introducing into the cell a nucleic acid encoding a target protein, wherein the cell produces the target protein containing Gal$_2$GlcNAc$_2$Man$_3$GlcNAc$_2$ N-glycans. The fungal cell can be further deficient in OCH1 activity and/or further include a nucleic acid encoding an α-1,3-glucosyltransferase such as ALG6. The fungal cell further can include a nucleic acid encoding the α and β subunits of a Glucosidase II, wherein expression of the α and β subunits of the Glucosidase II in the fungal cell produces the target protein containing Gal$_2$GlcNAc$_2$Man$_3$GlcNAc$_2$ N-glycans.

In another aspect, this document features an isolated fungal cell genetically engineered to produce proteins containing GlcNAcMan$_3$GlcNAc$_2$ N-glycans. The fungal cell can be deficient in OCH1 activity and include a nucleic acid encoding an α-1,2-mannosidase, a GlcNAc-transferase I, and a mannosidase II, wherein the nucleic acid encoding the α-1,2-mannosidase, the GlcNAc-transferase I, and the mannosidase II includes a nucleotide sequence encoding a targeting sequence, or nucleotide sequences encoding targeting sequences, to target each encoded protein to an intracellular compartment, wherein expression of the α-1,2-mannosidase, the GlcNAc-transferase I, and the mannosidase II in the fungal cell produces proteins containing GlcNAcMan$_3$GlcNAc$_2$ N-glycans. The fungal cell further can include a nucleic acid encoding a target protein, wherein the cell produces the target protein modified to contain GlcNAcMan$_3$GlcNAc$_2$ N-glycans.

In some embodiments, such a fungal cell further includes a nucleic acid encoding a GlcNAc-transferase II, wherein the nucleic acid encoding the GlcNAc-transferase II includes a nucleotide sequence encoding a targeting sequence to target the encoded GlcNAc-transferase II to an intracellular compartment, wherein expression of the GlcNAc-transferase II in the fungal cell produces proteins containing GlcNAc$_2$Man$_3$GlcNAc$_2$ N-glycans.

In some embodiments, such a fungal cell further includes a nucleic acid encoding a galactosyltransferase, wherein the nucleic acid encoding the galactosyltransferase includes a nucleotide sequence encoding a targeting sequence to target the encoded galactosyltransferase to the Golgi apparatus, wherein expression of the galactosyltransferase in the fungal cell produces proteins containing Gal$_2$GlcNAc$_2$Man$_3$GlcNAc$_2$ N-glycans.

In yet another aspect, this document features an isolated fungal cell genetically engineered to produce proteins containing GlcNAc$_2$Man$_3$GlcNAc$_2$ N-glycans. The fungal cell is genetically engineered to be deficient in ALG3 activity and includes a nucleic acid encoding a GlcNAc-transferase I and a GlcNAc-transferase II, wherein the nucleic acid encoding the GlcNAc-transferase I and the GlcNAc-transferase II includes a nucleotide sequence encoding a targeting sequence, or nucleotide sequences encoding targeting sequences, to target each encoded protein to an intracellular compartment, wherein expression of the GlcNAc-transferase I, and the GlcNAc-transferase II in the fungal cell produces proteins containing GlcNAc$_2$Man$_3$GlcNAc$_2$ N-glycans. The genetically engineered fungal cell further can be deficient in OCH1 activity and/or further include a nucleic acid encoding an α-1,3-glucosyltransferase. A genetically engineered fungal cell also can include a nucleic acid encoding a target protein, wherein the cell produces the target protein modified to contain GlcNAc$_2$Man$_3$GlcNAc$_2$ N-glycans. A fungal cell further can include a nucleic acid encoding the α and β subunits of a Glucosidase II, wherein expression of the α and β subunits of the Glucosidase II in the fungal cell produces the protein containing GlcNAc$_2$Man$_3$GlcNAc$_2$ N-glycans. The fungal cell further can include a nucleic acid encoding a galactosyltransferase, wherein the nucleic acid encoding the galactosyltransferase includes a nucleotide sequence encoding a targeting sequence to target the encoded galactosyltransferase to the Golgi apparatus, wherein expression of the galactosyltransferase in the fungal cell produces proteins containing Gal$_2$GlcNAc$_2$Man$_3$GlcNAc$_2$ N-glycans.

This document also features a substantially pure culture of *Yarrowia lipolytica* cells, a substantial number of which are genetically engineered to produce glycoproteins containing Gal$_2$GlcNac$_2$Man$_3$GlcNAc$_2$ N-glycans. The cells are genetically engineered to be deficient in ALG3 activity and include a nucleic acid encoding a GlcNAc-transferase I, a GlcNAc-transferase II, and a galactosyltransferase, wherein the nucleic acid encoding the GlcNAc-transferase I, the GlcNAc-transferase II, and the galactosyltransferase include a nucleotide sequence encoding a targeting sequence, or nucleotides sequences encoding targeting sequences, to target each encoded protein to an intracellular compartment, wherein expression of the GlcNAc-transferase I, the GlcNAc-transferase II, and the galactosyltransferase in the cell produces proteins containing Gal$_2$GlcNAc$_2$Man$_3$GlcNAc$_2$ N-glycans. The genetically engineered fungal cell further can be deficient in OCH1 activity and/or further include a nucleic acid encoding an α-1,3-glucosyltransferase (e.g., ALG6). The cells further can include a nucleic acid encoding the α and β subunits of a Glucosidase II, wherein expression of the α and β subunits of the Glucosidase II in the fungal cell produces the target protein containing Gal$_2$GlcNAc$_2$Man$_3$GlcNAc$_2$ N-glycans.

In another aspect, this document features a substantially pure culture of *Yarrowia lipolytica* cells, a substantial number of which are genetically engineered to produce glycoproteins containing Gal$_2$GlcNAc$_2$Man$_3$GlcNAc$_2$ N-glycans, wherein the cells are genetically engineered to be deficient in OCH1 activity and include a nucleic acid encoding an α-1,2-mannosidase, a GlcNAc-transferase I, a mannosidase II, a GlcNAc-transferase II, and a galactosyltransferase, wherein the nucleic acid encoding the α-1,2-mannosidase, the GlcNAc-transferase I, the mannosidase II, the GlcNAc-transferase II, and the galactosyltransferase includes a nucleotide sequence encoding a targeting sequence, or nucleotide sequences encoding targeting sequences, to target each encoded protein to an intracellular compartment, wherein expression of the α-1,2-mannosidase, GlcNAc-transferase I, mannosidase II, GlcNAc-transferase II, and galactosyltransferase in the cells produces proteins comprising Gal$_2$GlcNAc$_2$Man$_3$GlcNAc$_2$ N-glycans.

This document also features a composition that includes a glycoprotein, wherein at least 50% (e.g., at least 70% or at least 85% of the N-glycans on the glycoprotein are GlcNAc$_2$Man$_3$GlcNAc$_2$ N-glycans.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, Genbank® Accession Nos, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

DESCRIPTION OF DRAWINGS

FIG. 7 is a depiction of the amino acid sequence (SEQ ID NO:3) and *Yarrowia* codon optimized nucleotide sequence (SEQ ID NO:4) of the fusion protein between the 100 N-terminal amino acids of Kre2p and the catalytic domain of human GlcNAc-transferase I. In bold: Kre2p part of fusion protein; in normal font: GnT I part of fusion protein; underlined: start and stop codons.

FIG. 10 is a depiction of the amino acid sequence (SEQ ID NO:7) and *Yarrowia* codon optimized nucleotide sequence (SEQ ID NO:8) of the fusion protein between the 36 N-terminal amino acids of Mnn2p and the catalytic domain of *Drosophila melanogaster* mannosidase II. In bold: Mnn2p part of fusion protein; in normal font: Man II part of fusion protein; underlined: start and stop codons.

FIG. 13 is the amino acid sequence (SEQ ID NO:9) and *Yarrowia* codon optimized nucleotide sequence (SEQ ID NO:10) of the fusion protein between the 46 N-terminal amino acids of Mnn2p, the *Schizosaccharomyces pombe* UDP-Glc-4-epimerase-like protein and the catalytic domain of human β-1,4-galactosyl transferase I. The Mnn2p part of the fusion protein is from 1-46, linker sequences are from 47-49 and 405-408, epimerase sequences of the fusion protein are from 50-404, and the Man II part of the fusion protein is from 409-763 of SEQ ID NO:9. The Mnn2p part is from nucleotides 1-138, linker sequences are from nucleotides 139-147 and 1213-1224, epimerase sequences are from nucleotides 148-1212, and Man II part is from 1225-2289 of SEQ ID NO:10. Start and stop codons are underlined.

FIG. 22 is the amino acid sequence (SEQ ID NO:17) and *Yarrowia* codon optimized nucleotide sequence (SEQ ID NO:18) of the fusion protein between the 36 N-terminal amino acids of Mnn2p and the catalytic domain of rat GlcNAc-transferase II. In bold: Mnn2p part of fusion protein; in normal font: GnT II part of fusion protein; underlined: start and stop codons.

FIG. 30A is the nucleotide sequence of the synthetic preproLip2-light chain (LC) (SEQ ID NO:32).

FIG. 30B is the amino acid sequence of the synthetic preproLip2-LC (SEQ ID NO:33)

FIG. 31A is the nucleotide sequence of the synthetic preproLip2-heavy chain (HC) (SEQ ID NO:34).

FIG. 31B is the amino acid sequence of the synthetic preproLip2-HC (SEQ ID NO:35).

FIGS. 34A-1, 34A-2, 34B-1, and 34B-2 are a series of electroferograms depicting the N-glycan profile analysis of the secretome at different time-points within the G096 fed-batch fermentation.

DETAILED DESCRIPTION

Figure 1A:
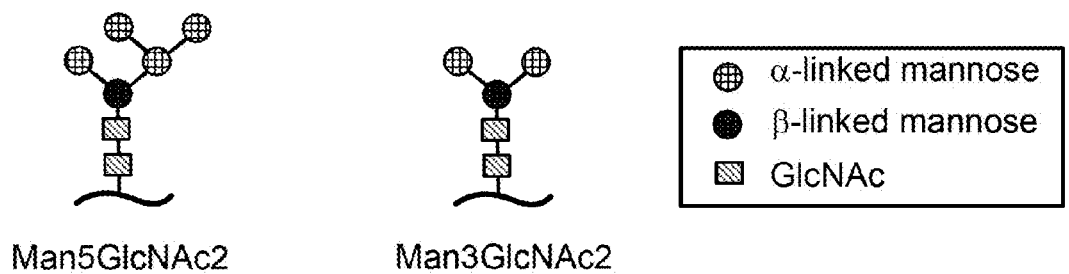
FIG. 1A is a representation of Man$_5$GLcNAc$_2$ and Man$_3$GlcNAc$_2$ structures.

As described herein, in vivo synthesis of mammalian-like complex N-glycans on yeast-secreted glycoproteins can be based on either a Man$_5$GlcNAc$_2$ or Man$_3$GlcNAc$_2$ base structure (see FIG. 1A, "Man" refers to mannose, and "GlcNAc" refers to N-glucosamine). To produce the Man$_5$GlcNAc$_2$ base structure, yeast cells can be engineered such that α-1,2-mannosidase activity is increased in an intracellular compartment and Outer CHain elongation (OCH1) activity is decreased. To produce the Man$_3$GlcNAc$_2$ base structure, activity of Asparagine Linked Glycosylation 3 (ALG3) and, in some embodiments, OCH1 is decreased, activity of α-1,2-mannosidase and, in some embodiments, activity of α-1,3-glucosyltransferase is increased. The N-glycan profile of proteins produced in such yeast cells can be altered by further engineering the yeast cells to contain one or more of the following activities: GlcNAc transferase I (GnT I) activity, mannosidase II activity, GlcNAc transferase II (GnT II) activity, glucosidase II activity, and galactosyltransferase (Gal T) activity. For example, expressing GnT I in a yeast cell producing Man$_5$GlcNAc$_2$ or Man$_3$GlcNAc$_2$ N-glycans results in the transfer of a GlcNAc moiety to the Man$_5$GlcNAc$_2$ or Man$_3$GlcNAc$_2$ N-glycans such that GlcNAcMan$_5$GlcNAc$_2$ or GlcNAcMan$_3$GlcNAc$_2$ N-glycans, respectively, are produced. In cells producing GlcNAcMan$_5$GlcNAc$_2$ N-glycans, expressing a mannosidase II results in two mannose residues being removed from GlcNAcMan$_5$GlcNAc$_2$ N-glycans to produce GlcNAcMan$_3$GlcNAc$_2$ N-glycans. In cells producing GlcNAcMan$_3$GlcNAc$_2$ N-glycans, expressing GnT II results in the transfer of another GlcNAc moiety to GlcNAcMan$_3$GlcNAc$_2$ N-glycans to produce GlcNAc$_2$Man$_3$GlcNAc$_2$ N-glycans. Expressing Gal T in cells producing GlcNAcMan$_3$GlcNAc$_2$ or GlcNAc$_2$Man$_3$GlcNAc$_2$ N-glycans results in the transfer of galactose to the GlcNAcMan$_3$GlcNAc$_2$ or GlcNAc$_2$Man$_3$GlcNAc$_2$ N-glycans to produce GalGlcNAcMan$_3$GlcNAc$_2$ or Gal$_2$GlcNAc$_2$Man$_3$GlcNAc$_2$ N-glycans. In some embodiments, glucosidase II (e.g., by expressing α and β subunits) can be expressed to increase production of the Man$_3$GlcNAc$_2$ base structure.

Target Molecules

Target molecules, as used herein, refer to any molecules that undergo N-glycosylation in a genetically engineered cell (e.g., a fungal cell such as Yarrowia lipolytica, Arxula adeninivorans, or other related species dimorphic yeast cell; a plant cell, or an animal cell). In some embodiments, the target molecules are capable of being trafficked through one or more steps of the Yarrowia lipolytica or Arxula adeninivorans (or other related species dimorphic yeast) secretory pathway, resulting in their N-glycosylation by the host cell machinery. The target molecules can be endogenous or exogenous.

Suitable target proteins include pathogen proteins (e.g., tetanus toxoid; diptheria toxoid; viral surface proteins (e.g., cytomegalovirus (CMV) glycoproteins B, H and gCIII; human immunodeficiency virus 1 (HIV-1) envelope glycoproteins; *Rous sarcoma* virus (RSV) envelope glycoproteins; herpes simplex virus (HSV) envelope glycoproteins; Epstein Barr virus (EBV) envelope glycoproteins; varicellazoster virus (VZV) envelope glycoproteins; human papilloma virus (HPV) envelope glycoproteins; Influenza virus glycoproteins; and Hepatitis family surface antigens), lysosomal proteins (e.g., glucocerebrosidase, cerebrosidase, or galactocerebrosidase), insulin, glucagon, growth factors, cytokines, chemokines, a protein binding to an Fc receptor, antibodies or fragments thereof, or fusions of any of the proteins to antibodies or fragments of antibodies (e.g., protein-Fc). Growth factors include, e.g., vascular endothelial growth factor (VEGF), Insulin-like growth factor (IGF), bone morphogenic protein (BMP), Granulocyte-colony stimulating factor (G-CSF), Granulocyte-macrophage colony stimulating factor (GM-CSF), Nerve growth factor (NGF); a Neurotrophin, Platelet-derived growth factor (PDGF), Erythropoietin (EPO), Thrombopoietin (TPO), Myostatin (GDF-8), Growth Differentiation factor-9 (GDF9), basic fibroblast growth factor (bFGF or FGF2), Epidermal growth factor (EGF), Hepatocyte growth factor (HGF). Cytokines include, e.g., interleukins (e.g., IL-1 to IL-33 such as IL-1, IL-2, IL-3, IL-4, IL-5, IL-6, IL-7, IL-8, IL-9, IL-10, IL-12, IL-13, or IL-15) and interferons (e.g., interferon β or interferon γ). Chemokines include, e.g., I-309, TCA-3, MCP-1, MIP-1α, MIP-1β, RANTES, C10, MRP-2, MARC, MCP-3, MCP-2, MRP-2, CCF18, MIP-1γ, Eotaxin, MCP-5, MCP-4, NCC-1, Ckβ10, HCC-1, Leukotactin-1, LEC, NCC-4, TARC, PARC, or Eotaxin-2. Also included are tumor glycoproteins (e.g., tumor-associated antigens), for example, carcinoembryonic antigen (CEA), human mucins, HER-2/neu, and prostate-specific antigen (PSA) [Henderson and Finn, *Advances in Immunology*, 62, pp. 217-56 (1996)]. In one embodiment, the target protein is an anti-HER2/neu antibody. In some embodiments, the target protein can be one associated with a lysosomal storage disorder, which target proteins include, e.g., alpha-L-iduronidase, beta-D-galactosidase, beta-glucosidase, beta-hexosaminidase, beta-D-mannosidase, alpha-L-fucosidase, arylsulfatase B, arylsulfatase A, alpha-N-acetylgalactosaminidase, aspartylglucosaminidase, iduronate-2-sulfatase, alpha-glucosaminide-N-acetyltransferase, beta-D-glucoronidase, hyaluronidase, alpha-L-mannosidase, alphaneuraminidase, phosphotransferase, acid lipase, acid ceramidase, sphingomyelinase, thioesterase, cathepsin K, and lipoprotein lipase.

Target proteins also can be fusion proteins. Fusions proteins include, e.g., a fusion of (i) any protein described herein or fragment thereof with (ii) an antibody or fragment thereof. As used herein, the term "antibody fragment" refers to (a) an antigen-binding fragment or (b) an Fc part of the antibody that can interact with an Fc receptor. An antigen binding fragment can be, for example, a Fab, F(ab')$_2$, Fv, and single chain Fv (scFv) fragment. An scFv fragment is a single polypeptide chain that includes both the heavy and light chain variable regions of the antibody from which the scFv is derived. In addition, diabodies [Poljak (1994) *Structure* 2(12):1121-1123; Hudson et al. (1999) *J. Immunol. Methods* 23(1-2):177-189] and intrabodies [Huston et al. (2001) *Hum. Antibodies* 10(3-4):127-142; Wheeler et al. (2003) *Mol. Ther.* 8(3):355-366; Stocks (2004) *Drug Discov. Today* 9(22): 960-966] can be used in the methods of the invention.

Target proteins can also be joined to one or more of a polymer, a carrier, an adjuvant, an immunotoxin, or a detectable (e.g., fluorescent, luminescent, or radioactive) moiety. For example, a target protein can be joined to polyethyleneglycol, which can be used to increase the molecular weight of small proteins and/or increase circulation residence time.

In some embodiments, the target molecule can be, or contain, dolichol.

Genetically Engineered Cells

Genetically engineered cells described herein can be used to produce target molecules that contain mammalian-like N-glycans or target molecules that contain intermediates within the mammalian glycosylation pathway. For example, as described herein, nucleic acids encoding one or more enzymes can be introduced into a fungal cell such that the cell produces the desired N-glycan (e.g., GlcNAcMan$_5$GlcNAc$_2$, GlcNAcMan$_3$GlcNAc$_2$, GlcNAc$_2$Man$_3$GlcNAc$_2$, GalGlcNAcMan$_3$GlcNAc$_2$ or Gal$_2$GlcNAc$_2$Man$_3$GlcNAc$_2$ N-glycans). Thus, in any of the embodiments described herein, a fungal cell may contain a nucleic acid encoding one enzyme, or a nucleic acid may encode multiple enzymes. Each such nucleic acid also can contain a targeting sequence as discussed below. In addition, a nucleic acid encoding a target molecule also can be introduced into the fungal cell such that the target molecule is produced and modified to contain the desired N-glycan (e.g., GlcNAcMan$_5$GlcNAc$_2$, GlcNAcMan$_3$GlcNAc$_2$, GlcNAc$_2$Man$_3$GlcNAc$_2$, GalGlcNAcMan$_3$GlcNAc$_2$ or Gal$_2$GlcNAc$_2$Man$_3$GlcNAc$_2$ N-glycans).

The terms "nucleic acid" and "polynucleotide" are used interchangeably herein, and refer to both RNA and DNA, including cDNA, genomic DNA, synthetic DNA, and DNA (or RNA) containing nucleic acid analogs. Nucleic acids can have any three-dimensional structure. A nucleic acid can be double-stranded or single-stranded (i.e., a sense strand or an antisense strand). Non-limiting examples of nucleic acids include genes, gene fragments, exons, introns, messenger RNA (mRNA), transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs. "Polypeptide" and "protein" are used interchangeably herein and mean any peptide-linked chain of amino acids, regardless of length or post-translational modification.

An "isolated nucleic acid" refers to a nucleic acid that is separated from other nucleic acid molecules that are present in a naturally-occurring genome, including nucleic acids that normally flank one or both sides of the nucleic acid in a naturally-occurring genome (e.g., a yeast genome). The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., any paramyxovirus, retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

The term "exogenous" as used herein with reference to nucleic acid and a particular host cell refers to any nucleic acid that does not occur in (and cannot be obtained from) that particular cell as found in nature. Thus, a non-naturally-occurring nucleic acid is considered to be exogenous to a host cell once introduced into the host cell. It is important to note that non-naturally-occurring nucleic acids can contain nucleic acid subsequences or fragments of nucleic acid sequences that are found in nature provided that the nucleic acid as a whole does not exist in nature. For example, a nucleic acid molecule containing a genomic DNA sequence within an expression vector is non-naturally-occurring nucleic acid, and thus is exogenous to a host cell once introduced into the host cell, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular cell. For example, an entire chromosome isolated from a cell of yeast x is an exogenous nucleic acid with respect to a cell of yeast y once that chromosome is introduced into a cell of yeast.

Cells suitable for genetic engineering include, e.g., fungal cells (e.g., *Yarrowia lipolytica* or any other related dimorphic yeast cells described herein), plant cells, or animal cells. The cells can be primary cells, immortalized cells, or transformed cells. The cells can be those in an animal, e.g., a non-human mammal. Such cells, prior to the genetic engineering as specified herein, can be obtained from a variety of commercial sources and research resource facilities, such as, for example, the American Type Culture Collection (Rockville, Md.).

Genetic engineering of a cell can include genetic modifications such as: (i) deletion of an endogenous gene encoding a protein having N-glycosylation activity; (ii) introduction of a recombinant nucleic acid encoding a mutant form of a protein (e.g., endogenous or exogenous protein) having N-glycosylation activity (i.e., expressing a mutant protein having an N-glycosylation activity); (iii) introduction or expression of an RNA molecule that interferes with the functional expression of a protein having the N-glycosylation activity; (iv) introduction of a recombinant nucleic acid encoding a wild-type (e.g., endogenous or exogenous) protein having N-glycosylation activity (i.e., expressing a protein having an N-glycosylation activity); or (v) altering the promoter or enhancer elements of one or more endogenous genes encoding proteins having N-glycosylation activity to thus alter the expression of their encoded proteins. RNA molecules include, e.g., small-interfering RNA (siRNA), short hairpin RNA (shRNA), anti-sense RNA, or micro RNA (miRNA). It is understood that item (ii) includes, e.g., replacement of an endogenous gene with a gene encoding a protein having greater N-glycosylation activity relative to the endogenous gene so replaced. Genetic engineering also includes altering an endogenous gene encoding a protein having an N-glycosylation activity to produce a protein having additions (e.g., a heterologous sequence), deletions, or substitutions (e.g., mutations such as point mutations; conservative or non-conservative mutations). Mutations can be introduced specifically (e.g., site-directed mutagenesis or homologous recombination) or can be introduced randomly (for example, cells can be chemically mutagenized as described in, e.g., Newman and Ferro-Novick (1987) *J. Cell Biol.* 105(4):1587.

The genetic modifications described herein can result in one or more of (i) an increase in one or more N-glycosylation activities in the genetically modified cell, (ii) a decrease in one or more N-glycosylation activities in the genetically modified cell, (iii) a change in the localization or intracellular distribution of one or more N-glycosylation activities in the genetically modified cell, or (iv) a change in the ratio of one or more N-glycosylation activities in the genetically modified cell. It is understood that an increase in the amount of an N-glycosylation activity can be due to overexpression of one or more proteins having N-glycosylation activity, an increase in copy number of an endogenous gene (e.g., gene duplication), or an alteration in the promoter or enhancer of an endogenous gene that stimulates an increase in expression of the protein encoded by the gene. A decrease in one or more N-glycosylation activities can be due to overexpression of a mutant form (e.g., a dominant negative form) of one or more proteins having N-glysosylation altering activities, introduction or expression of one or more interfering RNA molecules that reduce the expression of one or more proteins having an N-glycosylation activity, or deletion of one or more endogenous genes that encode a protein having N-glycosylation activity.

Methods of deleting or disrupting one or more endogenous genes are described in the accompanying Examples. For example, to disrupt a gene by homologous recombination, a "gene replacement" vector can be constructed in such a way to include a selectable marker gene. The selectable marker gene can be operably linked, at both 5' and 3' end, to portions of the gene of sufficient length to mediate homologous recombination. The selectable marker can be one of any number of genes which either complement host cell auxotrophy or provide antibiotic resistance, including URA3, LEU2 and HIS3 genes. Other suitable selectable markers include the CAT gene, which confers chloramphenicol resistance to yeast cells, or the lacZ gene, which results in blue colonies due to the expression of β-galactosidase. Linearized DNA fragments of the gene replacement vector are then introduced into the cells using methods well known in the art (see below). Integration of the linear fragments into the genome and the disruption of the gene can be determined based on the selection marker and can be verified by, for example, Southern blot analysis.

As detailed in the accompanying examples, subsequent to its use in selection, a selectable marker can be removed from the genome of the host cell by, e.g., Cre-loxP systems (see below). This process of marker removal is referred to as "curing" throughout the Examples.

Alternatively, a gene replacement vector can be constructed in such a way as to include a portion of the gene to be disrupted, where the portion is devoid of any endogenous gene promoter sequence and encodes none, or an inactive fragment of, the coding sequence of the gene. An "inactive fragment" is a fragment of the gene that encodes a protein having, e.g., less than about 10% (e.g., less than about 9%, less than about 8%, less than about 7%, less than about 6%, less than about 5%, less than about 4%, less than about 3%, less than about 2%, less than about 1%, or 0%) of the activity of the protein produced from the full-length coding sequence of the gene. Such a portion of the gene is inserted in a vector in such a way that no known promoter sequence is operably linked to the gene sequence, but that a stop codon and a transcription termination sequence are operably linked to the portion of the gene sequence. This vector can be subsequently linearized in the portion of the gene sequence and transformed into a cell. By way of single homologous recombination, this linearized vector is then integrated in the endogenous counterpart of the gene.

Expression vectors can be autonomous or integrative.

A recombinant nucleic acid can be in introduced into the cell in the form of an expression vector such as a plasmid, phage, transposon, cosmid or virus particle. The recombinant nucleic acid can be maintained extrachromosomally or it can be integrated into the yeast cell chromosomal DNA. Expression vectors can contain selection marker genes encoding proteins required for cell viability under selected conditions (e.g., URA3, which encodes an enzyme necessary for uracil biosynthesis or TRP1, which encodes an enzyme required for tryptophan biosynthesis) to permit detection and/or selection of those cells transformed with the desired nucleic acids (see, e.g., U.S. Pat. No. 4,704,362). Expression vectors can also include an autonomous replication sequence (ARS). For example, U.S. Pat. No. 4,837,148 describes autonomous replication sequences which provide a suitable means for maintaining plasmids in *Pichia pastoris*.

Integrative vectors are disclosed, e.g., in U.S. Pat. No. 4,882,279. Integrative vectors generally include a serially arranged sequence of at least a first insertable DNA fragment, a selectable marker gene, and a second insertable DNA fragment. The first and second insertable DNA fragments are each about 200 (e.g., about 250, about 300, about 350, about 400, about 450, about 500, or about 1000 or more) nucleotides in length and have nucleotide sequences which are homologous to portions of the genomic DNA of the species to be transformed. A nucleotide sequence containing a gene of interest (e.g., a gene encoding a protein having N-glycosylation activity) for expression is inserted in this vector between the first and second insertable DNA fragments whether before or after the marker gene. Integrative vectors can be linearized prior to yeast transformation to facilitate the integration of the nucleotide sequence of interest into the host cell genome.

An expression vector can feature a recombinant nucleic acid under the control of a yeast (e.g., *Yarrowia lipolytica*, *Arxula adeninivorans*, or other related dimorphic yeast species) promoter, which enables them to be expressed in yeast. Suitable yeast promoters include the TEF1, HP4D, GAP, POX2, ADC1, TPI1, ADH2, POX, and Gal10 promter. See, e.g., Madzak et al., (2000) *J. Mol. Microbiol. Biotechnol.* 2:207-216; Guarente et al. (1982) *Proc. Natl. Acad. Sci. USA* 79(23):7410. Additional suitable promoters are described in, e.g., Zhu and Zhang (1999) *Bioinformatics* 15(7-8):608-611 and U.S. Pat. No. 6,265,185. Where the expression vector is to be introduced into an animal cell, such as a mammalian cell, the expression vector can feature a recombinant nucleic acid under the control of an animal cell promoter suitable for expression in the host cell of interest. Examples of mammalian promoters include the SV40 and cytomegalovirus (CMV) promoters.

A promoter can be constitutive or inducible (conditional). A constitutive promoter is understood to be a promoter whose expression is constant under the standard culturing conditions. Inducible promoters are promoters that are responsive to one or more induction cues. For example, an inducible promoter can be chemically regulated (e.g., a promoter whose transcriptional activity is regulated by the presence or absence of a chemical inducing agent such as an alcohol, tetracycline, a steroid, a metal, or other small molecule) or physically regulated (e.g., a promoter whose transcriptional activity is regulated by the presence or absence of a physical inducer such as light or high or low temperatures). An inducible promoter can also be indirectly regulated by one or more transcription factors that are themselves directly regulated by chemical or physical cues.

Genetic engineering of a cell also includes activating an endogenous gene (e.g., a gene encoding a protein having N-glycosylation activity) that is present in the host cell, but is normally not expressed in the cells or is not expressed at significant levels in the cells. For example, a regulatory sequence (e.g., a gene promoter or an enhancer) of a endogenous gene can be modified such that the operably-linked coding sequence exhibits increased expression. Homologous recombination or targeting can be used to replace or disable the regulatory region normally associated with the gene with a regulatory sequence which causes the gene to be expressed at levels higher than evident in the corresponding non-genetically engineered cell, or causes the gene to display a pattern of regulation or induction that is different than evident in the corresponding non-genetically engineered cell. Suitable methods for introducing alterations of a regulatory sequence (e.g., a promoter or enhancer) of a gene are described in, e.g., U.S. Application Publication No. 20030147868.

It is understood that other genetically engineered modifications also can be conditional. For example, a gene can be conditionally deleted using, e.g., a site-specific DNA recombinase such as the Cre-loxP system (see, e.g., Gossen et al. (2002) *Ann. Rev. Genetics* 36:153-173 and U.S. Application Publication No. 20060014264).

A recombinant nucleic acid can be introduced into a cell described herein using a variety of methods such as the spheroplast technique or the whole-cell lithium chloride yeast transformation method. Other methods useful for transformation of plasmids or linear nucleic acid vectors into cells are described in, for example, U.S. Pat. No. 4,929,555; Hinnen et al. (1978) *Proc. Nat. Acad. Sci. USA* 75:1929; Ito et al. (1983) *J. Bacteriol.* 153:163; U.S. Pat. No. 4,879,231; and Sreekrishna et al. (1987) *Gene* 59:115. Electroporation and PEG1000 whole cell transformation procedures may also be used, as described by Cregg and Russel, Methods in Molecular Biology: Pichia Protocols, Chapter 3, Humana Press, Totowa, N.J., pp. 27-39 (1998). Transfection of animal cells can feature, for example, the introduction of a vector to the cells using calcium phosphate, electroporation, heat shock, liposomes, or transfection reagents such as FUGENE® or LIPOFECTAMINE®, or by contacting naked nucleic acid vectors with the cells in solution (see, e.g., Sambrook et al., Molecular Cloning: A Laboratory Manual Second Edition vol. 1, 2 and 3. Cold Spring Harbor Laboratory Press: Cold Spring Harbor, N.Y., USA, November 1989.

Transformed yeast cells can be selected for by using appropriate techniques including, but not limited to, culturing auxotrophic cells after transformation in the absence of the biochemical product required (due to the cell's auxotrophy), selection for and detection of a new phenotype, or culturing in the presence of an antibiotic which is toxic to the yeast in the absence of a resistance gene contained in the transformants. Transformants can also be selected and/or verified by integration of the expression cassette into the genome, which can be assessed by, e.g., Southern blot or PCR analysis.

Prior to introducing the vectors into a target cell of interest, the vectors can be grown (e.g., amplified) in bacterial cells such as *Escherichia coli* (*E. coli*). The vector DNA can be isolated from bacterial cells by any of the methods known in the art which result in the purification of vector DNA from the bacterial milieu. The purified vector DNA can be extracted extensively with phenol, chloroform, and ether, to ensure that no *E. coli* proteins are present in the plasmid DNA preparation, since these proteins can be toxic to mammalian cells.

Genetic engineering, as described herein, can be used to express (e.g., overexpress), introduce modifications into, or delete any number of genes encoding proteins having N-glycosylation activity. Such proteins include, for example, OCH1, ALG3, α-1,3-glucosyltransferase, GnT I, mannosidase II, GnT II, glucosidase II, or Gal T. The genes encoding proteins having N-glycosylation activity can be from any species containing such genes. Exemplary fungal species from which genes encoding proteins having N-glycosylation activity can be obtained include, without limitation, *Pichia anomala, Pichia bovis, Pichia canadensis, Pichia carsonii, Pichia farinose, Pichia fermentans, Pichia fluxuum, Pichia membranaefaciens, Pichia membranaefaciens, Candida valida, Candida albicans, Candida ascalaphidarum, Candida amphixiae, Candida Antarctica, Candida atlantica, Candida atmosphaerica, Candida blattae, Candida carpophila, Candida cerambycidarum, Candida chauliodes, Candida corydalis, Candida dosseyi, Candida dubliniensis, Candida ergatensis, Candida fructus, Candida glabrata, Candida fermentati, Candida guilliermondii, Candida haemulonii, Candida insectamens, Candida insectorum, Candida intermedia, Candida jeffresii, Candida kefyr, Candida krusei, Candida lusitaniae, Candida lyxosophila, Candida maltosa, Candida membranifaciens, Candida milleri, Candida oleophila, Candida oregonensis, Candida parapsilosis, Candida quercitrusa, Candida shehatae, Candida temnochilae, Candida tenuis, Candida tropicalis, Candida tsuchiyae, Candida sinolaborantium, Candida sojae, Candida viswanathii, Candida utilis, Pichia membranaefaciens, Pichia silvestris, Pichia membranaefaciens, Pichia chodati, Pichia membranaefaciens, Pichia menbranaefaciens, Pichia minuscule, Pichia pastoris, Pichia pseudopolymorpha, Pichia quercuum, Pichia robertsii, Pichia saitoi, Pichia silvestrisi, Pichia strasburgensis, Pichia terricola, Pichia vanriji, Pseudozyma Antarctica, Rhodosporidium toruloides, Rhodotorula glutinis, Saccharomyces bayanus, Saccharomyces bayanus, Saccharomyces momdshuricus, Saccharomyces uvarum, Saccharomyces bayanus, Saccharomyces cerevisiae, Saccharomyces bisporus, Saccharomyces chevalieri, Saccharomyces delbrueckii, Saccharomyces exiguous, Saccharomyces fermentati, Saccharomyces fragilis, Saccharomyces marxianus, Saccharomyces mellis, Saccharomyces rosei, Saccharomyces rouxii, Saccharomyces uvarum, Saccharomyces willianus, Saccharomycodes ludwigii, Saccharomycopsis capsularis, Saccharomycopsis fibuligera, Saccharomycopsis fibuligera, Endomycopsis hordei, Endomycopsis fobuligera. Saturnispora saitoi, Schizosaccharomyces octosporus, Schizosaccharomyces pombe, Schwanniomyces occidentalis, Torulaspora delbrueckii, Torulaspora delbrueckii, Saccharomyces dairensis, Torulaspora delbrueckii, Torulaspora fermentati, Saccharomyces fermentati, Torulaspora delbrueckii, Torulaspora rosei, Saccharomyces rosei, Torulaspora delbrueckii, Saccharomyces rosei, Torulaspora delbrueckii, Saccharomyces delbrueckii, Torulaspora delbrueckii, Saccharomyces delbrueckii, Zygosaccharomyces mongolicus, Dorulaspora globosa, Debaryomyces globosus, Torulopsis globosa, Trichosporon cutaneum, Trigonopsis variabilis, Williopsis californica, Williopsis saturnus, Zygosaccharomyces bisporus, Zygosaccharomyces bisporus, Debaryomyces disporua. Saccharomyces bisporas, Zygosaccharomyces bisporus, Saccharomyces bisporus, Zygosaccharomyces mellis, Zygosaccharomyces priorianus, Zygosaccharomyces rouxiim, Zygosaccharomyces rouxii, Zygosaccharomyces barkeri, Saccharomyces rouxii, Zygosaccharomyces rouxii, Zygosaccharomyces major, Saccharomyces rousii, Pichia anomala, Pichia bovis, Pichia Canadensis, Pichia carsonii, Pichia farinose, Pichia fermentans, Pichia fiuxuum, Pichia membranaefaciens, Pichia pseudopolymorpha, Pichia quercuum, Pichia robertsii, Pseudozyma Antarctica, Rhodosporidium toruloides, Rhodosporidium toruloides, Rhodotorula glutinis, Saccharomyces bayanus, Saccharomyces bayanus, Saccharomyces bisporus, Saccharomyces cerevisiae, Saccharomyces chevalieri, Saccharomyces delbrueckii, Saccharomyces fermentati, Saccharomyces fragilis, Saccharomycodes ludwigii, Schizosaccharomyces pombe, Schwanniomyces occidentalis, Torulaspora delbrueckii, Torulaspora globosa, Trigonopsis variabilis, Williopsis californica, Williopsis saturnus, Zygosaccharomyces bisporus, Zygosaccharomyces mellis, Zygosaccharomyces rouxii*, or any other fungi (e.g., yeast) known in the art or described herein. Exemplary lower eukaryotes also include various species of *Aspergillus* including, but not limited to, *Aspergillus caesiellus, Aspergillus candidus, Aspergillus carneus, Aspergillus clavatus, Aspergillus deflectus, Aspergillus flavus, Aspergillus fumigatus, Aspergillus glaucus, Aspergillus nidulans, Aspergillus niger, Aspergillus ochraceus, Aspergillus oryzae, Aspergillus parasiticus, Aspergillus penicilloides, Aspergillus restrictus, Aspergillus sojae, Aspergillus sydowi, Aspergillus tamari, Aspergillus terreus, Aspergillus ustus*, or *Aspergillus versicolor*. Exemplary protozoal genera from which genes encoding proteins having N-glycosylation activity can be obtained include, without limitation, *Blastocrithidia, Crithidia, Endotrypanum, Herpetomonas, Leishmania, Leptomonas, Phytomonas, Trypanosoma* (e.g., *T. bruceii, T. gambiense, T. rhodesiense*, and *T. cruzi*), and *Wallaceina*. For example, the gene encoding GnT I can be obtained from human (Swiss Protein Accession No. P26572), rat, *Arabidopsis*, mouse, or *Drosophila*; the gene encoding GntII can be obtained from human, rat (Swiss Protein Accession No. Q09326), *Arabidopsis*, or mouse; the gene encoding Man II can be obtained from human, rat, *Arabidopsis*, mouse, *Drosophila* (Swiss Protein Accession No. Q24451); and the gene encoding GalT can be obtained from human (Swiss Protein Accession No. P15291), rat, mouse, or bovine.

In some embodiments, a genetically engineered cell lacks the OCH1 (GenBank Accession No: AJ563920) gene or gene product (mRNA or protein) thereof. In some embodiments, a genetically engineered cell lacks the ALG3 (Genbank® Accession Nos: XM_503488, Genolevures Ref: YALI0E03190g) gene or gene product (mRNA or protein) thereof. In some embodiments, a genetically engineered cell expresses (e.g., overexpresses) an α-1,3-glucosyltransferase (e.g., ALG6, Genbank® Acccession Nos: XM_502922, Genolevures Ref: YALI0D17028g) protein. In some embodiments, a genetically engineered cell expresses an α-1,2-mannosidase (e.g., Genbank Acccession No.AF212153) protein. In some embodiments, a genetically engineered cell expresses a GlcNAc-transferase I (e.g., Swiss Prot. Accession No. P26572) protein. In some embodiments, a genetically engineered cell expresses a mannosidase II protein or catalytic domain thereof (e.g., Swiss Prot. Accession No. Q24451). In some embodiments, a genetically engineered cell expresses a galactosyltransferase I protein or catalytic domain thereof (e.g., Swiss Prot. Accession No. P15291). In some embodiments, the genetically engineered cell expresses a GlcNAc-transferase II protein or catalytic domain thereof (e.g., Swiss Prot. Accession No. Q09326). In some embodiments, the genetically engineered cell expresses an alpha or beta subunit (or both the alpha and the beta subunit) of a glucosidase II such as the glucosidase II of *Yarrowia lipolytica, Trypanosoma brucei* or *Aspergillus niger*. A genetically engineered cell can have any combination of these modifications.

For example, in some embodiments, a genetically engineered cell can lack the OCH1 gene and express an α-1,2-mannosidase, GlcNAc-transferase I, mannosidase II, and a galactosyltransferase I. In some embodiment, a genetically engineered cell can lack the ALG3 gene, and express an α-1,2-mannosidase, GlcNAc-transferase I, GlcNAc-transferase I, and a galactosyltransferase I. Such a genetically engineered cell further can express an α-1,3-glucosyltransferase and/or express alpha and beta subunits of a glucosidase II and/or lack the OCH1 gene.

One of more of such proteins can be fusion proteins that contain a heterologous targeting sequence. For example, the α-1,2-mannosidase can have an HDEL endoplasmic reticulum (ER)-retention amino acid sequence (see Examples). It is understood that any protein having N-glycosylation activity can be engineered into a fusion protein comprising an HDEL sequence. Other proteins can have heterologous sequences that target the protein to the Golgi apparatus. For example, the first 100 N-terminal amino acids encoded by the yeast Kre2p gene, the first 36 N-terminal amino acids (Swiss Prot. Accession No. P38069) encoded by the *S. cerevisiae* Mnn2 gene, or the first 46 N-terminal amino acids encoded by the *S. cerevisiae* Mnn2p gene can be used to target proteins to the Golgi. As such, nucleic acids encoding a protein to be expressed in a fungal cell can include a nucleotide sequence encoding a targeting sequence to target the encoded protein to an intracellular compartment. For example, the α-1,2-mannosidase can be targeted to the ER, while the GnT I, GnTII, mannosidase, and Gal T can be targeted to the Golgi.

In embodiments where a protein having N-glycosylation activity is derived from a cell that is of a different type (e.g., of a different species) than the cell into which the protein is to be expressed, a nucleic acid encoding the protein can be codon-optimized for expression in the particular cell of interest. For example, a nucleic acid encoding a protein having N-glycosylation from *Trypanosoma brucei* can be codon-optimized for expression in a yeast cell such as *Yarrowia lipolytica*. Such codon-optimization can be useful for increasing expression of the protein in the cell of interest. Methods for codon-optimizing a nucleic acid encoding a protein are known in the art and described in, e.g., Gao et al. (*Biotechnol. Prog.* (2004) 20(2): 443-448), Kotula et al. (*Nat. Biotechn.* (1991) 9, 1386-1389), and Bennetzen et al. (*J. Biol. Chem.* (1982) 257(6):2036-3031). Table 1 shows the codon usage for *Yarrowia lipolytica*. Data was derived from 2,945,919 codons present in 5,967 coding sequences. The contents of Table 1 were obtained from a Codon Usage Database, which can be found at world wide web at kazusa.or.jp/codon/cgi-bin/showcodon.cgi?species=284591.

TABLE 1

*Yarrowia lipolytica* Codon Usage Table

| | | | |
|---|---|---|---|
| UUU 15.9(46804) | CU 21.8(64161) | AU 6.8(20043) | GU 6.1(17849) |
| UUC 23.0(67672) | CC 20.6(60695) | AC 23.1(68146) | GC 6.1(17903) |
| UUA 1.8(5280) | CA 7.8(22845) | AA 0.8(2494) | GA 0.4(1148) |
| UUG 10.4(30576) | CG 15.4(45255) | AG 0.8(2325) | GG 12.1(35555) |
| CUU 13.2(38890) | CU 17.4(51329) | AU 9.6(28191) | GU 6.0(17622) |
| CUC 22.6(66461) | CC 23.3(68633) | AC 14.4(42490) | GC 4.4(12915) |
| CUA 5.3(15548) | CA 6.9(20234) | AA 9.8(28769) | GA 21.7(63881) |
| CUG 33.5(98823) | CG 6.8(20042) | AG 32.1(94609) | GG 7.7(22606) |
| AUU 22.4(66134) | CU 16.2(47842) | AU 8.9(26184) | GU 6.7(19861) |
| AUC 24.4(71810) | CC 25.6(75551) | AC 31.3(92161) | GC 9.8(28855) |
| AUA 2.2(6342) | CA 10.5(30844) | AA 12.4(36672) | GA 8.4(24674) |
| AUG 22.6(66620) | CG 8.5(25021) | AG 46.5(136914) | GG 2.4(7208) |
| GUU 15.8(46530) | CU 25.5(75193) | AU 21.5(63259) | GU 16.6(48902) |
| GUC 21.5(63401) | CC 32.7(96219) | AC 38.3(112759) | GC 21.8(64272) |
| GUA 4.0(11840) | CA 11.2(32999) | AA 18.8(55382) | GA 20.9(61597) |
| GUG 25.7(75765) | CG 8.9(26190) | AG 46.2(136241) | GG 4.4(12883) |

Tablefields are shown as [triplet] [frequency: per thousand] ([number]).

In some embodiments, human proteins can be introduced into the cell and one or more endogenous yeast proteins having N-glycosylation activity can be suppressed (e.g., deleted or mutated). Techniques for "humanizing" a fungal glycosylation pathway are described in, e.g., Choi et al. (2003) *Proc. Natl. Acad. Sci. USA* 100(9):5022-5027; Vervecken et al. (2004) *Appl. Environ. Microb.* 70(5):2639-2646; and Gerngross (2004) *Nature Biotech.* 22(11):1410-1414.

Where the genetic engineering involves, e.g., changes in the expression of a protein or expression of an exogenous protein (including a mutant form of an endogenous protein), a variety of techniques can be used to determine if the genetically engineered cells express the protein. For example, the presence of mRNA encoding the protein or the protein itself can be detected using, e.g., Northern Blot or RT-PCR analysis or Western Blot analysis, respectively. The intracellular localization of a protein having N-glycosylation activity can be analyzed by using a variety of techniques, including subcellular fractionation and immunofluorescence.

Methods for detecting glycosylation of a target molecule include DNA sequencer-assisted (DSA), fluorophore-assisted carbohydrate electrophoresis (FACE) or surface-enhanced laser desorption/ionization time-of-flight mass spectrometry (SELDI-TOF MS). For example, an analysis can utilize DSA-FACE in which, for example, glycoproteins are denatured followed by immobilization on, e.g., a membrane. The glycoproteins can then be reduced with a suitable reducing agent such as dithiothreitol (DTT) or β-mercaptoethanol. The sulfhydryl groups of the proteins can be carboxylated using an acid such as iodoacetic acid. Next, the N-glycans can be released from the protein using an enzyme such as N-glycosidase F. N-glycans, optionally, can be reconstituted and derivatized by reductive amination. The derivatized N-glycans can then be concentrated. Instrumentation suitable for N-glycan analysis includes, e.g., the ABI PRISM® 377 DNA sequencer (Applied Biosystems). Data analysis can be performed using, e.g., GENESCAN® 3.1 software (Applied Biosystems). Optionally, isolated mannoproteins can be further treated with one or more enzymes to confirm their N-glycan status. Additional methods of N-glycan analysis include, e.g., mass spectrometry (e.g., MALDI-TOF-MS), high-pressure liquid chromatography (HPLC) on normal phase, reversed phase and ion exchange chromatography (e.g., with pulsed amperometric detection when glycans are not labeled and with UV absorbance or fluorescence if glycans are appropriately labeled). See also Callewaert et al. (2001) *Glycobiology* 11(4):275-281 and Freire et al. (2006) *Bioconjug. Chem.* 17(2):559-564.

Where any of the genetic modifications of the genetically engineered cell are inducible or conditional on the presence of an inducing cue (e.g., a chemical or physical cue), the genetically engineered cell can, optionally, be cultured in the presence of an inducing agent before, during, or subsequent to the introduction of the nucleic acid. For example, following introduction of the nucleic acid encoding a target protein, the cell can be exposed to a chemical inducing agent that is capable of promoting the expression of one or more proteins having N-glycosylation activity. Where multiple inducing cues induce conditional expression of one or more proteins having N-glycosylation activity, a cell can be contacted with multiple inducing agents.

Target molecules modified to include the desired N-glycan can be isolated from the genetically engineered cell. The modified target molecule can be maintained within the yeast cell and released upon cell lysis or the modified target molecule can be secreted into the culture medium via a mechanism provided by a coding sequence (either native to the exogenous nucleic acid or engineered into the expression vector), which directs secretion of the molecule from the cell. The presence of the modified target molecule in the cell lysate or culture medium can be verified by a variety of standard protocols for detecting the presence of the molecule. For example, where the altered target molecule is a protein, such protocols can include, but are not limited to, immunoblotting or radioimmunoprecipitation with an antibody specific for the altered target protein (or the target protein itself), binding of a ligand specific for the altered target protein (or the target protein itself), or testing for a specific enzyme activity of the modified target protein (or the target protein itself).

In some embodiments, at least about 25% of the target molecules isolated from the genetically engineered cell contain the desired N-glycan. For example, at least about 27%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, or at least about 99% of the target molecules isolated from the genetically engineered cell can contain the desired N-glycan.

In some embodiments, in the target molecules produced using the methods described herein, at least 50% (e.g., at least 55, 60, 65, 70, 75, 80, or 85%) of the N-glycans on the glycoprotein can be $GlcNAc_2Man_3GlcNAc_2$ N-glycans. The percentage of $GlcNAc_2Man_3GlcNAc_2$ N-glycans can be estimated from the peak areas in the DSA-FACE electropherograms. See Example 13.

In some embodiments, the isolated modified target molecules can be frozen, lyophilized, or immobilized and stored under appropriate conditions, e.g., which allow the altered target molecules to retain biological activity.

Cultures of Engineered Cells

This document also provides a substantially pure culture of any of the genetically engineered cells described herein. As used herein, a "substantially pure culture" of a genetically engineered cell is a culture of that cell in which less than about 40% (i.e., less than about: 35%; 30%; 25%; 20%; 15%; 10%; 5%; 2%; 1%; 0.5%; 0.25%; 0.1%; 0.01%; 0.001%; 0.0001%; or even less) of the total number of viable cells in the culture are viable cells other than the genetically engineered cell, e.g., bacterial, fungal (including yeast), mycoplasmal, or protozoan cells. The term "about" in this context means that the relevant percentage can be 15% percent of the specified percentage above or below the specified percentage. Thus, for example, about 20% can be 17% to 23%. Such a culture of genetically engineered cells includes the cells and a growth, storage, or transport medium. Media can be liquid, semi-solid (e.g., gelatinous media), or frozen. The culture includes the cells growing in the liquid or in/on the semi-solid medium or being stored or transported in a storage or transport medium, including a frozen storage or transport medium. The cultures are in a culture vessel or storage vessel or substrate (e.g., a culture dish, flask, or tube or a storage vial or tube).

The genetically engineered cells described herein can be stored, for example, as frozen cell suspensions, e.g., in buffer containing a cryoprotectant such as glycerol or sucrose, as lyophilized cells. Alternatively, they can be stored, for example, as dried cell preparations obtained, e.g., by fluidized bed drying or spray drying, or any other suitable drying method.

Disorders Treatable by Altered N-Glycosylation Molecules

The isolated, target molecules modified to contain the desired N-glycan can be used to treat a variety of disorders, including metabolic disorders, cancer, and inflammatory disorders.

(i) Metabolic Disorders

A metabolic disorder is one that affects the production of energy within individual human (or animal) cells. Most metabolic disorders are genetic, though some can be "acquired" as a result of diet, toxins, infections, etc. Genetic metabolic disorders are also known as inborn errors of metabolism. In general, the genetic metabolic disorders are caused by genetic defects that result in missing or improperly constructed enzymes necessary for some step in the metabolic process of the cell. The largest classes of metabolic disorders are disorders of carbohydrate metabolism, disorders of amino acid metabolism, disorders of organic acid metabolism (organic acidurias), disorders of fatty acid oxidation and mitochondrial metabolism, disorders of porphyrin metabolism, disorders of purine or pyrimidine metabolism, disorders of steroid metabolism disorders of mitochondrial function, disorders of peroxisomal function, and lysosomal storage disorders (LSDs).

Examples of metabolic disorders that can be treated through the administration of one or more glycosylated molecules (or pharmaceutical compositions of the same) described herein can include hereditary hemochromatosis, oculocutaneous albinism, protein C deficiency, type I hereditary angioedema, congenital sucrase-isomaltase deficiency, Crigler-Najjar type II, Laron syndrome, hereditary Myeloperoxidase, primary hypothyroidism, congenital long QT syndrome, tyroxine binding globulin deficiency, familial hypercholesterolemia, familial chylomicronemia, abeta-lipoproteinema, low plasma lipoprotein A levels, hereditary emphysema with liver injury, congenital hypothyroidism, osteogenesis imperfecta, hereditary hypofibrinogenemia, alpha-1antichymotrypsin deficiency, nephrogenic diabetes insipidus, neurohypophyseal diabetes insipidus, adenosine deaminase deficiency, Pelizaeus Merzbacher disease, von Willebrand disease type IIA, combined factors V and VIII deficiency, spondylo-epiphyseal dysplasia tarda, choroideremia, I cell disease, Batten disease, ataxia telangiectasias, ADPKD-autosomal dominant polycystic kidney disease, microvillus inclusion disease, tuberous sclerosis, oculocerebro-renal syndrome of Lowe, amyotrophic lateral sclerosis, myelodysplastic syndrome, Bare lymphocyte syndrome, Tangier disease, familial intrahepatic cholestasis, X-linked adreno-leukodystrophy, Scott syndrome, Hermansky-Pudlak syndrome types 1 and 2, Zellweger syndrome, rhizomelic chondrodysplasia puncta, autosomal recessive primary hyperoxaluria, Mohr Tranebjaerg syndrome, spinal and bullar muscular atrophy, primary ciliary diskenesia (Kartagener's syndrome), giantism and acromegaly, galactorrhea, Addison's disease, adrenal virilism, Cushing's syndrome, ketoacidosis, primary or secondary aldosteronism, Miller Dieker syndrome, lissencephaly, motor neuron disease, Usher's syndrome, Wiskott-Aldrich syndrome, Optiz syndrome, Huntington's disease, hereditary pancreatitis, anti-phospholipid syndrome, overlap connective tissue disease, Sjögren's syndrome, stiff-man syndrome, Brugada syndrome, congenital nephritic syndrome of the Finnish type, Dubin-Johnson syndrome, X-linked hypophosphatemia, Pendred syndrome, persistent hyperinsulinemic hypoglycemia of infancy, hereditary spherocytosis, aceruloplasminemia, infantile neuronal ceroid lipofuscinosis, pseudoachondroplasia and multiple epiphyseal, Stargardt-like macular dystrophy, X-linked Charcot-Marie-Tooth disease, autosomal dominant retinitis pigmentosa, Wolcott-Rallison syndrome, Cushing's disease, limb-girdle muscular dystrophy, mucoploy-saccharidosis type IV, hereditary familial amyloidosis of Finish, Anderson disease, sarcoma, chronic myelomonocytic leukemia, cardiomyopathy, faciogenital dysplasia, Torsion disease, Huntington and spinocerebellar ataxias, hereditary hyperhomosyteinemia, polyneuropathy, lower motor neuron disease, pigmented retinitis, seronegative polyarthritis, interstitial pulmonary fibrosis, Raynaud's phenomenon, Wegner's granulomatosis, preoteinuria, CDG-Ia, CDG-Ib, CDG-Ic, CDG-Id, CDG-Ie, CDG-If, CDG-IIa, CDG-IIb, CDG-IIc, CDG-IId, Ehlers-Danlos syndrome, multiple exostoses, Griscelli syndrome (type 1 or type 2), or X-linked non-specific mental retardation. In addition, metabolic disorders can also include lysosomal storage disorders such as, but not limited to, Fabry disease, Farber disease, Gaucher disease, $GM_1$-gangliosidosis, Tay-Sachs disease, Sandhoff disease, $GM_2$ activator disease, Krabbe disease, metachromatic leukodystrophy, Niemann-Pick disease (types A, B, and C), Hurler disease, Scheie disease, Hunter disease, Sanfilippo disease, Morquio disease, Maroteaux-Lamy disease, hyaluronidase deficiency, aspartylglucosaminuria, fucosidosis, mannosidosis, Schindler disease, sialidosis type 1, Pompe disease, Pycnodysostosis, ceroid lipofuscinosis, cholesterol ester storage disease, Wolman disease, Multiple sulfatase deficiency, galactosialidosis, mucolipidosis (types II, III, and IV), cystinosis, sialic acid storage disorder, chylomicron retention disease with Marinesco-Sjögren syndrome, Hermansky-Pudlak syndrome, Chediak-Higashi syndrome, Danon disease, or Geleophysic dysplasia.

Symptoms of a metabolic disorder are numerous and diverse and can include one or more of, e.g., anemia, fatigue, bruising easily, low blood platelets, liver enlargement, spleen enlargement, skeletal weakening, lung impairment, infections (e.g., chest infections or pneumonias), kidney impairment, progressive brain damage, seizures, extra thick meconium, coughing, wheezing, excess saliva or mucous production, shortness of breath, abdominal pain, occluded bowel or gut, fertility problems, polyps in the nose, clubbing of the finger/toe nails and skin, pain in the hands or feet, angiokeratoma, decreased perspiration, corneal and lenticular opacities, cataracts, mitral valve prolapse and/or regurgitation, cardiomegaly, temperature intolerance, difficulty walking, difficulty swallowing, progressive vision loss, progressive hearing loss, hypotonia, macroglossia, areflexia, lower back pain, sleep apnea, orthopnea, somnolence, lordosis, or scoliosis. It is understood that due to the diverse nature of the defective or absent proteins and the resulting disease phenotypes (e.g., symptomatic presentation of a metabolic disorder), a given disorder will generally present only symptoms characteristic to that particular disorder. For example, a patient with Fabry disease can present a particular subset of the above-mentioned symptoms such as, but not limited to, temperature intolerance, corneal whirling, pain, skin rashes, nausea, or dirarrhea. A patient with Gaucher syndrome can present with splenomegaly, cirrhosis, convulsions, hypertonia, apnea, osteoporosis, or skin discoloration.

In addition to the administration of one or more molecules described herein, a metabolic disorder can also be treated by proper nutrition and vitamins (e.g., cofactor therapy), physical therapy, and pain medications.

Depending on the specific nature of a given metabolic disorder, a patient can present these symptoms at any age. In many cases, symptoms can present in childhood or in early adulthood. For example, symptoms of Fabry disease can present at an early age, e.g., at 10 or 11 years of age.

As used herein, a subject "at risk of developing a metabolic disorder" is a subject that has a predisposition to develop a disorder, i.e., a genetic predisposition to develop metabolic disorder as a result of a mutation in a enzyme such as alpha-L-iduronidase, beta-D-galactosidase, beta-glucosidase, beta-hexosaminidase, beta-D-mannosidase, alpha-L-fucosidase, arylsulfatase B, arylsulfatase A, alpha-N-acteylgalactosaminidase, aspartylglucosaminidase, iduronate-2-sulfatase, alpha-glucosaminide-N-acetyltransferase, beta-D-glucoronidase, hyaluronidase, alpha-L-mannosidase, alpha-neurominidase, phosphotransferase, acid lipase, acid ceramidase, sphinogmyelinase, thioesterase, cathepsin K, or lipoprotein lipase. Clearly, subjects "at risk of developing a metabolic disorder" are not all the subjects within a species of interest.

A subject "suspected of having a disorder" is one having one or more symptoms of a disorder such as any of those described herein.

(ii) Cancer

Cancer is a class of diseases or disorders characterized by uncontrolled division of cells and the ability of these to spread, either by direct growth into adjacent tissue through invasion, or by implantation into distant sites by metastasis (where cancer cells are transported through the bloodstream or lymphatic system). Cancer can affect people at all ages, but risk tends to increase with age. Types of cancers can include, e.g., lung cancer, breast cancer, colon cancer, pancreatic cancer, renal cancer, stomach cancer, liver cancer, bone cancer, hematological cancer, neural tissue cancer, melanoma, thyroid cancer, ovarian cancer, testicular cancer, prostate cancer, cervical cancer, vaginal cancer, or bladder cancer.

As used herein, a subject "at risk of developing a cancer" is a subject that has a predisposition to develop a cancer, i.e., a genetic predisposition to develop cancer such as a mutation in a tumor suppressor gene (e.g., mutation in BRCA1, p53, RB, or APC) or has been exposed to conditions that can result in cancer. Thus, a subject can also be one "at risk of developing a cancer" when the subject has been exposed to mutagenic or carcinogenic levels of certain compounds (e.g., carcinogenic compounds in cigarette smoke such as Acrolein, Arsenic, Benzene, Benz{a}anthracene, Benzo{a}pyrene, Polonium-210 (Radon), Urethane, or Vinyl Chloride). Moreover, the subject can be "at risk of developing a cancer" when the subject has been exposed to, e.g., large doses of ultraviolet light or X-irradiation, or exposed (e.g., infected) to a tumor-causing/associated virus such as papillomavirus, Epstein-Barr virus, hepatitis B virus, or human T-cell leukemia-lymphoma virus. From the above it will be clear that subjects "at risk of developing a cancer" are not all the subjects within a species of interest.

A subject "suspected of having a cancer" is one having one or more symptoms of a cancer. Symptoms of cancer are well-known to those of skill in the art and include, without limitation, breast lumps, nipple changes, breast cysts, breast pain, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, and pancreas metastases, difficulty swallowing, and the like. From the above it will be clear that subjects "suspected of having a cancer" are not all the subjects within a species of interest.

In addition to the administration of one or more altered N-glycosylation molecules described herein, a cancer can also be treated by chemotherapeutic agents, ionizing radiation, immunotherapy agents, or hyperthermotherapy agents. Chemotherapeutic agents include, e.g., cisplatin, carboplatin, procarbazine, mechlorethamine, cyclophosphamide, camptothecin, adriamycin, ifosfamide, melphalan, chlorambucil, bisulfan, nitrosurea, dactinomycin, daunorubicin, doxorubicin, bleomycin, plicomycin, mitomycin, etoposide, verampil, podophyllotoxin, tamoxifen, taxol, transplatinum, 5-flurouracil, vincristin, vinblastin, and methotrexate.

(iii) Inflammatory Disorders

An "inflammatory disorder," as used herein, refers to a process in which one or more substances (e.g., substances not naturally occurring in the subject), via the action of white blood cells (e.g., B cells, T cells, macrophages, monocytes, or dendritic cells) inappropriately trigger a pathological response, e.g., a pathological immune response. Accordingly, such cells involved in the inflammatory response are referred to as "inflammatory cells." The inappropriately triggered inflammatory response can be one where no foreign substance (e.g., an antigen, a virus, a bacterium, a fungus) is present in or on the subject. The inappropriately triggered response can be one where a self-component (e.g., a self-antigen) is targeted (e.g., an autoimmune disorder such as multiple sclerosis) by the inflammatory cells. The inappropriately triggered response can also be a response that is inappropriate in magnitude or duration, e.g., anaphylaxis. Thus, the inappropriately targeted response can be due to the presence of a microbial infection (e.g., viral, bacterial, or fungal). Types of inflammatory disorders (e.g., autoimmune disease) can include, but are not limited to, osteoarthritis, rheumatoid arthritis (RA), spondyloarthropathies, POEMS syndrome, Crohn's disease, multicentric Castleman's disease, systemic lupus erythematosus (SLE), multiple sclerosis (MS), muscular dystrophy (MD), insulin-dependent diabetes mellitus (IDDM), dermatomyositis, polymyositis, inflammatory neuropathies such as Guillain Bane syndrome, vasculitis such as Wegener's granulomatosus, polyarteritis nodosa, polymyalgia rheumatica, temporal arteritis, Sjogren's syndrome, Bechet's disease, Churg-Strauss syndrome, or Takayasu's arteritis. Also included in inflammatory disorders are certain types of allergies such as rhinitis, sinusitis, urticaria, hives, angioedema, atopic dermatitis, food allergies (e.g., a nut allergy), drug allergies (e.g., penicillin), insect allergies (e.g., allergy to a bee sting), or mastocytosis. Inflammatory disorders can also include ulcerative colitis and asthma.

A subject "at risk of developing an inflammatory disorder" refers to a subject with a family history of one or more inflammatory disorders (e.g., a genetic predisposition to one or more inflammatory disorders) or one exposed to one or more inflammation-inducing conditions. For example, a subject can have been exposed to a viral or bacterial superantigen such as, but not limited to, staphylococcal enterotoxins (SEs), a *streptococcus* pyogenes exotoxin (SPE), a staphylococcus aureus toxic shock-syndrome toxin (TSST-1), a streptococcal mitogenic exotoxin (SME) and a streptococcal superantigen (SSA). From the above it will be clear that subjects "at risk of developing an inflammatory disorder" are not all the subjects within a species of interest.

A subject "suspected of having an inflammatory disorder" is one who presents with one or more symptoms of an inflammatory disorder. Symptoms of inflammatory disorders are well known in the art and include, but are not limited to, redness, swelling (e.g., swollen joints), joints that are warm to the touch, joint pain, stiffness, loss of joint function, fever, chills, fatigue, loss of energy, headaches, loss of appetite, muscle stiffness, insomnia, itchiness, stuffy nose, sneezing, coughing, one or more neurologic symptoms such as dizziness, seizures, or pain. From the above it will be clear that subjects "suspected of having an inflammatory disorder" are not all the subjects within a species of interest.

In addition to the administration of one or more molecules described herein, an inflammatory disorder can also be treated by non-steroidal anti-inflammatory drug (NSAID), a disease-modifying anti-rheumatic drug (DMARD), a biological response modifier, or a corticosteroid. Biological response modifiers include, e.g., an anti-TNF agent. Non-limiting examples of anti-TNF agents include a soluble TNF receptor or an antibody specific for TNF such as adulimumab, infliximab, or etanercept.

Methods suitable for treating (e.g., preventing or ameliorating one or more symptoms of) any of the disorders described herein using any of the altered N-glycosylation molecules (or pharmaceutical compositions thereof) are set forth in the following section.

Pharmaceutical Compositions and Methods of Treatment

A target molecule modified to have the desired N-glycan can be incorporated into a pharmaceutical composition containing a therapeutically effective amount of the molecule and one or more adjuvants, excipients, carriers, and/or diluents. Acceptable diluents, carriers and excipients typically do not adversely affect a recipient's homeostasis (e.g., electrolyte balance). Acceptable carriers include biocompatible, inert or bioabsorbable salts, buffering agents, oligo- or polysaccharides, polymers, viscosity-improving agents, preservatives and the like. One exemplary carrier is physiologic saline (0.15 M NaCl, pH 7.0 to 7.4). Another exemplary carrier is 50 mM sodium phosphate, 100 mM sodium chloride. Further details on techniques for formulation and administration of pharmaceutical compositions can be found in, e.g., Remington's Pharmaceutical Sciences (Maack Publishing Co., Easton, Pa.). Supplementary active compounds can also be incorporated into the compositions.

Administration of a pharmaceutical composition containing molecules with N-glycans can be systemic or local. Pharmaceutical compositions can be formulated such that they are suitable for parenteral and/or non-parenteral administration. Specific administration modalities include subcutaneous, intravenous, intramuscular, intraperitoneal, transdermal, intrathecal, oral, rectal, buccal, topical, nasal, ophthalmic, intra-articular, intra-arterial, sub-arachnoid, bronchial, lymphatic, vaginal, and intra-uterine administration.

Administration can be by periodic injections of a bolus of the pharmaceutical composition or can be uninterrupted or continuous by intravenous or intraperitoneal administration from a reservoir which is external (e.g., an IV bag) or internal (e.g., a bioerodable implant, a bioartificial organ, or a colony of implanted altered N-glycosylation molecule production cells). See, e.g., U.S. Pat. Nos. 4,407,957, 5,798,113, and 5,800,828. Administration of a pharmaceutical composition can be achieved using suitable delivery means such as: a pump (see, e.g., Annals of Pharmacotherapy, 27:912 (1993); Cancer, 41:1270 (1993); Cancer Research, 44:1698 (1984); microencapsulation (see, e.g., U.S. Pat. Nos. 4,352,883; 4,353,888; and 5,084,350); continuous release polymer implants (see, e.g., Sabel, U.S. Pat. No. 4,883,666); macroencapsulation (see, e.g., U.S. Pat. Nos. 5,284,761, 5,158,881, 4,976,859 and 4,968,733 and published PCT patent applications WO92/19195, WO 95/05452); injection, either subcutaneously, intravenously, intra-arterially, intramuscularly, or to other suitable site; or oral administration, in capsule, liquid, tablet, pill, or prolonged release formulation.

Examples of parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aerosolizer, electroporation, and transdermal patch.

Formulations suitable for parenteral administration conveniently contain a sterile aqueous preparation of the altered N-glycosylation molecule, which preferably is isotonic with the blood of the recipient (e.g., physiological saline solution). Formulations can be presented in unit-dose or multi-dose form.

Formulations suitable for oral administration can be presented as discrete units such as capsules, cachets, tablets, or lozenges, each containing a predetermined amount of the altered N-glycosylation molecule; or a suspension in an aqueous liquor or a non-aqueous liquid, such as a syrup, an elixir, an emulsion, or a draught.

A molecule having N-glycans suitable for topical administration can be administered to a mammal (e.g., a human patient) as, e.g., a cream, a spray, a foam, a gel, an ointment, a salve, or a dry rub. A dry rub can be rehydrated at the site of administration. Such molecules can also be infused directly into (e.g., soaked into and dried) a bandage, gauze, or patch, which can then be applied topically. Such molecules can also be maintained in a semi-liquid, gelled, or fully-liquid state in a bandage, gauze, or patch for topical administration (see, e.g., U.S. Pat. No. 4,307,717).

Therapeutically effective amounts of a pharmaceutical composition can be administered to a subject in need thereof in a dosage regimen ascertainable by one of skill in the art. For example, a composition can be administered to the subject, e.g., systemically at a dosage from 0.01 µg/kg to 10,000 µg/kg body weight of the subject, per dose. In another example, the dosage is from 1 µg/kg to 100 µg/kg body weight of the subject, per dose. In another example, the dosage is from 1 µg/kg to 30 µg/kg body weight of the subject, per dose, e.g., from 3 µg/kg to 10 µg/kg body weight of the subject, per dose.

In order to optimize therapeutic efficacy, a molecule containing an N-glycan can be first administered at different dosing regimens. The unit dose and regimen depend on factors that include, e.g., the species of mammal, its immune status, the body weight of the mammal. Typically, levels of such a molecule in a tissue can be monitored using appropriate screening assays as part of a clinical testing procedure, e.g., to determine the efficacy of a given treatment regimen.

The frequency of dosing for a molecule is within the skills and clinical judgement of medical practitioners (e.g., doctors or nurses). Typically, the administration regime is established by clinical trials which may establish optimal administration parameters. However, the practitioner may vary such administration regimes according to the subject's age, health, weight, sex and medical status. The frequency of dosing can be varied depending on whether the treatment is prophylactic or therapeutic.

Toxicity and therapeutic efficacy of such molecules or pharmaceutical compositions thereof can be determined by known pharmaceutical procedures in, for example, cell cultures or experimental animals. These procedures can be used, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Pharmaceutical compositions that exhibit high therapeutic indices are preferred. While pharmaceutical compositions that exhibit toxic side effects can be used, care should be taken to design a delivery system that targets such compounds to the site of affected tissue in order to minimize potential damage to normal cells (e.g., non-target cells) and, thereby, reduce side effects.

The data obtained from the cell culture assays and animal studies can be used in formulating a range of dosage for use in appropriate subjects (e.g., human patients). The dosage of such pharmaceutical compositions lies generally within a range of circulating concentrations that include the ED50 with little or no toxicity. The dosage may vary within this range depending upon the dosage form employed and the route of administration utilized. For a pharmaceutical composition used as described herein (e.g., for treating a metabolic disorder in a subject), the therapeutically effective dose can be estimated initially from cell culture assays. A dose can be formulated in animal models to achieve a circulating plasma concentration range that includes the IC50 (i.e., the concentration of the pharmaceutical composition which achieves a half-maximal inhibition of symptoms) as determined in cell culture. Such information can be used to more accurately determine useful doses in humans. Levels in plasma can be measured, for example, by high performance liquid chromatography.

As defined herein, a "therapeutically effective amount" of a molecule containing an N-glycan is an amount of the molecule that is capable of producing a medically desirable result (e.g., amelioration of one or more symptoms of a metabolic disorder) in a treated subject. A therapeutically effective amount (i.e., an effective dosage) can includes milligram or microgram amounts of the compound per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

The subject can be any mammal, e.g., a human (e.g., a human patient) or a non-human primate (e.g., chimpanzee, baboon, or monkey), a mouse, a rat, a rabbit, a guinea pig, a gerbil, a hamster, a horse, a type of livestock (e.g., cow, pig, sheep, or goat), a dog, a cat, or a whale.

A molecule or pharmaceutical composition thereof described herein can be administered to a subject as a combination therapy with another treatment, e.g., a treatment for a metabolic disorder (e.g., a lysosomal storage disorder). For example, the combination therapy can include administering to the subject (e.g., a human patient) one or more additional agents that provide a therapeutic benefit to the subject who has, or is at risk of developing, (or suspected of having) a metabolic disorder (e.g., a lysosomal storage disorder). Thus, the compound or pharmaceutical composition and the one or more additional agents can be administered at the same time. Alternatively, the molecule can be administered first and the one or more additional agents administered second, or vice versa.

It will be appreciated that in instances where a previous therapy is particularly toxic (e.g., a treatment for a metabolic disorder with significant side-effect profiles), administration of a molecule described herein can be used to offset and/or lessen the amount of the previously therapy to a level sufficient to give the same or improved therapeutic benefit, but without the toxicity.

Any of the pharmaceutical compositions described herein can be included in a container, pack, or dispenser together with instructions for administration.

The following are examples of the practice of the invention. They are not to be construed as limiting the scope of the invention in any way.

EXAMPLES

Table 2 contains a list of all of the strains used in the experiments described below. In Table 2, MH=HDEL-tagged α-1,2-mannosidase; ζ=random integration via zeta sequences; docking Δ=integration into a specific locus; and (H)=hygromycin resistant.

TABLE 2

| | | Listing of Strains Used in Examples | | |
|---|---|---|---|---|
| Number | Short name | Description | Markers | Expected N-Glycans |
| G013 | Po1d lnuga Δoch1(URA3) cl 26.1 | Po1d lnuga transformed with SpeI/Bst1107I- digested pYLOCH1PUT-TOPO | URA3$^+$ leu2$^-$ ade2$^-$ gut2$^-$ | Mainly Man$_8$GlcNAc$_2$ |
| G014 | Po1d lnuga Δoch1 (cured) cl 7 | Po1d lnuga Δoch1 (G013) cured from the URA3 marker using pUB4-Cre | ura3$^-$ leu2$^-$ ade2$^-$ gut2$^-$ | Mainly Man$_8$GlcNAc$_2$ |
| G016 | Po1d lnuga Δoch1 TefMH (ζ-Not) cl 1.4 | Po1d lnuga Δoch1 (cured) (G014) transformed with NotI-digested pYLTUXL2preManHDEL(Y1) | URA3$^+$ leu2$^-$ ade2$^-$ gut2$^-$ | Man$_5$GlcNAc$_2$ |
| G018 | Po1d lnuga Δoch1 Hp4dMH (ζ-Not) cl 11.2 | Po1d lnuga Δoch1 (cured) (G014) transformed with NotI-digested pYLHUXL2preManHDEL(Y1) | URA3$^+$ leu2$^-$ ade2$^-$ gut2$^-$ | Man$_5$GlcNAc$_2$ |
| G036 | Po1d lnuga Δoch1 Hp4dMH (ζ-Not)(cured) cl 2.2 (1 copy ManHDEL) | Po1d lnuga Δoch1 Hp4dMH (Not) cl 11.2 (G018) cured from the URA3 marker using pRRQ2 | ura3$^-$ leu2$^-$ ade2$^-$ gut2$^-$ | Man$_5$GlcNAc$_2$ |
| G039 | Po1d lnuga Δoch1 Hp4dMH (ζ-cured) Δalg3ALG6 cl 24.1 | Po1d lnuga Δoch1 Hp4dMH (ζ-Not-cured) cl 2.2 (G036) transformed with NotI/PacI-digested pYlALG3PUT-ALG6 | URA3$^+$ leu2$^-$ ade2$^-$ gut2$^-$ | Glc$_{1-2}$Man$_5$GlcNAc$_2$ and Man$_3$GlcNAc$_2$ |
| G040 | Po1d lnuga Δoch1 Hp4dMH (ζ-cured) TefhGnTI cl 5.4 (1 copy GnT I) | Po1d lnuga Δoch1 Hp4dMH (ζ-Not-cured) cl 2.2 (G036) transformed with NotI-digested pYLTmAx hGnTI | URA3$^+$ leu2$^-$ ade2$^-$ gut2$^-$ | GlcNAcMan$_5$GlcNAc$_2$ |
| G043 | Po1d lnuga Δoch1 Hp4dMH (ζ-cured) TefhGnTI TefManII cl 15 | Po1d lnuga Δoch1 Hp4dMH (ζ-cured) TefhGnTI cl 5.4 (G040) transformed with NotI-digested pYLTmAXDmManII (LEU2 ex) | URA3$^+$ LEU2$^+$ ade2$^-$ gut2$^-$ | GlcNAcMan$_3$GlcNAc$_2$ |
| G044 | Po1d lnuga Δoch1 Hp4dMH (ζ-cured) TefhGnTI TefGalTI cl 12 | Po1d lnuga Δoch1 Hp4dMH (ζ-cured) TefhGnTI cl 5.4 (G040) transformed with NotI-digested pYLTmAXSpGal10hGalTI (ADE2 ex) | URA3$^+$ leu2$^-$ ADE2$^+$ gut2$^-$ | GalGlcNAcMan$_5$GlcNAc$_2$ |

TABLE 2-continued

Listing of Strains Used in Examples

| Number | Short name | Description | Markers | Expected N-Glycans |
|---|---|---|---|---|
| G045 | Po1d lnuga Δoch1 Hp4dMH (ζ-cured) Δalg3ALG6 cl 2.16 (cured) | Po1d lnuga Δoch1 Hp4dMH (ζ-cured) Δalg3ALG6 cl 24.1 (G039) cured from the URA3 marker using pRRQ2 | ura3⁻ leu2⁻ ade2⁻ gut2⁻ | Glc$_{1-2}$Man$_5$GlcNAc$_2$ and Man$_3$GlcNAc$_2$ |
| G046 | Po1d lnuga Δoch1 Hp4dMH (docking Δleu2) | Po1d lnuga Δoch1 (cured) (G014) transformed with NotI-digested JME926 pPTleu2-ADE2Ex-Hp4dManHDEL(Yl) | ura3⁻ leu2⁻ ADE2⁺ gut2⁻ | Man$_5$GlcNAc$_2$ |
| G047 | Po1d lnuga Δoch1 Hp4dMH (ζ-cured) Δalg3ALG6 TefhGnTI(H) cl2 (1 copy GnT I) | Po1d lnuga Δoch1 Hp4dMH (ζ-cured) Δalg3ALG6 cl 24.1 (G039) transformed with NotI-digested pYLTmAXhGnTI (Hyg$^R$ ex) | URA3⁺ leu2⁻ ade2⁻ gut2⁻ Hyg$^R$ | Glc$_{1-2}$Man$_5$GlcNAc$_2$ and GlcNAcMan$_3$GlcNAc$_2$ |
| G048 | Po1d lnuga Δoch1 Hp4dMH (ζ-cured) Δalg3ALG6 (cured) TefhGnTI clone 7.3 | Po1d lnuga Δoch1 Hp4dMH (ζ-cured) Δalg3ALG6 cl 2.16 (cured) (G045) transformed with NotI-digested pYLTmAXhGnTI | URA3⁺ leu2⁻ ade2⁻ gut2⁻ | Glc$_{1-2}$Man$_5$GlcNAc$_2$ and GlcNAcMan$_3$GlcNAc$_2$ |
| G050 | Po1d lnuga Δoch1 Hp4dMH (ζ-cured) Δalg3ALG6 (cured) TefhGnTI TefrGnTII cl. 42.3 | Po1d lnuga Δoch1 Hp4dMH (ζ-cured) Δalg3ALG6 cl 2.16 (cured) (G045) transformed with NotI-digested pYLTmAXhGnTI and pYLTmAXrGnTII (ADE2 Ex) | URA3⁺ leu2⁻ ADE2⁺ gut2⁻ | Glc$_{1-2}$Man$_5$GlcNAc$_2$ and GlcNAc$_2$Man$_3$GlcNAc$_2$ |
| G051 | Po1d lnuga Δoch1 Hp4dMH (ζ-cured) Δalg3ALG6 TefhGnTI(H) TefrGnTII clone 4.5 | Po1d lnuga Δoch1 Hp4dMH (ζ-cured) Δalg3ALG6 TefhGnTI cl2 (G047) transformed with NotI-digested pYLTmAXrGnTII (ADE2 Ex) | URA3⁺ leu2⁻ ADE2⁺ gut2⁻ Hyg$^R$ | Glc$_{1-2}$Man$_5$GlcNAc$_2$ and GlcNAc$_2$Man$_3$GlcNAc$_2$ |
| G052 | Po1d lnuga Δoch1 Hp4dMH (ζ-cured) Hp4dhGnTI (ζ) cl one 16 | Po1d lnuga Δoch1 Hp4dMH (ζ-Not-cured) cl 2.2 (G036) transformed with NotI-digested pYLHp4mAxhGnTI | URA3⁺ leu2⁻ ade2⁻ gut2⁻ | GlcNAcMan$_5$GlcNAc$_2$ |
| G053 | Po1d lnuga Δoch1 Hp4dMH (docking Δaxp1) | Po1d lnuga Δoch1 (cured) (G014) transformed with NotI-digested OXYP289-pPTAxp1-Leu2Ex-Hp4dManHDEL(Yl) | ura3⁻ LEU2⁺ ade2⁻ gut2⁻ | Man$_5$GlcNAc$_2$ |
| G054 | Po1d lnuga Δoch1 Hp4dMH (docking Δaxp1) (cured) | Po1d lnuga Δoch1 Hp4dMH (docking Δaxp1) (G053) cured from the LEU2 marker using pUB4-Cre | ura3⁻ leu2⁻ ade2⁻ gut2⁻ | Man$_5$GlcNAc$_2$ |
| G055 | Po1d lnuga Δoch1 Hp4dMH (docking Δleu2-cured) | Po1d lnuga Δoch1 Hp4dMH (docking Δleu2) (G046) cured from the ADE2 marker using pRRQ2 | ura3⁻ leu2⁻ ade2⁻ gut2⁻ | Man$_5$GlcNAc$_2$ |
| G056 | Po1d lnuga Δoch1 Hp4dMH (ζ-cured) Δalg3ALG6 Hp4dGnTI (ζ) clone E | Po1d lnuga Δoch1 Hp4dMH (ζ-cured) Δalg3ALG6 cl 2.16 (cured) (G045) transformed with NotI-digested pYLHp4mAxhGnTI | URA3⁺ leu2⁻ ade2⁻ gut2– | Glc$_{1-2}$Man$_5$GlcNAc$_2$ and GlcNAcMan$_3$GlcNAc$_2$ |
| G057 | Po1d lnuga Δoch1 Hp4dMH (ζ-cured) Δalg3ALG6 Hp4dGnTI (docking Δade2) clone G | Po1d lnuga Δoch1 Hp4dMH (ζ-cured) Δalg3ALG6 cl 2.16 (cured) (G045) transformed with NotI-digested JME925 pPTade2-URA3ex-Hp4dhGnTI | URA3⁺ leu2⁻ ade2⁻ gut2⁻ | Glc$_{1-2}$Man$_5$GlcNAc$_2$ and GlcNAcMan$_3$GlcNAc$_2$ |
| G058 | Po1d lnuga Δoch1 Hp4dMH (ζ-cured) Δalg3ALG6 Hp4dGnTI (ζ-cured) | Po1d lnuga Δoch1 Hp4dMH (ζ-cured) Δalg3ALG6 Hp4dGnTI (ζ) (G056) cured from the URA3 marker using pRRQ2 | ura3⁻ leu2⁻ ade2⁻ gut2⁻ | Glc$_{1-2}$Man$_5$GlcNAc$_2$ and GlcNAcMan$_3$GlcNAc$_2$ |
| G059 | Po1d lnuga Δoch1 Hp4dMH (ζ-cured) Δalg3ALG6 Hp4dGnTI (docking Δade2-cured) | Po1d lnuga Δoch1 Hp4dMH (ζ-cured) Δalg3ALG6 Hp4dGnTI (docking Δade2) (G057) cured from the URA3 marker using pRRQ2 | ura3⁻ leu2⁻ ade2⁻ gut2⁻ | Glc$_{1-2}$Man$_5$GlcNAc$_2$ and GlcNAcMan$_3$GlcNAc$_2$ |
| G060 | Po1d lnuga Δoch1 Hp4dMH (ζ-cured) Δalg3ALG6 Hp4dGnTI (docking Δade2) Hp4dGls2α/β (ζ) clone 6 | Po1d lnuga Δoch1 Hp4dMH (ζ-cured) Δalg3ALG6 Hp4dGnTI (docking Δade2) (G057) transformed with Not-digested Zeta-LEU2Ex-Hp4dL2preAnGlcII a + b(alt) | URA3+ LEU2+ ade2– gut2– | GlcNAcMan$_3$GlcNAc$_2$ |

TABLE 2-continued

Listing of Strains Used in Examples

| Number | Short name | Description | Markers | Expected N-Glycans |
|---|---|---|---|---|
| G061 | Po1d lnuga Δoch1 Hp4dMH (ζ-cured) Δalg3ALG6 Hp4dGnTI (docking Δade2) Hp4d Gls2α/β (docking Δura3) clone 18 | Po1d lnuga Δoch1 Hp4dMH (ζ-cured) Δalg3ALG6 Hp4dGnTI (docking Δade2) (G057) transformed with NotI-digested JME923 pPTUra3-Leu2Ex-Hp4d L2preAnGlcIIa + b(alt) | URA3+ LEU2+ ade2– gut2– | GlcNAcMan$_3$GlcNAc$_2$ |
| G070 | Po1d lnuga Δoch1 Hp4dMH (1 copy-ζ-cured) Δalg3ALG6 (cured) Hp4dGnTI (docking Δade2) Hp4dGls2α/β (docking Δura3) Hp4dGnTII (ζ) cl 6 | Po1d lnuga Δoch1 Hp4dMH (1 copy-ζ-cured) Δalg3ALG6 (cured) Hp4dGnTI (docking Δade2) Hp4d Gls2α/β (docking Δura3) (G061) transformed with Not-digested pYLHp4mAXrGnTII (ADE2ex) | URA3$^+$ LEU2$^+$ ADE2$^+$ gut2$^-$ | GlcNAc$_2$Man$_3$GlcNAc$_2$ |
| G071 | Po1d lnuga Δoch1 Hp4dMH (1 copy-ζ-cured) Δalg3ALG6 (cured) Hp4dGnTI (docking Δade2) Hp4d Gls2α/β (docking Δura3) Hp4dGnTII (integration in Axp1 locus was aimed at) cl 8 | Po1d lnuga Δoch1 Hp4dMH (1 copy-ζ-cured) Δalg3ALG6 (cured) Hp4dGnTI (docking Δade2) Hp4d Gls2α/β (docking Δura3) (G061) transformed with Not-digested OXYP289 pPTAxp1-ADE2ex-Hp4dGnTII | URA3$^+$ LEU2$^+$ ADE2$^+$ gut2$^-$ | GlcNAc$_2$Man$_3$GlcNAc$_2$ |
| G096 | Po1d lnuga Δoch1 Hp4dMH (1 copy-ζ-cured) Δalg3ALG6 (cured) Hp4dGnTI (docking Δade2) Hp4d Gls2α/β (docking Δura3) Hp4dGnTII (integration in Axp1 locus was aimed at) Hp4dPP-HC/LC clone 13 | Po1d lnuga Δoch1 Hp4dMH (1 copy-ζ-cured) Δalg3ALG6 (cured) Hp4dGnTI (docking Δade2) Hp4d Gls2α/β (docking Δura3) Hp4dGnTII (docking Δaxp1) (G071) transformed with NotI digested pYLHp4L2preproHerHC&LC (Gut2ex)-ori2 | URA3$^+$ LEU2$^+$ ADE2$^+$ GUT2$^+$ | GlcNAc$_2$Man$_3$GlcNAc$_2$ |

Example 1: *Yarrowia lipolytica* OCH1 Disruption

Figure 1B:
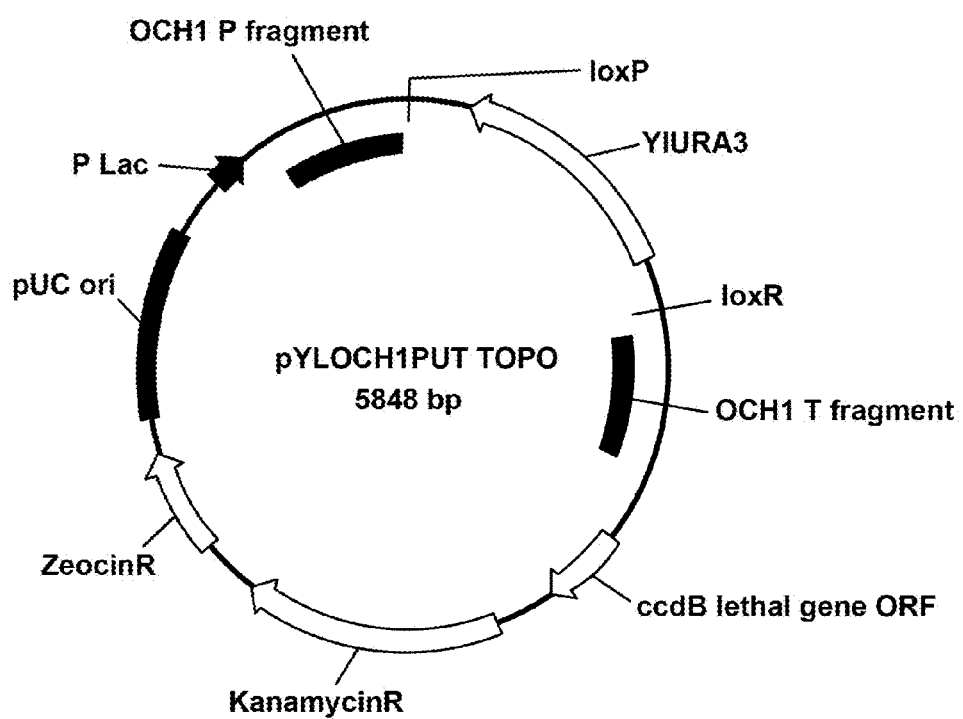
FIG. 1B is a schematic diagram of plasmid pYlOCH1 PUT TOPO.

The generation of a glyco-engineered protein expression strain was done in *Yarrowia lipolytica* strain po1d lnuga (a strain having the auxotrophies leu2-, ura3-, gut2- and ade2-). A strategy to knock out the OCH1 (GenBank Accession No: AJ563920) gene in *Yarrowia lipolytica* was set up as described for the LIP2 gene (Fickers et al., 2003 *J Microbiol Methods.* 55(3):727-37). The gene construction strategy followed for the OCH1 gene is described in U.S. Patent Publication No. 20090069232-A1. The resulting vector was called pYlOCH1 PUT TOPO (FIG. 1B).

Figure 2:
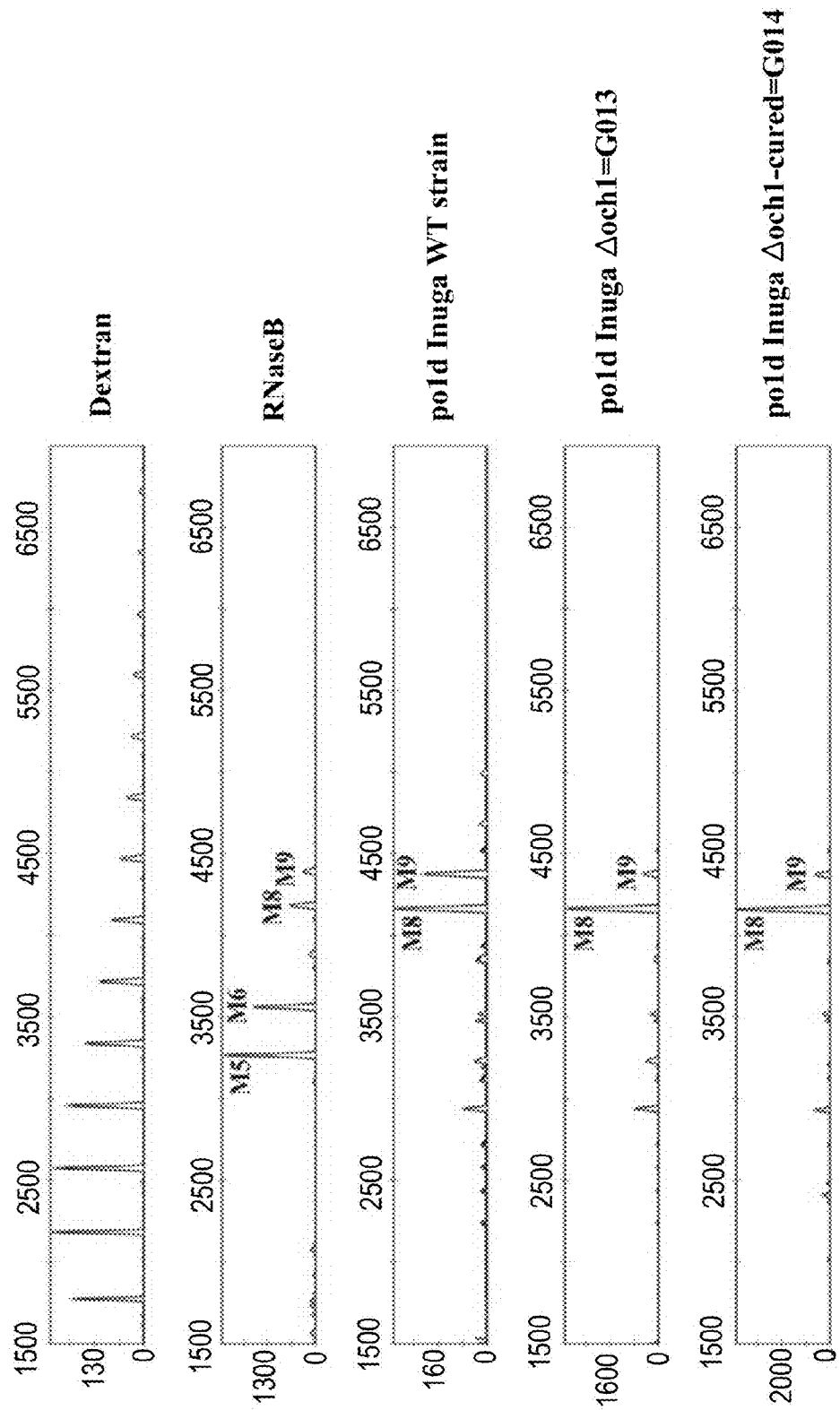
FIG. 2 is a series of electroferograms depicting N-glycan analysis of secreted proteins obtained from po1d 1nuga *Yarrowia lipolytica* wild-type cells or Δoch1 po1d 1nuga *Yarrowia lipolytica* cells. The main N-glycan upon OCH1 inactivation becomes Man$_8$GlcNAc$_2$. Analysis was performed using DNA sequencer-assisted, fluorophore-assisted carbohydrate electrophoresis (DSA-FACE). "M5," "M6," "M8," and "M9," refer to the number of mannose residues conjugated to the base N-acetylglucosamine structure. The Y-axis represents the relative fluorescence units as an indication of the amount of each N-glycan structure. The X-axis represents the relative mobility of each N-glycan structure through a capillary. The top electroferogram is an analysis of dextran for use as a mobility standard.

The OCH1 KO fragment was isolated from the plasmid by a SpeI/Bst1107I restriction digest and transformed to *Yarrowia lipolytica* strain po1d lnuga. Several uracil prototrophic strains were obtained and screened by PCR on genomic DNA (gDNA) using primers Yloch1 prom fw (5'-TCGCTATCACGTCTCTAGC-3', SEQ ID NO:1) and Yloch1 term rev (5'-ACTCTGTATACTTGTATGTACTGT-GAGAC-3', SEQ ID NO:2) to analyze the genomic integration of the plasmid. A fragment of the correct size (i.e., 2328 bp vs. 1894 bp in the wild type) was amplified for several clones tested. The knock-out of the OCH1 gene also was confirmed by N-glycan analysis of the total glycoprotein pool secreted into the growth medium (=secretome): the Man$_8$GlcNAc$_2$ structure has become the predominant N-glycan within the sugar profile (FIG. 2). This profile differs from that of the wild-type strain, which contains a higher amount of Man$_9$GlcNAc$_2$—the latter most probably containing an additional mannose as a result of Och1p activity—as well as some structures with an even higher number of mannose residues.

To remove the URA3 gene, a positive Δoch1 clone (called G013, see Table 2) was transformed with the episomal plasmid pUB4-Cre (Fickers et al., 2003, supra) that contains an expression cassette for the Cre recombinase. Removal of the URA3 gene was screened for by PCR on gDNA using primers Yloch1 prom fw and Yloch1 term rev (see above). Clones in which the URA3 marker was excised no longer resulted in the amplification of a 2328 bp band; instead a PCR-fragment of 1075 bp (excl. URA3) was obtained. Positive clones were checked at the N-glycan level of the secretome and show a profile very similar to that of the non-cured strain (FIG. 2). One of the cured strains (called G014, see Table 2) was selected for further N-glycan engineering.

Example 2: Overexpression of an ER-Retained α-1,2-Mannosidase by Either Random Integration or Targeted/Docked Integration To enable the generation of Man$_5$GlcNAc$_2$ attached to glycoproteins expressed by a Δoch1 strain, an α-1,2-mannosidase was expressed to cleave Man$_8$GlcNAc$_2$ to Man$_5$GlcNAc$_2$ (i.e., a Golgi type α-1,2-mannosidase activity). Such a mannosidase should be targeted to the secretion system. *Trichoderma reesei* α-1,2-mannosidase (Genbank accession no. AF212153), fused to the *S. cerevisiae* prepro mating factor and tagged with a HDEL sequence (SEQ ID NO:21) to localize it into the ER, is able to trim Man$_8$GlcNAc$_2$ to Man$_5$GlcNAc$_2$ in vivo in *Pichia pastoris* as well as in *Trichoderma reesei* and *Aspergillus niger*. Expression constructs were made where a codon-optimized version of the HDEL-tagged *T. reesei* α-1,2-mannosidase was fused to the *Y. lipolytica* LIP2 pre signal sequence and placed under the transcriptional control of either the TEF1, Hp4d (Madzak et al., 2000, *J. Mol. Microbiol. Biotechnol.*

2:207-216), GAP or POX2 promotor. The construction strategy of these plasmids is described in U.S. Patent Publication No. 20090069232-A1.

Figure 3:
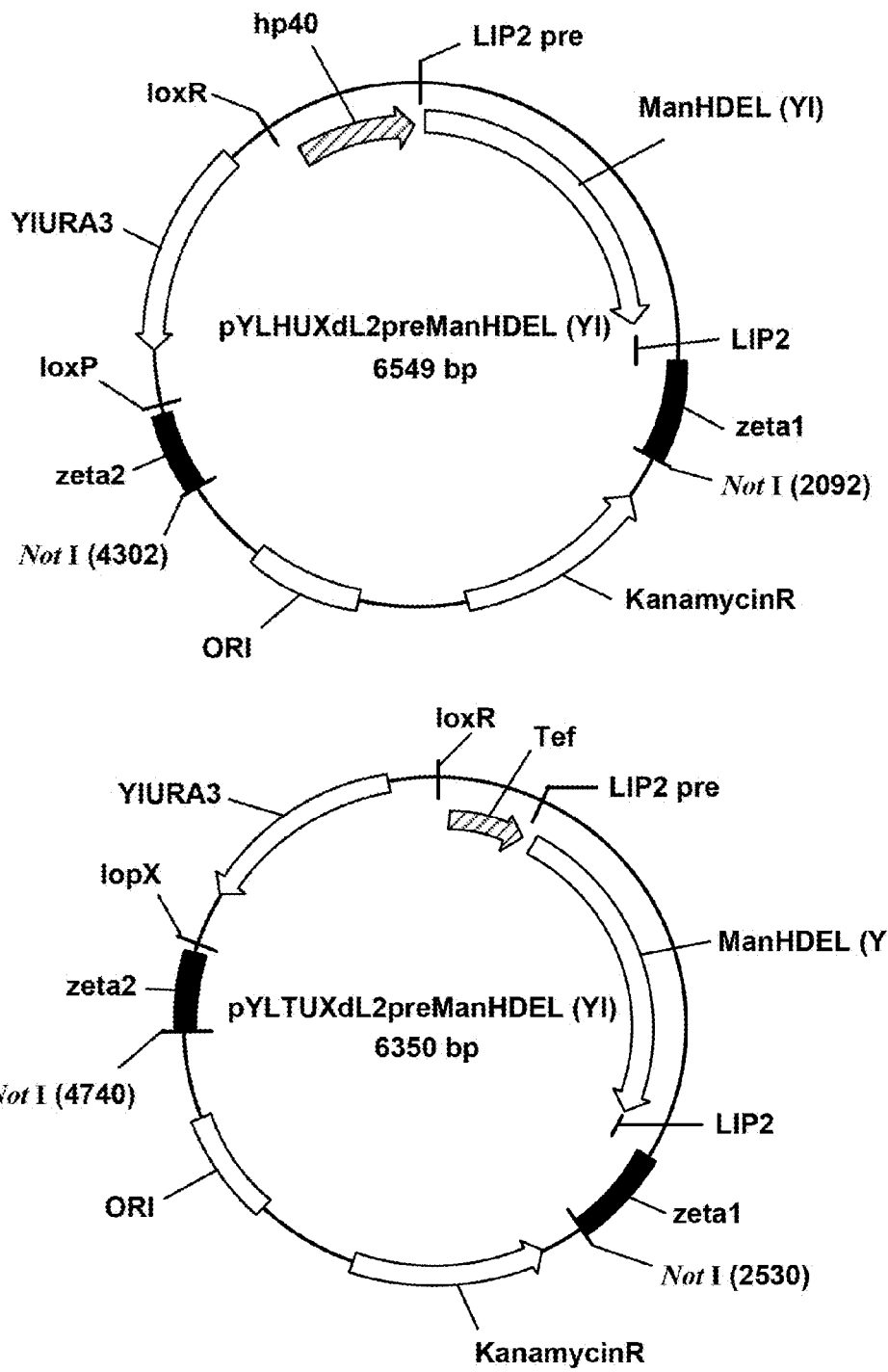
FIG. 3 is a schematic diagram of plasmids pYLHUXdL2preManHDEL and pYLTUXdL2preManHDEL.
Figure 4:
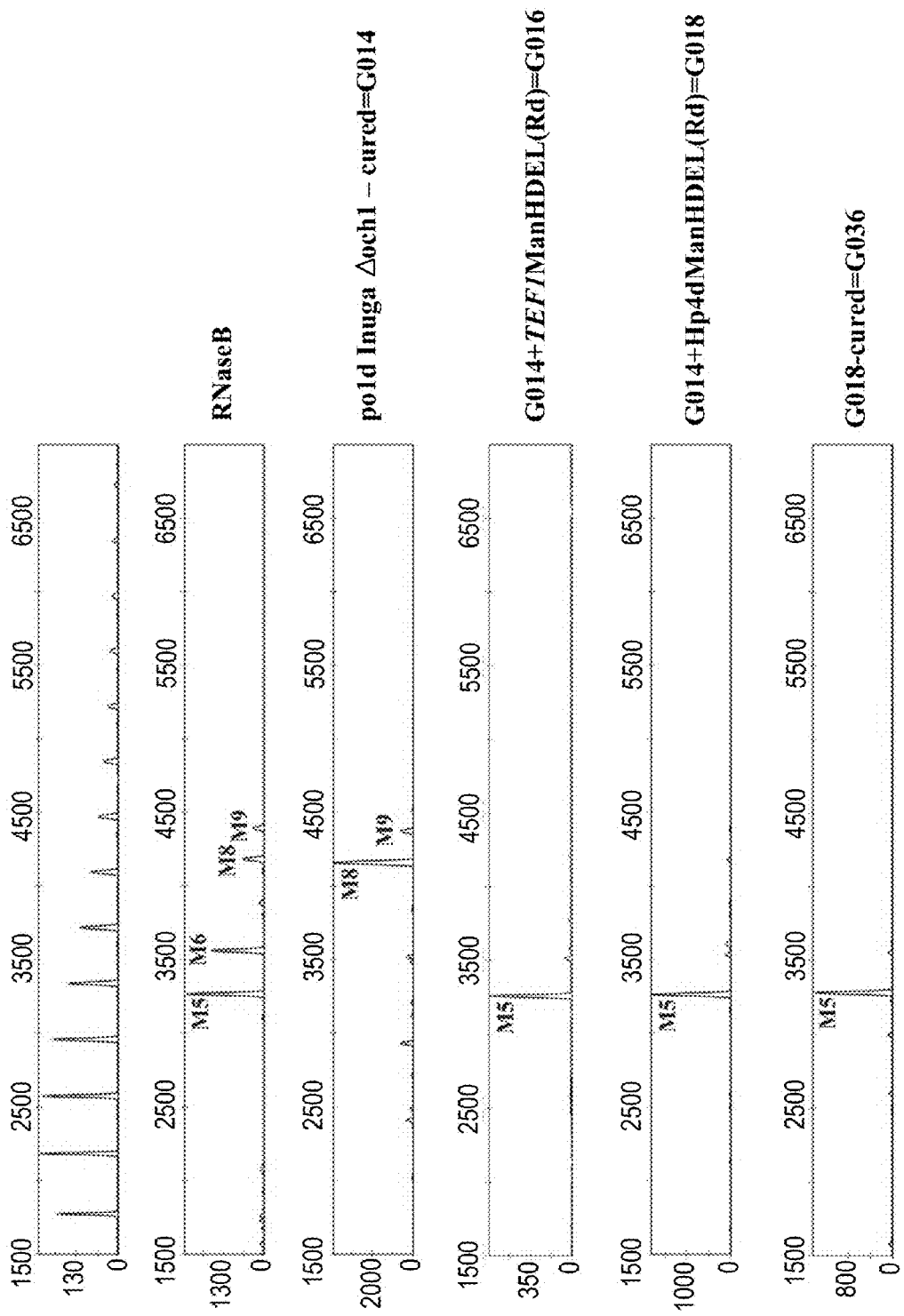
FIG. 4 is a series of electroferograms depicting the N-glycan profile after introduction of a ManHDEL (=HDEL-tagged α-1,2-mannosidase) expression cassette (either under TEF1 or Hp4d promoter control) into strain G014. "Rd" stands for "random integration" via the zeta sequences present on the vectors shown in FIG. 3. The major N-glycan upon mannosidase expression is Man$_5$GlcNAc$_2$. Curing of the URA3 marker from one of these strains (G018, see Table 2) does not change the N-glycan profile.

Two of these vectors, pYLHUXdL2preManHDEL and pYLTUXdL2preManHDEL (FIG. 3)—with the mannosidase under the transcriptional control of the Hp4d resp. TEF1 promotor, were used to transform strain G014 (derived from Example 1). The vectors were digested with NotI to allow random integration into the genome via the zeta sequences. URA3 prototrophic transformants were selected for N-glycan analysis. Several transformants show a clear conversion of $Man_8GlcNAc_2$ towards $Man_5GlcNAc_2$ (FIG. 4). Since clones expressing the mannosidase under TEFL promotor control showed a slow and clumpy growth phenotype (one of these clones was called G016), further steps in glyco-engineering were done in a strain background where the gene is under Hp4d transcriptional control.

One positive clone expressing the ManHDEL under control of the hp4d promoter (G018) was chosen, from which the URA3 marker was cured via transient transformation of plasmid pRRQ2 (Richard et al., 2001 *J. Bacteriol.* 183: 3098-3107), expressing the Cre-recombinase. Several ura3- clones were selected after the procedure and one clone (G036), showing a clear $Man_5GlcNAc_2$ profile on the secretome, was used for further engineering work (FIG. 4). Southern analysis of this clone revealed the presence of one randomly integrated mannosidase expression cassette. This Southern analysis was performed on Hind III digested genomic DNA using a DIG-labeled mannosidase-specific PCR fragment that was generated using primers Man for (5'-GCCTTCCAGACCTCTTGGAACGCCTACCACC-3', SEQ ID NO:22) and Man rev (5'-GCCAGGTGGCCGC-CTCGTCGAGAAGAAGATCG-3', SEQ ID NO:23).

Figure 5:
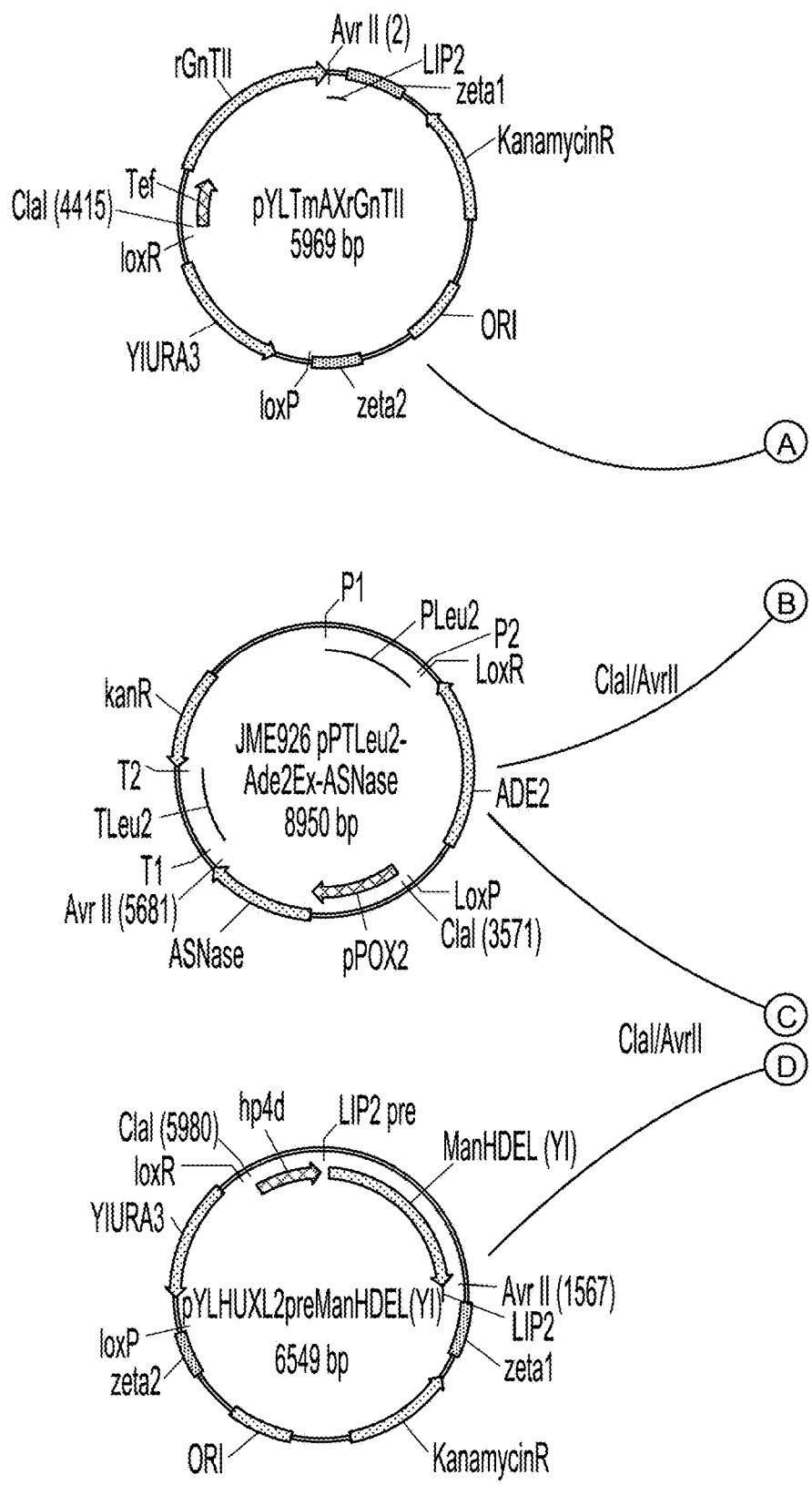
FIG. 5 is a schematic of the construction strategy for plasmids JME926 pPTLeu2-ADE2ex-Hp4dManHDEL(Y1) and OXYP289 pPTAxp1-LEU2ex-Hp4dManHDEL(Y1). See FIG. 23 for the construction of vector pYLTmAXrGn-TII.
Figure 5:
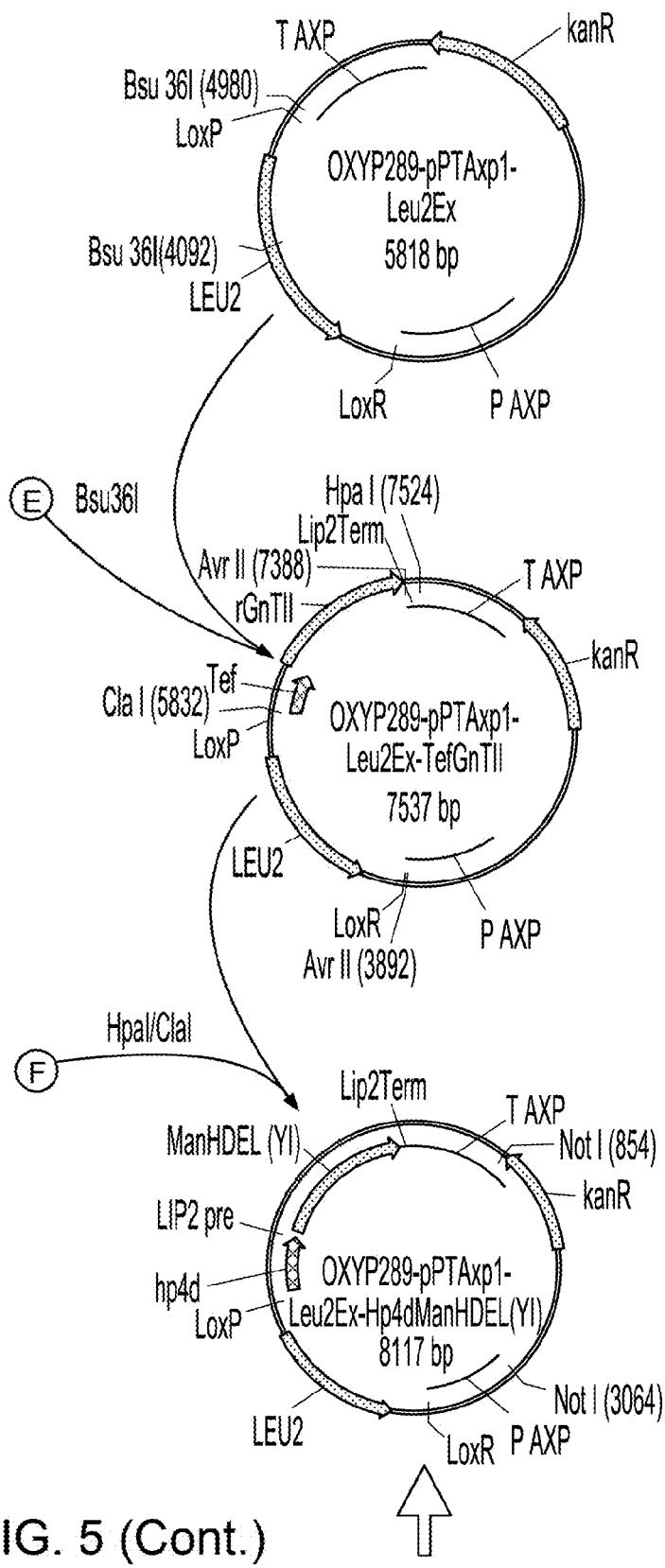
Figure 6:
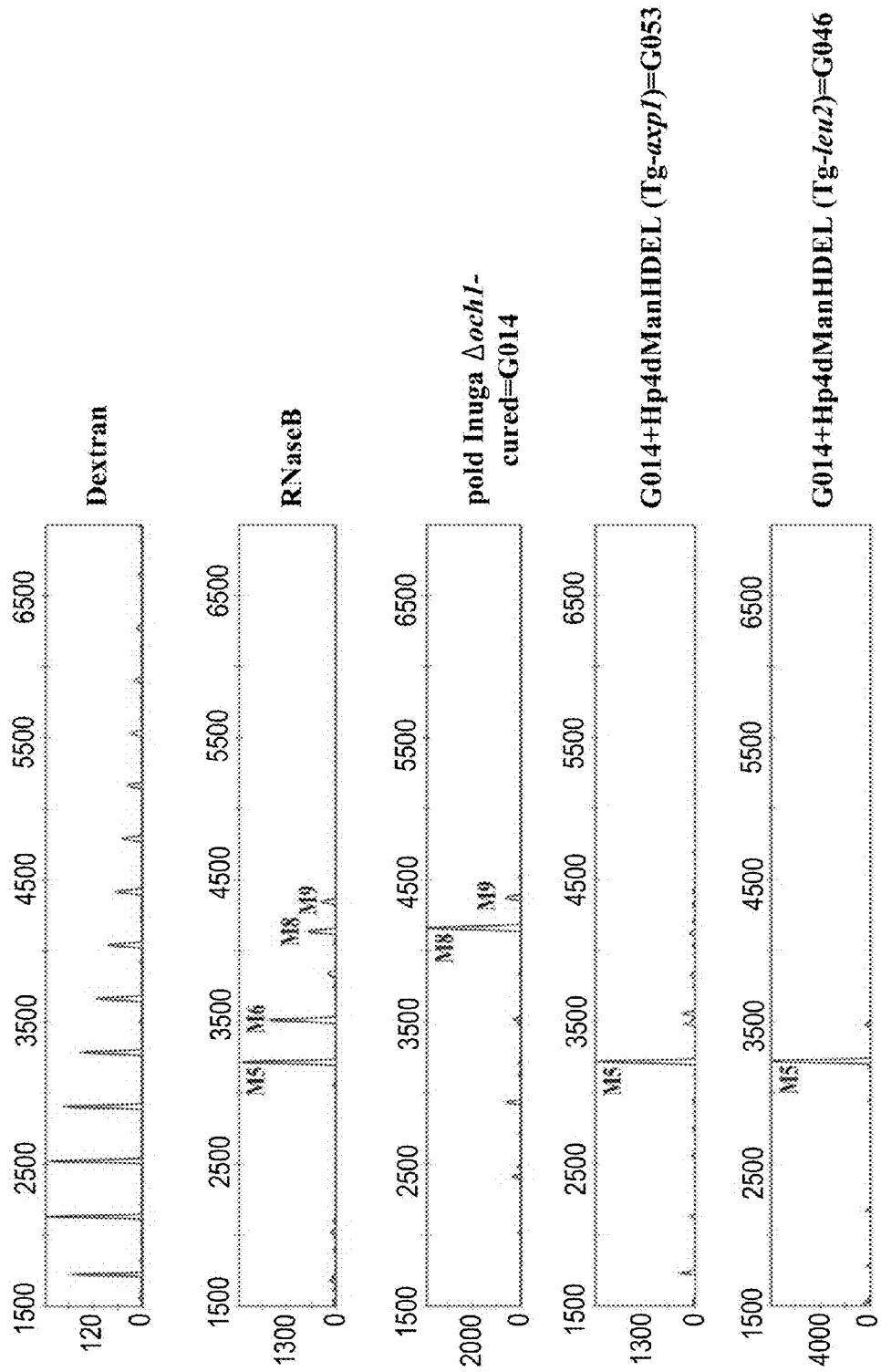
FIG. 6 is a series of electroferograms depicting the N-glycan profile after introduction of a ManHDEL (=HDEL-tagged α-1,2-mannosidase) expression cassette (under Hp4d promoter control) into strain G014 by targeted integration (Tg) in either the LEU2 or the AXP1 locus. Man$_5$GlcNAc$_2$ becomes the main N-glycan.

In an alternative strategy, two constructs were generated that allow targeted integration of the Hp4d-driven mannosidase expression cassette into either the LEU2 or AXP1 locus of the *Yarrowia* genome. Construction of these plasmids, JME926_pPTLeu2-ADE2ex-Hp4dManHDEL(Y1) and OXYP289_pPTAxp1-LEU2ex-Hp4dManHDEL(Y1), is described in FIG. 5. Prior to transformation to strain G014, both constructs were digested with NotI and the respective expression cassettes were isolated. Selected ADE2 prototrophic clones had potentially integrated the mannosidase expression cassette into the LEU2 locus, whereas LEU2 prototrophs potentially had integrated the cassette into the AXP1 locus. The transformants were checked by Southern analysis to assess proper targeting into the genome. This was performed on BamHI digested (integration in LEU2 locus) or HindIII digested (integration in AXP1 locus) genomic DNA using a DIG-labeled mannosidase-specific PCR fragment that was generated using primers Man for (5'-GCCT-TCCAGACCTCTTGGAACGCCTACCACC-3', SEQ ID NO:22) and Man rev (5'-GCCAGGTGGCCGCCTCGTC-GAGAAGAAGATCG-3', SEQ ID NO:23). The selected clones also were checked for the nature of the N-glycans synthesized onto the secreted glycoproteins. In most cases, correctly targeted Hp4d-driven α-1,2-mannosidase expression resulted into the synthesis of predominantly $Man_5GlcNAc_2$ oligosaccharides (FIG. 6). For each targeting locus, one mannosidase expressing clone (G046 in case of LEU2 docking; G053 in case of AXP1 docking) was selected for curing via transient expression of the Cre recombinase using plasmid pRRQ2 for strain G046 and pUB4-Cre for strain G053. The resulting cured strains (G055 abd G054, respectively) were re-checked via Southern blotting and their $Man_5GlcNAc_2$ profile confirmed via N-glycan analysis using DSA-FACE.

Example 3: Expression of GlcNAc-Transferase I

Figure 8:
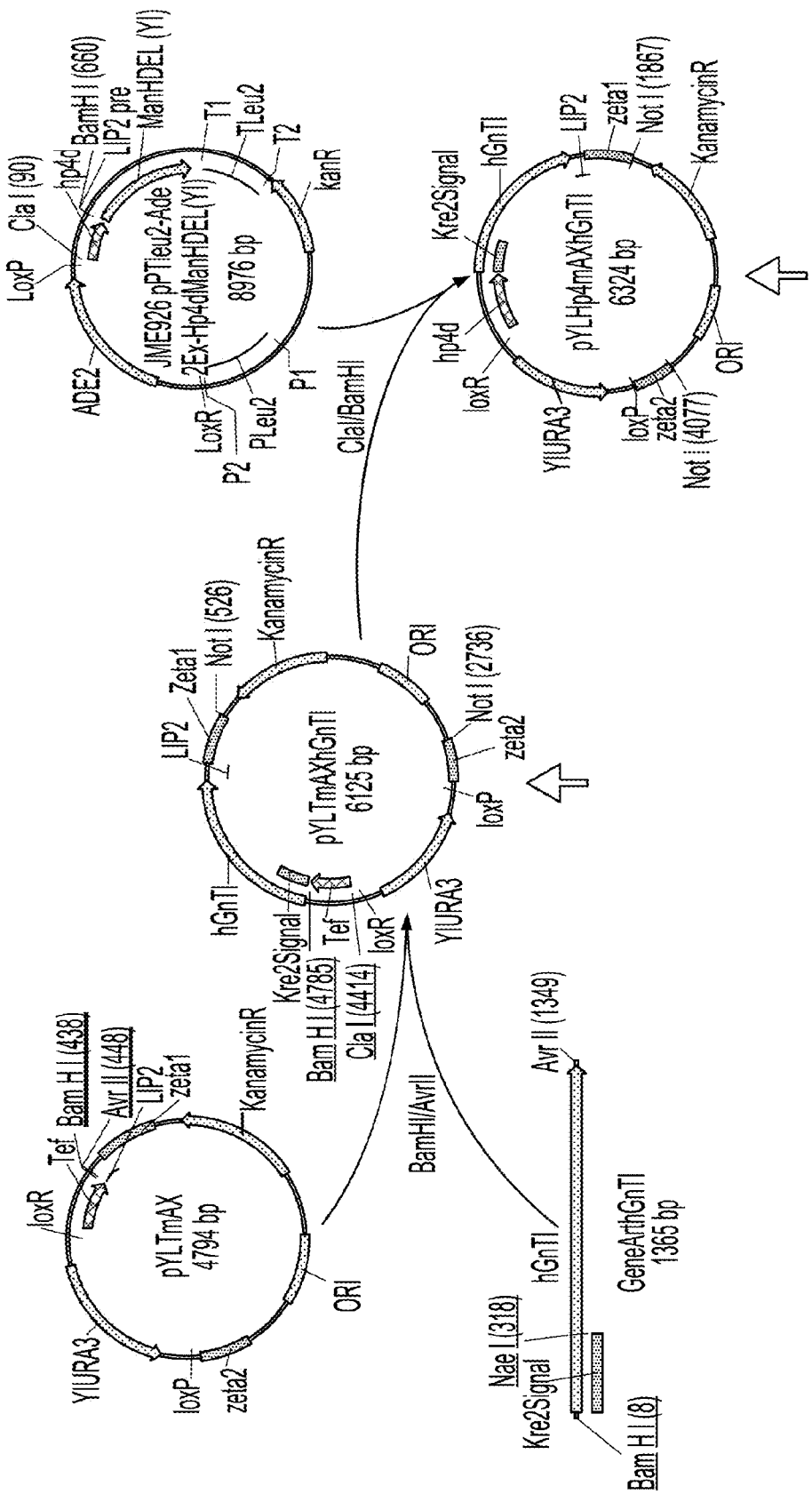
FIG. 8 is a schematic diagram of the construction strategy for plasmids pYLTmAXhGnTI and pYLHp4mAXhGnTI.

A *Yarrowia* codon-optimized sequence was generated for the expression of a fusion protein consisting of the first 100 N-terminal amino acids of the *S. cerevisiae* Kre2 protein (SwissProt AccNo P27809) followed by the catalytic domain of human GlcNAc-transferase I (SwissProt AccNo P26572) (FIG. 7, SEQ ID NO:3 and SEQ ID NO:4). The yeast Kre2p 100 N-terminal amino acids serve as a Golgi localization signal for the catalytic GnT I domain. In this way, it is ensured that the GnT I fusion protein is localized later in the secretion pathway than the ER-retained HDEL-tagged α-1,2-mannosidase in order to enable the enzyme converting the protein-linked N-glycans from $Man_5GlcNAc_2$ to $GlcNAcMan_5GlcNAc_2$. The codon optimized synthetic gene for the expression of the fusion protein was placed under the transcriptional control of either the TEF1 or the Hp4d promoter, resulting into the plasmids pYLTmAXhGnTI and pYLHp4mAXhGnTI. The construction strategy is shown in FIG. 8. Functional expression of the Kre2-GnT I fusion protein should result in the addition of a β-1,2-linked GlcNAc residue onto the available $Man_5GlcNAc_2$ glycans resulting in the synthesis of $GlcNAcMan_5GlcNAc_2$.

Figure 9:
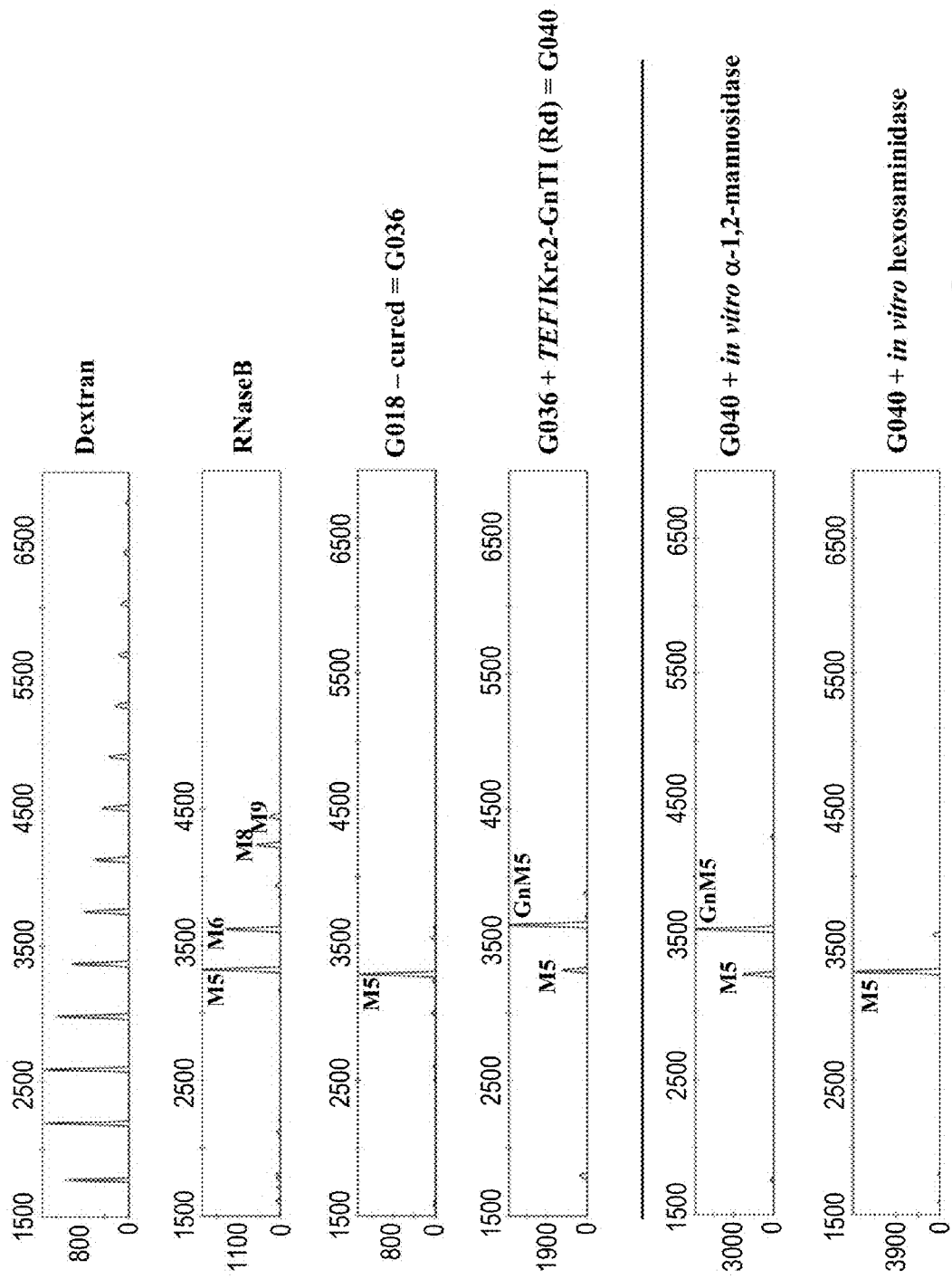
FIG. 9 is a series of electroferograms depicting the N-glycan profile after introduction of the GnT I activity into strain G036 by transformation with a vector expressing GnT I. "Rd" stands for "random integration" via the zeta sequences present on the vectors shown in FIG. 8. The major N-glycan upon expression of the GnT I activity is GlcNAcMan$_5$GlcNAc$_2$. In vitro treatment with α-1,2-mannosidase does not change the profile significantly, indicating that only small amounts of high-mannose N-glycans other than Man$_5$GlcNAc$_2$ are present. In vitro hexosaminidase treatment results in a shift from GlcNAcMan$_5$GlcNAc$_2$ towards Man$_5$GlcNAc$_2$.

The plasmids pYLTmAXhGnTI and pYLHp4mAXGnTI were NotI digested before transformation to strain G036 (cf. Example 2), known to produce $Man_5GlcNAc_2$ N-glycans on its secreted proteins. Transformants were selected for uracil prototrophy. Analysis of the N-glycosylation profile on the secretome of several of these clones showed a clear change in the N-glycan pattern: the $Man_5GlcNAc_2$ was significantly reduced and a new peak, representing an N-glycan with higher molecular weight (about one glucose unit extra), appeared. Treatment of the isolated N-glycans with Jack Bean β-N-acetylhexosaminidase, an enzyme capable of removing terminal β-linked GlcNAc residues, indicated that the new N-glycan is $GlcNAcMan_5GlcNAc_2$: the new peak disappeared and was completely converted into $Man_5GlcNAc_2$ (FIG. 9). Depending on the cultivation method used, about 70% of the total N-glycan pool proved to be $GlcNAcMan_5GlcNAc_2$ (with approximately 77% of the available $Man_5GlcNAc_2$ being converted).

One transformant expressing the Kre2-GnT I fusion protein under control of the TEF1 promotor was named strain G040 and selected for further use. Genomic analysis of this strain via Southern blot indicated the presence of one expression cassette. Southern analysis was done on BamHI digested genomic DNA using a DIG-labeled GnT I-specific PCR fragment that was generated using primers 5'-GGAT-GATCACACAATGGCCCTGTTTCTG-3' (SEQ ID NO:5) and 5'-TGCTCTAGACTAGTTCCAAGAGGGGTC-3' (SEQ ID NO:6). Analysis of the glycosylation profile on the secretome of strain G040 versus strains carrying 1 to 3 copies (confirmed by the same southern blot) of the Hp4d-driven Kre2-GnT I expression cassette, did not show significant difference in GlcNAc-transfer capacity.

Example 4: Expression of Mannosidase II

A *Yarrowia* codon-optimized sequence was generated for the expression of a fusion protein consisting of the first 36 N-terminal amino acids of the *S. cerevisiae* Mnn2 protein (SwissProt AccNo P38069) followed by the catalytic domain of *Drosophila melanogaster* mannosidase II (SwissProt AccNo Q24451)(FIG. 10, SEQ ID NO:7 and SEQ ID NO:8). The yeast Mnn2 36 N-terminal amino acids serve as a Golgi localization signal for the catalytic Man II domain.

Figure 11:
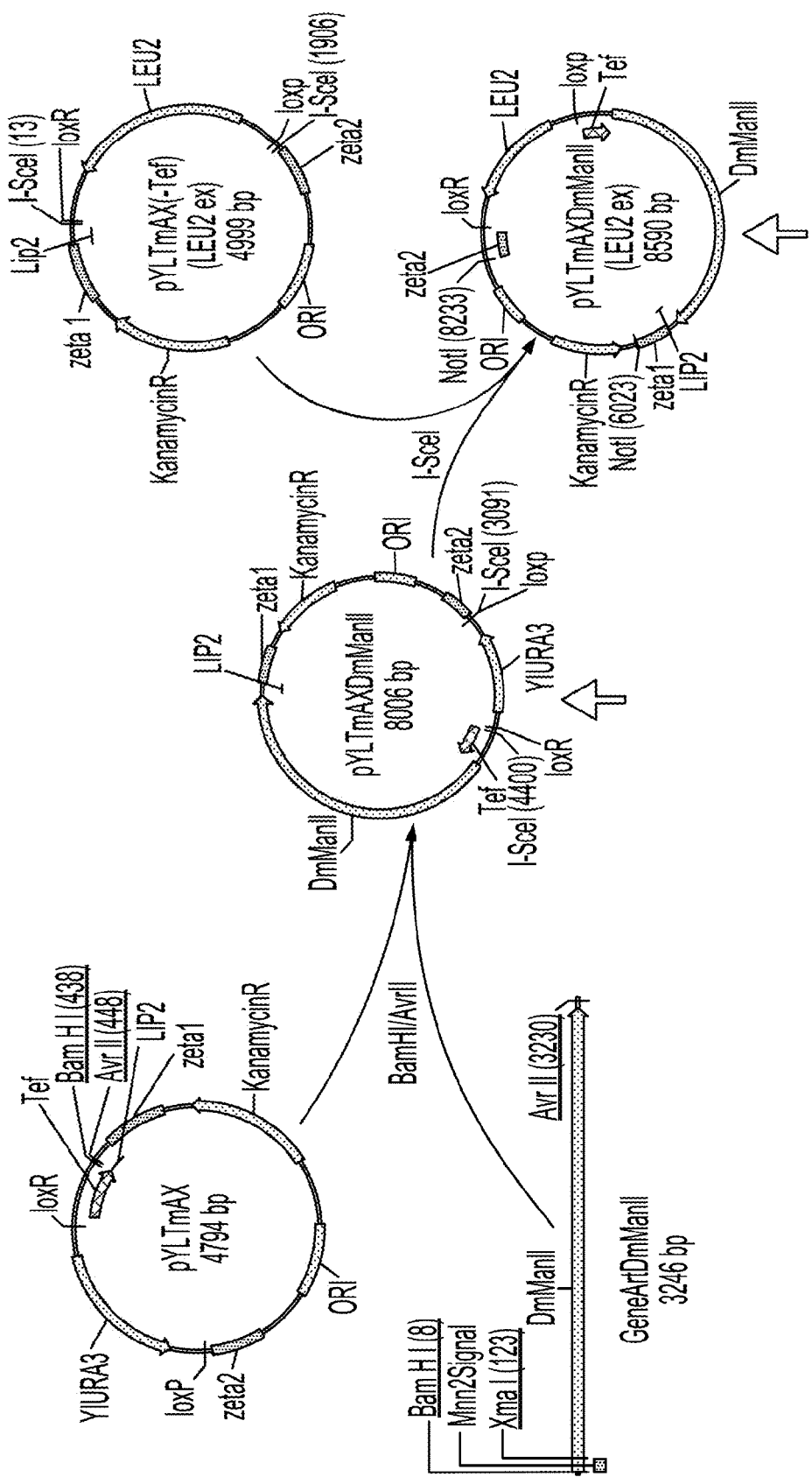
FIG. 11 is a schematic depiction of the construction strategy for plasmids pYLTmAXDmManII and pYLTmAXDmManII (LEU2ex).

In this way, it is ensured that the Mnn2-Man II fusion protein is localized at the same or even a later position in the secretion pathway than the Kre2-GnT I fusion protein and is therefore able to convert GlcNAcMan$_5$GlcNAc$_2$ into GlcNAcMan$_3$GlcNAc$_2$. The *Yarrowia* codon optimized synthetic gene for the expression of the fusion protein was placed under the transcriptional control of the TEF1 promoter, resulting into the plasmids pYLTmAXDmManII and pYLTmAXDmManII (LEU2ex). The construction strategy is shown in FIG. 11.

Figure 12:
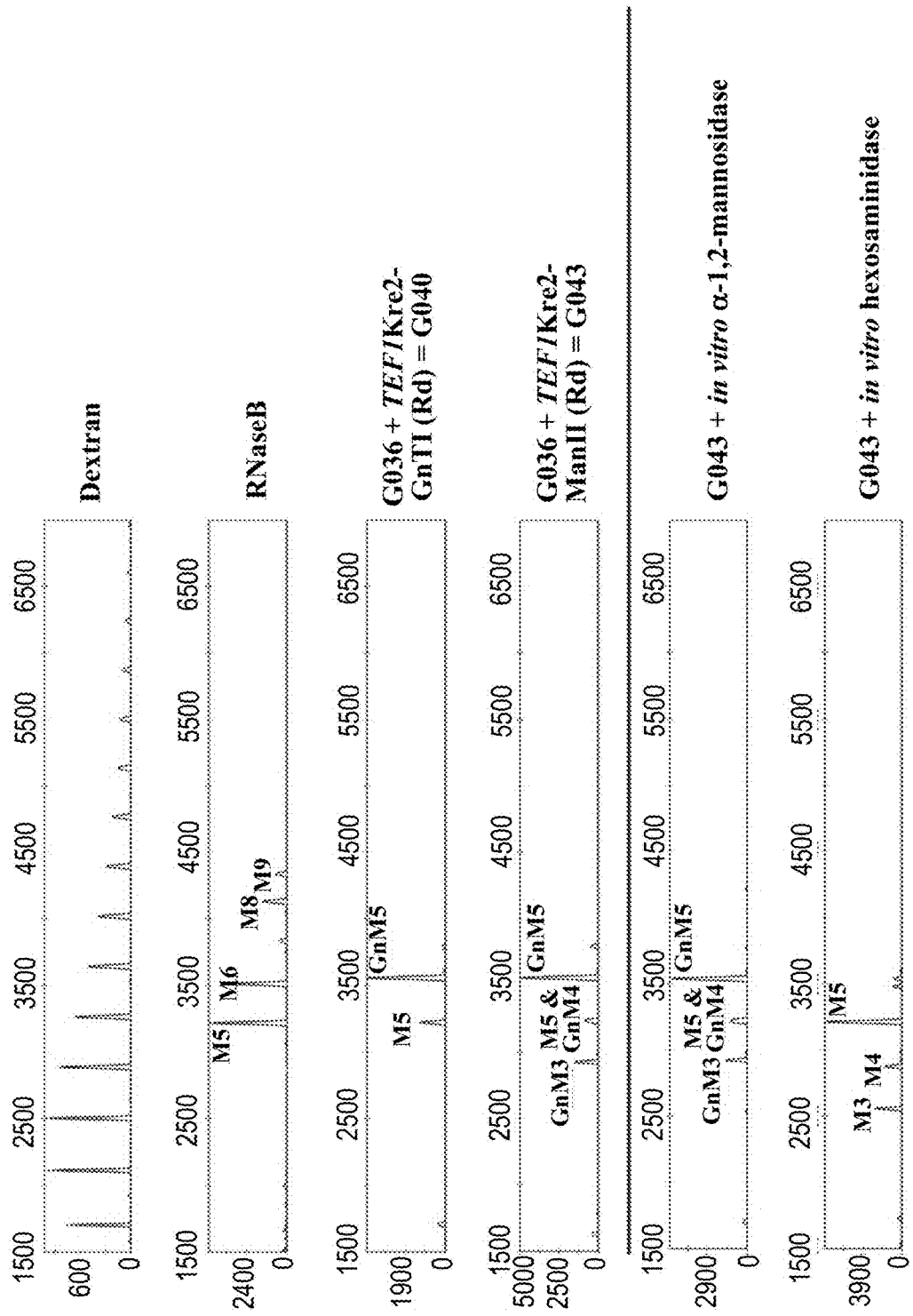
FIG. 12 is a series of electroferograms depicting the N-glycan profile after introduction of the Man II activity into strain G040 by transformation with a Man II-expressing vector. "Rd" stands for "random integration" via the zeta sequences present on the vectors shown in FIG. 11. Upon expression of the Man II activity a new peak appears with higher electrophoretic mobility, as well as a 'shoulder' peak running at almost the same position as Man$_5$GlcNAc$_2$. In vitro hexosaminidase treatment results in a shift forward for these peaks (next to the observed shift from GlcNAcMan$_5$GlcNAc$_2$ towards Man$_5$GlcNAc$_2$), indicating the presence of terminal GlcNAc and thus identifying the peaks as GlcNAcMan$_3$GlcNAc$_2$ and GlcNAcMan$_4$GlcNAc$_2$. In vitro treatment with α-1,2-mannosidase does not change the profile significantly, indicating that only small amounts of high-mannose N-glycans other than Man$_5$GlcNAc$_2$ are present.

Plasmid pYLTmAXDmManII (LEU2ex) was NotI digested before transformation to strain G040 (see Example 3), which was known to produce GlcNAcMan$_5$GlcNAc$_2$ N-glycans on its secreted proteins. Transformants were selected for leucine prototrophy. Analysis of the N-glycosylation profile on the secretome of several of these clones showed a change in the N-glycan pattern: a new peak representing an N-glycan with a lower molecular weight of about two glucose units appeared, which could indicate the formation of GlcNAcMan$_3$GlcNAc$_2$ and thus partial mannosidase II activity. Also another peak appears, running at almost the same position as Man$_5$GlcNAc$_2$ (i.e. a shoulder to the peak), potentially representing GlcNAcMan$_4$GlcNAc$_2$. The latter structure could be the result of a partial trimming event, where the mannosidase II activity has only removed one mannose residue instead of two. Treatment of the isolated N-glycans with Jack Bean β-N-acetylhexosaminidase resulted in a leftward shift of the glycan pattern with about one glucose unit and thus a higher electrophoretic mobility due to the loss of a terminal GlcNAc residue (FIG. 12). This further confirms the generation of GlcNAcMan$_4$GlcNAc$_2$ and GlcNAcMan$_3$GlcNAc$_2$ from GlcNAcMan$_5$GlcNAc$_2$ due to the expression of a functional mannosidase II activity. Depending on the cultivation method used, about 15% of the total N-glycan pool proved to be GlcNAcMan$_3$GlcNAc$_2$: approximately 35% of the available GlcNAcMan$_5$GlcNAc$_2$ lost 1 or 2 mannose residues, with 20% being completely trimmed towards GlcNAcMan$_3$GlcNAc$_2$.

Example 5: Expression of Galactosyltransferase I

Synthesis of N-glycans with terminal galactose residues not only depends on the presence of a functional and well-localized galactosyltransferase within the secretion pathway, but also on the availability of UDP-Gal, the donor substrate that is used by the enzyme. Although UDP-Glc and UDP-GlcNAc are generally thought to be sufficiently available in the Golgi apparatus of yeast organisms, this is less known for UDP-Gal. To overcome potential UDP-Gal deficiency during glyco-engineering, attempts have been made previously in *Pichia pastoris* to target a fusion protein of the *Schizosaccharomyces pombe* UDP-Glc-4-epimerase (encoded by the GAL10 like gene SPBC365.14c-SwissProt AccNo Q9Y7X5) and the catalytic domain of the human β-1,4-galactosyltransferase I (GalT I) (SwissProt AccNo P15291) into the yeast Golgi apparatus (Bobrowicz et al., *Glycobiology* 14(9):757-766, 2004). Localization of the Gal10p-GalT I fusion protein within the secretion pathway, preferably at a position where GlcNAc-transfer and mannosidase II activity has already acted on the N-glycans of proteins destined for secretion, was accomplished by using the first 46 N-terminal amino acids of *S. cerevisiae* Mnn2p as N-terminal targeting signal.

Figure 14:
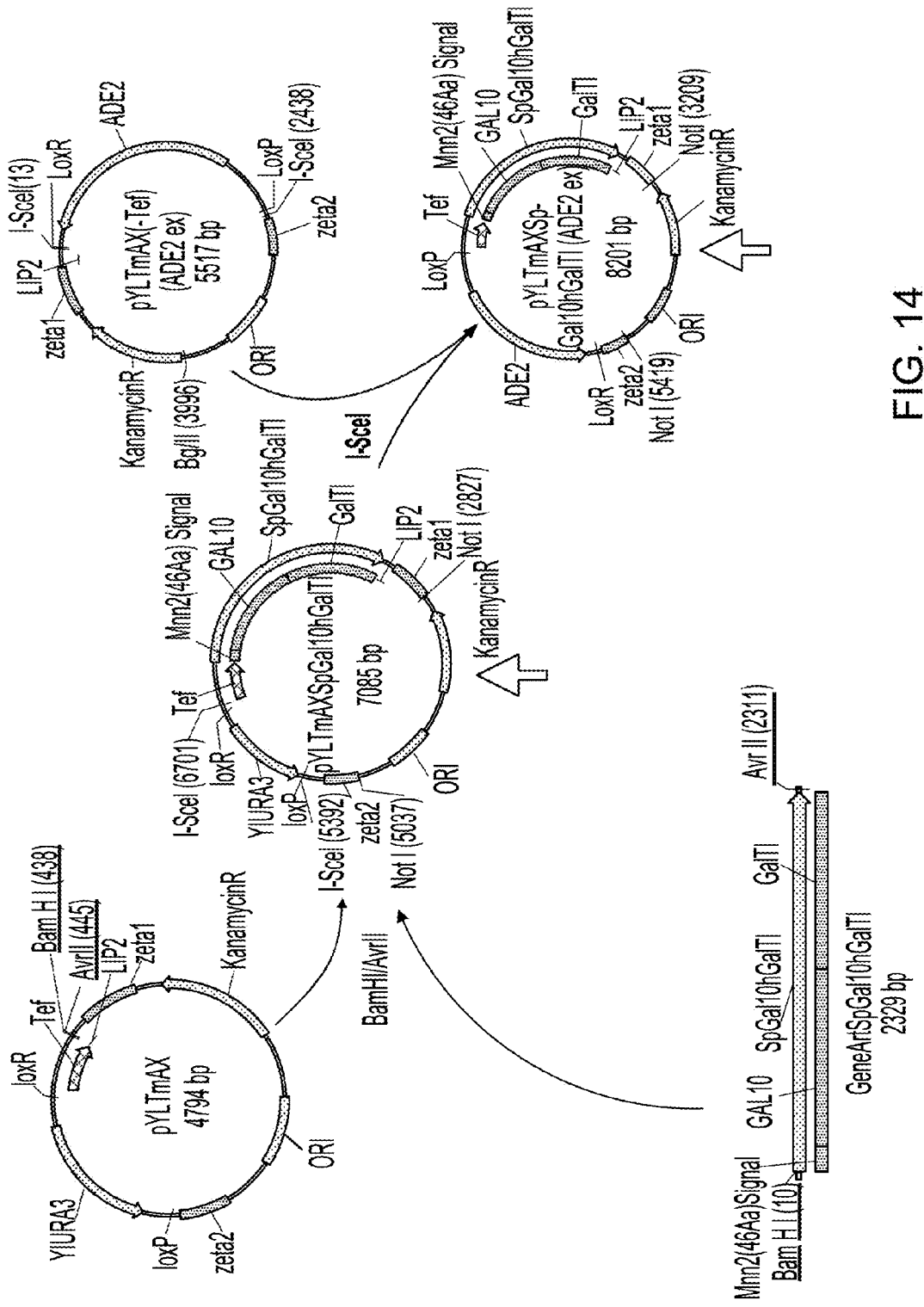
FIG. 14 is a schematic depiction of the construction strategy for plasmids pYLTmAXSpGal10hGalTI and pYLTmAXSpGal10hGalTI (ADE2ex).

Hence, a *Yarrowia* codon-optimized sequence was generated for the expression of a fusion protein consisting of the first 46 N-terminal amino acids of the *S. cerevisiae* Mnn2 protein, followed by the *S. pombe* Gal10-like protein and the catalytic domain of human GalT I (FIG. 13). The resulting synthetic gene was placed under the transcriptional control of the TEF1 promoter, resulting into the plasmids pYLTmAXSpGal10hGalTI and pYLTmAXSpGal10hGalTI (ADE2ex). The construction strategy is shown in FIG. 14.

Figure 15:
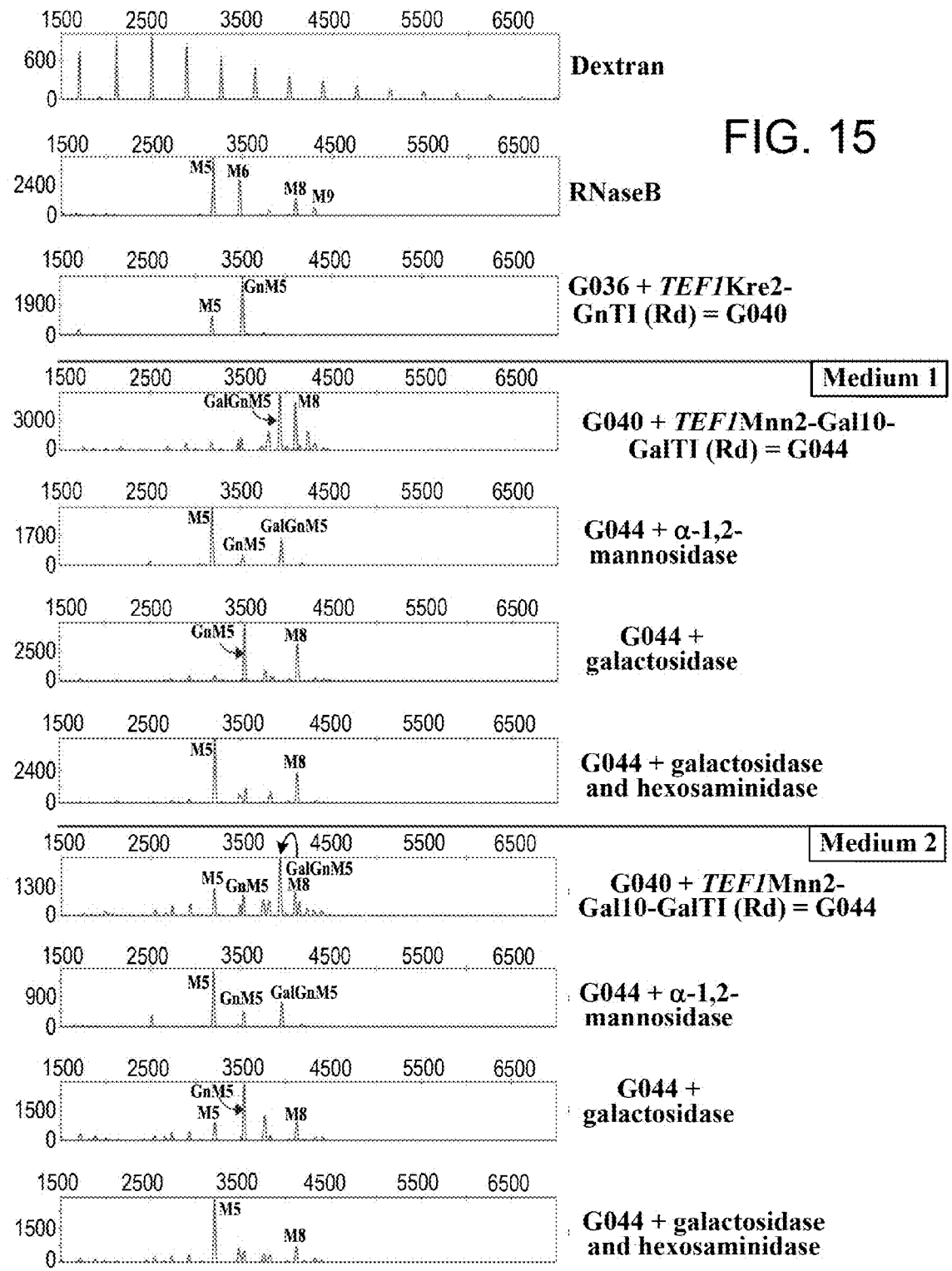
FIG. 15 is a series of electroferograms depicting the N-glycan profile after introduction of the Gal10-GalTI activity into strain G040. The resulting transformant G044 was cultivated in 2 different media. "Rd" stands for "random integration" via the zeta sequences present on the vectors shown in FIG. 14. Upon expression of the Gal10-GalTI activity a new peak appears running at a position between Man$_7$GlcNAc$_2$ and Man$_8$GlcNAc$_2$. In vitro galactosidase treatment results in a shift forward for this peak and an equal increase of GlcNAcMan$_5$GlcNAc$_2$ (the latter being confirmed as representing this N-glycan by the double treatment with galactosidase and hexosaminidase). This indicates the presence of terminal galactose and thus identifying the new peak of the G044 profile as GalGlcNAcMan$_5$GlcNAc$_2$. In vitro treatment with α-1,2-mannosidase indicates the presence of a large amount of high-mannose N-glycans (especially Man$_8$GlcNAc$_2$) that were not yet trimmed to Man$_5$GlcNAc$_2$.

Plasmid pYLTmAXSpGal10hGalTI (ADE2ex) was NotI digested before transformation to strain G040 (see Example 3), known to produce GlcNAcMan$_5$GlcNAc$_2$ N-glycans on its secreted proteins. Transformants were selected for their adenine prototrophy. Analysis of the N-glycosylation profile on the secretome of several of these clones showed a change in the N-glycan pattern: a new peak appears, running at a position between Man$_7$GlcNAc$_2$ and Man$_8$GlcNAc$_2$ (FIG. 15). Treatment of the N-glycans with *Streptococcus pneumonia* β-1,4-galactosidase indicates that the peak represents GalGlcNAcMan$_5$GlcNAc$_2$ since this in vitro digest results in the disappearance of this new peak and an equally high increase in GlcNAcMan$_5$GlcNAc$_2$.

Using this set-up and depending on the growth conditions, about 75% of GlcNAcMan$_5$GlcNAc$_2$ was converted into GalGlcNAcMan$_5$GlcNAc$_2$. The total amount of the galactosylated structure accounted for about 25% of the total N-glycan pool. From an in vitro α-1,2-mannosidase digest it is clear, however, that a significant amount of high-mannose N-glycans was not converted to Man$_5$GlcNAc$_2$ (FIG. 15). Depending on the cultivation medium used, the conversion rate of Man$_5$GlcNAc$_2$ towards GlcNAcMan$_5$GlcNAc$_2$ also is lower than that observed in the G040 parent strain. This is most probably related to the slower growth rate observed for transformants of this Mnn2-Gal10-GalT I fusion protein.

Example 6: Knock-Out of YlALG3 and Simultaneous Overexpression of YlALG6

To allow the generation of a Man$_3$GlcNAc$_2$ platform, the ALG3 gene of strain G036 (po1d lnuga Δoch1+Hp4d-driven α-1,2-mannosidase) needs to be inactivated. This results into the loss of the ER-localized Alg3p α-1,6-mannosyltransferase activity and changes the composition of the lipid-linked N-glycan precursor structure. Transfer of this structure to an N-glycosylation site of a nascent polypeptide chain makes it possible to convert the yeast glycosylation profile into mammalian-like N-glycan structures without the need to express the Mannosidase II. However, since this new lipid-linked structure is not transferred as efficiently to nascent polypeptides, the *Yarrowia* ALG6 gene (encoding an ER-localized Alg6p α-1,3-glucosyl transferase) needs to be overexpressed simultaneously to reduce potential protein underglycosylation as much as possible.

Figure 16:
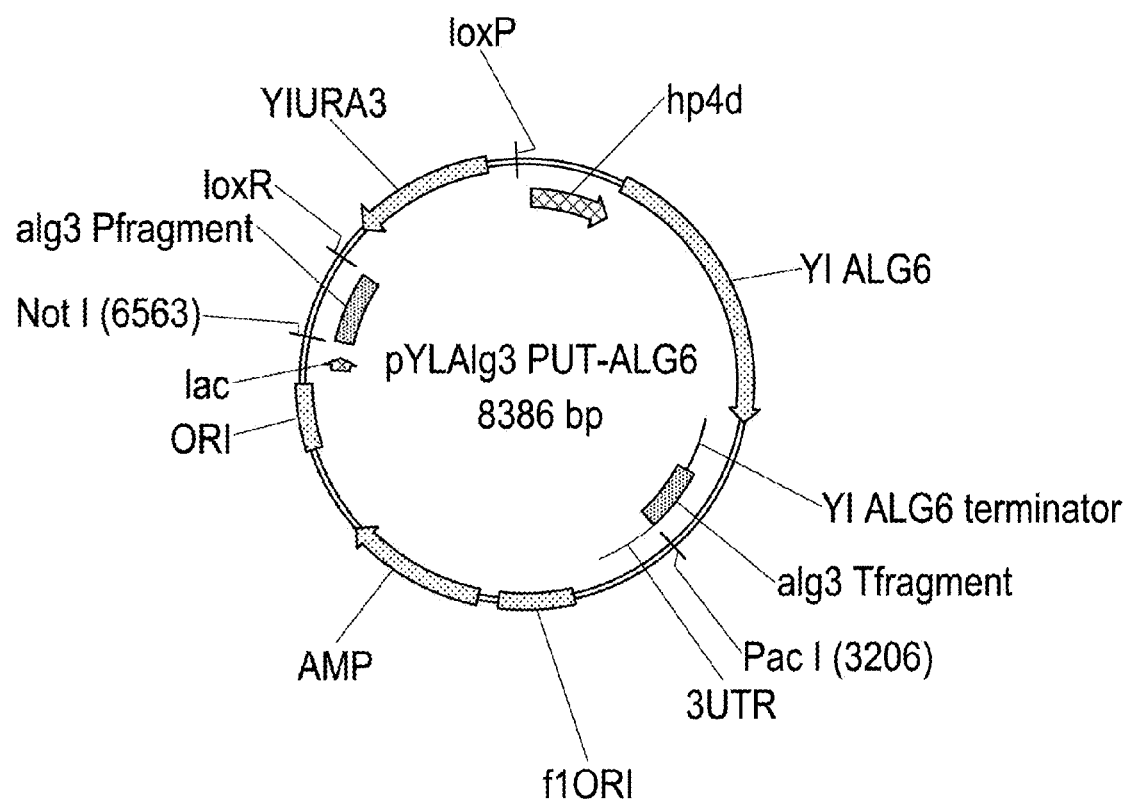
FIG. 16 is a schematic depiction of plasmid pYLalg3PUT-ALG6.
Figure 17:
FIG. 17 is a series of electroferograms depicting the N-glycan profile after introduction of pYLalg3PUT-ALG6 into strain G036. Overexpression of ALG6 results in a significant amount of glucosylated peaks (GlcMan$_5$GlcNAc$_2$ and Glc$_2$Man$_5$GlcNAc$_2$), indicating that the Glc$_3$Man$_5$GlcNAc$_2$ structure that was transferred to the nascent protein is not completely trimmed towards Man$_5$GlcNAc$_2$ by glucosidase II. Depending on the growth medium, the generated Man$_5$GlcNAc$_2$ is partially (still some Man$_5$GlcNAc$_2$ and Man$_4$GlcNAc$_2$) or almost completely trimmed towards Man$_3$GlcNAc$_2$ by the action of the ER-localized HDEL-tagged *T. reesei* α-1,2-mannosidase. The Man$_5$GlcNAc$_2$ and Man$_4$GlcNAc$_2$ peaks are identified as such, by their sensitivity towards α-1,2-mannosidase. Because of the capping glucoses, GlcMan$_5$GlcNAc$_2$ and Glc$_2$Man$_5$GlcNAc$_2$ are insensitive towards this treatment. Jack Bean mannosidase is partially capable of removing the free α-1,6-linked mannose while it also converts Man$_{3-5}$'GlcNAc$_2$ into Man$_1$GlcNAc$_2$.

A vector called pYLalg3PUT-ALG6 (FIG. 16) was constructed previously to allow simultaneous knock-out of YlALG3 and Hp4d-driven overexpression of YlALG6. See U.S. Patent Publication No. 20090069232-A1. A NotI/PacI fragment of this vector, containing this knock-out/knock-in cassette, was transformed into *Yarrowia lipolytica* G036 and transformants were selected based on their uracil prototrophy. Clones that had correctly integrated the construct were directly screened via N-glycan analysis on the secretome. Out of 80 screened clones, 2 clones showed an N-glycosylation profile that could fit with the inactivation of YlALG3 in a strain expressing an ER-located α-1,2-mannosidase. Apart from a fraction Man$_3$GlcNAc$_2$ glycans, there was still some Man$_4$GlcNAc$_2$ and Man$_5$GlcNAc$_2$ as well as a significant amount of glucosylated N-glycans (GlcMan$_5$GlcNAc$_2$ and Glc$_2$Man$_5$GlcNAc$_2$). The latter are the result of an inefficient trimming by glucosidase II (Grinna and Robbins, *J. Biol. Chem.* 255, 2255-2258, 1980). The nature of the structures of Man$_4$GlcNAc$_2$ and Man$_5$GlcNAc$_2$ was confirmed by in vitro treatment of the N-glycans with α-1,2-mannosidase (FIG. 17). Depending on the growth conditions used, the level of Man$_3$GlcNAc$_2$ could increase to up to 60% of the total N-glycan pool, with the glucosylated peaks being insensitive towards α-1,2-mannosidase and only slightly sensitive towards Jack Bean α-mannosidase treatment (aspecific α-mannosidase that can act on α-1,2-, α-1,3- and α-1,6-linked mannose residues). In contrast, the latter enzyme converts the generated Man$_3$GlcNAc$_2$ into Man$_1$GlcNAc$_2$ (FIG. 17).

One of the two positive transformants was called G039 and used for further glyco-engineering work. The strain was transformed transiently with pRRQ2 expressing the Cre-recombinase to allow the curing of the URA3 marker that was introduced upon transformation of G036 with vector pYLalg3PUT-ALG6. Analysis shows that the glycosylation profile remains the same after curing. One cured strain was selected for further use and designated G045.

Figure 18:
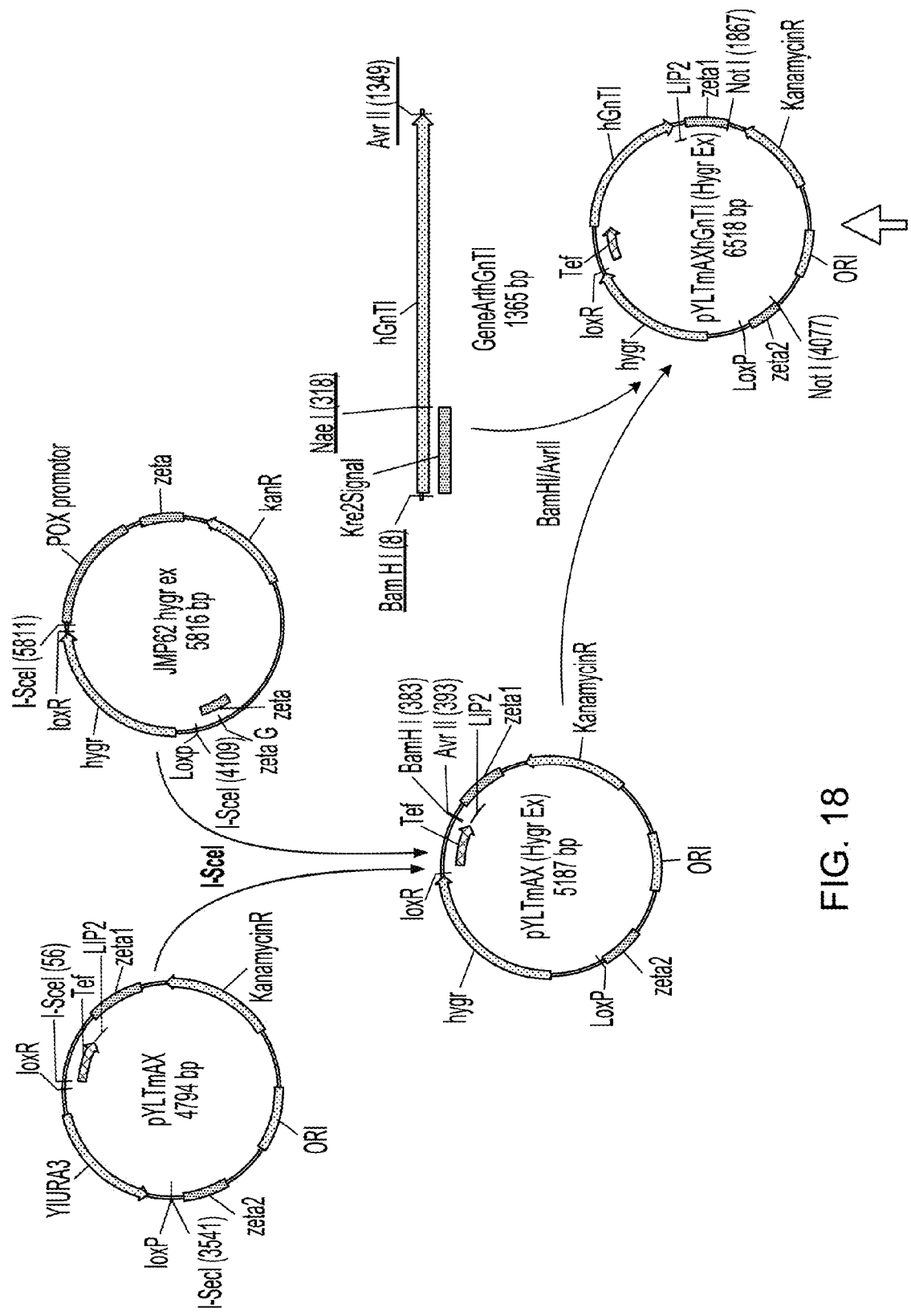
FIG. 18 is a schematic depiction of the construction strategy for plasmid pYLTmAXhGnTI (Hygr ex).

Example 7: Expression of GlcNAc-Transferase I in a Man$_3$GlcNAc$_2$ Producing Strain Similar to what was done in example 3, the introduction of a GnT I activity was accomplished via the expression of the Kre2-GnT I fusion protein. Random integration of such an expression construct for GnT I was accomplished in three ways: 1) the non cured strain G039 (see Example 6) was transformed with the NotI digested vector pYLTmAXhGnTI (Hygr ex) and GnT I expressing clones were initially selected based on their ability to survive 300 µg/ml of hygromycin added to the selection plates, 2) the cured strain G045 (see Example 6) was transformed with the NotI digested vector pYLTmAXhGnTI (see also Example 3) and GnT I expressing clones were initially selected based on their uracil prototrophy or 3) the cured strain G045 (see Example 6) was transformed with the NotI digested vector pYLHp4mAXhGnTI and GnT I expressing clones were initially selected based on their uracil prototrophy. The construction strategy for pYLTmAXhGnTI (Hygr ex) is shown in FIG. 18. When using plasmids pYLTmAXhGnTI (Hygr ex) and pYLTmAXhGnTI, the expression of GnT I was under the transcriptional control of the TEF1 promoter; when using plasmid pYLHp4mAXhGnTI, the GnT I expression was under the control of the Hp4d promoter.

Figure 19:
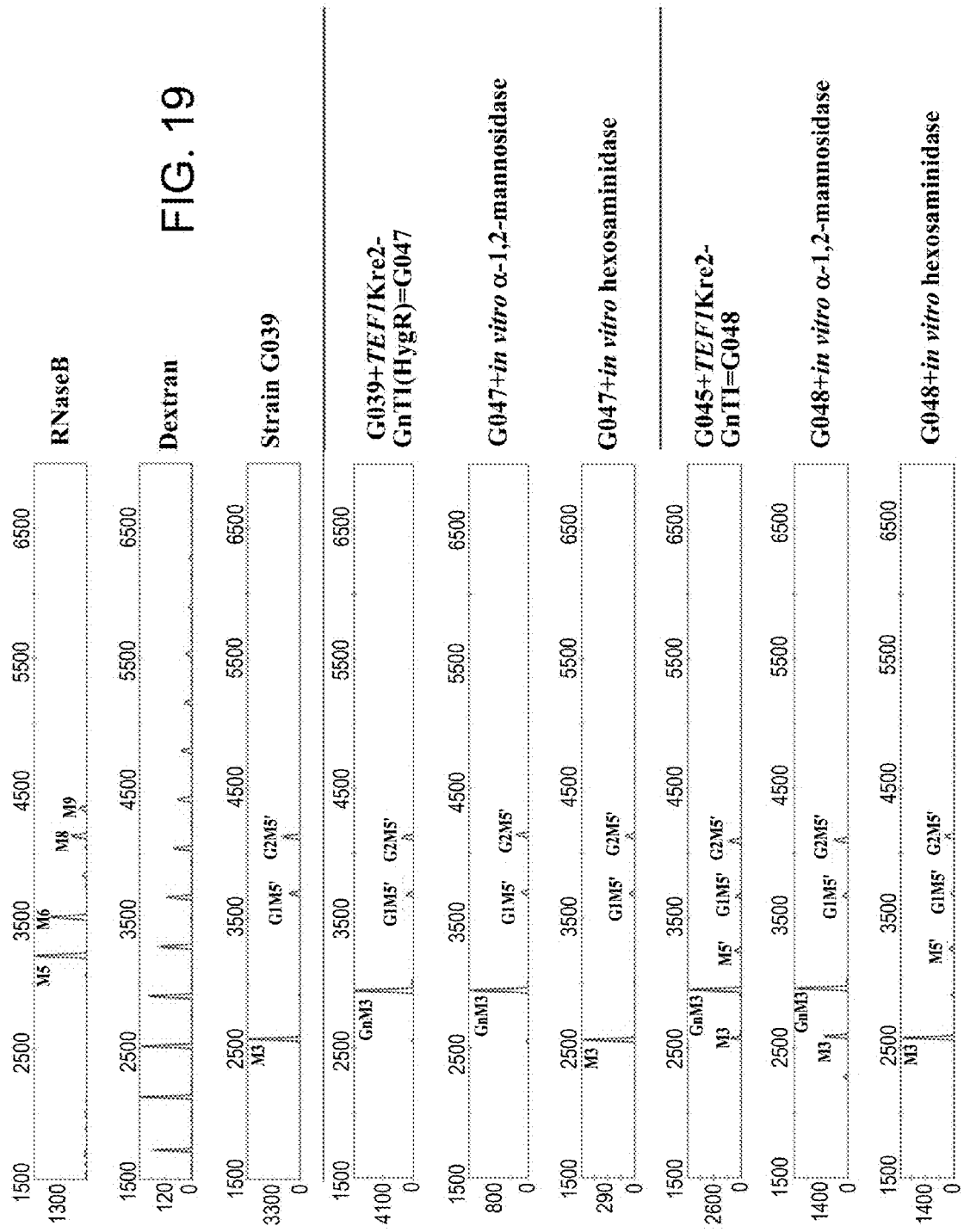
FIG. 19 is a series of electroferograms depicting the N-glycan profiles after introduction of the GnT I activity into either the non-cured (G039) or cured (G045) version of the Δalg3-Hp4dALG6 strain by transformation with a GnT I-expressing vector. The generation of GlcNAcMan$_3$GlcNAc$_2$ was proven via a hexosaminidase digest. The new peak completely shifts back towards Man$_3$GlcNAc$_2$. In strain G048 conversion towards GlcNAcMan$_3$GlcNAc$_2$ was not complete since some Man$_3$GlcNAc$_2$ could still be observed. This strain also has some remnant Man$_5$GlcNAc$_2$ as shown by the α-1,2-mannosidase digest.

Transformation of G039 with pYLTmAXhGnTI (Hygr ex) resulted in three clones that only emerged on the culture plates after a longer incubation period than what was expected. However, analysis of the N-glycosylation profile of the secretome of these clones showed a clear change in the N-glycan pattern: the Man$_3$GlcNAc$_2$ present in the non-transformed G039 strain was significantly reduced or almost completely absent while a new peak, representing an N-glycan with higher molecular weight (about one glucose unit extra), appeared. Treatment of the isolated N-glycans with Jack Bean β-N-acetylhexosaminidase, an enzyme capable of removing terminal β-linked GlcNAc residues, indicated that the new N-glycan indeed is GlcNAcMan$_3$GlcNAc$_2$. The new peak disappeared and was completely converted into Man$_3$GlcNAc$_2$ (FIG. 19). One of the evaluated transformants was used for further glyco-engineering work and named G047. Similar results were also obtained when the cured strain G045 was transformed with pYLTmAXhGnTI (G048) or with pYLHp4mAXhGnTI (G056). Strain G056 was selected for curing via transient expression of the Cre recombinase using plasmid pRRQ2. The resulting strain was called G058.

Depending on the cultivation method used, about 70% of the total N-glycan pool of strain G047 proved to be GlcNAcMan$_3$GlcNAc$_2$ with some remaining Glc$_{1-2}$Man$_5$GlcNAc$_2$ and almost no Man$_3$GlcNAc$_2$ was present (conversion rate >>90%) (FIG. 19). Regardless of the high conversion rate, only one copy of the GnT I expression cassette could be identified in this strain via Southern blot. Southern analysis was done on BamHI digested genomic DNA using a DIG-labeled GnT I-specific PCR fragment that was generated using primers 5'-GGATGATCACACAATG-GCCCTGTTTCTG-3'(SEQ ID NO:11) and 5'-TGCTCTA-GACTAGTTCCAAGAGGGGTC-3' (SEQ ID NO:12).

Figure 20:
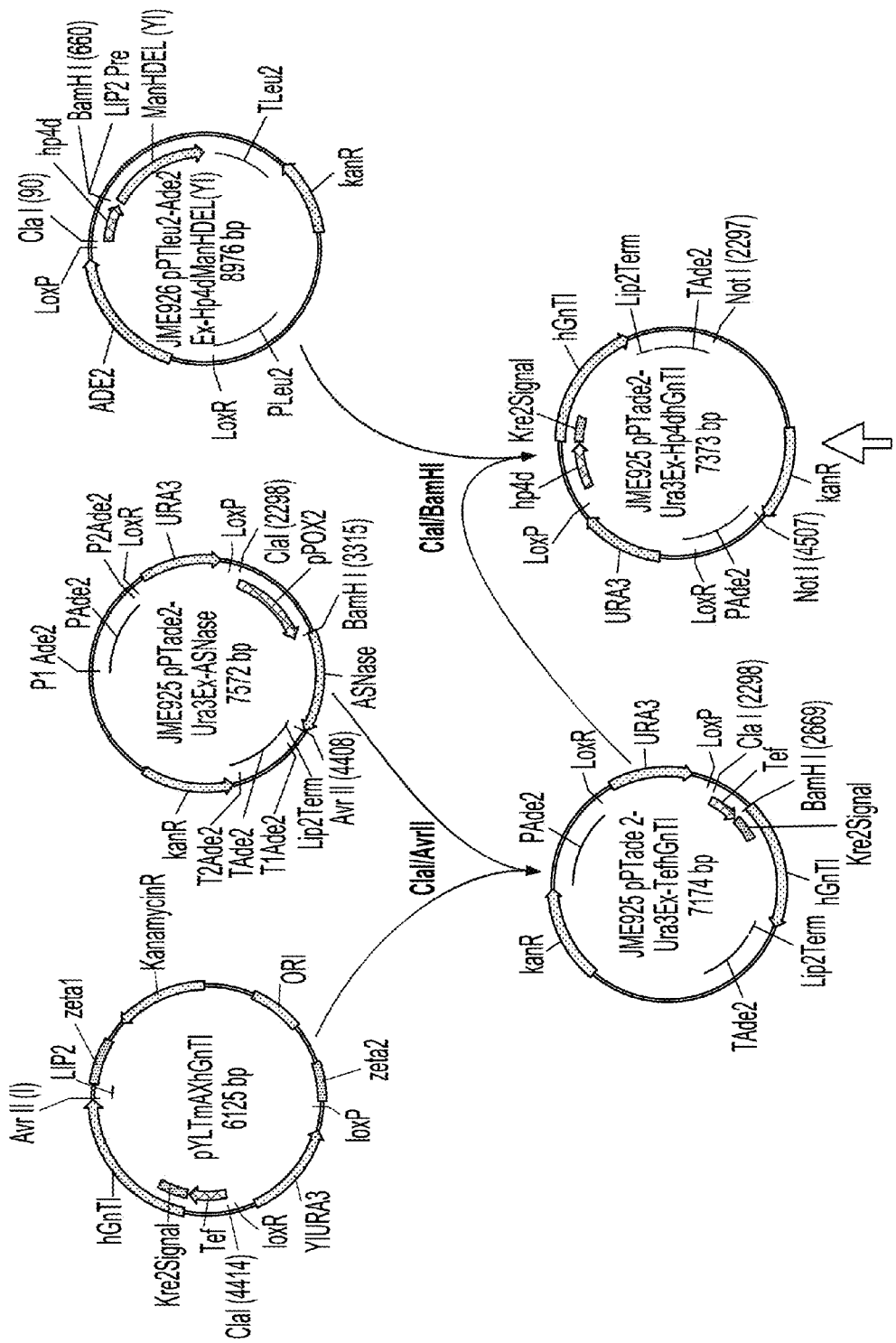
FIG. 20 is a schematic depiction of the construction strategy for plasmid JME925 pPTAde2-URA3 ex-Hp4dhGnTI.
Figure 21:
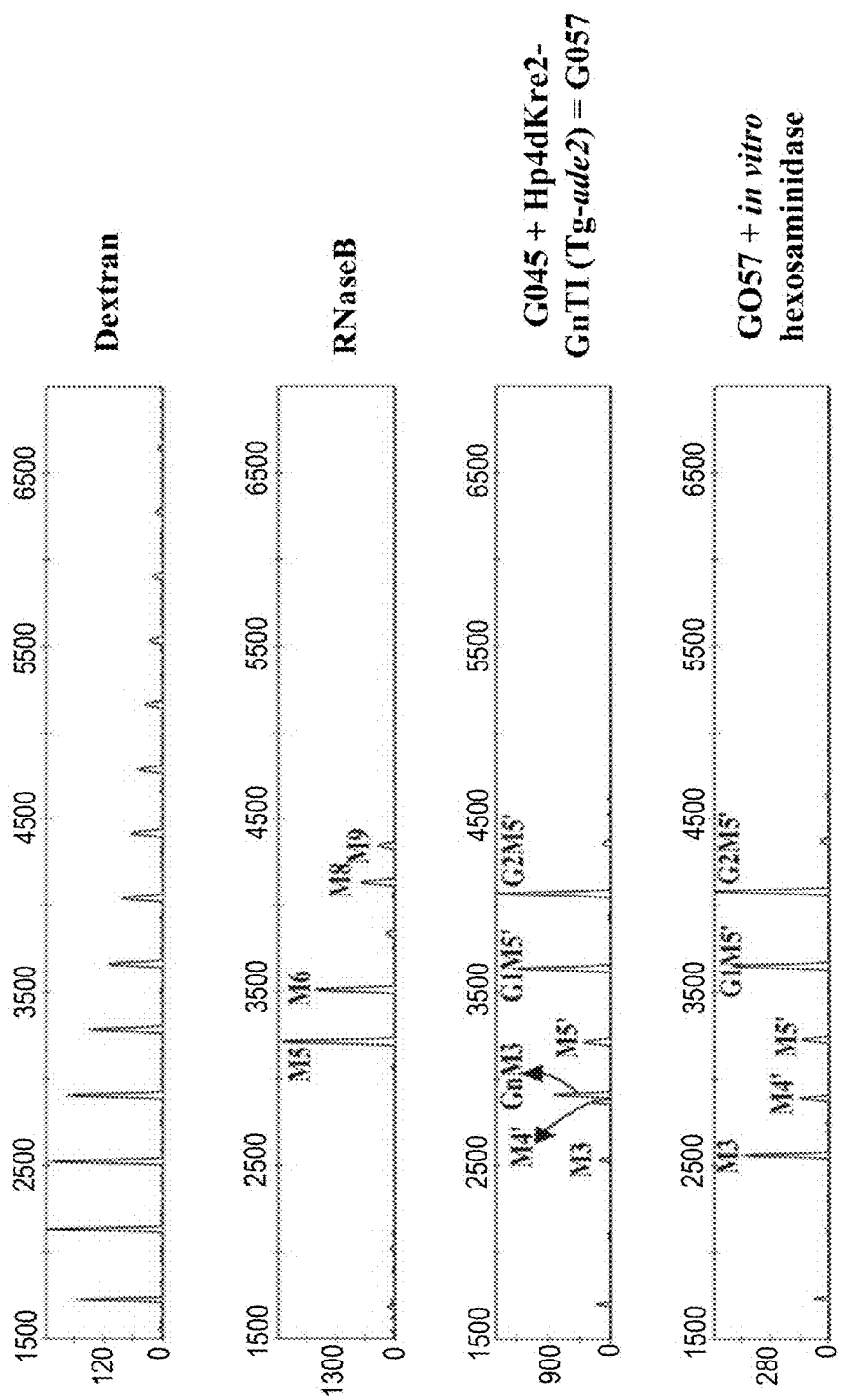
FIG. 21 is a series of electroferograms depicting N-glycan profiles after introduction of the GnT I activity into the cured version of the Δalg3-Hp4dALG6 strain (=G045); integration of an Hp4d-driven expression construct into the ADE2 locus (Tg-ade2). In this cultivation the amount of glucosylated N-glycans was high and conversion of Man$_{4'-5'}$GlcNAc$_2$ to Man$_3$GlcNAc$_2$ was not complete. A new peak running next to Man$_4$GlcNAc$_2$ was observed in transformant G057 and could be designated as GlcNAcMan$_3$GlcNAc$_2$ based on the result if the hexosaminidase digest: the new peak completely shifts back towards Man$_3$GlcNAc$_2$.

In an alternative strategy, a construct JME925 pPTAde2-URA3ex-Hp4dhGnTI was generated to allow targeted integration of the Hp4d-driven GnT I expression cassette into the ADE2 locus of the *Yarrowia* genome. The construction strategy is depicted in FIG. 20. Prior to transformation to strain G045, the plasmid was NotI digested and the targeting/expression cassette was isolated. Transformants were selected based on their adenine prototrophy. Correct integration of the expression cassette into the ADE2 locus was checked via PCR using forward primer Ver1Ade2 (5'-CGACGATAGAGCAGGTCTCACTGTTGGGAAT-GCTG-3', SEQ ID NO:13) reverse primer Ver2Ade2 (5'-CTACACTGACGAAGTGGACATCCCGGCTTGGACTG-3', SEQ ID NO:14) and further confirmed via Southern blotting. This was done on BamHI/SpeI digested genomic DNA using a DIG-labeled GnT I-specific PCR fragment that was generated using primers 5'-GGATGATCACACAATGGC-CCTGTTTCTG-3' (SEQ ID NO:15) and 5'-TGCTCTA-GACTAGTTCCAAGAGGGGTC-3' (SEQ ID NO:16). Synthesis of GlcNAcMan$_3$GlcNAc$_2$ onto the secretome was confirmed via N-glycan analysis and in vitro Jack Bean β-N-acetylhexosaminidase treatment (FIG. 21). One GnT I expressing transformant (called G057) was selected for curing via transient expression of the Cre recombinase using plasmid pRRQ2. The resulting strain was called G059.

Example 8: Expression of GlcNAc-Transferase II

Figure 23:
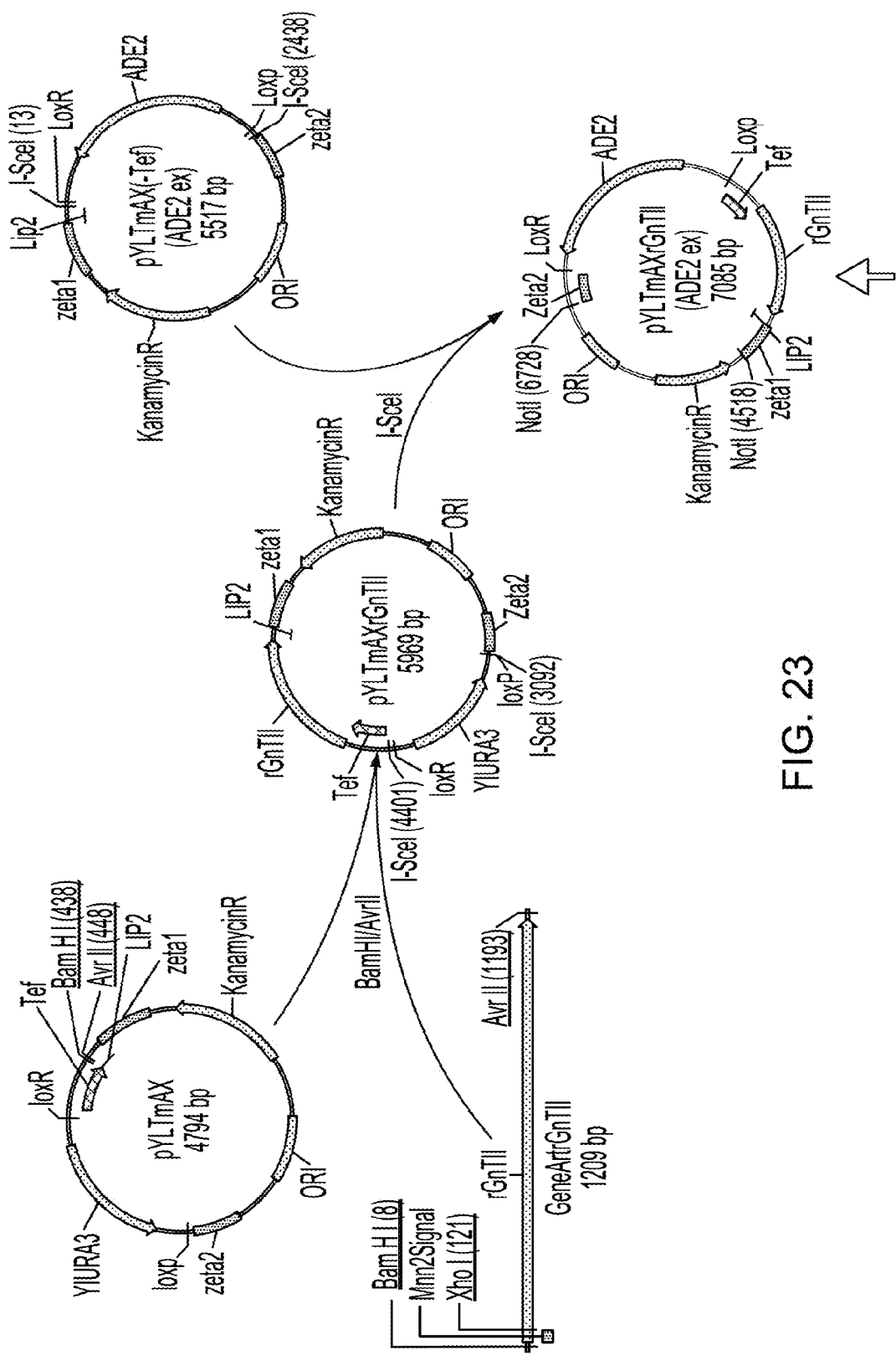
FIG. 23 is a schematic depiction of the construction strategy for plasmids pYLTmAXrGnTII and pYLTmAXrGnTII (ADE2 ex).

A *Yarrowia* codon-optimized sequence was generated for the expression of a fusion protein consisting of the first 36 N-terminal amino acids of the *S. cerevisiae* Mnn2 protein (SwissProt AccNo P38069) followed by the catalytic domain of rat GlcNAc-transferase II (GnT II) (SwissProt AccNo Q09326) (FIG. 22, SEQ ID NO:17 and SEQ ID NO:18). The yeast Mnn2 36 N-terminal amino acids serve as a Golgi localization signal for the catalytic GnT II domain. In this way, it was ensured that the Mnn2-GnT II fusion protein was localized at the same or even a later position in the secretion pathway than the Kre2-GnT I (and Mnn2-Man II) fusion protein and was therefore able to convert GlcNAcMan$_3$GlcNAc$_2$ into GlcNAc$_2$Man$_3$GlcNAc$_2$. The synthetic gene for the expression of the fusion protein was placed under the transcriptional control of the TEF1 promoter, resulting into the plasmids pYLTmAXrGnTII and pYLTmAXrGnTII (ADE2ex). The construction strategy is shown in FIG. 23.

Figure 24:
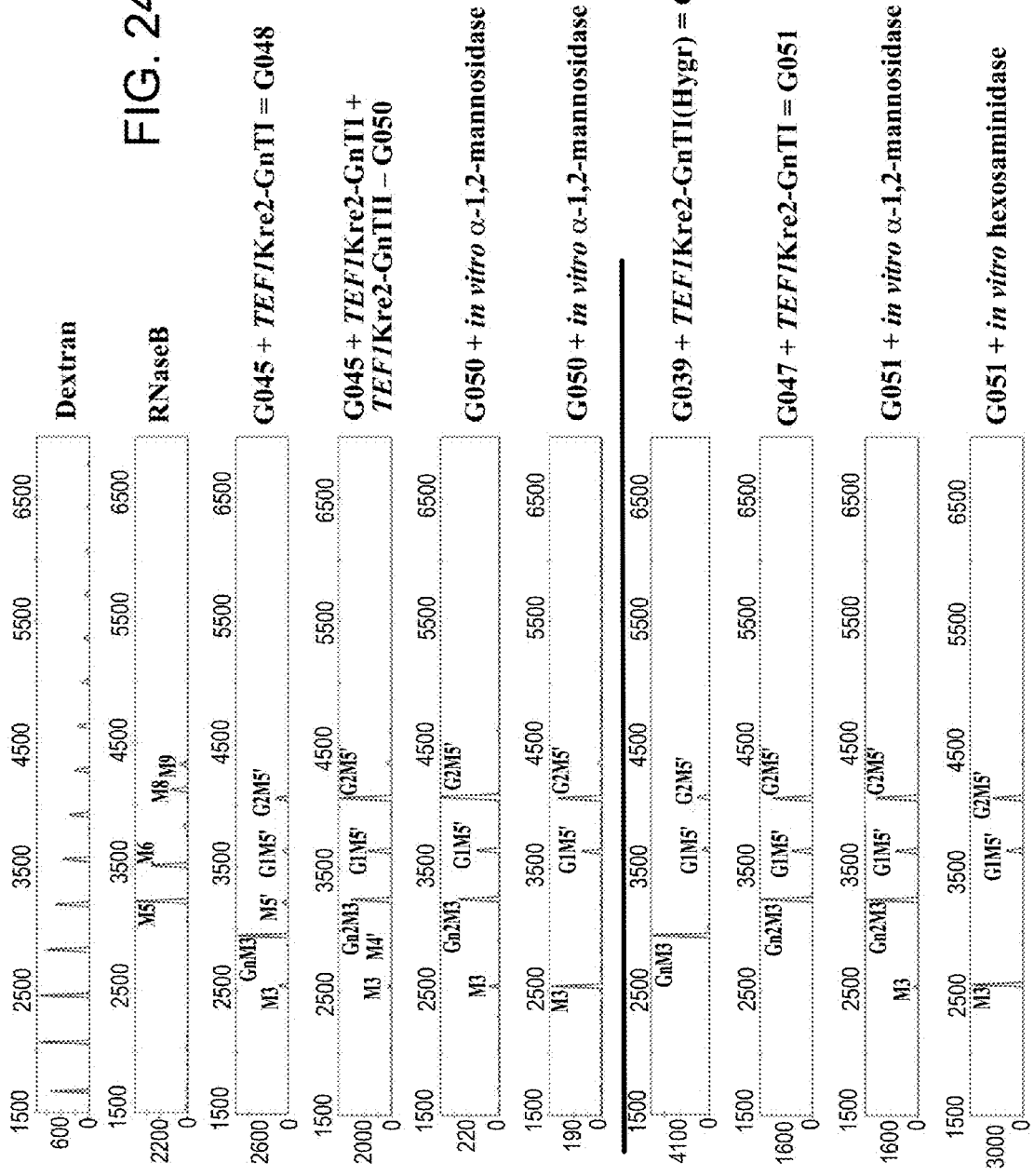
FIG. 24 is a series of electroferograms depicting N-glycan profiles after introduction of the GnT II activity into a strain synthesizing GlcNAcMan$_3$GlcNAc$_2$. The resulting strains were either obtained via double transformation of G045 with the GnTI and GnT II expression constructs or via transformation of G047 with the GnTII expression construct. In both cases, the peak representing GlcNAcMan$_3$GlcNAc$_2$ almost completely disappeared and a new peak, about one glucose unit larger, appeared. Hexosaminidase treatment indicates the presence of two terminal GlcNAc residues onto the new N-glycan; the peak shifts about two glucose units to the left and thus represents GlcNAc$_2$Man$_3$GlcNAc$_2$. α-1,2-mannosidase treatment does not result into major differences, indicating that there are only limited amounts of Man$_{4'\text{-}5'}$GlcNAc$_2$ present.

A strain expressing the GnT II activity was generated in two different ways: 1) strain G045 (see Example 6) was transformed simultaneously with NotI digested pYLTmAX-hGnTI and NotI digested pYLTmAXrGnTII (ADE2 ex) and transformants were selected based on their uracil and adenine prototrophy or 2) strain G047 (Example 7) was transformed with NotI digested pYLTmAXrGnTII (ADE2 ex) and transformants were selected based on their adenine prototrophy. Integration of the expression cassettes was checked using forward primer TefPromFW 5'-GTC-CCCGAATTACCTTTCC-3' (SEQ ID NO:19) and reverse primer Lip2TermRV 5'-AGGTAGAAGTTG-TAAAGAGTG-3' (SEQ ID NO:20). N-glycan analysis on the secretome in combination with in vitro treatment of the isolated sugars with Jack Bean β-N-acetylhexosaminidase indicated that several transformants were capable of producing GlcNAc$_2$Man$_3$GlcNAc$_2$ and thus of expressing a functional GnT II activity (FIG. 24). In one selected condition, about 40% of the total N-glycan pool consisted of GlcNAc$_2$Man$_3$GlcNAc$_2$. The conversion rate of the substrate GlcNAcMan$_3$GlcNAc$_2$ to GlcNAc$_2$Man$_3$GlcNAc$_2$ was 90%. The final selected strains were called G050 (double transformation of G045) and G051 (GnT II expression in G047).

Example 9: Expression of Glucosidase II Alpha and Beta Subunits (Gls2α and Gls2β)

Figure 25:
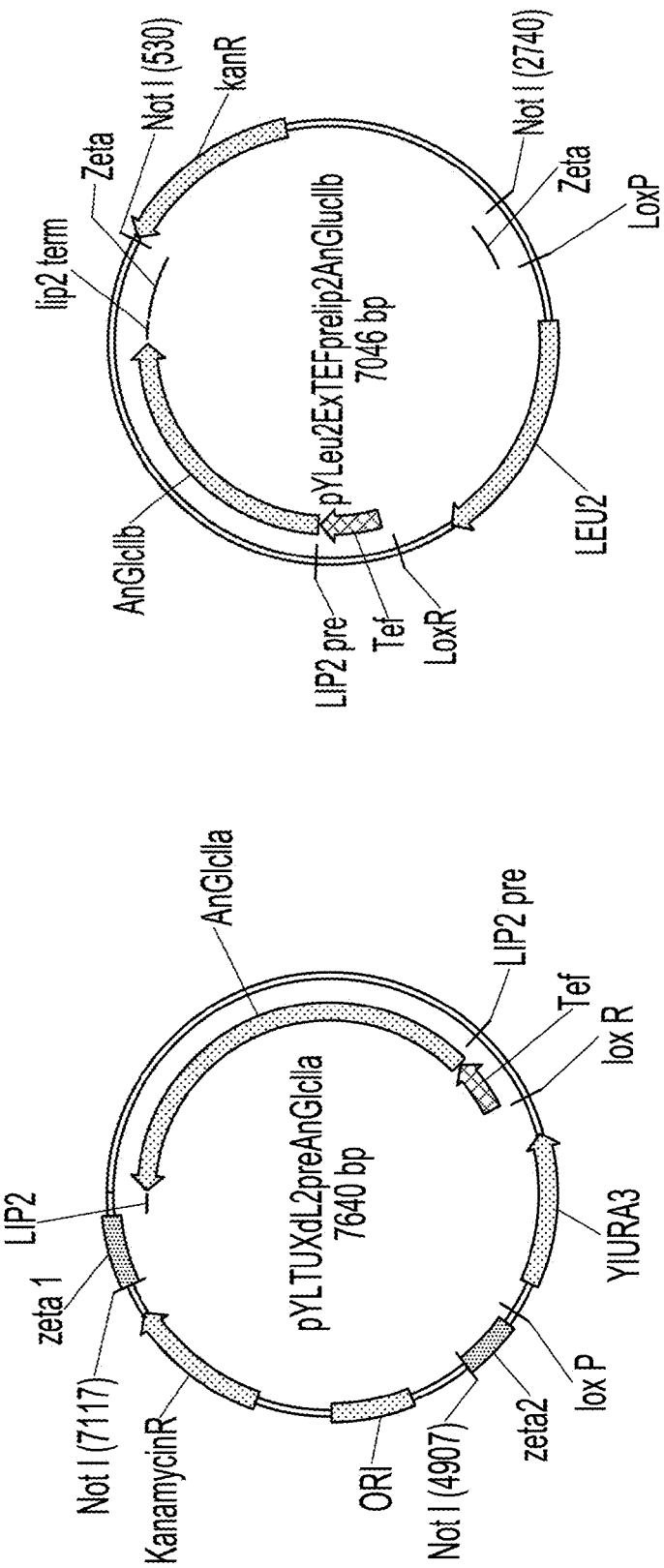
FIG. 25 is a schematic diagram of plasmids pYLTUXdL2preAnGlcII and pYLeu2ExTEFpreLip2-AnGlucIIβ for expression of the glucosidase II activity.

Based on the experiments described in Examples 6 to 8, the strategy involving the knock-out of YlALG3 and simultaneous overexpression of YlALG6 results into the generation of N-glycans carrying one or two terminal glucose residues (Glc$_{1-2}$Man$_5$GlcNAc$_2$). The presence of these glucose residues hampers the conversion towards Man$_3$GlcNAc$_2$ by the ER-localized HDEL-tagged α-1,2-mannosidase. In order for the glucose residues to be removed, the glucosidase II activity within the ER needs to be increased. In a background without α-1,2-mannosidase expression, overexpression of the *Aspergillus niger* glucosidase II alpha and beta subunit resulted in the highest conversion of Glc$_{1-2}$Man$_5$GlcNAc$_2$ into Man$_5$GlcNAc$_2$ (U.S. Patent Publication No. 20090069232-A1). Constructs for the overexpression of the *A. niger* gls2 subunits were produced as follows: 1) a *Yarrowia* codon-optomized cDNA was generated for the expression of the mature (lacking the signal peptide) *A. niger* gls2α and gls2β subunit; 2) the cDNA's were cloned in-frame to the *Y. lipolytica* LIP2pre-sequence; 3) the resulting LIP2pre-gls2α and LIP2pre-gls2β sequences were cloned under the transcriptional control of the constitutive TEF1 promoter. The resulting plasmids were called pYLTUXdL2preAnGlcIIα and pYLeu2ExTEFpreLip2AnGlucIIβ (FIG. 25).

Figure 26:
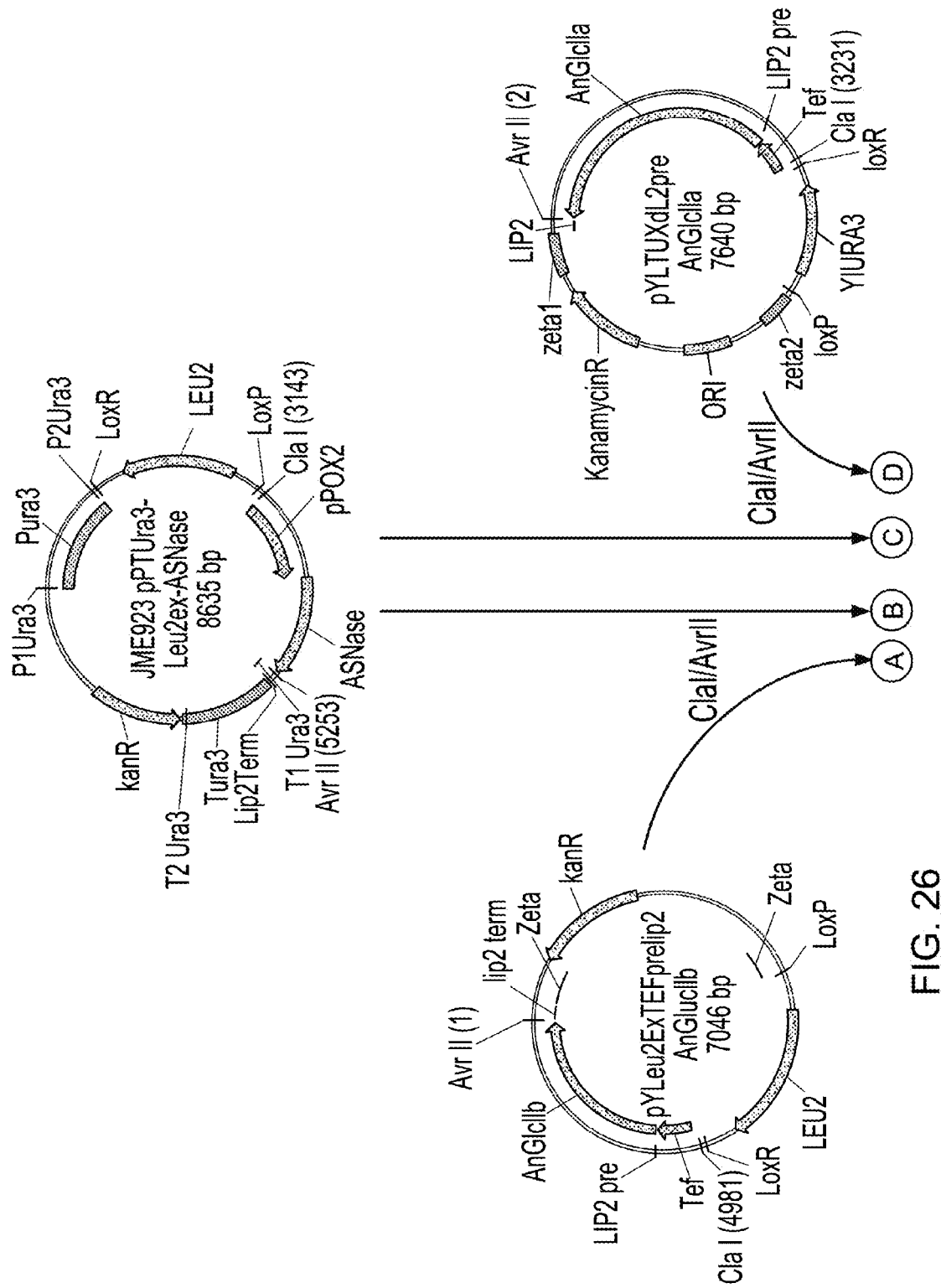
FIG. 26 is a schematic of the construction strategy for plasmids JME923 pPTura3-LEU2ex-TefL2preAnGlcHa+b [alt1].
Figure 26:
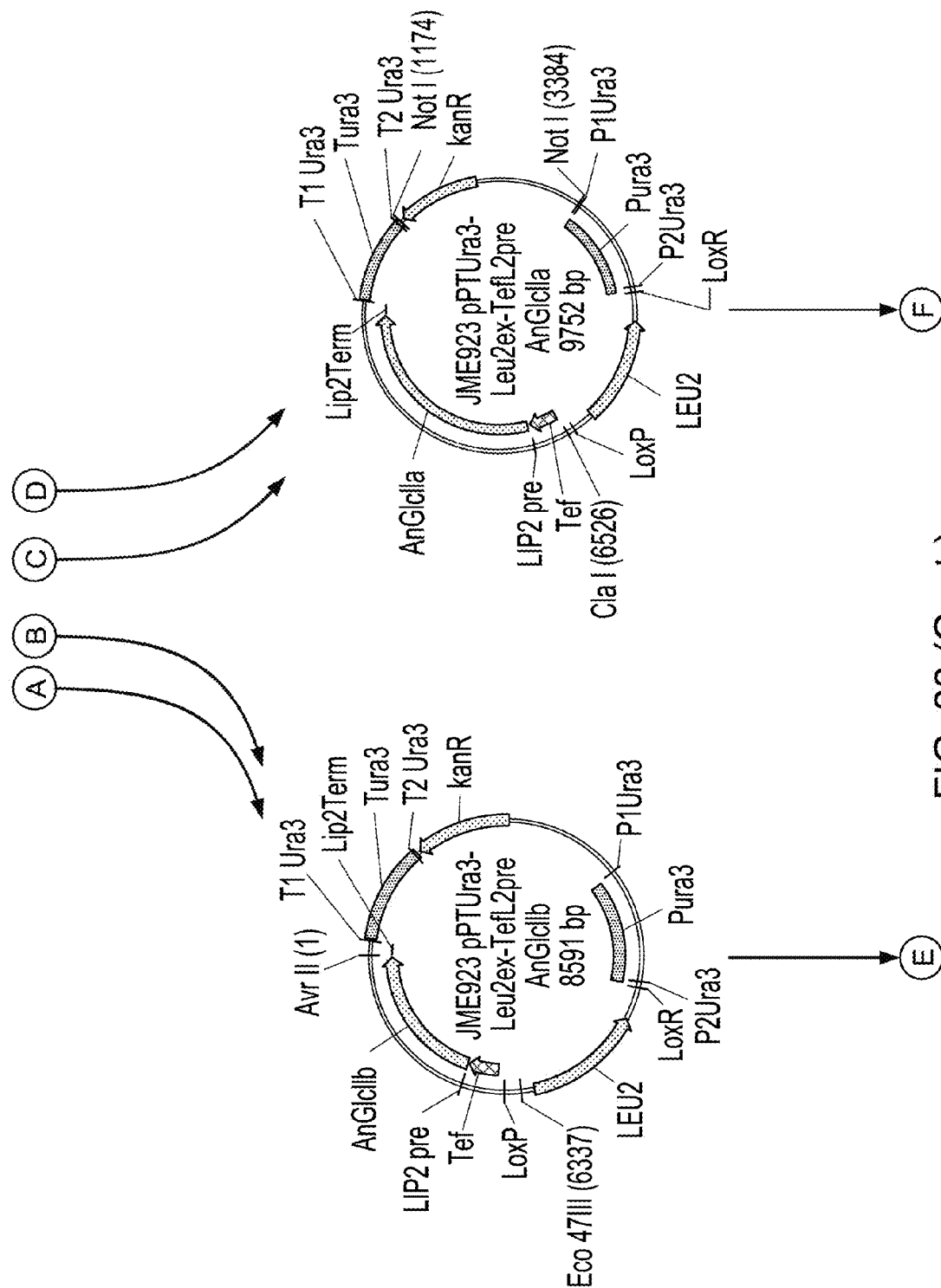
Figure 26:
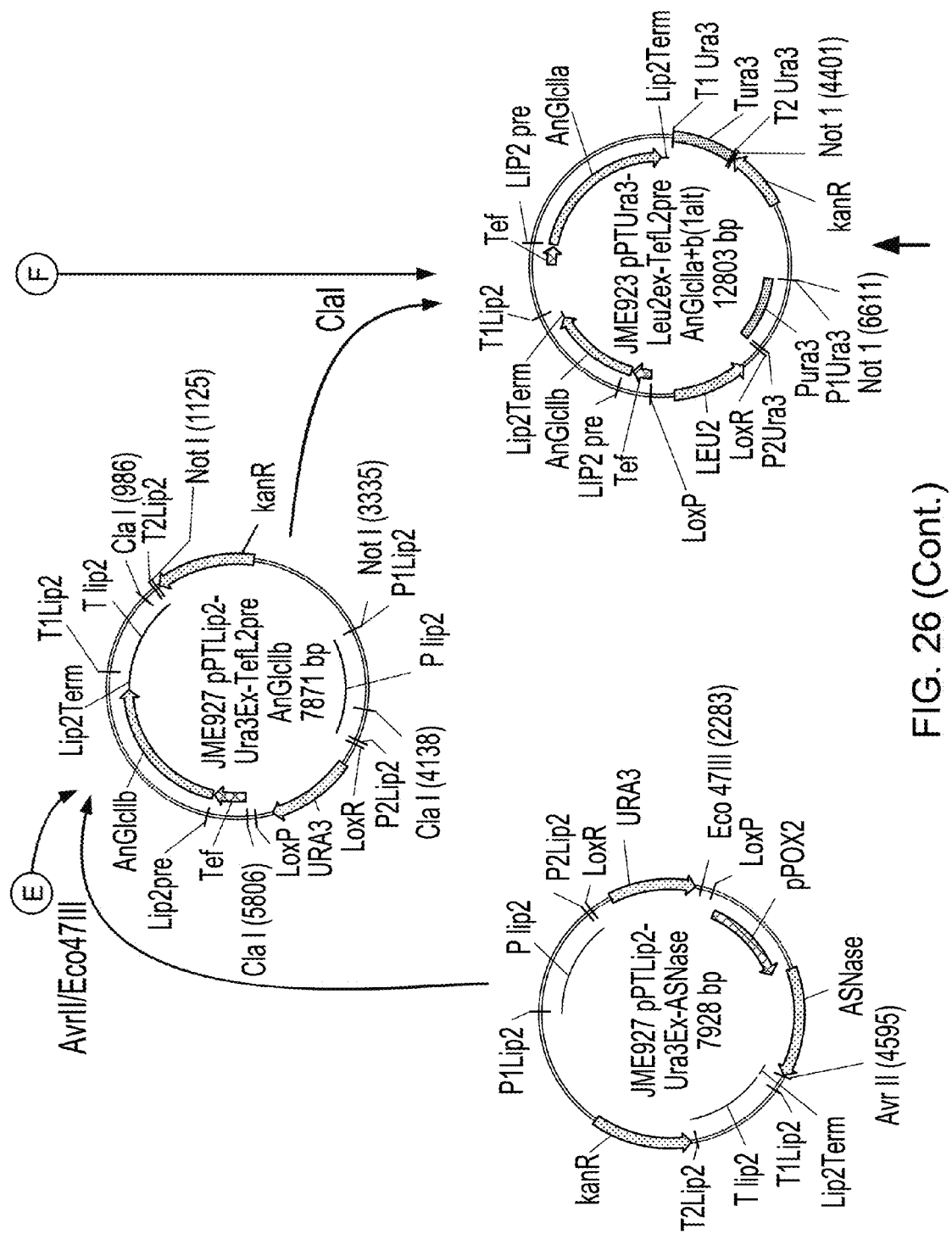
Figure 27:
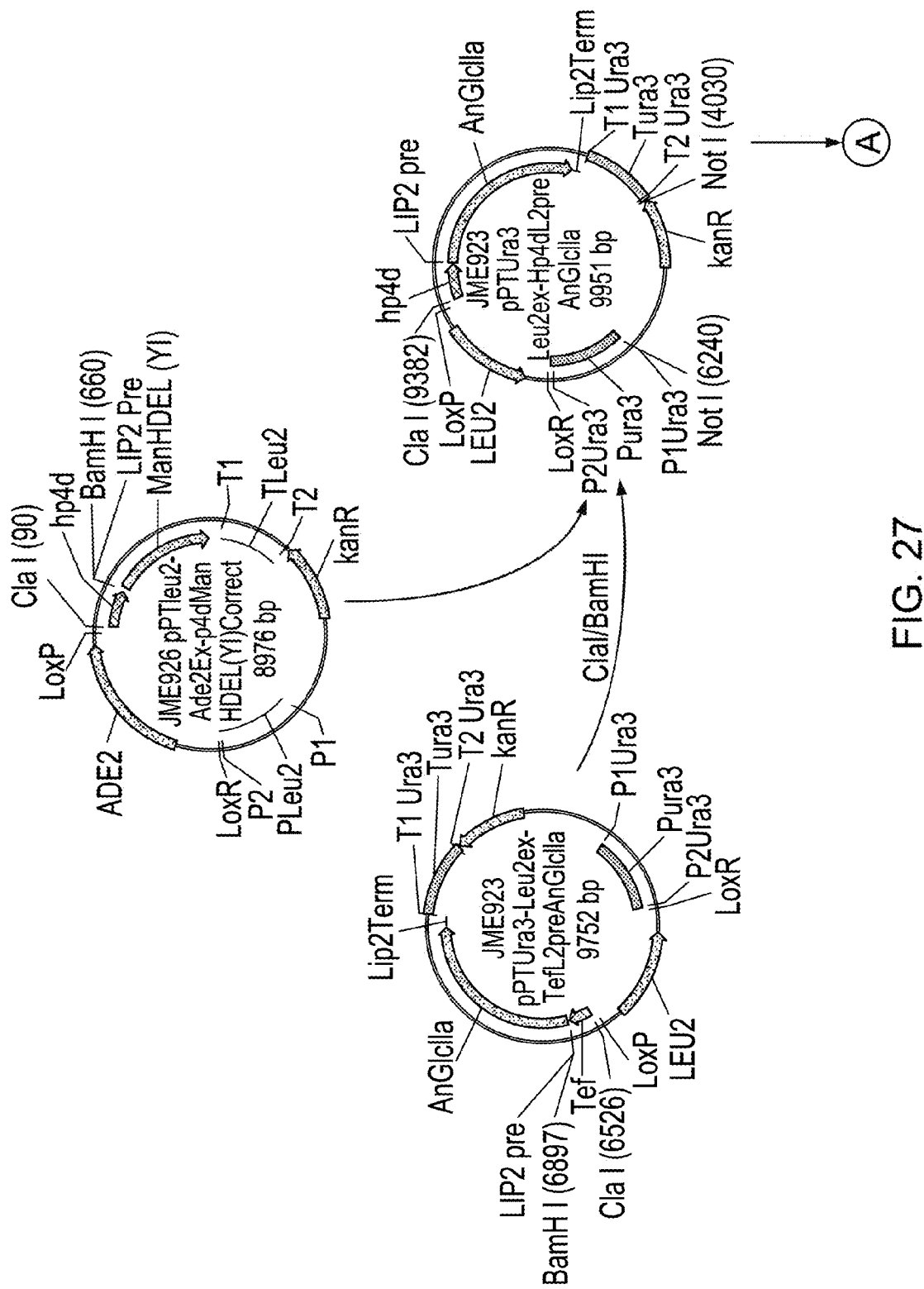
FIG. 27 is a schematic of the construction strategy for plasmids JME923 pPTura3-LEU2ex-Hp4dL2preAnGlcIIa+b[alt1] and Zeta-LEU2ex-Hp4dL2preAnGlcIIa+b[alt].
Figure 27:
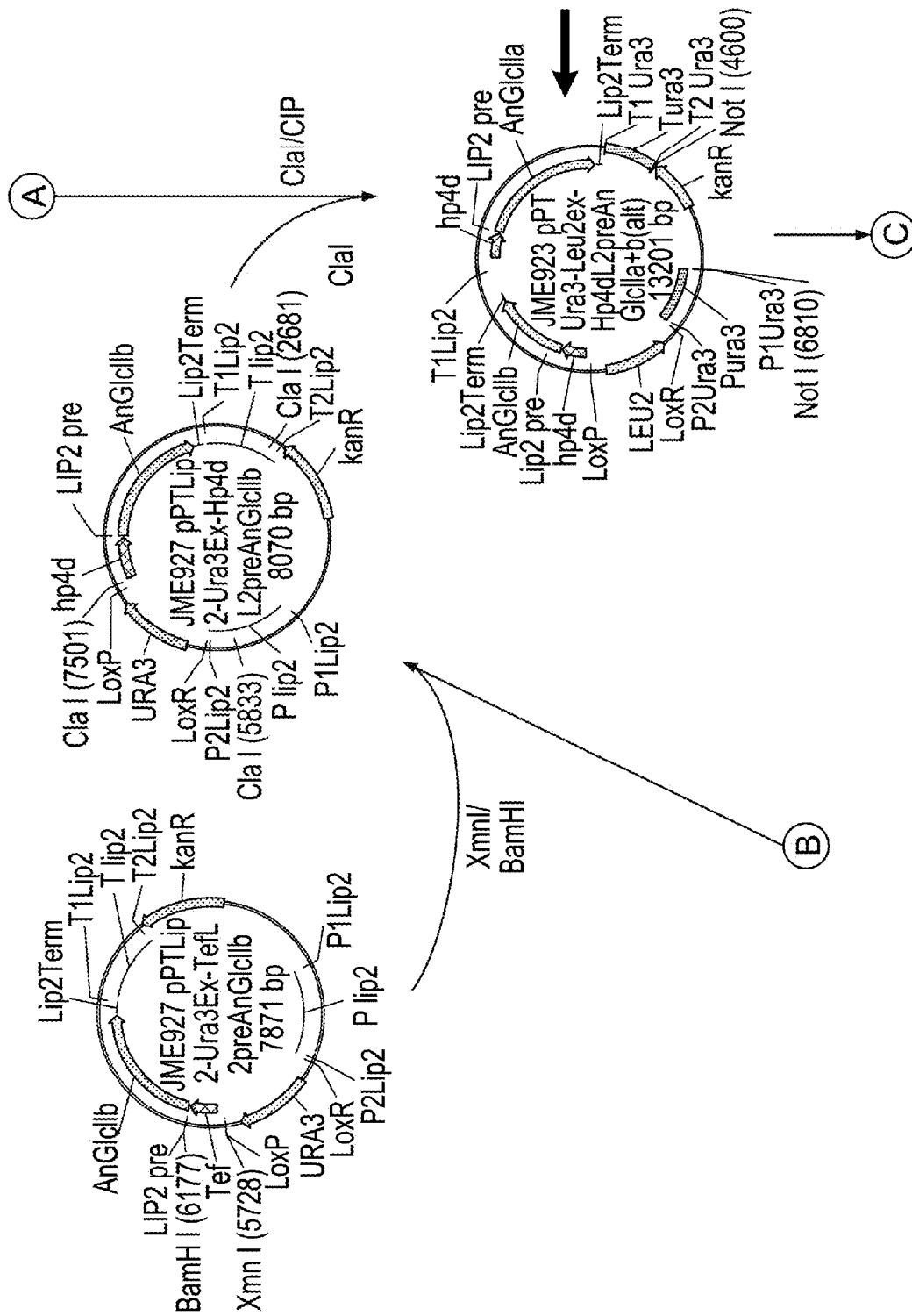
Figure 27:
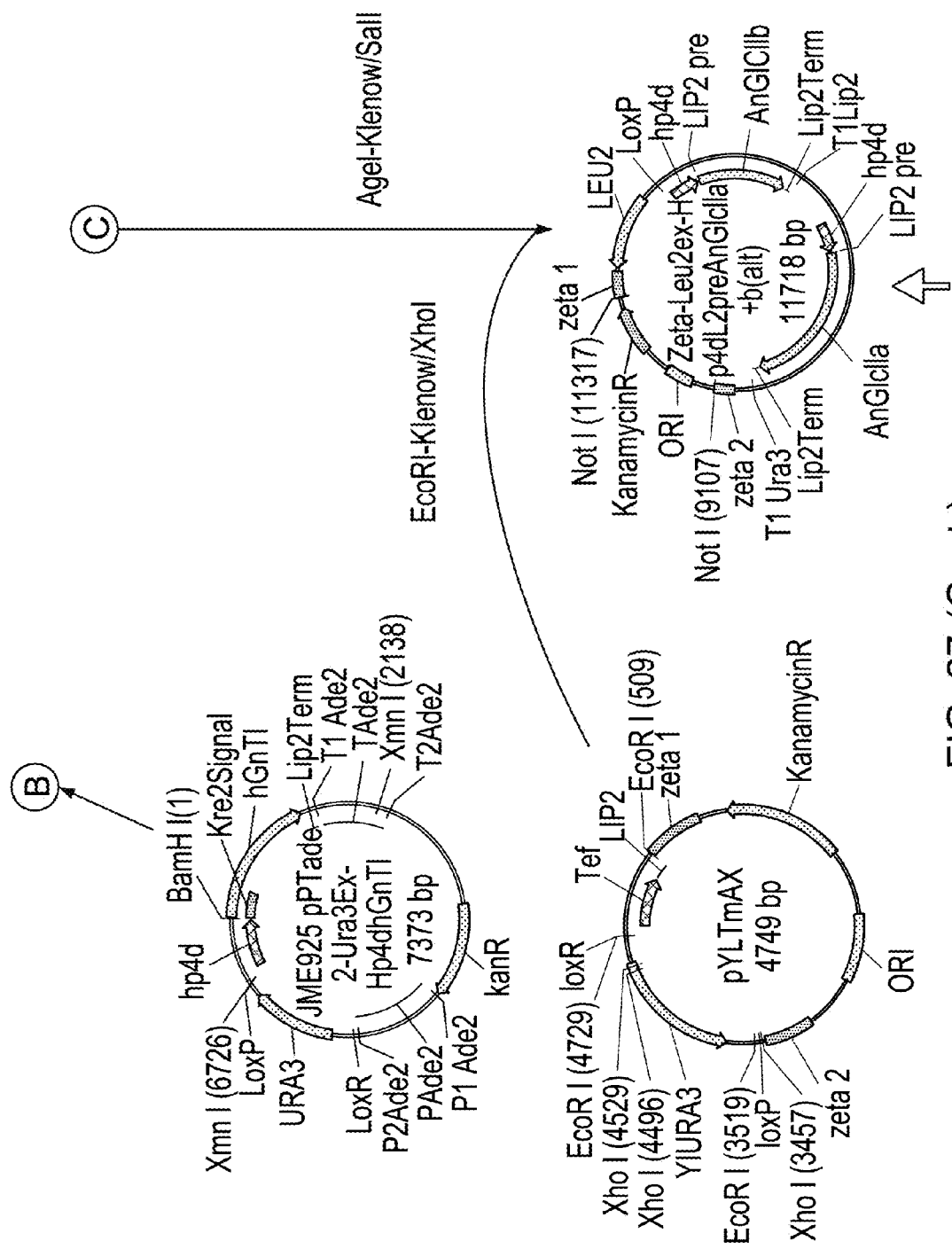

Based on these plasmids, new constructs were generated for the simultaneous overexpression of the *A. niger* gls2α and gls2β subunits under either TEF1 promoter control (vector JME923 pPTura3-LEU2ex-TefL2preAnGlcIIa+b [alt1] for targeted integration—FIG. 26) or Hp4d promoter control (vector JME923 pPTura3-LEU2ex-Hp4dL2preAnGlcIIa+b[alt1] for targeted integration and vector Zeta-LEU2ex-Hp4dL2preAnGlcIIa+b[alt] for random integration—FIG. 27).

Strain G057 (see example 7) was transformed with NotI digested plasmids JME923 pPTura3-LEU2ex-Hp4dL2preAnGlcIIa+b[alt1] and Zeta-LEU2ex-Hp4dL2preAnGlcIIa+b[alt] and transformants were selected based on their leucine prototrophy. Several clones were analyzed genomically via PCR and Southern analysis to evaluate the integration of the gls2α and gls2β expression cassette. PCR-analysis and DIG probe generation for the gls2α subunit was done using primers AnGls2α-FW (5'-GCTGGACTCTTCTTCTATCC-3') (SEQ ID NO:24) and AnGls2α-RV (5'-GGTCTCCTTCAGAGACAGG-3') (SEQ ID NO:25); for the gls2β subunit we made use of primers AnGls2β-FW (5'-CCAAGTTCTACAAGGACACC-3') (SEQ ID NO:26) and AnGlc2β-RV (5'-CCCTTGACGAC-CTTAGAGG-3') (SEQ ID NO:27). Southern analysis to check for targeted integration of the dual Hp4dGls2α/β expression cassette was done on Eco47III-digested gDNA when using the gls2α probe, and on SpeI/SfiI-digested gDNA when using the gls2β probe. The majority of the selected clones showed correct integration of the dual expression cassette into the URA3 locus. Southern analysis for random integration of the dual Hp4dGls2α/β expression cassettes was checked on PvuI-digested gDNA with both probes. In all cases, only one copy of the dual expression cassette was integrated.

Figure 28:
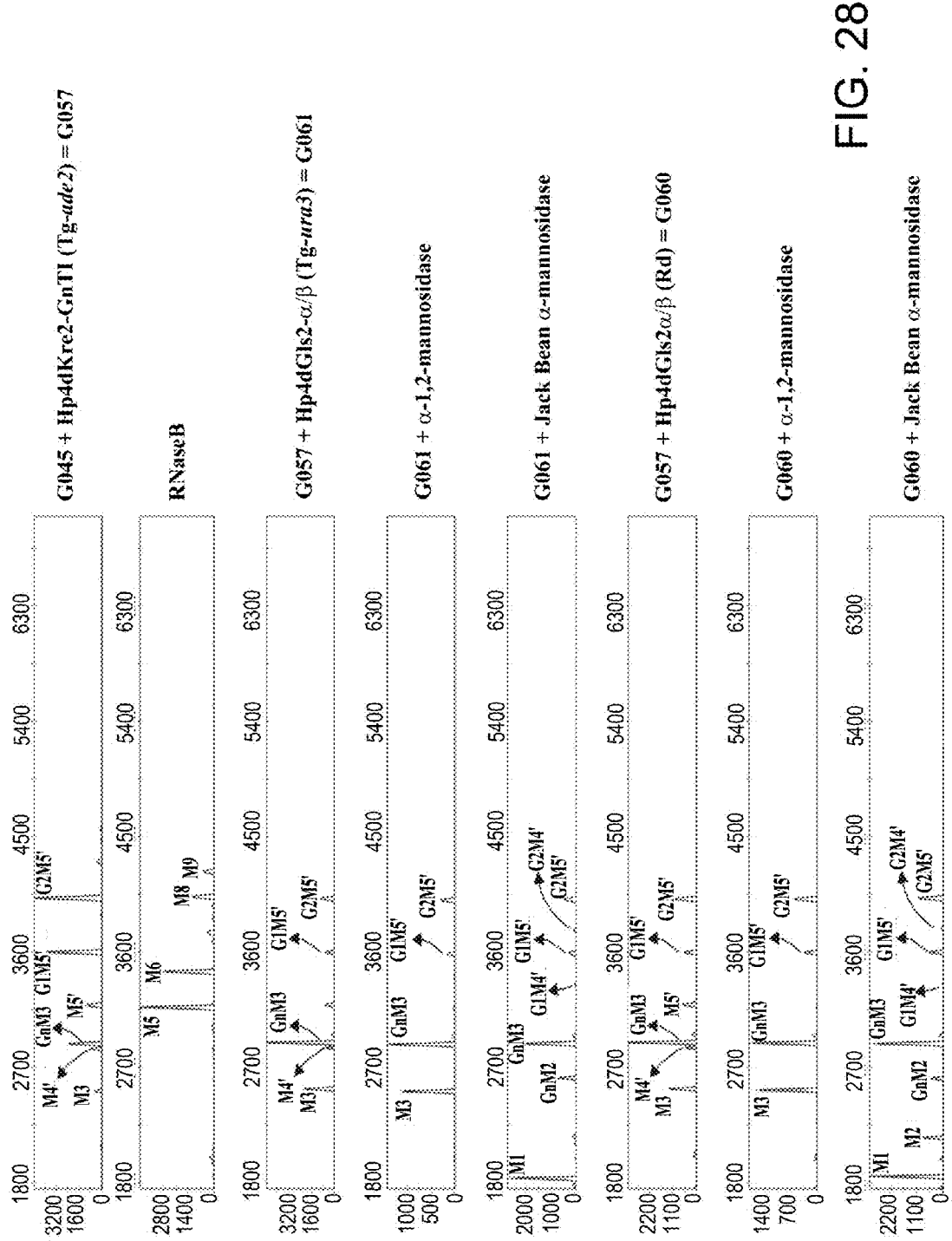
FIG. 28 is a series of electroferograms depicting N-glycan profiles after introduction of the glucosidase II activity into a strain synthesizing GlcNAcMan3GlcNAc2. The resulting strains were either obtained via random (G060) or targeted (G061) integration of a dual expression construct for the gls2α and gls2β subunit. In both cases, a reduction of glucosylated peaks is observed. α-1,2-mannosidase treatment indicates that not all of the generated Man$_5$GlcNAc$_2$ was converted towards Man$_3$GlcNAc$_2$ by the heterologous HDEL-tagged α-1,2-mannosidase. Because of the capping glucoses, GlcMan$_5$GlcNAc$_2$ and Glc$_2$Man$_5$GlcNAc$_2$ are insensitive towards this treatment. Jack Bean mannosidase is partially capable of removing the free α-1,6-linked mannose on both the remaining glucosylated N-glycans and GlcNAcMan$_3$GlcNAc$_2$. Furthermore, this treatment converts Man$_{3\text{-}5}$GlcNAc$_2$ into Man$_1$GlcNAc$_2$. "Rd" stands for "random integration" via the zeta sequences present on the vectors shown in FIG. 27. "Tg-ade2" and "Tg-ura3" stands for targeted integration in the ADE2 resp. URA3 locus.

Next, N-glycan analysis was performed on several clones confirmed to have the dual Hp4dGls2α/β expression cassette (correctly) integrated. N-glycosylation was examined on total secreted protein after three days of falcon cultivation. Several clones showed a significant reduction of the glucosylated sugars and an increase of Man$_3$GlcNAc$_2$ and GlcNAcMan$_3$GlcNAc$_2$. The profiles of a clone that has integrated the dual expression cassette randomly (=strain G060) on the one hand and in a targeted way (=strain G061) on the other, are shown in FIG. 28. The two smaller peaks represent Man$_4$GlcNAc$_2$ and Man$_5$GlcNAc$_2$, since they shift to Man$_3$GlcNAc$_2$ resp. Man$_1$GlcNAc$_2$ upon treatment with α-1,2-mannosidase and Jack Bean mannosidase. The latter treatment also results in a partial conversion of the remaining Glc$_{1-2}$Man$_5$GlcNAc$_2$ into Glc$_{1-2}$Man$_4$GlcNAc$_2$ and of GlcNAcMan$_3$GlcNAc$_2$ into GlcNAcMan$_2$GlcNAc$_2$. Presence of Man$_4$GlcNAc$_2$ and Man$_5$GlcNAc$_2$ however indicates incomplete conversion towards Man$_3$GlcNAc$_2$ by the heterologously co-expressed HDEL-tagged α-1,2-mannosidase. Similarly, the presence of Man$_3$GlcNAc$_2$ indicates incomplete transfer of a GlcNAc-residue by recombinant human GnT I to obtain GlcNAcMan$_3$GlcNAc$_2$. However, based on results described above (e.g. G047 cultivation in Example 7, FIG. 19), it is clear that differences in cultivation conditions can increase the conversion rates significantly and thus improve the end result.

Example 10: Expression of GlcNAc-Transferase II in the GlcNAcMan$_3$GlcNAc$_2$ Producing Strain G061

As described in Example 8, a *Yarrowia* codon-optimized sequence was generated for the expression of a fusion protein consisting of the first 36 N-terminal amino acids of the *S. cerevisiae* Mnn2 protein (SwissProt AccNo P38069) followed by the catalytic domain of rat GlcNAc-transferase II (GnT II) (SwissProt AccNo Q09326) (FIG. 22, SEQ ID NO:17 and SEQ ID NO:18, respectively). The yeast Mnn2 36 N-terminal amino acids serve as a Golgi localization signal for the catalytic GnT II domain. In this way, it was ensured that the Mnn2-GnT II fusion protein was localized at the same or even a later position in the secretion pathway than the Kre2-GnT I fusion protein and was therefore able to convert GlcNAcMan$_3$GlcNAc$_2$ into GlcNAc$_2$Man$_3$GlcNAc$_2$. The synthetic gene for the expression of the fusion protein was placed under the transcriptional control of the Hp4d promoter resulting in plasmid pYLHp4mAXrGnT II, which was used for random integration of the Hp4d-driven GnT II expression cassette into the *Yarrowia* genome. In an alternative strategy, construct OXYP289 pPTAxp1-ADE2ex-Hp4dhGnTII was generated to allow targeted integration of the Hp4d-driven GnT II expression cassette into the AXP1 locus of the *Yarrowia* genome.

Prior to transformation of strain G061 (see Example 9), the plasmids were NotI digested and the targeting/expression cassette was isolated. Transformants were selected based on their adenine prototrophy. Correct integration of the expression cassette into the ADE2 locus was confirmed by Southern blot analysis after digesting the genomic DNA with XmnI. A DIG-labeled probe with specificity for the GnT II coding sequence was generated using forward primer rGnTII-FW (5'-GACCAGATGCTGCGAAACG-3') (SEQ ID NO: 28) and reverse primer rGnTII-RV (5'-CTT-GACGTCCACCTTGTCG-3') (SEQ ID NO: 29). This strategy produces a band of 3172 bp when the gene is successfully integrated into the Axp1 locus.

In an alternative strategy, correct integration into the Axp1 locus can be examined via a PCR reaction on genomic DNA using the forward primer AXPVer1b (5'-GCCTGAACG-GCACGATGCGATCGTGGCAATCC-3') (SEQ ID NO: 30) and the reversed primer AXPVer2b (5'-CAAGAAGC-CTCAGGCTCGGCGAATCTCCA TC-3') (SEQ ID NO: 31). In case of correct targeting into the Axp1 locus, a PCR fragment of 6489 bp is expected.

Figure 29:
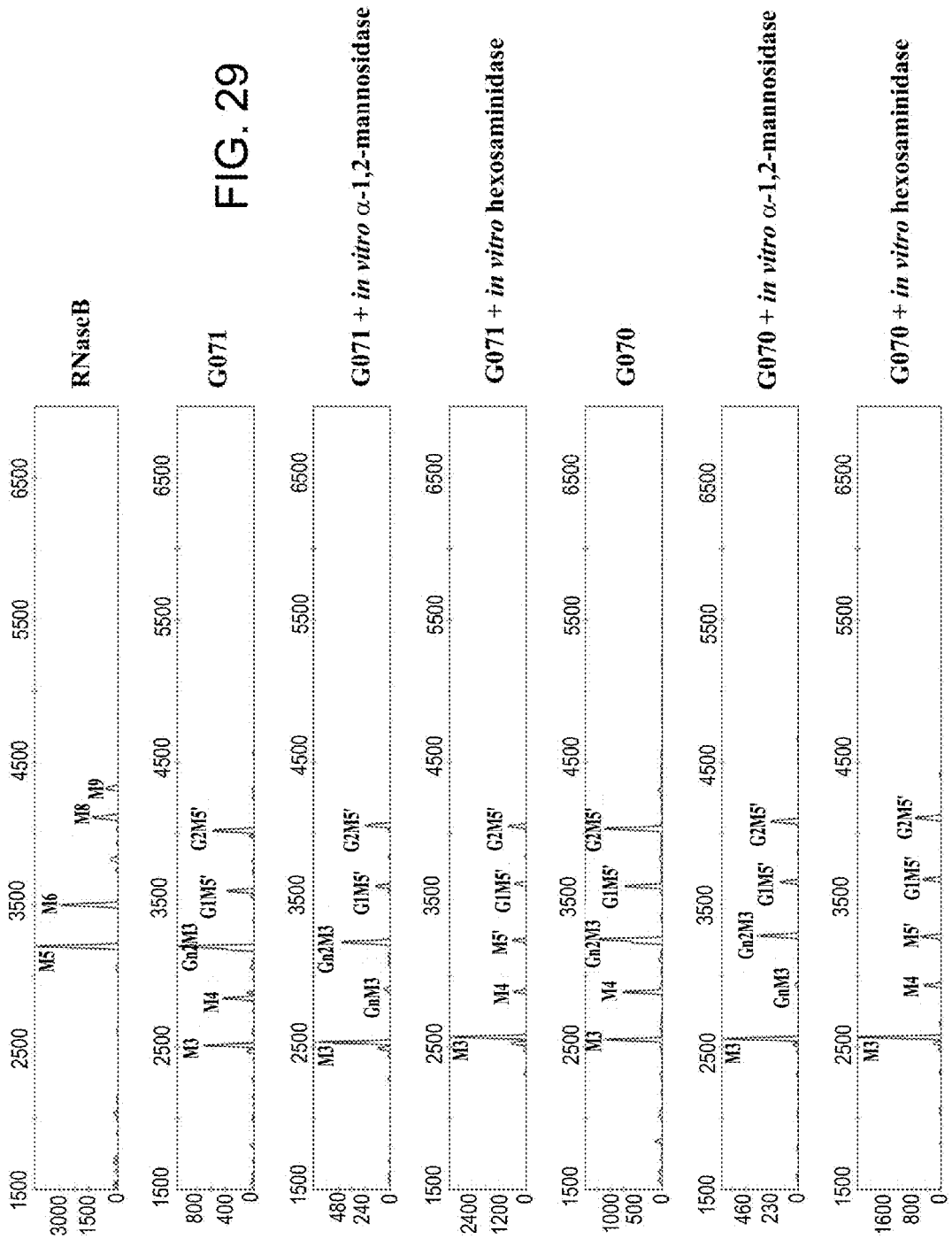
FIG. 29 is a series of electroferograms depicting the N-glycan profile of the secretome of strains G070 and G071, which were generated via the introduction of GlcNAc-transferase II into strain G061. The N-glycans were treated with either α-1,2-mannosidase (removing all terminal α-1,2-linked mannose residues) or hexosaminidase (which removes terminal β-1,2-linked GlcNAc residues) to allow identification of the peaks in the G070 and G071 native profiles. The glucose-containing N-glycans are not sensitive to either of the two enzymes. The α-1,2-mannosidase treatment results in the trimming of Man5'GlcNAc2 and Man4GlcNAc2 towards Man3GlcNAc2. The hexosaminidase treatment removes the β-1,2-linked terminal GlcNAc residues that have been added by GlcNAc-transferase I and II to generate Man3GlcNAc2.

N-glycan analysis on the secretome, in combination with in vitro treatment of the isolated sugars with Jack Bean β-N-acetylhexosaminidase or *T. reesei* α-1,2-mannosidase, indicated that several transformants were capable of producing GlcNAc$_2$Man$_3$GlcNAc$_2$ and thus of expressing a functional GnT II activity (FIG. 29). The analyses indicated that about 25 to 30% of the total N-glycan pool consisted of GlcNAc$_2$Man$_3$GlcNAc$_2$, with a GlcNAcMan$_3$GlcNAc$_2$ to GlcNAc$_2$Man$_3$GlcNAc$_2$ conversion rate of about 90%. The final selected strains were called G070 (integration of pYLHp4mAXrGnTII into G061) and G071 (integration of OXYP289 pPTAxp1-ADE2ex-Hp4dhGnTII into G061).

Example 11: Construction of a Tandem Plasmid for Simultaneous Hp4d-Driven Expression of the Anti-HER2 Heavy Chain (HC) and Light Chain (LC) into *Yarrowia lipolytica*

The amino acid sequences for the anti-HER2 antibody heavy and light chains were obtained from Carter et al., *Proc Natl Acad Sci USA.*, 89(10): 4285-4289 (1992); and Ward et al., *Appl Environ Microbiol.*, 70(5): 2567-2576 (2004). The relevant amino acid sequences were reverse translated, codon-optimized for *Yarrowia lipolitica*, and synthesized by GenArt, Regensburg Germany. Regions of very high (>80%) or very low (<30%) GC content were avoided where possible. During the optimization processes, the following cis-acting sequence motifs were avoided: internal TATA-boxes, chi-sites and ribosomal entry sites, AT-rich or GC-rich sequence stretches, repeat sequences and RNA secondary structures as well as (cryptic) splice donor and acceptor sites. In order to allow secretion of the ectopic proteins, the coding sequence of the Lip2 protein 'prepro' signal (followed by that of a peptide linker 'GGG') was added to the 5' region of the coding sequences. 'GGG' was added to enhance the changes for correct Kex2 processing. FIG. 30A contains the nucleotide sequence of the synthetic prepro-Lip2-LC (=750 bp) (SEQ ID NO: 32). FIG. 30B contains the amino acid sequence of the preproLip2-LC (=250 Aa; MW=27.011 Da; pI=8.46) (SEQ ID NO: 33). FIG. 31A contains the nucleotide sequence of the synthetic prepro-Lip2-HC (=1458 bp) (SEQ ID NO: 34). FIG. 31B contains the amino acid sequence of the preproLip2-HC (=486 Aa; MW=52.853 Da; pI=8.65) (SEQ ID NO: 35). The coding sequences for preproLip2-HC and -LC were introduced into the same vector, called pYLHp4L2preproHerHC/LC (GUT2ex)-ori2.

Example 12: Expression of the Anti-HER2 Antibody HC and LC into *Yarrowia lipolvtica* Strains with a Varying Degree of Glyco-Engineering Plasmid pYLHp4L2preproHerHC&LC (GUT2ex)-ori2 was digested with NotI and the HC-/LC-tandem expression cassette was isolated before transforming *Yarrowia lipolytica* strains G045, G057, G061 and G071 (see Table 2). Transformants containing the randomly integrated HC-/LC-expression cassette were selected based on their ability to grow on glycerol as the sole carbon source. Expression analysis of the HC and LC was done via western blotting after a 4 day shake flask cultivation of the selected transformants in rich medium containing glycerol as the only carbon source (SuperT/glycerol medium: 0.5% yeast extract; 2% malt extract; 1% trypton; 1.5% glycerol; 200 mM phosphate buffer pH 6.8). LC-detection was performed using a mouse monoclonal to Kappa Free Light Chains (4C11) (Abcam) while HC-detection was done using mouse monoclonal anti-human IgG (γ-chain specific) (Sigma).

Figure 32:
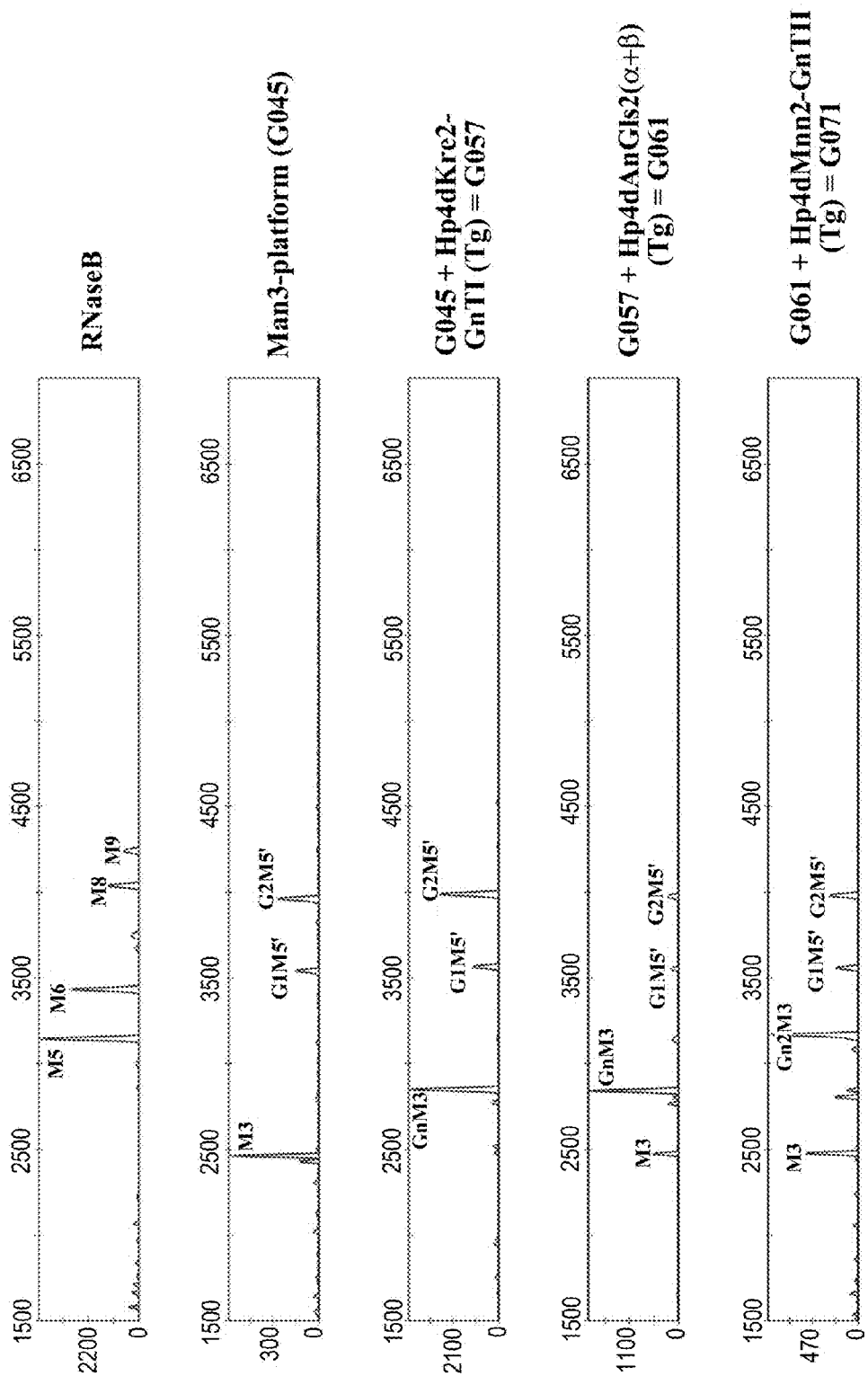
FIG. 32 is a series of electroferograms depicting the N-glycan profile analysis of SuperT/glycerol shake-flask cultivations of glyco-engineered strains G045, G057, G061 and G071 that were transformed with pYLHp4L2preproHerHC/LC (GUT2ex)-ori2. See Table 2 for a description of strains G045, G057, G061 and G071.

The N-glycans of the secretome of the anti-HER2 antibody producing strains showed a similar profile as the corresponding glyco-engineered strains that were not expressing any HC and LC (FIG. 32). The percentages of N-glycans in strains with the G045, G057, G061, and G071 background were determined after a 6-day shake flask cultivation in SuperT/glycerol medium. In a G045 background, 54.6% of the N-glycans were Man$_3$GlcNAc$_2$. In the G057 background, 47.5% of the N-glycans were GlcNAc$_1$Man$_3$GlcNAc$_2$. In a G061 background, 58.9% of the N-glycans were GlcNAc$_1$Man$_3$GlcNAc$_2$. In a G071 background, 37.6% of the N-glycans were GlcNAc$_2$Man$_3$GlcNAc$_2$.

Example 13: Fermentation of *Yarrowia* Strain G096, a GlcNAc$_2$Man$_3$GlcNAc$_2$ Synthesizing Strain Expressing the Anti-HER2 Antibody HC and LC Several pYLHp4L2preproHerHC&LC (GUT2ex)-ori2 transformants of *Yarrowia lipolytica* G071, a strain capable of synthesizing GlcNAc$_2$Man$_3$GlcNAc$_2$, were analyzed for HC and LC expression levels. One of these clones, G096, was chosen for further analysis.

Fermentation was done in a 14-liter stirred tank bioreactor (MAVAG AG) equipped with a process control and management system (Lucillus PIMS). The relative partial oxygen pressure in the medium, the $CO_2$ and $O_2$ concentrations in the exhaust gas, pH value, temperature, reactor overpressure, reactor weight, feed weight and base weight were all monitored on-line. Foam generation was counteracted by adding the antifoaming agent polypropylene glycol (PPG). Adjustments in pH were done by either the addition of a 25% ammonia solution or a 8.5% phosphoric acid solution.

A seed culture of G096 was grown at 28° C. in a shake flask containing rich medium. The seed culture was inoculated into the fermentor containing mineral medium to start a batch phase at 28° C. with unrestricted growth, using glycerol as only carbon source. This phase was used to rapidly reach a high biomass concentration. From that point onward, the process was shifted to an exponential glycerol fed batch (with glycerol as sole carbon and energy source;

pH 6), with a constant growth rate of 0.02. As an example, the results for a fed batch fermentation at 28° C. are described below.

The fed-batch phase lasted for 148 hours. At different time-points of the fermentation, samples were taken to follow up the following parameters: 1) expression of the LC and HC protein backbones via western blot; 2) expression of functional anti-HER2 antibody via an ELISA; and 3) evolution of the N-glycosylation profile of the secretome. The full-length HC expression level reached a maximum around timepoint 7 (39 hrs) and remains approximately equal from then onwards. The LC expression reached a maximum between time-points 7 (39 hrs) and 10 (73 hrs), but decreased somewhat in the later time-points. Some LC-dimers were produced between time-points 5 (25 hrs) and 9 (62 hrs), but disappeared again from that point onwards.

Figure 33:
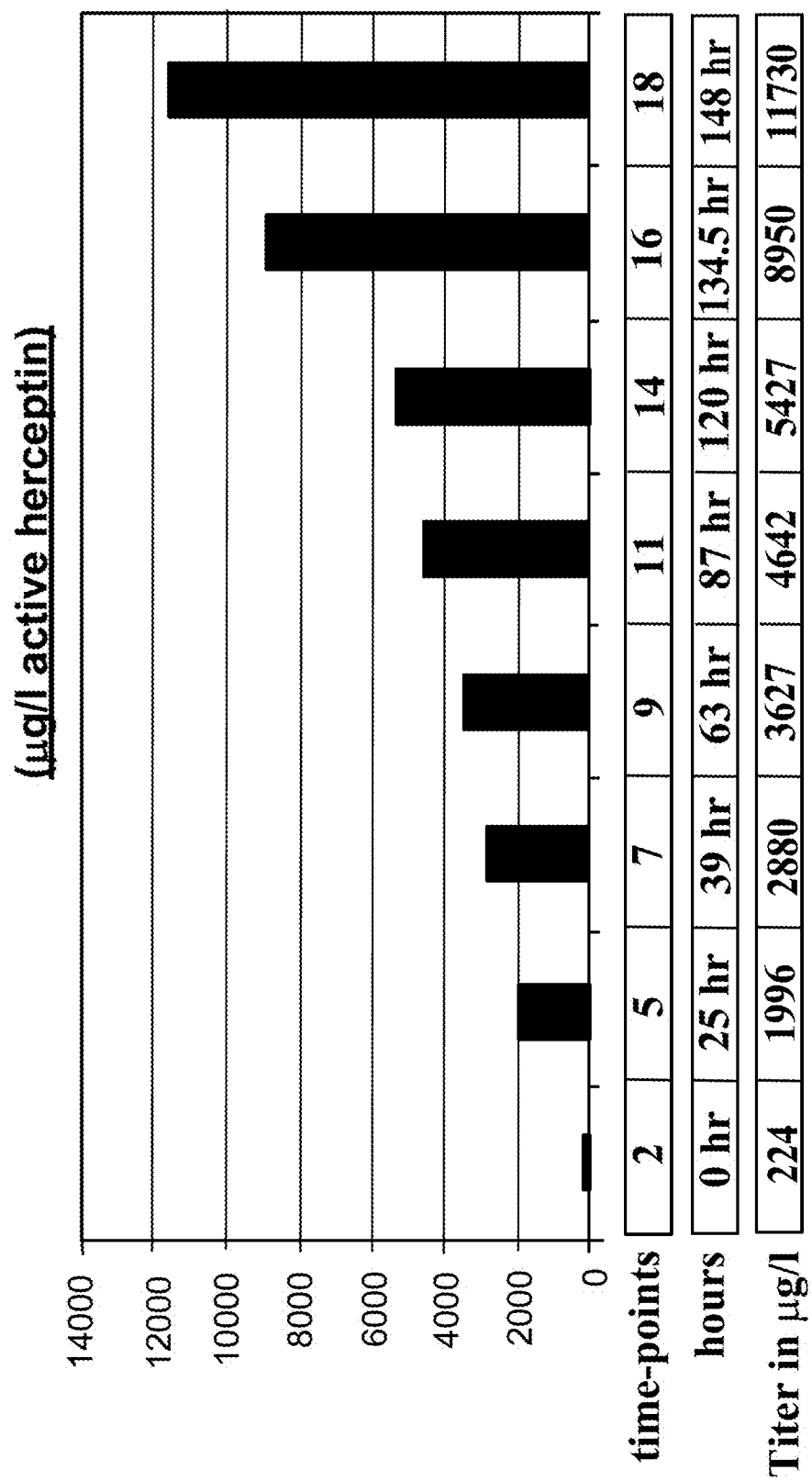
FIG. 33 is a graph of the results from a functional ELISA at different time-points in the G096 fed-batch fermentation.

A functional ELISA was developed to measure the production of anti-HER2 antibody that has at least one functional antigen binding domain. Plates were coated with a recombinant variant of the natural HER2 antigen, the recombinant human ErbB2/Fc chimera (R&D systems). Then a dilution of the medium, harvested at different time-points, was added to the coated plates. Assessment of the amount of antigen binding protein was done using a HRP-conjugated anti-human kappa LC antibody (Sigma). The evolution of the amount of ErbB2/Fc chimera binding protein (a measure of the amount of secreted functional anti-HER2 antibody) within the fed-batch fermentation is shown in FIG. 33. The data show a gradual increase in the levels of anti-HER2 antibody, with a maximum of 10 to 12 mg/L at the end of the production phase.

Figures 1, 34A:
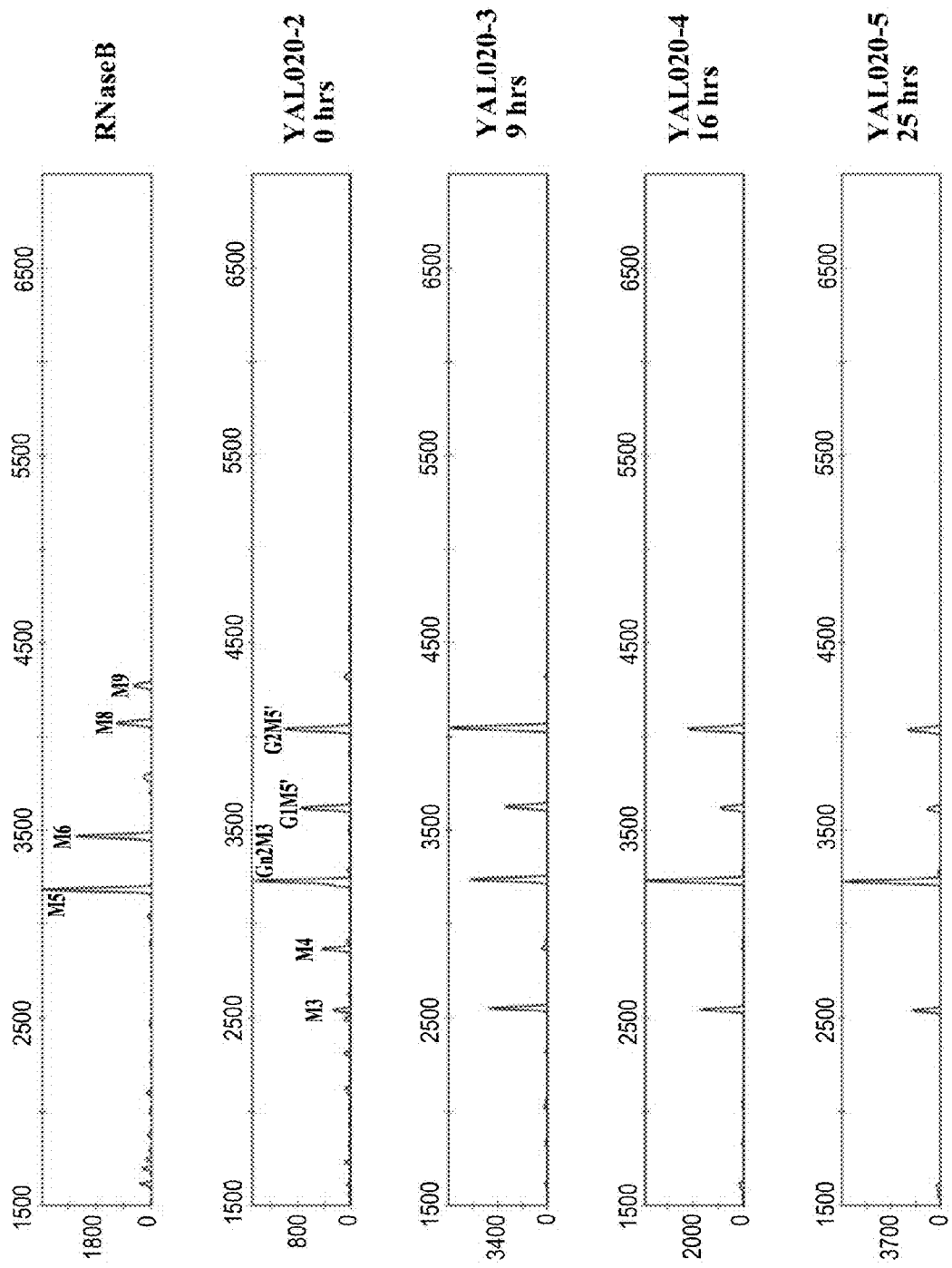
Figures 2, 34A:
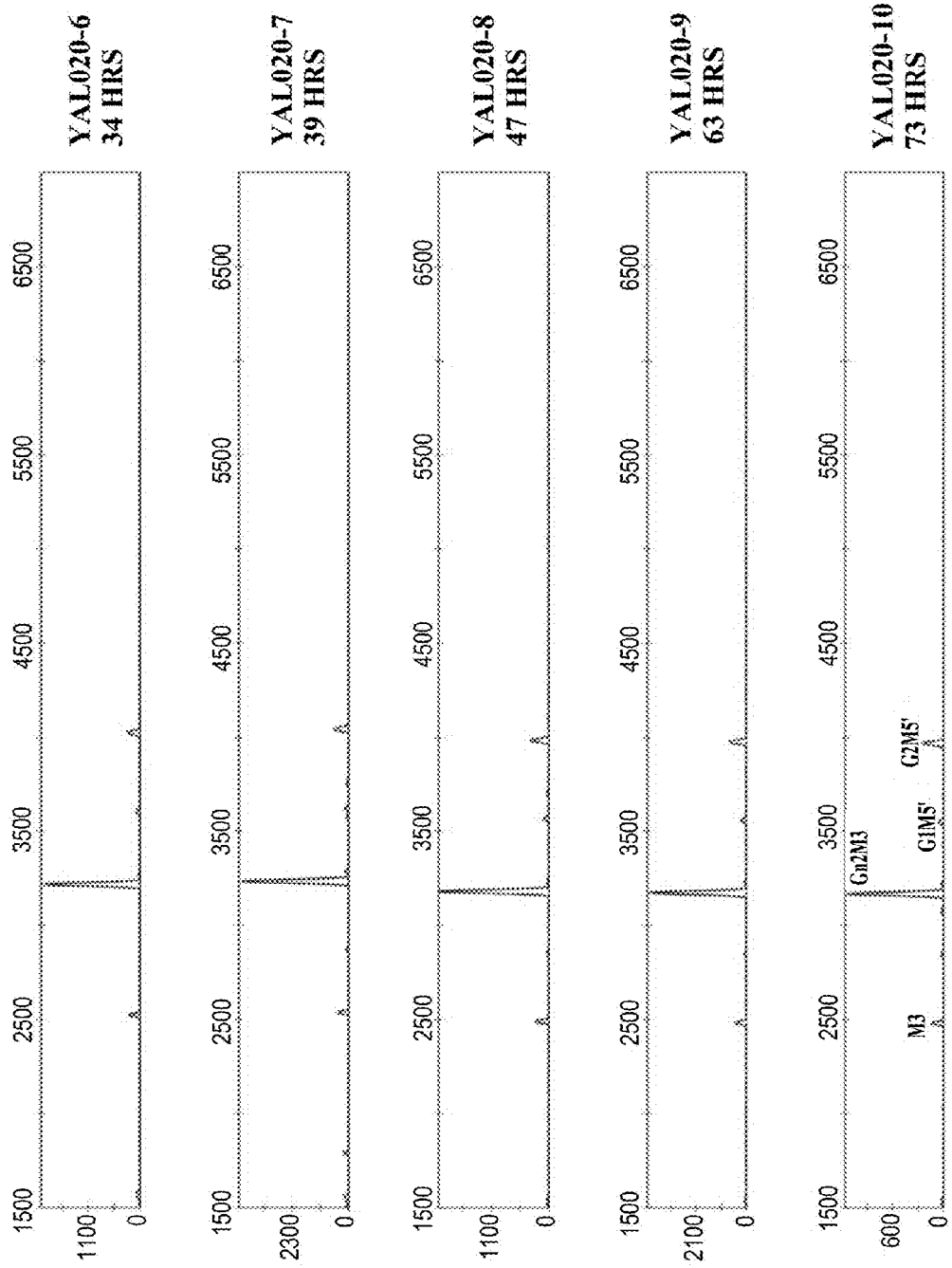
Figures 1, 34B:
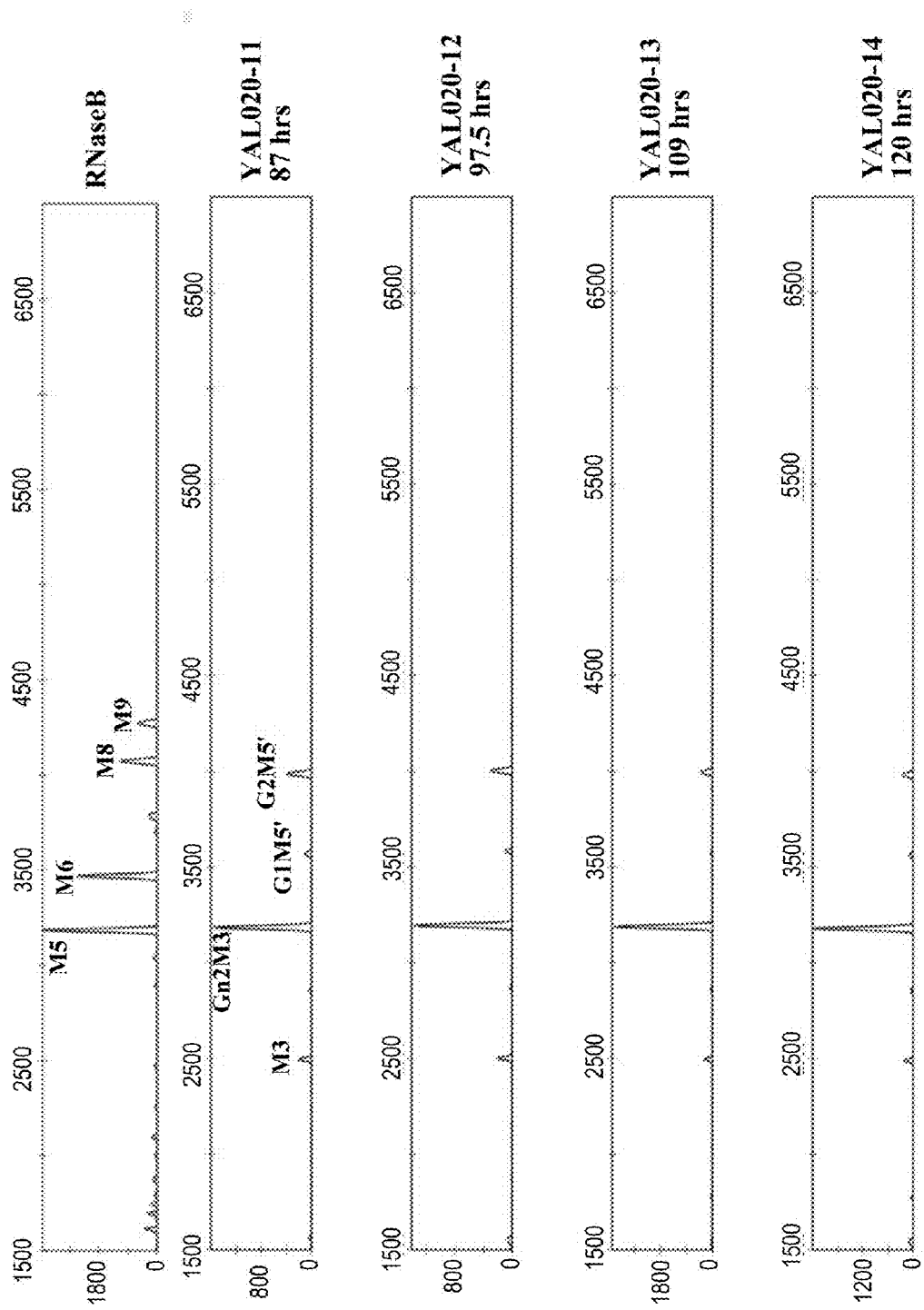
Figures 2, 34B:
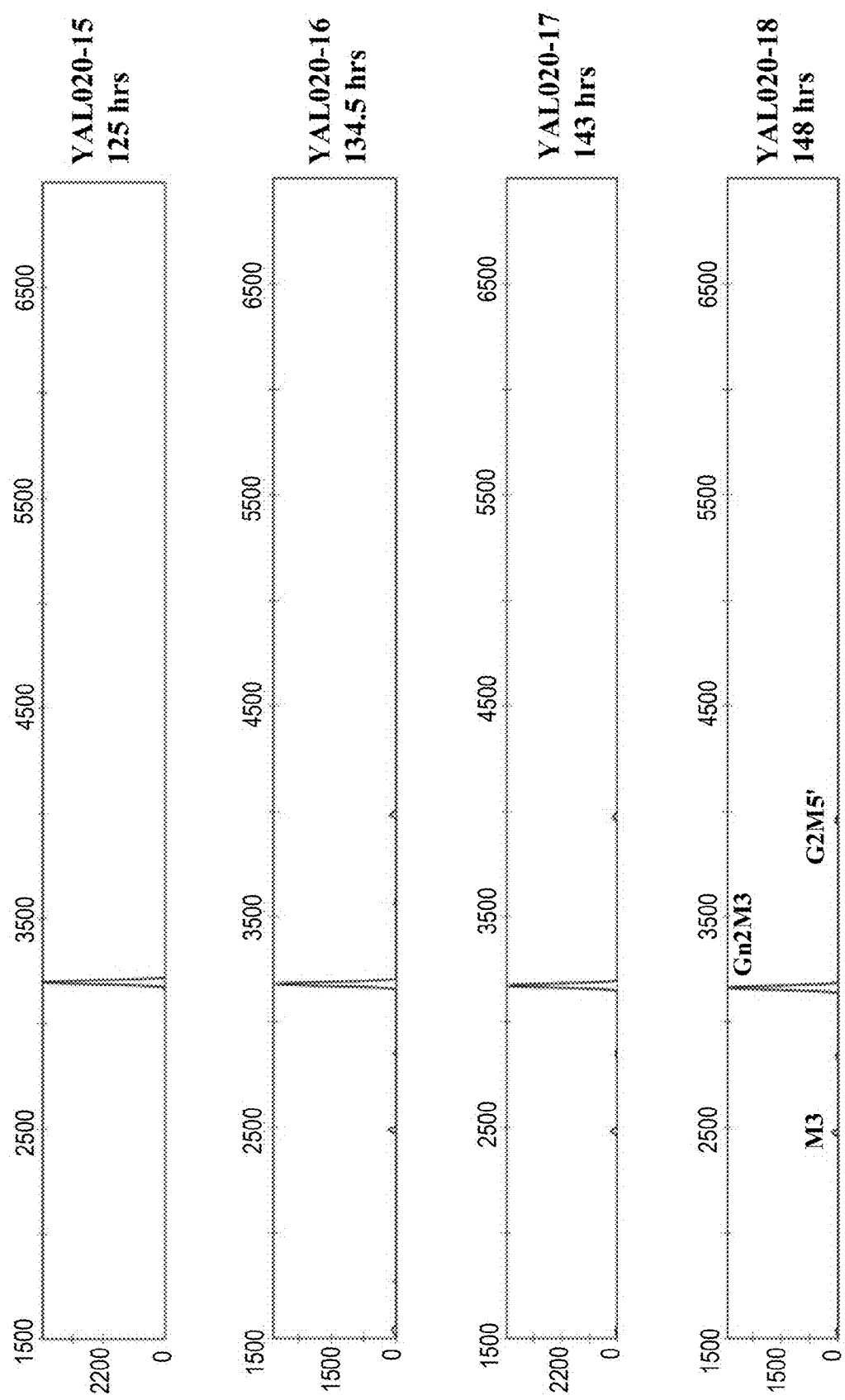

N-glycan analysis was done on samples taken at several time-points during the fed-batch fermentation. The results are shown in FIGS. 34A and 34B. At the beginning of the fed-batch phase, there was a significant amount of glucose-containing N-glycans present. From time-point 6 onward (34 hrs after start of exponential feeding), the level of glucosylated N-glycans decreased significantly with hardly any left at the time of harvest (time-point 18, 148 hrs). This indicated that proteins originally carrying glucose-containing N-glycans, were diluted out by the end of the fermentation. At that point about 86% of the N-glycans isolated from the secretome had the structure $GlcNAc_2Man_3GlcNAc_2$.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A substantially pure culture of *Yarrowia lipolytica* cells, a substantial number of which are genetically engineered to produce glycoproteins comprising GalGlcNAc$_2$Man$_3$GlcNAc$_2$ or Gal$_2$GlcNAc$_2$Man$_3$GlcNAc$_2$ N-glycans, wherein said cells are genetically engineered to be deficient in Outer CHain elongation (OCH1) activity and in Asparagine Linked Glycosylation 3 (ALG3) activity and to comprise one or more nucleic acids encoding an α-1,2-mannosidase, a nucleic acid encoding Asparagine Linked Glycosylation 6 (ALG6), and one or more nucleic acids encoding each of a GlcNAc-transferase I, a GlcNAc-transferase II, and a galactosyltransferase, wherein each of said one or more nucleic acids encoding said α-1,2-mannosidase, said GlcNAc-transferase I, said GlcNAc-transferase II, and said galactosyltransferase comprises nucleotide sequences encoding targeting sequences to target each encoded protein to an intracellular compartment, wherein said cells produce proteins comprising GalGlcNAc$_2$Man$_3$GlcNAc$_2$ or Gal$_2$GlcNAc$_2$Man$_3$GlcNAc$_2$ N-glycans.

2. The culture of claim 1, wherein each of said cells further comprises a nucleic acid encoding a target protein, wherein each of said cells produces said target protein comprising GalGlcNAc$_2$Man$_3$GlcNAc$_2$ or Gal$_2$GlcNAc$_2$Man$_3$GlcNAc$_2$ N-glycans.

3. The culture of claim 2, wherein the target protein is a protein selected from the group consisting of a therapeutic glycoprotein, an antibody or fragment thereof, interferon-β, granulocyte-macrophage colony-stimulating factor (GM-CSF), interferon-γ, and erythropoietin.

4. The culture of claim 2, wherein said target protein is an antibody or fragment thereof comprising an Fc part that can interact with an Fc receptor.

5. The culture of claim 1, wherein said intracellular compartment is the Golgi apparatus.

6. The culture of claim 1, wherein said coding sequence encoding said α-1,2-mannosidase comprises an endoplasmic reticulum targeting sequence to target the encoded α-1,2-mannosidase to the endoplasmic reticulum.

7. The culture of claim 6, wherein said endoplasmic reticulum targeting sequence is an HDEL endoplasmic reticulum-retention (HDEL) sequence (SEQ ID NO: 21).

8. The culture of claim 1, wherein each of said cells further comprise a nucleic acid encoding the α and β subunits of a Glucosidase II.

9. An isolated *Yarrowia lipolytica* cell genetically engineered to produce proteins comprising GalGlcNAc$_2$Man$_3$GlcNAc$_2$ or Gal$_2$GlcNAc$_2$Man$_3$GlcNAc$_2$ N-glycans, wherein said cell is genetically engineered to be deficient in Outer CHain elongation (OCH1) activity and in Asparagine Linked Glycosylation 3 (ALG3) activity and to comprise one or more nucleic acids encoding an α-1,2-mannosidase, a nucleic acid encoding Asparagine Linked Glycosylation 6 (ALG6), and one or more nucleic acids encoding each of a GlcNAc-transferase I, a GlcNAc-transferase II, and a galactosyltransferase, wherein each of said one or more nucleic acids encoding said α-1,2-mannosidase, said GlcNAc-transferase I, said GlcNAc-transferase II, and said galactosyltransferase comprises nucleotide sequences encoding targeting sequences to target each encoded protein to an intracellular compartment, wherein said cell produces proteins comprising GalGlcNAc$_2$Man$_3$GlcNAc$_2$ or Gal$_2$GlcNAc$_2$Man$_3$GlcNAc$_2$ N-glycans.

10. The *Yarrowia lipolytica* cell of claim 9, wherein said cell further comprises a nucleic acid encoding a target protein, wherein each of said cells produces said target protein comprising GalGlcNAc2Man3GlcNAc2 or Gal2GlcNAc2Man3GlcNAc2 N-glycans.

11. The *Yarrowia lipolytica* cell of claim 10, wherein the target protein is a protein selected from the group consisting of a therapeutic glycoprotein, an antibody or fragment thereof, interferon-β, granulocyte-macrophage colony-stimulating factor (GM-CSF), interferon-γ, and erythropoietin.

12. The *Yarrowia lipolytica* cell of claim 10, wherein said target protein is an antibody or fragment thereof comprising an Fc part that can interact with an Fc receptor.

13. The *Yarrowia lipolytica* cell of claim 9, wherein said intracellular compartment is the Golgi apparatus.

14. The *Yarrowia lipolytica* cell of claim 9, wherein said coding sequence encoding said α-1,2-mannosidase is linked to an endoplasmic reticulum targeting sequence to target the encoded α-1,2-mannosidase to the endoplasmic reticulum.

15. The *Yarrowia lipolytica* cell of claim 14, wherein said endoplasmic reticulum targeting sequence is an HDEL endoplasmic reticulum-retention (HDEL) sequence (SEQ ID NO: 21).

16. The *Yarrowia lipolytica* cell of claim 9, wherein said cell further comprises a nucleic acid encoding the α and β subunits of a Glucosidase II.

* * * * *

UNITED STATES PATENT AND TRADEMARK OFFICE
CERTIFICATE OF CORRECTION

PATENT NO. : 10,287,557 B2
APPLICATION NO. : 14/641002
DATED : May 14, 2019
INVENTOR(S) : Steven Christian Jozef Geysens and Wouter Vervecken Page 1 of 1

It is certified that error appears in the above-identified patent and that said Letters Patent is hereby corrected as shown below:

In the Specification

Column 1, Line 4:
After "RELATED" insert -- APPLICATIONS --.

Column 1, Line 10:
After "2010," delete "2002,".

In the Claims

Column 82, Line 30:
In Claim 10, delete "GalGlcNAc2Man3GlcNAc2 or Gal2GlcNAc2Man3GlcNAc2" and insert -- GalGlcNAc$_2$Man$_3$GlcNAc$_2$ or Gal$_2$GlcNAc$_2$Man$_3$GlcNAc$_2$ --, therefor.

Signed and Sealed this
Third Day of December, 2019

Andrei Iancu
*Director of the United States Patent and Trademark Office*